(12) United States Patent
Sabatini et al.

(10) Patent No.: US 11,225,469 B2
(45) Date of Patent: Jan. 18, 2022

(54) INHIBITORS OF PHOSPHOGLYCERATE DEHYDROGENASE (PHGDH) AND USES THEREOF

(71) Applicants: Whitehead Institute for Biomedical Research, Cambridge, MA (US); Dana-Farber Cancer Institute, Inc., Boston, MA (US); The United States of America, as represented by the Secretary, Department of Health and Human Services, Bethesda, MD (US)

(72) Inventors: David M. Sabatini, Cambridge, MA (US); Michael Pacold, Cambridge, MA (US); Matthew B. Boxer, New Market, MD (US); Jason M. Rohde, Poolesville, MD (US); Kyle R. Brimacombe, Highland, NY (US); Min Shen, Boyds, MD (US); Ganesha Bantukallu, Falls Church, VA (US); Li Liu, Germantown, MD (US)

(73) Assignees: Whitehead Institute for Biomedical Research, Cambridge, MA (US); Dana-Farber Cancer Institute, Inc., Boston, MA (US); The United States of America, as represented by the Secretary, Department of Health and Human Services, Silver Spring, MD (US)

( * ) Notice: Subject to any disclaimer, the term of this patent is extended or adjusted under 35 U.S.C. 154(b) by 0 days.

(21) Appl. No.: 15/543,643

(22) PCT Filed: Jan. 15, 2016

(86) PCT No.: PCT/US2016/013602
§ 371 (c)(1),
(2) Date: Jul. 14, 2017

(87) PCT Pub. No.: WO2016/115463
PCT Pub. Date: Jul. 21, 2016

(65) Prior Publication Data
US 2018/0105508 A1    Apr. 19, 2018

Related U.S. Application Data

(60) Provisional application No. 62/103,990, filed on Jan. 15, 2015.

(51) Int. Cl.
| | | |
|---|---|---|
| *C07D 401/12* | (2006.01) |
| *C07D 213/75* | (2006.01) |
| *C07D 213/40* | (2006.01) |
| *A61K 45/06* | (2006.01) |
| *C07D 233/88* | (2006.01) |
| *C07D 213/78* | (2006.01) |
| *C07D 235/30* | (2006.01) |
| *C07D 249/14* | (2006.01) |
| *C07D 231/40* | (2006.01) |
| *A61P 43/00* | (2006.01) |
| *A61P 35/00* | (2006.01) |

(52) U.S. Cl.
CPC ............ *C07D 401/12* (2013.01); *A61K 45/06* (2013.01); *A61P 35/00* (2018.01); *A61P 43/00* (2018.01); *C07D 213/40* (2013.01); *C07D 213/75* (2013.01); *C07D 213/78* (2013.01); *C07D 231/40* (2013.01); *C07D 233/88* (2013.01); *C07D 235/30* (2013.01); *C07D 249/14* (2013.01)

(58) Field of Classification Search
CPC .. C07D 495/10; C07D 401/12; A61K 31/496; A61K 31/4545; A61P 35/00
USPC .............. 544/360; 546/189; 514/252.13, 318
See application file for complete search history.

(56) References Cited

U.S. PATENT DOCUMENTS

2014/0323467 A1    10/2014   Salituro et al.

OTHER PUBLICATIONS

Pccompound-selected items 1-6, Create Date Jul. 14, 2005 to Create Date Jul. 29, 2011.*
Cecil Textbook of Medicine, edited by Bennet, J.C., and Plum F., 20th edition,vol. 1, 1004-1010, 1996.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
PuBChen CID4985294 Bioactivity—Create Date Feb. 14, 2011.*

(Continued)

*Primary Examiner* — Paul V Ward
(74) *Attorney, Agent, or Firm* — Wolf, Greenfield & Sacks, P.C.

(57) ABSTRACT

The present invention provides compounds of Formula (II), and pharmaceutically acceptable salts, solvates, hydrates, polymorphs, co-crystals, tautomers, stereoisomers, isotopically labeled derivatives, pro-drugs, and compositions thereof. Also provided are methods and kits involving the compounds of Formula (I), (II) or (III) for treating diseases associated with the over-expression of phosphoglycerate dehydrogenase (PHGDH) in a subject, such as proliferative diseases (e.g., cancers (e.g., breast cancer, ER negative breast cancer, melanoma, cervical cancer), benign neoplasms, diseases associated with angiogenesis, inflammatory diseases, autoinflammatory diseases, and autoimmune diseases). Treatment of a subject with a proliferative disease using a compound or composition of the invention may inhibit the activity of PHGDH or inhibit the serine biosynthetic pathway, or both.

25 Claims, 45 Drawing Sheets
Specification includes a Sequence Listing.

(56) References Cited

OTHER PUBLICATIONS

Pccompound selected items 1-24, Create Date Feb. 14, 2011 to Mar. 6, 2020.*
PCT/US2016/013602, dated May 6, 2016, International Search Report and Written Opinion.
PCT/US2016/013602, dated Jul. 27, 2017, International Preliminary Report on Patentability.
[No Author Listed], CID 49853035. Compound Summary. Feb. 14, 2011. 2 pages.
[No Author Listed], CID 49853070. Compound Summary. Feb. 14, 2011. 1 page.
[No Author Listed], CID 49853091. Compound Summary. Feb. 14, 2011. 10 pages.
[No Author Listed], CID 49853099. Compound Summary. Feb. 14, 2011. 3 pages.
[No Author Listed], CID 49853203. Compound Summary. Feb. 14, 2011. 2 pages.
[No Author Listed], CID 49853258. Compound Summary. Feb. 14, 2011. 3 pages.
[No Author Listed], CID 49853284. Compound Summary. Feb. 14, 2011. 2 pages.
[No Author Listed], CID 53257117. Compound Summary. Jul. 29, 2011. 3 pages.
[No Author Listed], CID 8418019. Compound Summary. Jul. 30, 2006. 1 page.
Achouri et al., Cloning, sequencing and expression of rat liver 3-phosphoglycerate dehydrogenase. Biochem J. Apr. 15, 1997;323 ( Pt 2):365-70.
Birsoy et al., An Essential Role of the Mitochondrial Electron Transport Chain in Cell Proliferation Is to Enable Aspartate Synthesis. Cell. Jul. 30, 2015;162(3):540-51. doi: 10.1016/j.cell.2015.07.016.
Cantor et al., Cancer cell metabolism: one hallmark, many faces. Cancer Discov. Oct. 2012;2(10):881-98. doi: 10.1158/2159-8290.CD-12-0345. Epub Sep. 25, 2012.
Chakraborty et al., Characterization of a dihydrolipoyl dehydrogenase having diaphorase activity of Clostridium kluyveri. Biosci Biotechnol Biochem. Apr. 2008;72(4):982-8. Epub Apr. 7, 2008.
Chaneton et al., Serine is a natural ligand and allosteric activator of pyruvate kinase M2. Nature. Nov. 15, 2012;491(7424):458-462. doi: 10.1038/nature11540. Epub Oct. 14, 2012. Erratum in: Nature. Apr. 18, 2013;496(7445):386.
Chen et al., Phosphoglycerate dehydrogenase is dispensable for breast tumor maintenance and growth. Oncotarget. Dec. 2013;4(12):2502-11.
DeNicola et al., NRF2 regulates serine biosynthesis in non-small cell lung cancer. Nat Genet. Dec. 2015;47(12):1475-81. doi: 10.1038/ng.3421. Epub Oct. 19, 2015. Erratumin: Nat Genet. Apr. 2016;48(4):473.
Fan et al., Quantitative flux analysis reveals folate-dependent NADPH production. Nature. Jun. 12, 2014;510(7504):298-302. doi: 10.1038/nature13236. Epub May 4, 2014. Erratum in: Nature. Sep. 25, 2014;513(7519):574.
Farber et al., Temporary remissions in acute leukemia in children produced by folic acid antagonist, 4-aminopteroyl-glutamic acid. N Engl J Med. Jun. 3, 1948;238(23):787-93.
Fell et al., Control analysis of mammalian serine biosynthesis. Feedback inhibition on the final step. Biochem J. Nov. 15, 1988;256(1):97-101.
Foley et al., 4-(3-Chloro-5-(trifluoromethyl)pyridin-2-yl)-N-(4-methoxypyridin-2-yl)piperazine-1-carbothioamide (ML267), a potent inhibitor of bacterial phosphopantetheinyl transferase that attenuates secondary metabolism and thwarts bacterial growth. J Med Chem. Feb. 13, 2014;57(3):1063-78. doi: 10.1021/jm401752p. Epub Jan. 22, 2014.
Hamiaux et al., DAD2 is an α/β hydrolase likely to be involved in the perception of the plant branching hormone, strigolactone. Curr Biol. Nov. 6, 2012;22(21):2032-6. doi: 10.1016/j.cub.2012.08.007. Epub Sep. 6, 2012.
Kim et al., SHMT2 drives glioma cell survival in ischaemia but imposes a dependence on glycine clearance. Nature. Apr. 16, 2015;520(7547):363-7. doi: 10.1038/nature14363. Epub Apr. 8, 2015.
Labuschagne et al., Serine, but not glycine, supports one-carbon metabolism and proliferation of cancer cells. Cell Rep. May 22, 2014;7(4):1248-58. doi: 10.1016/j.celrep.2014.04.045. Epub May 10, 2014. Supplemental Information.
Locasale, Serine, glycine and one-carbon units: cancer metabolism in full circle. Nat Rev Cancer. Aug. 2013;13(8):572-83. doi: 10.1038/nrc3557. Epub Jul. 4, 2013.
Locasale et al., Phosphoglycerate dehydrogenase diverts glycolytic flux and contributes to oncogenesis. Nat Genet. Jul. 31, 2011;43(9):869-74. doi: 10.1038/ng.890.
Lund et al., The reactions of the phosphorylated pathway of L-serine biosynthesis: thermodynamic relationships in rabbit liver in vivo. Arch Biochem Biophys. Feb. 15, 1985;237(1):186-96.
Maddocks et al., Serine starvation induces stress and p53-dependent metabolic remodelling in cancer cells. Nature. Jan. 24, 2013;493(7433):542-6. doi: 10.1038/nature11743. Epub Dec. 16, 2012. Methods.
Mattaini et al., An epitope tag alters phosphoglycerate dehydrogenase structure and impairs ability to support cell proliferation. Cancer Metab. Apr. 29, 2015;3:5. doi: 10.1186/s40170-015-0131-7. eCollection 2015.
Narkewicz et al., Evidence for intracellular partitioning of serine and glycine metabolism in Chinese hamster ovary cells. Biochem J. Feb. 1, 1996;313 ( Pt 3):991-6.
Nilsson et al., Metabolic enzyme expression highlights a key role for MTHFD2 and the mitochondrial folate pathway in cancer. Nat Commun. 2014;5:3128. doi: 10.1038/ncomms4128.
Possemato et al., Functional genomics reveal that the serine synthesis pathway is essential in breast cancer. Nature. Aug. 18, 2011;476(7360):346-50. doi: 10.1038/nature10350.
Snell, Enzymes of serine metabolism in normal, developing and neoplastic rat tissues. Adv Enzyme Regul. 1984;22:325-400.
Snell et al., Enzymic imbalance in serine metabolism in rat hepatomas. Biochem J. Jan. 15, 1986;233(2):617-20.
Snell et al., Enzymic imbalance in serine metabolism in human colon carcinoma and rat sarcoma. Br J Cancer. Jan. 1988;57(1):87-90.
Sullivan et al., Supporting Aspartate Biosynthesis Is an Essential Function of Respiration in Proliferating Cells. Cell. Jul. 30, 2015;162(3):552-63. doi:10.1016/j.cell.2015.07.017.
Tibbetts et al., Compartmentalization of Mammalian folate-mediated one-carbon metabolism. Annu Rev Nutr. Aug. 21, 2010;30:57-81. doi:10.1146/annurev.nutr.012809.104810.
Vander Heiden, Targeting cancer metabolism: a therapeutic window opens. Nat Rev Drug Discov. Aug. 31, 2011;10(9):671-84. doi: 10.1038/nrd3504.
Wang et al., Genetic screens in human cells using the CRISPR-Cas9 system. Science. Jan. 3, 2014;343(6166):80-4. doi:10.1126/science.1246981. Epub Dec. 12, 2013.
Zhang et al., Glycine decarboxylase activity drives non-small cell lung cancer tumor-initiating cells and tumorigenesis. Cell. Jan. 20, 2012;148(1-2):259-72. doi: 10.1016/j.cell.2011.11.050. Epub Jan. 5, 2012. Erratum in:Cell. Mar. 2, 2012;148(5):1066. Mitchell, Wayne [added].
Hamanaka et al. Inhibition of Phosphoglycerate Dehydrogenase Attenuates Bleomycin-induced Pulmonary Fibrosis. Am J Respir Cell Mol Biol. May 2018;58(5):585-593. doi: 10.1165/rcmb.2017-0186OC.
Yoshino et al., PHGDH as a Key Enzyme for Serine Biosynthesis in HIF2α-Targeting Therapy for Renal Cell Carcinoma. Cancer Res. Nov. 15, 2017;77(22):6321-6329. doi: 10.1158/0008-5472.CAN-17-1589. Epub Sep. 26, 2017.

* cited by examiner

| Enzyme | Inactive | IC$_{50}$ ($\mu$M) NCT-502 | NCT-503 |
|---|---|---|---|
| PHGDH | >100 | 2.6 | 1.1 |
| GAPDH | >100 | >100 | >100 |
| LDHA | >57 | >57 | >57 |
| HSD17B4 | >57 | >57 | >57 |
| GPD1 | >100 | >100 | >100 |
| GPD1L | >100 | >100 | >100 |

*In vitro* and *in vivo* efficacy
of PHGDH inhibitors

| Low PHGDH | NCT-503 EC$_{50}$ ($\mu$M) |
|---|---|
| —△— MDA-MB-231 | ~100 |
| ··○·· ZR-75-1 | >100 |
| —□— SK-MEL-2 | >100 |
| High PHGDH | |
| —✱— HT1080 | 14 |
| —▲— HCC70 | 16 |
| —◇— BT-20 | 8 |
| ··●·· MDA-MB-468 | 8 |
| —■— MT-3 | 9 |

| Entry | R | IC$_{50}$[a] | % inhibition[b] |
|---|---|---|---|
| 1 | 4-Me-pyridin-2-yl-NH-C(=O)- | NA | 16 (max) |
| 2 | 4-Me-pyridin-2-yl-CH$_2$-C(=S)- | 39 | 37 |
| 3 | 4-Me-pyridin-2-yl-C(=S)- | NA | 9 (max) |
| 4 | 3-Me-phenyl-NH-C(=S)- | NA | 20 (max) |
| 5 | 4,6-diMe-pyridin-2-yl-NH-C(=S)- | 6.5 | 88 |

[a] IC$_{50}$ determined in diaphorase coupled assay
[b] % inhibition is enzyme inhibition at 57 μM of compound

*In vitro* ADME

| Assay | Subtype | units | NCT-502 | NCT-503 |
|---|---|---|---|---|
| Buffer Stability | PHGDH assay buffer (with EDTA) | % remaining at 48 hours | >95 | >95 |
| | Aq. buffered 5 mM Glutathione | | 76 | >95 |
| | Aq. buffered 500 uM DTT | | >95 | >95 |
| Liver Microsomal Stability | Mouse | % remaining at 15 minutes | 70 | 95 |
| | Rat | | 95 | 100 |
| | Human | | 97 | 98 |
| Passive Permeability | PAMPA | $\times 10^{-6}$ cm/s | 927 | 1874 |
| MDCK MDR1 Permeability | A-B | $\times 10^{-6}$ cm/s | 9.96 | 4.06 |
| | B-A | | 8.86 | 5.68 |
| | Efflux ratio | fold | 0.9 | 1.4 |
| Aqueous Solubility | | mg/mL | <1.0 | 10 | target engagement data

Fig. 6A

*In vivo* PK (30 mg/kg, IP, plasma)

| Parameter | units | NCT-503 |
|---|---|---|
| AUClast | hr*ng/mL | 14700 |
| SE_AUClast | hr*ng/mL | 660 |
| AUCINF_obs | hr*ng/mL | 14700 |
| AUC_%Extrap_obs | % | 0.1 |
| MRTINF_obs | hr | 2.4 |
| t1/2 | hr | 2.5 |
| $T_{max}$ | hr | 0.083 |
| $C_{max}$ | ng/mL | 7980 |

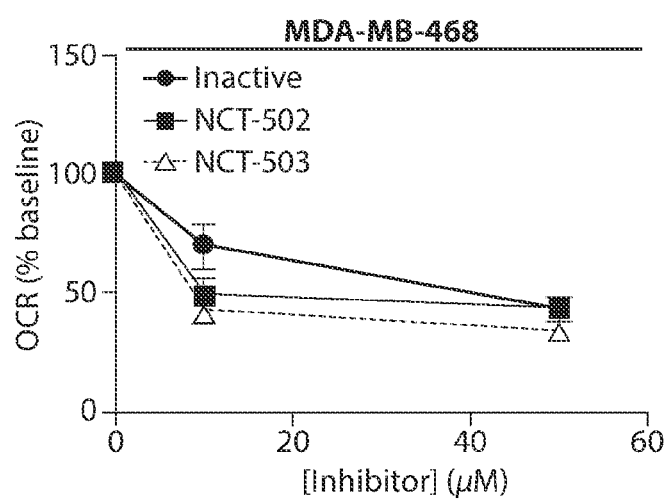
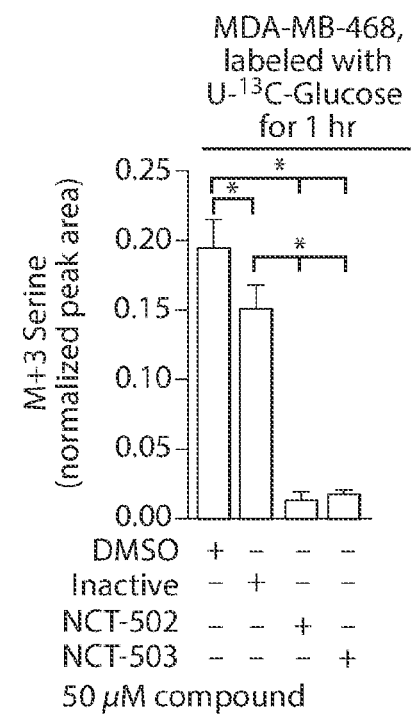
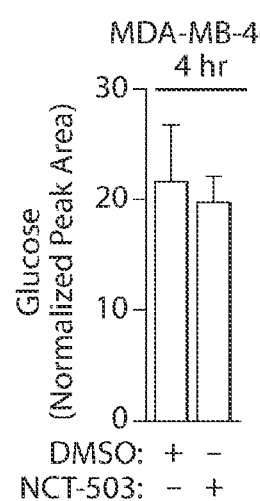
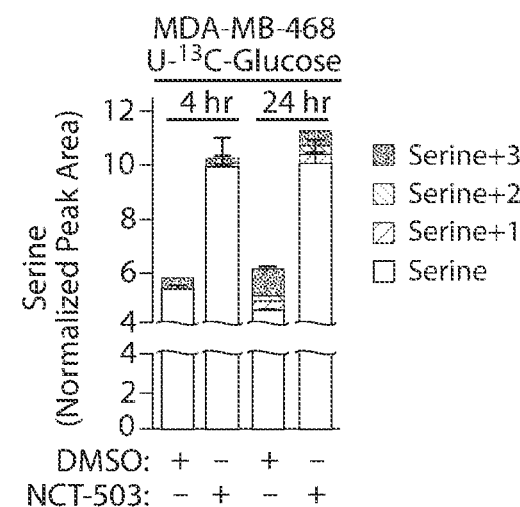
Fig. 6D  Fig. 6E
Fig. 6F  Fig. 6G

| Compound | Structure | MDA-MB-468 EC$_{50}$, Cytotoxicity (µM) | EC$_{50}$ (Flux, µM) |
|---|---|---|---|
| NCT-503 | 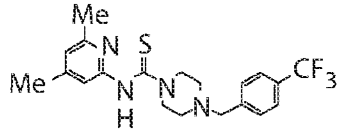 | 8 | 2.3 |
| NCGC00356258 | 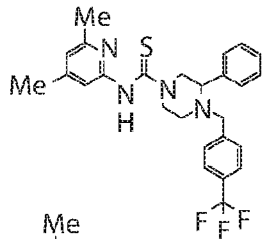 | 8.6 | 6.9 |
| NCGC00356790 | 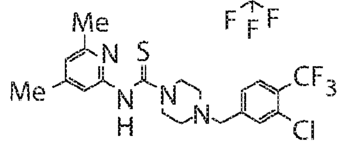 | 11 | 12.4 |
| NCGC00356789 | 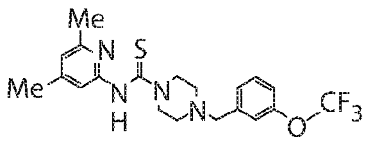 | 12.5 | 4.1 |
| NCGC00356793 | 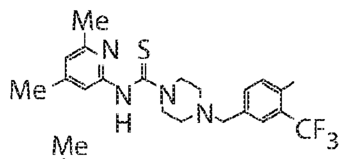 | 14.5 | 8.6 |
| NCT-502 | 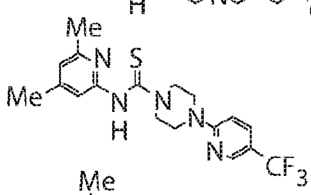 | 15.2 | 17.5 |
| NCGC00351759 | 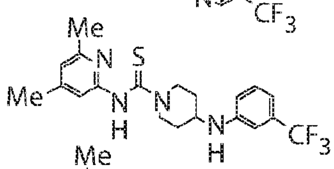 | 15.5 | 3.9 |
| NCGC00356785 | 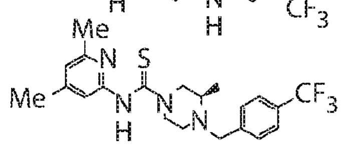 | 22.8 | 19.9 |
| NCGC00356356 | 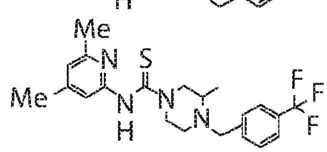 | 24.4 | 15.8 |
| NGCC00356784 | 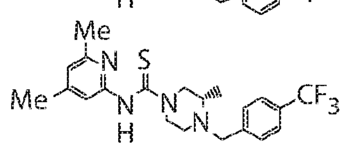 | 25.6 | 25.3 |
| NGGC00351951 | 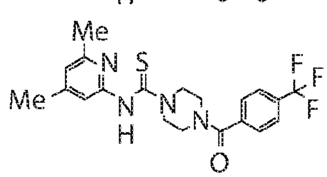 | 29.3 | 17 |

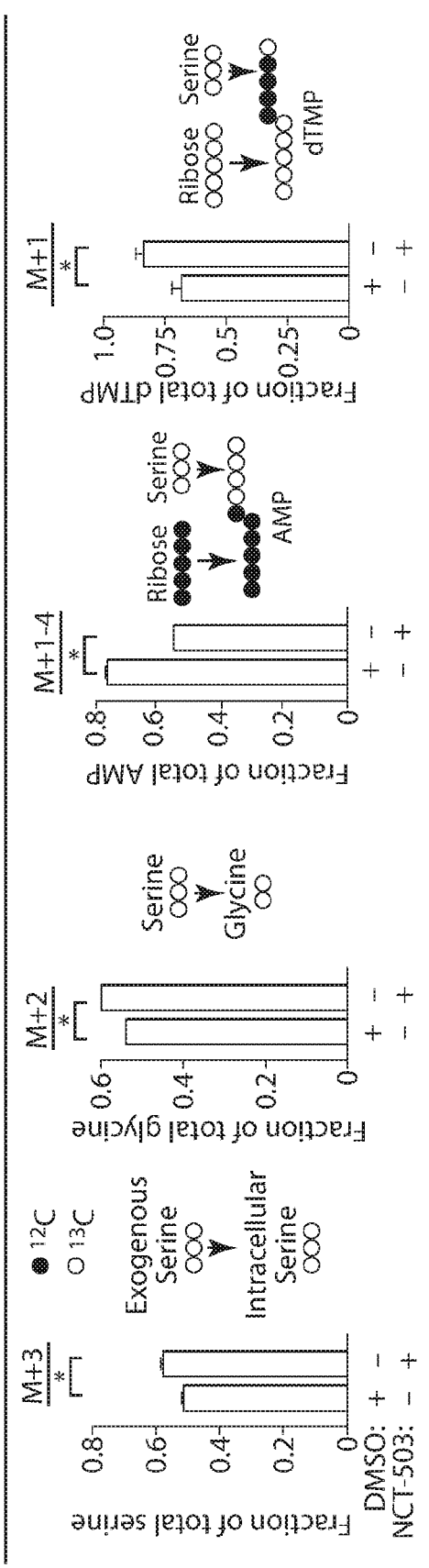
Fig. 10A
Fig. 10B

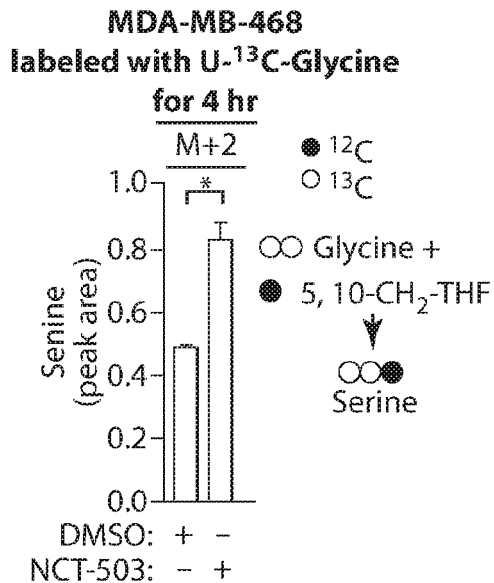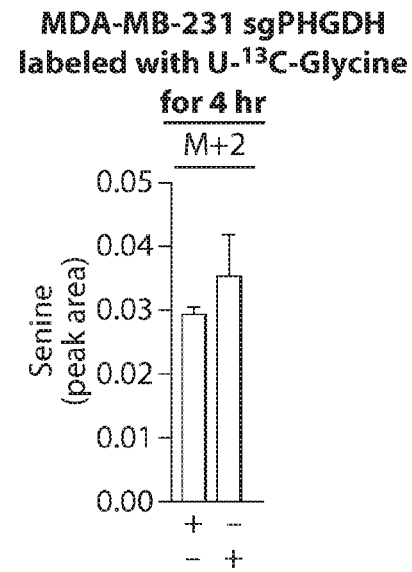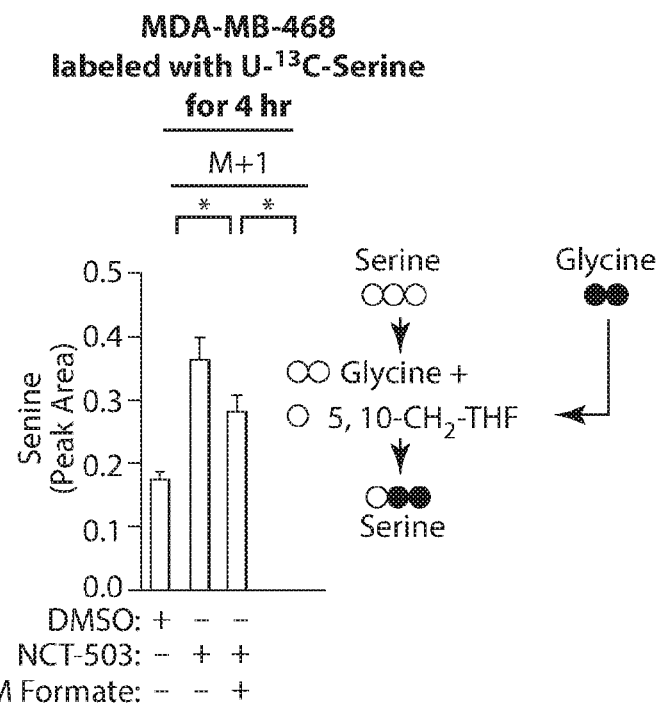
Fig. 13A
Fig. 13B
Fig. 13C

INHIBITORS OF PHOSPHOGLYCERATE DEHYDROGENASE (PHGDH) AND USES THEREOF

RELATED APPLICATIONS

The present application is a national stage filing under 35 U.S.C. § 371 of international PCT application, PCT/US2016/013602, filed Jan. 15, 2016, which claims priority under 35 U.S.C. § 119(e) to U.S. Provisional Application, U.S. Ser. No. 62/103,990, filed Jan. 15, 2015, each of which is incorporated herein by reference.

GOVERNMENT SUPPORT

This invention was made with Government support under grant number R03 DA034602-01A1 awarded by the National Institutes of Health, and grant number BC120208 awarded by the Department of Defense. The Government has certain rights in the invention.

BACKGROUND OF THE INVENTION

One-carbon metabolism uses the coenzyme tetrahydrofolate to carry reactive one-carbon units, which are essential for the synthesis of the dTMP and purines ultimately incorporated into DNA and RNA (See, e.g., Tibbetts, A. S. & Appling, D. R. "Compartmentalization of Mammalian folatemediated one-carbon metabolism." *Anna. Rev. Nutr.* 30, 57-81 (2010); Locasale, J. W. "Serine, glycine and one-carbon units: cancer metabolism in full circle." *Nat Rev Cancer* 13, 572-583 (2013)). Antifolates, such as methotrexate, target the enzymes responsible for tetrahydrofolate synthesis and have a long record of efficacy in the treatment of malignancies (See, e.g., Farber, S., Diamond, L. K., Mercer, R., Sylvester, R. & Wolff, J. "Temporary remissions in acute leukemia in children produced by folic acid antagonist, 4aminopteroyl-glutamic acid." *New England Journal of Medicine* 238, 787-793 (1948); Vander Heiden, M. G. "Targeting cancer metabolism: a therapeutic window opens." *Nat Rev Drug Discov* 10, 671-684 (2011)). The proteinogenic amino acids serine and glycine are also the source of the one-carbon units carried by tetrahydrofolate (See, e.g., Cantor, J. R. & Sabatini, D. M. "Cancer cell metabolism: one hallmark, many faces." *Cancer Discov* 2, 881-898 (2012)) and incorporated into nucleotides (See, e.g., Labuschagne, C. F., van den Broek, N. J. F., Mackay, G. M., Vousden, K. H. & Maddocks, O. D. K. "Serine, but not glycine, supports one-carbon metabolism and proliferation of cancer cells." *Cell Rep* 1, 1248-1258 (2014)). It is well appreciated that proliferating cells not only obtain serine exogenously (See, e.g., Maddocks, O. D. K. et al. "Serine starvation induces stress and p53-dependent metabolic remodelling in cancer cells." 493, 542-546 (2013)) but also synthesize serine from glucose via the canonical serine synthesis pathway, in which 3-phosphoglycerate dehydrogenase (PHGDH), which converts the glycolytic intermediate 3-phosphoglycerate (3-PG) to phosphohydroxypyruvate (P-Pyr), catalyzes the first, often rate limiting step (See, e.g., Snell, K., Natsumeda, Y., Eble, J. N., Glover, J. L. & Weber, G. "Enzymic imbalance in serine metabolism in human colon carcinoma and rat sarcoma." *Br J Cancer* 57, 87-90 (1988); Snell, K. & Weber, G. "Enzymic imbalance in serine metabolism in rat hepatomas." *Biochem J* 233, 617-620 (1986); Fell, D. A. & Snell, K. "Control analysis of mammalian serine biosynthesis. Feedback inhibition on the final step." *Biochem J* 256, 97-101 (1988)).

Recent work demonstrating that PHGDH loss is selectively toxic to tumor cell lines with high PHGDH expression or flux through the serine synthesis pathway has contributed to interest in understanding serine synthesis and downstream one-carbon metabolism (See, e.g., Possemato, R. et al. "Functional genomics reveal that the serine synthesis pathway is essential in breast cancer." 476, 346-350 (2011); Locasale, J. W. et al. "Phosphoglycerate dehydrogenase diverts glycolytic flux and contributes to oncogenesis." *Nat Genet* 43, 869-874 (2011); Chen, J. et al. "Phosphoglycerate dehydrogenase is dispensable for breast tumor maintenance and growth." *Oncotarget* 4, 2502-2511 (2013); Mattaini, K. R. et al. "An epitope tag alters phosphoglycerate dehydrogenase structure and impairs ability to support cell proliferation." *Cancer Metab* 3, 5 (2015); DeNicola, G. M. et al. "NRF2 regulates serine biosynthesis in non-small cell lung cancer." *Nat Genet* (2015); Zhang, W. C. et al. "Glycine decarboxylase activity drives non-small cell lung cancer tumor-initiating cells and tumorigenesis." *Cell* 148, 259-272 (2012); Kim, D. et al. "SHMT2 drives glioma cell survival in ischaemia but imposes a dependence on glycine clearance." 520, 363-367 (2015); Chaneton, B. et al. "Serine is a natural ligand and allosteric activator of pyruvate kinase M2." 491, 458-462 (2012); Fan, J. et al. "Quantitative flux analysis reveals folate-dependent NADPH production." 510, 298-302 (2014); Nilsson, R. et al. Metabolic enzyme expression highlights a key role for MTHFD2 and the mitochondrial folate pathway in cancer. *Nature Communications* 5, 3128 (2014)).

Cancer cells adapt their metabolic processes to drive macromolecular biosynthesis for rapid cell growth and proliferation. RNA interference screening has identified genomic targets for tumor suppression, including the PHGDH gene which is associated with aggressive breast cancer and is required for tumorigenesis. (Possemato et al. "Functional genomics reveal that the serine biosynthesis pathway is essential in breast cancer." *Nature* 476, 346-350 (2011)). PHGDH is in a genomic region of recurrent copy number gain in breast cancer, leading to over-expression. Phosphoglycerate dehydrogenase (PHGDH) is over-expressed in approximately 70% of breast cancers that test negative for expression of estrogen receptors (ER negative breast cancers), which account for 20% of breast cancers, but 50% of deaths. It is also over-expressed in approximately 5% of melanomas. Cell lines that over-express PHGDH and are addicted to the activity of this enzyme are sensitive to PHGDH knockdown and are likely sensitive to PHGDH inhibitors. Development of chemotherapeutics and methods that target PHGDH is needed in the treatment of cancers and other diseases associated with PHGDH over-expression.

SUMMARY OF THE INVENTION

Provided herein are novel inhibitors of PHGDH which can be used in the treatment of diseases (e.g., cancer) or in studying the biological consequences of PHGDH inhibition. The present invention provides compounds of Formula (I), (II) or (III), or of a sub-formula thereof, or pharmaceutically acceptable salts, solvates, hydrates, polymorphs, co-crystals, tautomers, stereoisomers, isotopically labeled derivatives, pro-drugs, and pharmaceutical compositions thereof. The compounds of Formula (I), (II), or (III), or of a sub-formula thereof, or pharmaceutically acceptable salts, solvates, hydrates, polymorphs, co-crystals, tautomers, stereoisomers, isotopically labeled derivatives, pro-drugs, and pharmaceutical compositions thereof, may inhibit the activity of a dehydrogenase or oxidoreductase. In certain embodiments, the inhibited protein is a phosphoglycerate dehydrogenase (PHGDH).

The compounds of Formula (I), (II), or (III), or of a sub-formula thereof, or pharmaceutically acceptable salts, solvates, hydrates, polymorphs, co-crystals, tautomers, stereoisomers, isotopically labeled derivatives, pro-drugs, and pharmaceutical compositions thereof, are useful in the treatment and prevention of diseases in subject. In certain embodiments, the disease is associated with the over-expression or aberrant activity (e.g., increased activity), or both, of phosphoglycerate dehydrogenase (PHGDH). In certain embodiments, the inventive compounds, or compositions thereof, are used for the treatment or prevention (or both) of proliferative diseases in a subject (e.g., cancer (e.g., breast cancer, ER negative breast cancer, melanoma, or cervical cancer), benign neoplasms, diseases associated with angiogenesis, inflammatory diseases, autoinflammatory diseases, autoimmune diseases). In certain embodiments, the inventive compounds, or compositions thereof, are used for the treatment or prevention (or both) of fibrotic diseases in a subject (e.g., idiopathic pulmonary fibrosis, nephrogenic systemic fibrosis, scleroderma).

The present invention also provides methods of using the inventive compounds, and pharmaceutically acceptable salts, solvates, hydrates, polymorphs, co-crystals, tautomers, stereoisomers, isotopically labeled derivatives, pro-drugs, and pharmaceutical compositions and formulations thereof, as therapeutics or prophylactics for the treatment and prevention of diseases in a subject. In certain embodiments, the disease is associated with the over-expression or aberrant activity (e.g., increased activity), or both, of phosphoglycerate dehydrogenase (PHGDH). In certain embodiments, the inventive compounds, or compositions thereof, are used for the treatment and prevention (or both) of proliferative diseases in a subject (e.g., cancer (e.g., breast cancer, ER negative breast cancer, melanoma, cervical cancer), benign neoplasms, diseases associated with angiogenesis, inflammatory diseases, autoinflammatory diseases, autoimmune diseases). In certain embodiments, the inventive compounds, or compositions thereof, are used for the treatment and prevention (or both) of fibrotic diseases in a subject (e.g., idiopathic pulmonary fibrosis, nephrogenic systemic fibrosis, scleroderma).

The present invention also provides uses of the inventive compounds, and pharmaceutically acceptable salts, solvates, hydrates, polymorphs, co-crystals, tautomers, stereoisomers, isotopically labeled derivatives, pro-drugs, and pharmaceutical compositions and formulations thereof, in the manufacture of medicaments for the treatment and prevention of diseases. In certain embodiments, the disease is associated with the over-expression or aberrant activity (e.g., increased activity), or both, of phosphoglycerate dehydrogenase (PHGDH). In certain embodiments, the use of the inventive compounds, salts, or compositions thereof, is for the treatment or prevention (or both) of a proliferative disease (e.g., cancer (e.g., breast cancer, ER negative breast cancer, melanoma, cervical cancer), benign neoplasms, diseases associated with angiogenesis, inflammatory diseases, autoinflammatory diseases, autoimmune diseases). In certain embodiments, the use of the inventive compounds, salts, or compositions thereof, is for the treatment or prevention (or both) of fibrotic diseases (e.g., idiopathic pulmonary fibrosis, nephrogenic systemic fibrosis, scleroderma).

The compounds of Formula (I), (II), or (III), or of a sub-formula thereof, or pharmaceutically acceptable salts, solvates, hydrates, polymorphs, co-crystals, tautomers, stereoisomers, isotopically labeled derivatives, pro-drugs, and pharmaceutical compositions thereof, are useful in research in the field of disease pathology, biochemistry, cell biology, oncology, and other fields associated with proliferative diseases. The compounds of the invention can be used to study the roles of biomolecules (e.g., PHGDH, serine). The compounds of the invention can be used to study biological pathways (e.g., PHGDH expression, serine biosynthetic pathway, TCA cycle, PSAT1 expression, PSPH expression). The compounds of the invention can be used to study aspects of proliferative or fibrotic diseases (e.g., tumorigenesis, cell proliferation, cell growth, cell death).

The compounds of Formula (I), (II), or (III), or of a sub-formula thereof, or pharmaceutically acceptable salts, solvates, hydrates, polymorphs, co-crystals, tautomers, stereoisomers, isotopically labeled derivatives, pro-drugs, and pharmaceutical compositions thereof, can be used to determine if a cancer over-expresses PHGDH, to determine if cancer cells have one or more extra copies of the PHGDH gene, or in a diagnostic test for determining if a subject has cancer that over-expresses PHGDH.

In additional aspects, the present invention provides methods of using the inventive compounds, or compositions thereof, to inhibit the activity of PHGDH, inhibit serine production in the serine biosynthetic pathway, inhibit cell growth, or induce cell death by administering the compound, or composition thereof, to a subject, or by contacting it with a biological sample (e.g., cells, tissues, biopsied tissues, blood, tumors). In certain embodiments, the method of treatment may further comprise determining if a cancer over-expresses PHGDH, determining if cancer cells have one or more extra copies of the PHGDH gene, or performing a diagnostic test to determining if a subject has cancer that over-expresses PHGDH.

In one aspect, the present invention provides compounds of Formula (I):

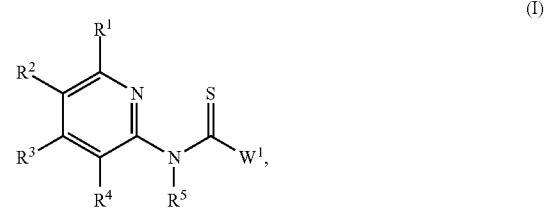

or pharmaceutically acceptable salts, solvates, hydrates, polymorphs, co-crystals, tautomers, stereoisomers, isotopically labeled derivatives, pro-drugs, and pharmaceutical compositions thereof, wherein:

$W^1$ is of formula:

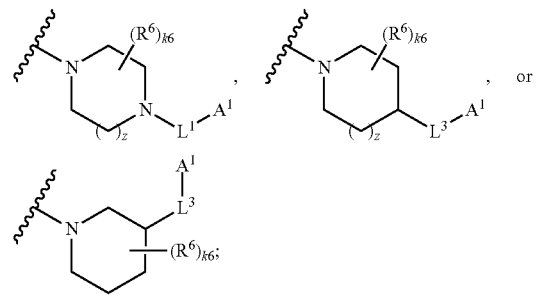

$L^1$ is a bond, optionally substituted alkylene, optionally substituted alkenylene, optionally substituted alkynylene, —C(=O)—, —C(=O)O—, —C(=O)NR$^a$—, —S(=O)—, —S(=O)O—, —S(=O)NR$^a$—, —S(=O)$_2$—, —S(=O)$_2$O—, or —S(=O)$_2$NR$^a$—;

$L^3$ is a bond, optionally substituted alkylene, optionally substituted alkenylene, optionally substituted alkynylene, —NR$^a$—, —O—, —S—, —C(=O)—, —C(=O)O—, —C(=O)NR$^a$—, —OC(=O)—, —NR$^a$C(=O)—, —OC(=O)O—, —NR$^a$C(=O)NR$^a$—, —NR$^a$C(=O)O—, —OC(=O)NR$^a$—, —S(=O)—, —S(=O)O—, —S(=O)NR$^a$—, —O(S=O)—, —NR$^a$S(=O)—, —S(=O)$_2$—, —S(=O)$_2$O—, —S(=O)$_2$NR$^a$, —OS(=O)$_2$—, or —NR$^a$S(=O)$_2$—;

$A^1$ is hydrogen, optionally substituted alkyl, optionally substituted alkenyl, optionally substituted alkynyl, optionally substituted carbocyclyl, optionally substituted heterocyclyl, optionally substituted aryl, or optionally substituted aryl;

$R^1$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —SCN, —NCS, —N$_3$, —NO$_2$, —OR$^b$, —NR$^c$R$^d$, —NR$^c$(OR$^b$), —SR$^e$, —SSR$^e$, —C(=O)R$^f$, —C(=O)OR$^b$, —C(=O)NR$^c$R$^d$, —C(=NR$^c$)R$^f$, —C(=NR$^c$)OR$^b$, —C(=NR$^c$)NR$^c$R$^d$, —OC(=O)R$^f$, —OC(=O)OR$^b$, —OC(=O)NR$^c$R$^d$, —OC(=NR$^c$)R$^f$, —OC(=NR$^c$)OR$^b$, —OC(=NR$^c$)NR$^c$R$^d$, —NR$^c$C(=O)R$^f$, —NR$^c$C(=O)OR$^b$, —NR$^c$C(=O)NR$^c$R$^d$, —NR$^c$C(=NR$^c$)R$^f$, —NR$^c$C(=NR$^c$)OR$^b$, —NR$^c$C(=NR$^c$)NR$^c$R$^d$, —C(=S)R$^f$, —C(=S)OR$^b$, —C(=O)SR$^e$, —C(=S)NR$^c$R$^d$, —NR$^c$C(=S)NR$^c$R$^d$, —Si(R$^f$)$_3$, —OSi(R$^f$)$_3$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

$R^2$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —SCN, —NCS, —N$_3$, —NO$_2$, —OR$^b$, —NR$^c$R$^d$, —NR$^c$(OR$^b$), —SR$^e$, —SSR$^e$, —C(=O)R$^f$, —C(=O)OR$^b$, —C(=O)NR$^c$R$^d$, —C(=NR$^c$)R$^f$, —C(=NR$^c$)OR$^b$, —C(=NR$^c$)NR$^c$R$^d$, —OC(=O)R$^f$, —OC(=O)OR$^b$, —OC(=O)NR$^c$R$^d$, —OC(=NR$^c$)R$^f$, —OC(=NR$^c$)OR$^b$, —OC(=NR$^c$)NR$^c$R$^d$, —NR$^c$C(=O)R$^f$, —NR$^c$C(=O)OR$^b$, —NR$^c$C(=O)NR$^c$R$^d$, —NR$^c$C(=NR$^c$)R$^f$, —NR$^c$C(=NR$^c$)OR$^b$, —NR$^c$C(=NR$^c$)NR$^c$R$^d$, —C(=S)R$^f$, —C(=S)OR$^b$, —C(=O)SR$^e$, —C(=S)NR$^c$R$^d$, —NR$^c$C(=S)NR$^c$R$^d$, —Si(R$^f$)$_3$, —OSi(R$^f$)$_3$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

$R^3$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —SCN, —NCS, —N$_3$, —NO$_2$, —OR$^b$, —NR$^c$R$^d$, —NR$^c$(OR$^b$), —SR$^e$, —SSR$^e$, —C(=O)R$^f$, —C(=O)OR$^b$, —C(=O)NR$^c$R$^d$, —C(=NR$^c$)R$^f$, —C(=NR$^c$)OR$^b$, —C(=NR$^c$)NR$^c$R$^d$, —OC(=O)R$^f$, —OC(=O)OR$^b$, —OC(=O)NR$^c$R$^d$, —OC(=NR$^c$)R$^f$, —OC(=NR$^c$)OR$^b$, —OC(=NR$^c$)NR$^c$R$^d$, —NR$^c$C(=O)R$^f$, —NR$^c$C(=O)OR$^b$, —NR$^c$C(=O)NR$^c$R$^d$, —NR$^c$C(=NR$^c$)R$^f$, —NR$^c$C(=NR$^c$)OR$^b$, —NR$^c$C(=NR$^c$)NR$^c$R$^d$, —C(=S)R$^f$, —C(=S)OR$^b$, —C(=O)SR$^e$, —C(=S)NR$^c$R$^d$, —NR$^c$C(=S)NR$^c$R$^d$, —Si(R$^f$)$_3$, —OSi(R$^f$)$_3$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

$R^4$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —SCN, —NCS, —N$_3$, —NO$_2$, —OR$^b$, —NR$^c$R$^d$, —NR$^c$(OR$^b$), —SR$^e$, —SSR$^e$, —C(=O)R$^f$, —C(=O)OR$^b$, —C(=O)NR$^c$R$^d$, —C(=NR$^c$)R$^f$, —C(=NR$^c$)OR$^b$, —C(=NR$^c$)NR$^c$R$^d$, —OC(=O)R$^f$, —OC(=O)OR$^b$, —OC(=O)NR$^c$R$^d$, —OC(=NR$^c$)R$^f$, —OC(=NR$^c$)OR$^b$, —OC(=NR$^c$)NR$^c$R$^d$, —NR$^c$C(=O)R$^f$, —NR$^c$C(=O)OR$^b$, —NR$^c$C(=O)NR$^c$R$^d$, —NR$^c$C(=NR$^c$)R$^f$, —NR$^c$C(=NR$^c$)OR$^b$, —NR$^c$C(=NR$^c$)NR$^c$R$^d$, —C(=S)R$^f$, —C(=S)OR$^b$, —C(=O)SR$^e$, —C(=S)NR$^c$R$^d$, —NR$^c$C(=S)NR$^c$R$^d$, —Si(R$^f$)$_3$, —OSi(R$^f$)$_3$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

$R^5$ is hydrogen, optionally substituted $C_1$-$C_6$ alkyl, or a nitrogen protecting group;

each $R^6$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^b$, —NR$^c$R$^d$, —SR$^e$, —C(=O)R$^f$, —C(=O)OR$^b$, or —C(=O)NR$^c$R$^d$;

each $R^a$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each $R^b$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each of $R^c$ and $R^d$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or $R^c$ and $R^d$ are joined to form an optionally substituted heterocyclic or optionally substituted heteroaryl ring;

each of $R^e$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a sulfur protecting group;

each of $R^f$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

k6 is 0, 1, 2, 3, or 4; and z is 1 or 2;

provided:

when $L^1$ is a bond, $A^1$ is not optionally substituted 1-isoquinolinyl, optionally substituted 4-isoquinolinyl, optionally substituted 4-quinolinyl, or optionally substituted 4-quinazolinyl; and the compound is not:

N-(3-fluoro-4-((2-(4-methylpiperazine-1-carbothioamido)pyridin-4-yl)oxy)phenyl)-2-oxo-1-phenyl-1,2-dihydropyridine-3-carboxamide.

In another aspect, the present invention provides compounds of Formula (II):

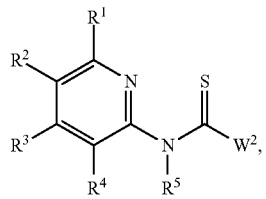

(II)

or pharmaceutically acceptable salts, solvates, hydrates, polymorphs, co-crystals, tautomers, stereoisomers, isotopically labeled derivatives, pro-drugs, and pharmaceutical compositions thereof, wherein:

$W^2$ is of formula:

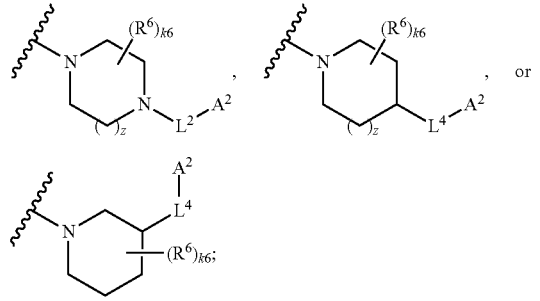

$L^2$ is optionally substituted alkylene, optionally substituted alkenylene, optionally substituted alkynylene, —C(=O)—, —C(=O)O—, —C(=O)NR$^a$—, —S(=O)—, —S(=O)O—, —S(=O)NR$^a$—, —S(=O)$_2$—, —S(=O)$_2$O—, or —S(=O)$_2$NR$^a$—;

$L^4$ is an optionally substituted alkylene, optionally substituted alkenylene, optionally substituted alkynylene, —NR$^a$—, —O—, —S—, —C(=O)—, —C(=O)O—, —C(=O)NR$^a$—, —OC(=O)—, —NR$^a$C(=O)—, —OC(=O)O—, —NR$^a$C(=O)NR$^a$—, —NR$^a$C(=O) O—, —OC(=O)NR$^a$—, —S(=O)—, —S(=O)O—, —S(=O)NR$^a$—, —O(S=O)—, —NR$^a$S(=O)—, —S(=O)$_2$—, —S(=O)$_2$O—, —S(=O)$_2$NR$^a$—, —OS(=O)$_2$—, or —NR$^a$S(=O)$_2$—;

$A^2$ is optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^1$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —SCN, —NCS, —N$_3$, —NO$_2$, —OR$^b$, —NR$^c$R$^d$, —NR$^c$(OR$^b$), —SR$^e$, —SSR$^e$, —C(=O)R$^f$, —C(=O)OR$^b$, —C(=O)NR$^c$R$^d$, —C(=NR$^c$)R$^f$, —C(=NR$^c$)OR$^b$, —C(=NR$^c$)NR$^c$R$^d$, —OC(=O)R$^f$, —OC(=O)OR$^b$, —OC(=O)NR$^c$R$^d$, —OC(=NR$^c$)R$^f$, —OC(=NR$^c$) OR$^b$, —OC(=NR$^c$)NR$^c$R$^d$, —NR$^c$C(=O)R$^f$, —NR$^c$C (=O)OR$^b$, —NR$^c$C(=O)NR$^c$R$^d$, —NR$^c$C(=NR$^c$)R$^f$, —NR$^c$C(=NR$^c$)OR$^b$, —NR$^c$C(=NR$^c$)NR$^c$R$^d$, —C(=S)R$^f$, —C(=S)OR$^b$, —C(=O)SR$^e$, —C(=S) NR$^c$R$^d$, —NR$^c$C(=S)NR$^c$R$^d$, —Si(R$^f$)$_3$, —OSi(R$^f$)$_3$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

$R^2$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —SCN, —NCS, —N$_3$, —NO$_2$, —OR$^b$, —NR$^c$R$^d$, —NR$^c$(OR$^b$), —SR$^e$, —SSR$^e$, —C(=O)R$^f$, —C(=O)OR$^b$, —C(=O)NR$^c$R$^d$, —C(=NR$^c$)R$^f$, —C(=NR$^c$)OR$^b$, —C(=NR$^c$)NR$^c$R$^d$, —OC(=O)R$^f$, —OC(=O)OR$^b$, —OC(=O)NR$^c$R$^d$, —OC(=NR$^c$)R$^f$, —OC(=NR$^c$) OR$^b$, —OC(=NR$^c$)NR$^c$R$^d$, —NR$^c$C(=O)R$^f$, —NR$^c$C (=O)OR$^b$, —NR$^c$C(=O)NR$^c$R$^d$, —NR$^c$C(=NR$^c$)R$^f$, —NR$^c$C(=NR$^c$)OR$^b$, —NR$^c$C(=NR$^c$)NR$^c$R$^d$, —C(=S)R$^f$, —C(=S)OR$^b$, —C(=O)SR$^e$, —C(=S) NR$^c$R$^d$, —NR$^c$C(=S)NR$^c$R$^d$, —Si(R$^f$)$_3$, —OSi(R$^f$)$_3$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

$R^3$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —SCN, —NCS, —N$_3$, —NO$_2$, —OR$^b$, —NR$^c$R$^d$, —NR$^c$(OR$^b$), —SR$^e$, —SSR$^e$, —C(=O)R$^f$, —C(=O)OR$^b$, —C(=O)NR$^c$R$^d$, —C(=NR$^c$)R$^f$, —C(=NR$^c$)OR$^b$, —C(=NR$^c$)NR$^c$R$^d$, —OC(=O)R$^f$, —OC(=O)OR$^b$, —OC(=O)NR$^c$R$^d$, —OC(=NR$^c$)R$^f$, —OC(=NR$^c$) OR$^b$, —OC(=NR$^c$)NR$^c$R$^d$, —NR$^c$C(=O)R$^f$, —NR$^c$C (=O)OR$^b$, —NR$^c$C(=O)NR$^c$R$^d$, —NR$^c$C(=NR$^c$)R$^f$, —NR$^c$C(=NR$^c$)OR$^b$, —NR$^c$C(=NR$^c$)NR$^c$R$^d$, —C(=S)R$^f$, —C(=S)OR$^b$, —C(=O)SR$^e$, —C(=S) NR$^c$R$^d$, —NR$^c$C(=S)NR$^c$R$^d$, —Si(R$^f$)$_3$, —OSi(R$^f$)$_3$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

$R^4$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —SCN, —NCS, —N$_3$, —NO$_2$, —OR$^b$, —NR$^c$R$^d$, —NR$^c$(OR$^b$), —SR$^e$, —SSR$^e$, —C(=O)R$^f$, —C(=O)OR$^b$, —C(=O)NR$^c$R$^d$, —C(=NR$^c$)R$^f$, —C(=NR$^c$)OR$^b$, —C(=NR$^c$)NR$^c$R$^d$, —OC(=O)R$^f$, —OC(=O)OR$^b$, —OC(=O)NR$^c$R$^d$, —OC(=NR$^c$)R$^f$, —OC(=NR$^c$) OR$^b$, —OC(=NR$^c$)NR$^c$R$^d$, —NR$^c$C(=O)R$^f$, —NR$^c$C —C(=O)OR$^b$, —NR$^c$C(=O)NR$^c$R$^d$, —NR$^c$C(=NR$^c$)R$^f$, —NR$^c$C(=NR$^c$)OR$^b$, —NR$^c$C(=NR$^c$)NR$^c$R$^d$, —C(=S)R$^f$, —C(=S)OR$^b$, —C(=O)SR$^e$, —C(=S)NR$^c$R$^d$, —NR$^c$C(=S)NR$^c$R$^d$, —Si(R$^f$)$_3$, —OSi(R$^f$)$_3$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

R$^5$ is hydrogen, optionally substituted C$_1$-C$_6$ alkyl, or a nitrogen protecting group;

each R$^6$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^b$, —NR$^c$R$^d$, —SR$^e$, —C(=O)R$^f$, —C(=O)OR$^b$, or —C(=O)NR$^c$R$^d$;

each R$^a$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each R$^b$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each of R$^c$ and R$^d$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or R$^c$ and R$^d$ are joined to form an optionally substituted heterocyclic or optionally substituted heteroaryl ring;

each R$^e$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a sulfur protecting group;

each R$^f$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

k6 is 0, 1, 2, 3, or 4; and z is 1 or 2;

provided:

A$^2$ is not substituted or unsubstituted pyridazinyl, and the compound is not:

N-(4,6-dimethylpyridin-2-yl)-4-(3-(trifluoromethyl)benzyl)piperazine-1-carbothioamide;

N-(4-methylpyridin-2-yl)-4-((3-(trifluoromethyl)phenyl)amino)piperidine-1-carbothioamide;

N-(4,6-dimethylpyridin-2-yl)-4-(3-(trifluoromethyl)phenyl)sulfonyl)piperazine-1-carbothioamide; or N-(pyridin-2-yl)-4-(tert-butoxycarbonyl)piperazine-1-carbothioamide.

In another aspect, the present invention provides compounds of Formula (I) according to Formula (III):

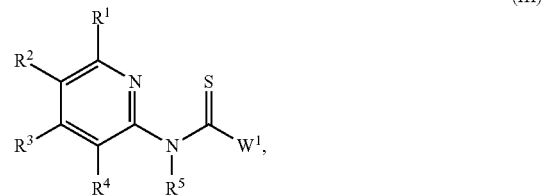

(III)

or pharmaceutically acceptable salts, solvates, hydrates, polymorphs, co-crystals, tautomers, stereoisomers, isotopically labeled derivatives, pro-drugs, and pharmaceutical compositions thereof, wherein:

W$^1$ is of formula:

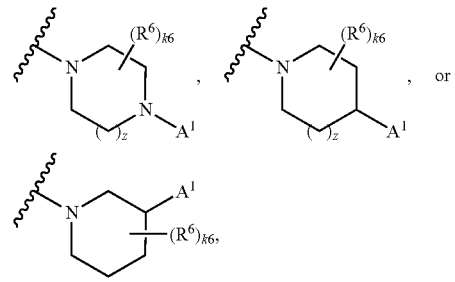

and A$^1$, R$^1$-R$^6$, R$^a$-R$^f$, k6, and z are as defined for compounds of Formula (I).

The present invention also provides pharmaceutical compositions including a compounds of Formula (I), (II), or (III), or pharmaceutically acceptable salts, solvates, hydrates, polymorphs, co-crystals, tautomers, stereoisomers, isotopically labeled derivatives, or thereof. The pharmaceutical compositions may contain a therapeutically or prophylactically effective amount of the compound. The composition may be useful in the treatment or prevention (or both) of a proliferative disease or fibrotic disease. In certain embodiments the composition may be useful for inhibiting the activity of PHGDH, inhibiting serine biosynthetis, inhibiting cell growth, or inducing cell death in a subject or biological sample.

Another aspect of the present disclosure relates to kits comprising a container with a compound, or pharmaceutically acceptable salt, or pharmaceutical composition thereof, of Formula (I), (II), or (III). The kits described herein may include a single or multiple dose of the compound or composition thereof. The kits may be useful in a method of the disclosure (e.g., treatment or prevention of a proliferative disease (e.g., treatment or prevention of cancer) or fibrotic disease). In certain embodiments, the kit may further comprise instructions for administering the compound or composition thereof. The kit described herein may also include information as required by a regulatory agency (e.g., the U.S. Food and Drug Administration).

The details of one or more embodiments of the invention are set forth herein. Other features, objects, and advantages of the invention will be apparent from the Detailed Description, the Examples, the Figures, the Definitions, and the Claims.

BRIEF DESCRIPTION OF THE DRAWINGS

The accompanying drawings, which constitute a part of this specification, illustrate several embodiments of the invention and together with the description, serve to explain the principles of the invention.

FIG. 6A. In vitro ADME of NCT-502 (Compound 72) and NCT-503 (Compound 267).

FIG. 6D. Both active and inactive PHGDH inhibitors decrease oxygen consumption rates in MDA-MB-468 cells.

FIG. 6E. NCT-502 (Compound 72) and NCT-503 (Compound 267) decrease M+3 labeled serine production from U-$^{13}$C glucose in MDA-MB-468 cells, Inactive compound does not greatly decrease M+3 labeled serine production from U-$^{13}$C glucose.

FIG. 6F. NCT-503 (Compound 267) does not change intracellular glucose concentrations in MDA-MB-468 cells.

FIG. 6G. NCT-503 (Compound 267) decreases production of M+3 serine from U-$^{13}$C glucose but increases M+1 serine.

FIGS. 10A-10E. PHGDH inhibition in a PHGDH-dependent cell line unexpectedly reduces the incorporation of exogenous serine into AMP and dTMP. Treatment of MDA-MB-468 cells with 10 μM NCT-503 (Compound 267) for 24 hours reduces the synthesis of glucose-derived serine and decreases $^{13}$C incorporation, via serine, into AMP. In addition, $^{13}$C from glucose-derived serine is not incorporated into dTMP. 10 μM NCT-503 (Compound 267) treatment for 24 hours in the presence of exogenous U-$^{13}$C-serine does not increases the proportion of labeled serine but increases the fraction of labeled glycine, consistent with decreased synthesis of unlabeled serine. NCT-503 (Compound 267) reduces the incorporation of one-carbon units from exogenous U-$^{13}$C-serine into AMP and dTMP. The dTMP fractional labeling does not change greatly but the decrease in dTMP pool size (FIG. 11D) decreases the accuracy of the dTMP fractional labeling. MDA-MB-231 cells lacking PHGDH do not exhibit an increase in M+2 glycine or a significant decrease in incorporation of exogenous serine into AMP or dTMP in the presence of 10 μM NCT-503 (Compound 267).

FIG. 13A. Increased synthesis of serine from glycine following PHGDH inhibition. Increased pool size of M+2 serine from U-$^{13}$C-glycine following PHGDH inhibitor treatment.

FIG. 13B. The M+2 glycine pool does not increase in MDA-MB-231 cells lacking PHGDH following NCT-503 (Compound 267) treatment.

FIG. 13C. Pool size data for likely SHMT1-mediated synthesis of M+l-serine from unlabeled glycine and $^{13}$C-serine-derived 5,10-methylene THF (5,10-CH$_2$-THF), which increases with PHGDH inhibition (10 µM NCT-503 (Compound 267)) and is suppressed by exogenous unlabeled formate.

DEFINITIONS

Chemical Terms

Figure 1A:
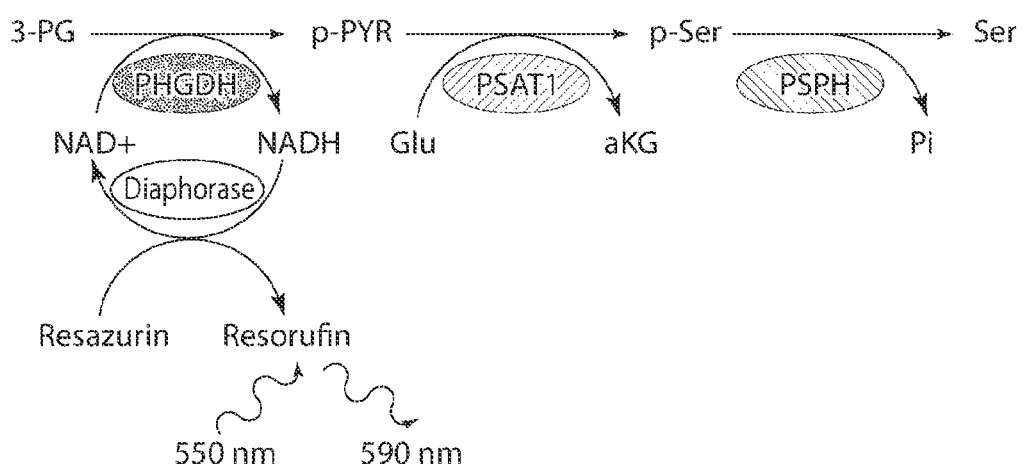
FIG. 1A. Coupled PHGDH assay with diaphorase/resazurin readout used for the primary screen.

Definitions of specific functional groups and chemical terms are described in more detail below. The chemical elements are identified in accordance with the Periodic Table of the Elements, CAS version, *Handbook of Chemistry and Physics*, 75 Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, CM, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of CM alkenyl groups include ethenyl ($C_2$), 1-propenyl (C3), 2-propenyl (C3), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted C2-10 alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("C2-9 alkynyl"). In some embodiments, an alkynyl group has 2 to 8 carbon atoms ("C2-8 alkynyl"). In some embodiments, an alkynyl group has 2 to 7 carbon atoms ("C2-7 alkynyl"). In some embodiments, an alkynyl group has 2 to 6 carbon atoms ("C2-6 alkynyl"). In some embodiments, an alkynyl group has 2 to 5 carbon atoms ("C2-5 alkynyl"). In some embodiments, an alkynyl group has 2 to 4 carbon atoms ("$C_{2-4}$ alkynyl"). In some embodiments, an alkynyl group has 2 to 3 carbon atoms ("C2-3 alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of C2-4 alkynyl groups include, without limitation, ethynyl (C2), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted C2-10 alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("C5-10 carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned C3-6 carbocyclyl groups as well as cycloheptyl ($C_7$), cycloheptenyl ($C_7$), cycloheptadienyl ($C_7$), cycloheptatrienyl (C7), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl (C9), cyclononenyl (C9), cyclodecyl ($C_{10}$), cyclodecenyl ($C_{10}$), octahydro-1H-indenyl (C9), decahydronaphthalenyl (C10), spiro[4.5]decanyl (C10), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted C3-10 carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("C5-6 cycloalkyl"). In some embodiments, a cycloalkyl group has 5 to 10 ring carbon atoms ("$C_{6-10}$ cycloalkyl"). Examples of C5-6 cycloalkyl groups include cyclopentyl ($C_5$) and cyclohexyl ($C_5$). Examples of $C_{3-6}$ cycloalkyl groups include the aforementioned C5-6 cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted C6-14 aryl. In certain embodiments, the aryl group is substituted $C_{6-14}$ aryl.

"Aralkyl" is a subset of alkyl and aryl, as defined herein, and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1∝ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl, as defined herein, and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as defined herein. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, as defined herein, which are divalent bridging groups are further referred to using the suffix -ene, e.g., alkylene, alkenylene, alkynylene, carbocyclylene, heterocyclylene, arylene, and heteroarylene.

As used herein, the term "optionally substituted" refers to substituted or unsubstituted.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl, or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$+X—, —N(OR$^{cc}$)R$^{bb}$, —SH, —SR$^{33}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S) SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O) (R$^{aa}$)$_2$, —OP(=O)(R$^{aa}$)$_2$, —OP(=O)(OR$^{cc}$)$_2$, —P(=O)$_2$N (R$^{bb}$)$_2$, —OP(=O)$_2$N(R$^{bb}$)$_2$, —P(=O)(NR$^{bb}$)$_2$, —OP(=O) (NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O) R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, Ce-M aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$) OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, CMO alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C6-M aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, Ce-M aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$X−, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{cc}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$) R$^{ee}$, —OC(=NR$^{ff}$)OR$^{ee}$, —C(=NR$^{ff}$)N(R$^{ff}$)$_2$, —OC (=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP (=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Acyl" as used herein refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, CHO alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxy acetamide, acetoacetamide, (N-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-f-BOC), 1,1-dimethyl-2,2,2-trichloroethyl carbamate (TCBOC), 1-methyl-1-(4-biphenylyl)ethyl carbamate (Bpoc), 1-(3,5-di-r-butylphenyl)-1-methylethyl carbamate (r-Bumeoc), 2-(2'- and 4'-pyridyl) ethyl carbamate (Pyoc), 2-(N,N-dicyclohexylcarboxamido) ethyl carbamate, f-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, f-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-r-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O) SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$) N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O) (OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy) ethyl, 1-methyl-1-methoxy ethyl, 1-methyl-1-benzyloxyethyl, 1-methy 1-1-benzyloxy-2-fluoroethy 1,2,2, 2-trichloroethyl, 2-trimethylsilylethyl, 2-(phenylselenyl) ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis (4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl 5-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1, 1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is an sulfur protecting group (also referred to as a thiol protecting group). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Figures, Examples, and Claims. The invention is not intended to be limited in any manner by the above exemplary listing of substituents.

Other Definitions

The following definitions are more general terms used throughout the present application.

As used herein, the term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, non-toxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid, or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula Rx H$_2$O, wherein R is the compound and wherein x is a number greater than 0. A given compound may form more than one type of hydrates, including, e.g., monohydrates (is 1), lower hydrates (is a number greater than 0 and smaller than 1, e.g., hemihydrates (R·0.5 H$_2$O)), and polyhydrates (is a number greater than 1, e.g., dihydrates (R·2 H$_2$O) and hexahydrates (R·6 H$_2$O)).

The term "tautomers" refers to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "isotopically labeled derivative" refers to a compound wherein one or more atoms in the compound has been replaced with an isotope of the same element. For the given element or position in the molecule the isotope will be enriched, or present in a higher percentage of all atoms of the element or of all atoms at the position in the molecule in a sample, relative to an unlabeled sample. In certain embodiments, the enriched isotope will be a radioactive isotope (e.g., a radionuclide).

The term "pro-drugs" refers to compounds, including derivatives of the compounds described herein, which have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offer advantages of solubility, tissue compatibility, or delayed release in the mammalian organism (see, Bundgard, H., *Design of Pro-drugs*, pp. 7-9, 21-24, Elsevier, Amsterdam 1985). Pro-drugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular pro-drugs. In some cases it is desirable to prepare double ester type pro-drugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is non-human animal. In certain embodiments, the animal is fish.

The terms "administer," "administering," or "administration," as used herein, refer to implanting, absorbing, ingesting, injecting, inhaling, or otherwise introducing an inventive compound, or a pharmaceutical composition thereof, in or on a subject.

As used herein, the terms "treatment," "treat," and "treating" refer to reversing, alleviating, delaying the onset of, or inhibiting the progress of a pathological condition (e.g., a disease, disorder, or condition, or one or more signs or symptoms thereof) described herein, such as a proliferative disease (e.g, cancer (e.g, breast cancer, ER negative breast cancer, melanoma, cervical cancer), benign neoplasms, diseases associated with angiogenesis, inflammatory diseases, autoinflammatory diseases, and autoimmune diseases) In some embodiments, the disease may be a disease associated with over-expression of phosphoglycerate dehydrogenase (PHGDH). In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of exposure to a pathogen). Treatment may also be continued after symptoms have resolved, for example, to delay or prevent recurrence.

As used herein, the terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "protein" or "peptide" comprises a polymer of amino acid residues linked together by peptide bonds. The term, as used herein, refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The term "aberrant activity" refers to activity deviating from normal activity, that is, abnormal activity. The term "increased activity" refers to activity higher than normal activity.

The terms "composition" and "formulation" are used interchangeably.

The term "biological sample" refers to any sample including tissue samples (such as tissue sections and needle biopsies of a tissue); cell samples (e.g., cells, cells in cell cultures, cytological smears (such as Pap or blood smears), or samples of cells obtained by microdissection); samples of whole organisms (such as samples of yeasts or bacteria); or cell fractions, cell extracts, fragments or organelles (such as obtained by lysing cells and separating the components thereof by centrifugation or otherwise). Other examples of biological samples include blood, serum, urine, semen, fecal matter, tumors, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from another biological sample.

The term "proliferative disease" refers to a disease that occurs due to abnormal growth or extension by the multiplication of cells (Walker, *Cambridge Dictionary of Biology*, Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, diseases associated with angiogenesis, inflammatory diseases, autoinflammatory diseaes, and autoimmune diseases.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, hematological malignancies. Additional exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast, triple negative breast cancer (TNBC), ER positive breast cancer, ER negative breast cancer, PR positive breast cancer, PR negative breast cancer, ER/PR positive breast cancer, ER/PR negative breast cancer, HER2 positive breast cancer, HER2 negative breast cancer); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma, squamous cell carcinoma of the cervix); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland cancer; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "fibrotic disease" or "fibrosis" refers to a class of diseases characterized by the formation of excess fibrous connective tissue. Exemplary fibrotic diseases include, but are not limited to: pulmonary fibrosis, idiopathic pulmonary fibrosis, cystic fibrosis, cirrhosis, endomyocardial fibrosis, atrial fibrosis, mediastinal fibrosis, myelofibrosis, retroperitoneal fibrosis, progressive massive fibrosis, nephrogenic systemic fibrosis, Crohn's disease, chronic kidney disease, keloid, scleroderma, systemic sclerosis, arthrofibrosis, Peyronie's disease, Dupuytren's contracture, asthma, and adhesive capsulitis.

PHGDH, phosphoglycerate dehydrogenase, is alternatively referred to as 3-PGDH, 3PGDHm HEL-S-113, NLS, PDG, PGAD, PGD, PGDH, PHGDHD, or SERA. The term "PHGDH" ecompasses mutants, variants, homologs, fragements, and synthetically modified phosphoglycerate dehydrogenases. In some instances, the term "PHGDH" is referring to the gene that encodes for the PHGDH protein. PHGDH is an oxidoreductase, which catalyzes the dehydrogenation of 3-phospho-D-glycerate to form 3-phosphonooxypyruvate. PHGDH also catalyzes the dehydrogenation of 2-hydroxygluturate to form 2-oxogluturate. NAD+ or NADP+ serve as co-factors. Non-limiting examples of the nucleotide and protein sequences for human PHGDH are described in GenBank Accession Numbers NG_009188.1 (nucleotide) and NP_006614.2 (protein), incorporated herein by reference. The amino acid sequence of this human PHGDH is as follows:

(SEQ ID NO: NP_006614.2)
MAFANLRKVLISDSLDPCCRKILQDGGLQVVEKQNLSKEELIAELQDCEG

LIVRSATKVTADVINAAEKLQVVGRAGTGVDNVDLEAATRKGILVMNTPN

GNSLSAAELTCGMIMCLARQIPQATASMKDGKWERKKFMGTELNGKTLGI

LGLGRIGREVATRMQSFGMKTIGYDPIISPEVSASFGVQQLPLEEIWPLC

DFITVHTPLLPSTTGLLNDNTFAQCKKGVRVVNCARGGIVDEGALLRALQ

SGQCAGAALDVFTEEPPRDRALVDHENVISCPHLGASTKEAQSRCGEEIA

VQFVDMVKGKSLTGVVNAQALTSAFSPHTKPWIGLAEALGTLMRAWAGSP

KGTIQVITQGTSLKNAGNCLSPAVIVGLLKEASKQADVNLVNAKLLVKEA

GLNVTISHSPAAPGEQGFGECLLAVALAGAPYQAVGLVQGTTPVLQGLNG

AVFRPEVPLRRDLPLLLFRTQTSDPAMLPTMIGLLAEAGVRLLSYQTSLV

SDGETWHVMGISSLLPSLEAWKQHVTEAFQFHF

MDA-MB-231 is a cell line of human breast adenocarcinoma epithelial cells isolated from a pleural effusion. MDA-MB-231 cells do not express PHGDH (or express so little as to be undectable by western blot). MDA-MB-231 cells are independent PHGDH-independent.

MDA-MB-468 is a cell line of human adenocarcinoma epithelial cells isolated from a pleural effusion. MDA-MB-468 cells have copy number amplications of PHGDH and, thus, over-express PHGDH. MDA-MB-468 has high flux through the serine biosynthesis pathway and are PHGDH-dependent, thus serving as a model for PHGDH-dependent breast cancer.

The present application refers to various issued patent, published patent applications, journal articles, and other publications, all of which are incorporated herein by reference.

DETAILED DESCRIPTION OF CERTAIN EMBODIMENTS OF THE INVENTION

Phosphoglycerate dehydrogenase (PHGDH) is an oxidoreductase which has been implicated as essential for tumorigenesis in some cancers. PHGDH over-expression has been identified in cancer cells, for example, cells from breast cancer tumors. (Possemato et al. "Functional genomics reveal that the serine biosynthesis pathway is essential in breast cancer." Nature 476, 346-350 (2011)) PHGDH is known to catalyze two reactions: (1) the dehydrogenation of 3-phospho-D-glycerate to form 3-phosphonooxypyruvate; and (2) the dehydrogenation of 2-hydroxygluturate to form 2-oxogluturate. Both reactions utilize the coenzyme $NAD^+$, and form NADH and a proton as co-products. The dehydrogenation of 3-phospho-D-glycerate is the first step in the biosynthesis of L-serine. Inhibition of PHGDH may have the effect of slowing serine biosynthesis or reducing levels of serine (or both). Inhibition of PHGDH may also reduce levels of NADH and NADPH. Serine and NADPH are necessary for the synthesis of a variety of biomolecules needed for cell proliferation. Therefore, modulation of serine and NADH/NADPH metabolisms (e.g., blocking flux through the serine biosynthetic pathway) may inhibit the growth of cells, in particular cancer cells. (Possemato et al.) Elevated serine biosynthetic activity has been observed in malignant cells. (Snell, "Enzymes of serine metabolism in normal, developing an neoplastic rat tissues." Adv. Enzyme Regul. 22, 325-400 (1984); Achouri et al. "Cloning, sequencing and expression of rat liver 3-phosphoglycerate dehydrogenase." Biochem. J. 323, 365-370 (1984)). Other enzymes in the serine biosynthetic pathway include phosphoserine aminotransferase (PSAT1) and phosphoserine phosphatase (PSPH). Suppressing the activity of PHGDH (and reducing levels of 3-phosphonooxypyruvate) may also effect the activity of PSAT1 and PSPH. The levels of the metabolic products of PSAT1 and PSPH are therefore likely to be reduced in cells where PHGDH activity is inhibited. Such products include a-ketoglutarate (produced by PSAT1), reduced production of which may have implications for tricarboxylic acid cycle (TCA cycle) mechanisms such as anaplerosis. For example, a reduction in flux of a-ketoglutarate from the serine pathway may lead to an increase in conversion of glutamate to a-ketoglutarate. (Possemato et all). The compounds, compositions, kits, uses, and methods of the invention inhibit PHGDH and therefore are potentially effective treatments for cancers associated with PHGDH-dependent cells and PHGDH over-expression (e.g., breast cancer, ER negative breast cancer, melanoma, cervical cancer)).

The present invention provides a family of inhibitors of 3-phosphoglycerate dehydrogenase (PHGDH) and uses thereof. The compounds are based on a carbiothioamide core and represent the first chemotype capable of inhibiting PHGDH. In certain embodiments, the compounds have in vitro $IC_{50}$'s of 1 to 5 µM. In certain embodiments, the compounds exhibit selective cytotoxicity towards cell lines with PHGDH over-expression. In certain embodiments, the compounds exhibit lower toxicity (e.g., an order of magnitude less) towards cell lines that do not over-express PHGDH.

In one aspect, the invention provides compounds of Formula (I), (II), or (III), or pharmaceutically acceptable salts, solvates, hydrates, polymorphs, co-crystals, tautomers, stereoisomers, isotopically labelled derivatives, pro-drugs, or pharmaceutical compositions thereof. In certain embodiments, the invention provides compounds of Formula (I), (II), or (III), or pharmaceutical acceptable salts or pharmaceutical compositions thereof. The compounds have been found to inhibit phosphoglycerate dehydrogenase (PHGDH) and thus may be useful for the treatment or prevention (or both) of diseases associated with PHGDH over-expression or aberrant activity (e.g., increased activity). In certain embodiments, the disease is a proliferative disease (e.g., cancer (e.g., breast cancer, ER negative breast cancer, melanoma, cervical cancer), benign neoplasms, diseases associated with angiogenesis, inflammatory diseases, autoinflammatory diseases, autoimmune diseases). In certain embodiments, the disease is a fibrotic disease (e.g., idiopathic pulmonary fibrosis, nephrogenic systemic fibrosis, scleroderma).

The invention also provides pharmaceutical compositions and kits comprising compounds of Formula (I), (II), or (III), or pharmaceutically acceptable salts, solvates, hydrates, polymorphs, co-crystals, tautomers, stereoisomers, isotopically labelled derivatives, or pro-drugs thereof, and uses thereof for the treatment of disease. In certain embodiments, the invention provides pharmaceutical compositions and kits comprising compounds of Formula (I), (II), or (III), or pharmaceutically acceptable salts thereof, and uses thereof for the treatment of disease.

In another aspect, the invention provides methods for treating a proliferative disease (e.g., cancer, (e.g., breast cancer, ER negative breast cancer, melanoma, cervical cancer), benign neoplasms, diseases associated with angiogenesis, inflammatory diseases, autoinflammatory diseases, autoimmune diseases) by administering a therapeutically effective amount of a compound of Formula (I), (II), or (III). Additional aspects of the invention include, methods for inhibiting PHGDH activity, inhibiting cell growth, inducing cell death, and inhibiting the serine biosynthetic pathway by administering the compound to a subject or contacting it with a biological sample (e.g., cells, tissues, blood, biopsied tissues, tumors).

In another aspect, the invention provides methods for treating a fibrotic disease (e.g., idiopathic pulmonary fibrosis, nephrogenic systemic fibrosis, scleroderma), by administering a therapeutically effective amount of a compound of Formula (I), (II), or (III).

Compounds

In one aspect of the present invention, the invention provides compounds of Formula (I):

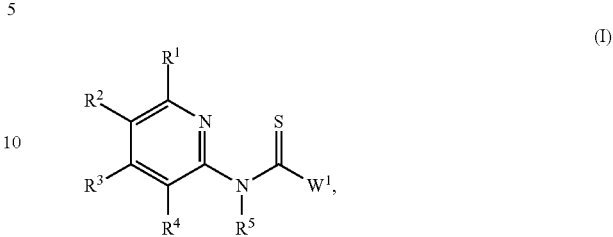

or pharmaceutically acceptable salts, solvates, hydrates, polymorphs, co-crystals, tautomers, stereoisomers, isotopically labeled derivatives, pro-drugs, and pharmaceutical compositions thereof, wherein:

$W^1$ is of formula:

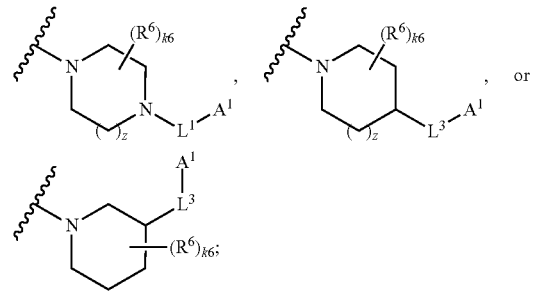

$L^1$ is a bond, optionally substituted alkylene, optionally substituted alkenylene, optionally substituted alkynylene, —C(=O)—, —C(=O)O—, —C(=O)NR$^a$—, —S(=O)—, —S(=O)O—, —S(=O)NR$^a$, —S(=O)$_2$—, —S(=O)$_2$O—, or —S(=O)$_2$NR$^a$—;

$L^3$ is a bond, optionally substituted alkylene, optionally substituted alkenylene, optionally substituted alkynylene, —NR$^a$—, —O—, —S—, —C(=O)—, —C(=O)O—, —C(=O)NR$^a$—, —OC(=O)—, —NR$^a$C(=O)—, —OC(=O)O—, —NR$^a$C(=O) NR$^a$—, —NR$^a$C(=O)O—, —OC(=O)NR$^a$—, —S(=O)—, —S(=O)O—, —S(=O)NR$^a$—, —O(S=O)—, —NR$^a$S(=O)—, —S(=O)$_2$—, —S(=O)$_2$O—, —S(=O)$_2$NR$^a$—, —OS(=O)$_2$—, or —NR$^a$S(=O)$_2$—;

$A^1$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^1$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —SCN, —NCS, —N$_3$, —NO$_2$, —OR$^b$, —NR$^c$R$^d$, —NR$^c$(OR$^b$), —SR$^e$, —SSR$^e$, —C(=O)R$^f$, —C(=O)OR$^b$, —C(=O)NR$^c$R$^d$, —C(=NR$^c$)R$^f$, —C(=NR$^c$)OR$^b$, —C(=NR$^c$)NR$^c$R$^d$, —OC(=O)R$^f$, —OC(=O)OR$^b$, —OC(=O)NR$^c$R$^d$, —OC(=NR$^c$)R$^f$, —OC(=NR$^c$)OR$^b$, —OC(=NR$^c$)NR$^c$R$^d$, —NR$^c$C(=O)R$^f$, —NR$^c$C(=O)OR$^b$, —NR$^c$C(=O)NR$^c$R$^d$, —NR$^c$C(=NR$^c$)R$^f$, —NR$^c$C(=NR$^c$)OR$^b$, —NR$^c$C(=NR$^c$)NR$^c$R$^d$, —C(=S)R$^f$, —C(=S)OR$^b$, —C(=O)SR$^e$, —C(=S)NR$^c$R$^d$, —NR$^c$C(=S)NR$^c$R$^d$, —Si(R$^f$)$_3$, —OSi(R$^f$)$_3$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

R$^2$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —SCN, —NCS, —N$_3$, —NO$_2$, —OR$^b$, —NR$^c$R$^d$, —NR$^c$(OR$^b$), —SR$^e$, —SSR$^e$, —C(=O)R$^f$, —C(=O)OR$^b$, —C(=O)NR$^c$R$^d$, —C(=NR$^c$)R$^f$, —C(=NR$^c$)OR$^b$, —C(=NR$^c$)NR$^c$R$^d$, —OC(=O)R$^f$, —OC(=O)OR$^b$, —OC(=O)NR$^c$R$^d$, —OC(=NR$^c$)R$^f$, —OC(=NR$^c$)OR$^b$, —OC(=NR$^c$)NR$^c$R$^d$, —NR$^c$C(=O)R$^f$, —NR$^c$C(=O)OR$^b$, —NR$^c$C(=O)NR$^c$R$^d$, —NR$^c$C(=NR$^c$)R$^f$, —NR$^c$C(=NR$^c$)OR$^b$, —NR$^c$C(=NR$^e$)NR$^c$R$^d$, —C(=S)R$^f$, —C(=S)OR$^b$, —C(=O)SR$^e$, —C(=S)NR$^c$R$^d$, —NR$^c$C(=S)NR$^c$R$^d$, —Si(R$^f$)$_3$, —OSi(R$^f$)$_3$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

R$^3$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —SCN, —NCS, —N$_3$, —NO$_2$, —OR$^b$, —NR$^c$R$^d$, —NR$^c$(OR$^b$), —SR$^e$, —SSR$^e$, —C(=O)R$^f$, —C(=O)OR$^b$, —C(=O)NR$^c$R$^d$, —C(=NR$^c$)R$^f$, —C(=NR$^c$)OR$^b$, —C(=NR$^c$)NR$^c$R$^d$, —OC(=O)R$^f$, —OC(=O)OR$^b$, —OC(=O)NR$^c$R$^d$, —OC(=NR$^c$)R$^f$, —OC(=NR$^c$)OR$^b$, —OC(=NR$^c$)NR$^c$R$^d$, —NR$^c$C(=O)R$^f$, —NR$^c$C(=O)OR$^b$, —NR$^c$C(=O)NR$^c$R$^d$, —NR$^c$C(=NR$^c$)R$^f$, —NR$^c$C(=NR$^c$)OR$^b$, —NR$^c$C(=NR$^e$)NR$^c$R$^d$, —C(=S)R$^f$, —C(=S)OR$^b$, —C(=O)SR$^e$, —C(=S)NR$^c$R$^d$, —NR$^c$C(=S)NR$^c$R$^d$, —Si(R$^f$)$_3$, —OSi(R$^f$)$_3$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

R$^4$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —SCN, —NCS, —N$_3$, —NO$_2$, —OR$^b$, —NR$^c$R$^d$, —NR$^c$(OR$^b$), —SR$^e$, —SSR$^e$, —C(=O)R$^f$, —C(=O)OR$^b$, —C(=O)NR$^c$R$^d$, —C(=NR$^c$)R$^f$, —C(=NR$^c$)OR$^b$, —C(=NR$^c$)NR$^c$R$^d$, —OC(=O)R$^f$, —OC(=O)OR$^b$, —OC(=O)NR$^c$R$^d$, —OC(=NR$^c$)R$^f$, —OC(=NR$^c$)OR$^b$, —OC(=NR$^c$)NR$^c$R$^d$, —NR$^c$C(=O)R$^f$, —NR$^c$C(=O)OR$^b$, —NR$^c$C(=O)NR$^c$R$^d$, —NR$^e$C(=NR$^c$)R$^f$, —NR$^c$C(=NR$^c$)OR$^b$, —NR$^c$C(=NR$^e$)NR$^c$R$^d$, —C(=S)R$^f$, —C(=S)OR$^b$, —C(=O)SR$^e$, —C(=S)NR$^c$R$^d$, —NR$^c$C(=S)NR$^c$R$^d$, —Si(R$^f$)$_3$, —OSi(R$^f$)$_3$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

R$^5$ is hydrogen, optionally substituted C$_1$-C$_6$ alkyl, or a nitrogen protecting group;

each R$^6$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^b$, —NR$^c$R$^d$, —SR$^e$, —C(=O)R$^f$, —C(=O)OR$^b$, or —C(=O)NR$^c$R$^d$;

each R$^a$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each R$^b$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each of R$^c$ and R$^d$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or R$^c$ and R$^d$ are joined to form an optionally substituted heterocyclic or optionally substituted heteroaryl ring;

each of R$^e$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a sulfur protecting group;

each of R$^f$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

k6 is 0, 1, 2, 3, or 4; and z is 1 or 2;

provided:

when L$^1$ is a bond, A$^1$ is not optionally substituted 1-isoquinolinyl, optionally substituted 4-isoquinolinyl, optionally substituted 4-quinolinyl, or optionally substituted 4-quinazolinyl; and the compound is not:
N-(3-fluoro-4-((2-(4-methylpiperazine-1-carbothioamido)pyridin-4-yl)oxy)phenyl)-2-oxo-1-phenyl-1,2-dihydropyridine-3-carboxamide.

In certain embodiments, the invention provides compounds of Formula (I) or pharmaceutically acceptable salts thereof. In certain embodiments, the invention provides compounds of Formula (I) or pharmaceutically acceptable salts thereof, or pharmaceutical compositions thereof.

In another aspect, the present invention provides compounds of Formula (I) according to Formula (III):

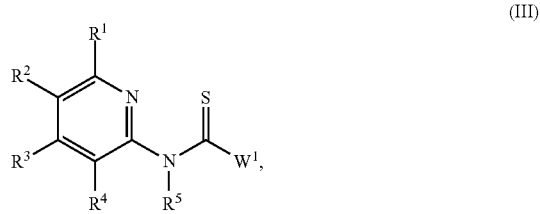

(III)

or pharmaceutically acceptable salts, solvates, hydrates, polymorphs, co-crystals, tautomers, stereoisomers, isotopi cally labeled derivatives, pro-drugs, and pharmaceutical compositions thereof, wherein:

$W^1$ is of formula:

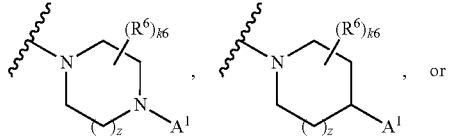

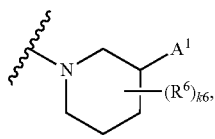

and $A^1$, $R^1$-$R^6$, $R^a$-$R^f$, k6, and z are as defined for compounds of Formula (I).

In certain embodiments, the invention provides compounds of Formula (III) or pharmaceutically acceptable salts thereof. In certain embodiments, the invention provides compounds of Formula (III) or pharmaceutically acceptable salts thereof, or pharmaceutical compositions thereof.

A compound not included in Formula (I) or (III) is N-(3-fluoro-4-((2-(4-methylpiperazine-1-carbothioamido)pyridin-4-yl)oxy)phenyl)-2-oxo-1-phenyl-1,2-dihydropyridine-3-carboxamide:

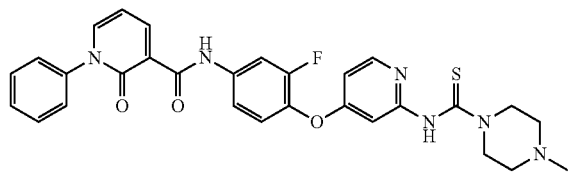

Compounds of Formula (I) or (III) do not include compounds, wherein $L^1$ is a bond and $A^1$ is an optionally substituted ring of formula:

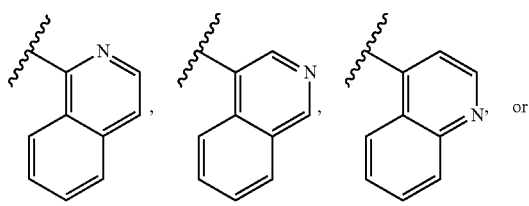

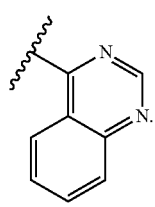

In certain embodiments, the compound of Formula (III) is of Formula (III-A):

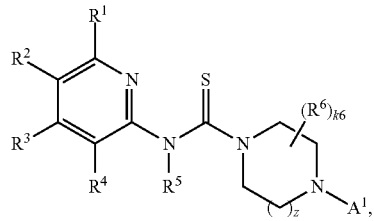
(III-A)

wherein $A^1$, $R^1$-$R^6$, $R^a$-$R^f$, k6, and z are as defined for compounds of Formula (I).

In certain embodiments, the compound of Formula (III) is of Formula (III-B):

(III-B)

wherein $A^1$, $R^1$-$R^6$, $R^a$-$R^f$, k6, and z are as defined for compounds of Formula (I).

In certain embodiments, the compound of Formula (III) is of Formula (III-C):

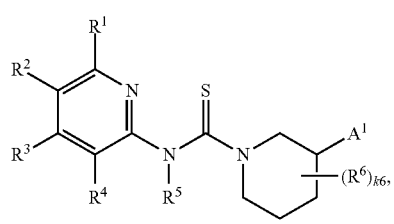
(III-C)

wherein $A^1$, $R^1$-$R^6$, $R^a$-$R^f$, k6, and z are as defined for compounds of Formula (I).

In another aspect, the compound of Formula (III) is of Formula (III'):

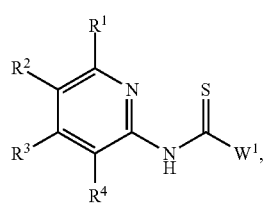
(III')

wherein:
W¹ is:

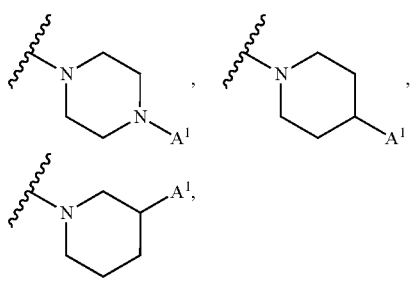

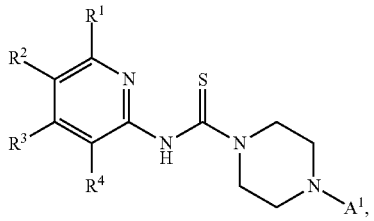

and A¹, R¹-R⁴, and Rᵃ-Rᶠ are as defined for compounds of Formula (I).

In certain embodiments, the compound of Formula (III′) is of Formula (III′-A):

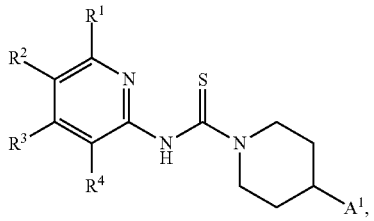
(III′-A)

wherein A¹, R¹-R⁴, and Rᵃ-Rᶠ are as defined for compounds of Formula (I).

In certain embodiments, the compound of Formula (III′) is of Formula (III′-B):

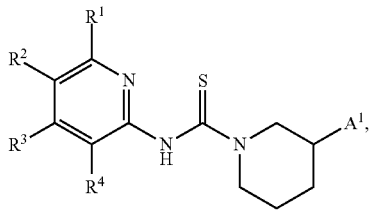
(III′-B)

wherein A¹, R¹-R⁴, and Rᵃ-Rᶠ are as defined for compounds of Formula (I).

In certain embodiments, the compound of Formula (III′) is of Formula (III′-C):

(III′-C)

wherein A¹, R¹-R⁴, and Rᵃ-Rᶠ are as defined for compounds of Formula (I).

Compounds of Formula (I) or (III) include group W¹. In certain embodiments, W¹ is of formula:

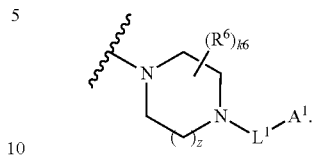

In certain embodiments, W¹ is of formula:

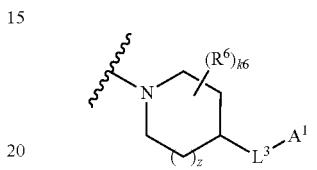

In certain embodiments, W¹ is of formula:

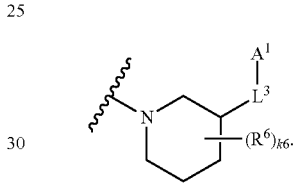

In certain embodiments, W¹ is of formula:

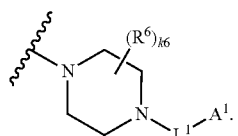

In certain embodiments, W¹ is of formula:

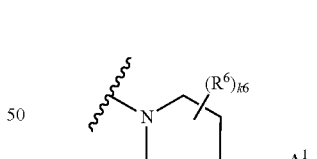

In certain embodiments, W¹ is of formula:

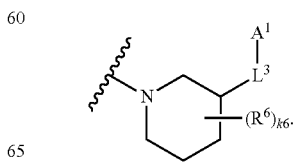

In certain embodiments, W¹ is of formula:

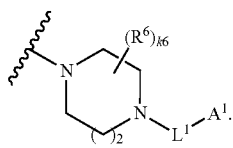

In certain embodiments, W¹ is of formula:

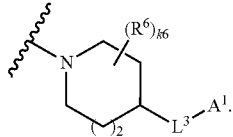

In certain embodiments, W¹ is of formula:

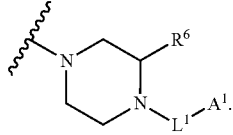

In certain embodiments, W¹ is of formula:

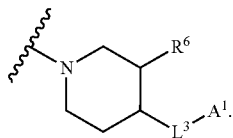

In certain embodiments, W¹ is of formula:

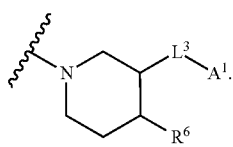

In certain embodiments, W¹ is of formula:

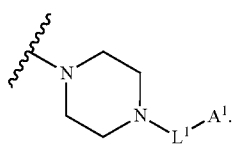

In certain embodiments, W¹ is of formula:

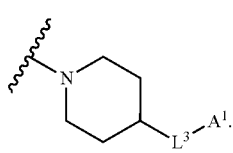

In certain embodiments, W¹ is of formula:

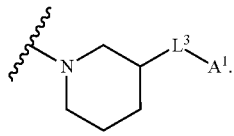

In certain embodiments, W¹ is of formula:

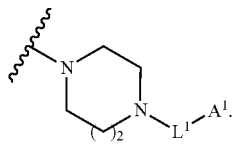

In certain embodiments, W¹ is of formula:

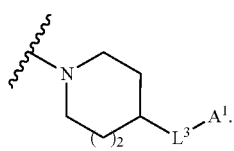

Compounds of Formula (I) or (III) include group W¹. In certain embodiments, W¹ is of formula:

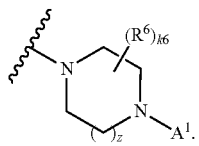

In certain embodiments, W¹ is of formula:

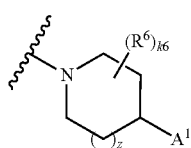

In certain embodiments, W¹ is of formula:

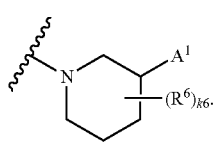

In certain embodiments, W¹ is of formula:

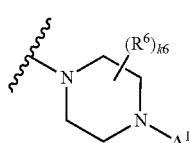

In certain embodiments, $W^1$ is of formula:

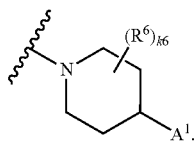

In certain embodiments, $W^1$ is of formula:

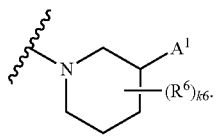

In certain embodiments, $W^1$ is of formula:

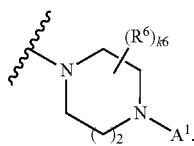

In certain embodiments, $W^1$ is of formula:

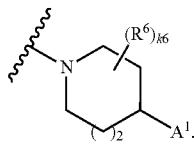

In certain embodiments, $W^1$ is of formula:

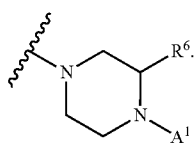

In certain embodiments, $W^1$ is of formula:

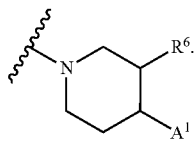

In certain embodiments, $W^1$ is of formula:

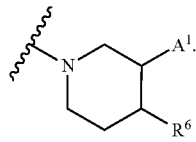

In certain embodiments, $W^1$ is of formula:

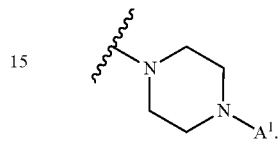

In certain embodiments, $W^1$ is of formula:

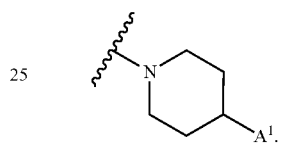

In certain embodiments, $W^1$ is of formula:

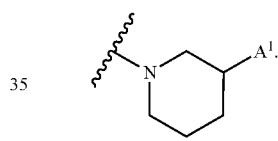

In certain embodiments, $W^1$ is of formula:

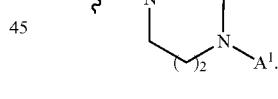

In certain embodiments, $W^1$ is of formula:

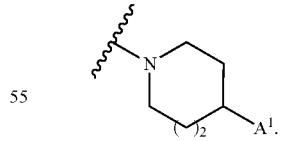

Compounds of Formula (I) include linker $L^1$. In certain embodiments, $L^1$ is optionally substituted alkylene, —C(=O)—, —C(=O)O—, or —C(=O)NR$^a$—. In certain embodiments, $L^1$ is optionally substituted alkylene. In certain embodiments, $L^1$ is optionally substituted $C_1$-$C_6$ alkylene. In certain embodiments, $L^1$ is alkylene. In certain embodiments, $L^1$ is $C_1$-$C_6$ alkylene. In certain embodiments, $L^1$ is methylene. In certain embodiments, $L^1$ is ethylene. In certain embodiments, $L^1$ is propylene. In certain embodiments, $L^1$ is butylene. In certain embodiments, $L^1$ is optionally substituted alkenylene. In certain embodiments, $L^1$ is optionally substituted alkynylene.

In certain embodiments, $L^1$ is —C(=O)—. In certain embodiments, $L^1$ is —C(=O)O—. In certain embodiments, $L^1$ is —C(=O)NR$^a$—. In certain embodiments, $L^1$ is —S(=O)—. In certain embodiments, $L^1$ is —S(=O)O—. In certain embodiments, $L^1$ is —S(=O)NR$^a$—. In certain embodiments, $L^1$ is —S(=O)$_2$—. In certain embodiments, $L^1$ is —S(=O)$_2$O—. In certain embodiments, $L^1$ is —S(=O)$_2$NR$^a$—. In certain embodiments, $L^1$ is —C(=O)NH—. In certain embodiments, $L^1$ is —S(=O)NH—. In certain embodiments, $L^1$ is —S(=O)$_2$NH—.

Compounds of Formula (I) include linker $L^3$. In certain embodiments, $L^3$ is optionally substituted alkylene, —NR$^a$—, —O—, —S—, —C(=O)—, —C(=O)O—, —C(=O)NR$^a$—, —OC(=O)—, or —NR$^a$C(=O)—. In certain embodiments, $L^3$ is optionally substituted alkylene. In certain embodiments, $L^3$ is optionally substituted $C_1$-$C_6$ alkylene. In certain embodiments, $L^3$ is alkylene. In certain embodiments, $L^3$ is $C_1$-$C_6$ alkylene. In certain embodiments, $L^3$ is methylene. In certain embodiments, $L^3$ is ethylene. In certain embodiments, $L^3$ is propylene. In certain embodiments, $L^3$ is butylene. In certain embodiments, $L^3$ is optionally substituted alkenylene. In certain embodiments, $L^3$ is optionally substituted alkynylene.

In certain embodiments, $L^3$ is —NR$^a$—. In certain embodiments, $L^3$ is —NH—. In certain embodiments, $L^3$ is —O—. In certain embodiments, $L^3$ is —S—. In certain embodiments, $L^3$ is —C(=O)—. In certain embodiments, $L^3$ is —C(=O)O—. In certain embodiments, $L^3$ is —C(=O)NR$^a$—. In certain embodiments, $L^3$ is —OC(=O)—. In certain embodiments, $L^3$ is —NR$^a$C(=O)—. In certain embodiments, $L^3$ is —OC(=O)—. In certain embodiments, $L^3$ is —NR$^a$C(=O)NR$^a$—. In certain embodiments, $L^3$ is —NR$^a$C(=O)O—. In certain embodiments, $L^3$ is —OC(=O)NR$^a$—. In certain embodiments, $L^3$ is —S(=O)—. In certain embodiments, $L^3$ is —S(=O)O—. In certain embodiments, $L^3$ is —S(=O)NR$^a$—. In certain embodiments, $L^3$ is —OS(=O)—. In certain embodiments, $L^3$ is —NR$^a$S(=O)—. In certain embodiments, $L^3$ is —S(=O)$_2$—. In certain embodiments, $L^3$ is —S(=O)$_2$O—. In certain embodiments, $L^3$ is —S(=O)$_2$NR$^a$—. In certain embodiments, $L^3$ is —OS(=O)$_2$—. In certain embodiments, $L^3$ is —NR$^a$S(=O)$_2$—. In certain embodiments, $L^3$ is —C(=O)NH—. In certain embodiments, $L^3$ is —S(=O)NH—. In certain embodiments, $L^3$ is —S(=O)$_2$NH—. In certain embodiments, $L^3$ is —NHC(=O)—. In certain embodiments, $L^3$ is —NHS(=O)—. In certain embodiments, $L^3$ is —NHS(=O)$_2$—. In certain embodiments, $L^3$ is —OC(=O)NH—. In certain embodiments, $L^3$ is —NHC(=O)O—. In certain embodiments, $L^3$ is —NHC(=O)NH—.

Compounds of Formula (I) or (III) may contain one or more independent groups $R^A$ within certain embodiments of group $A^1$. In such embodiments, $A^1$ are rings of formula:

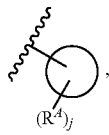

wherein the circle indicates a ring, and $R^A$ is an optional substituent. The ring may contain one or more heteroatoms at any position, wherein the heteroatoms are independently selected from N, O, and S, and may be monocyclic or polycyclic. Each $R^A$ is independently halogen, nitrile, nitro, optionally substituted alkyl, optionally substituted alkenyl, optionally substituted carbocyclyl, optionally substituted heterocyclyl, optionally substituted aryl, optionally substituted heteroaryl, —OR$^b$, —NR$^c$R$^d$, —SR$^e$, —C(=O)R$^f$, —C(=O)OR$^b$, —C(=O)NR$^c$R$^d$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$. The number of independently selected substituents is defined by j, which may be 0, 1, 2, 3, 4, 5, 6, 7, or 8, contingent on ring size and available valency.

Compounds of Formula (I) or (III) include group $A^1$. In certain embodiments, $A^1$ is optionally substituted alkyl, optionally substituted carbocyclyl, optionally substituted heterocyclyl, optionally substituted aryl, or optionally substituted heteroaryl. In certain embodiments, $A^1$ is optionally substituted alkyl. In certain embodiments, $A^1$ is optionally substituted alkyl, optionally substituted alkenyl. In certain embodiments, $A^1$ is optionally substituted alkynyl. In certain embodiments, $A^1$ is optionally substituted carbocyclyl. In certain embodiments, $A^1$ is optionally substituted heterocyclyl. In certain embodiments, $A^1$ is optionally substituted aryl. In certain embodiments, $A^1$ is optionally substituted heteroaryl.

In certain embodiments, $A^1$ is optionally substituted cyclohexyl. In certain embodiments, $A^1$ is optionally substituted piperidinyl. In certain embodiments, $A^1$ is optionally substituted piperizinyl. In certain embodiments, $A^1$ is optionally substituted morpholinyl. In certain embodiments, $A^1$ is of formula:

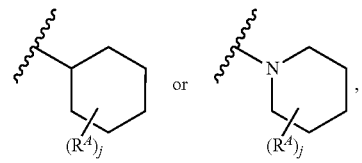

wherein j is 0-5. In certain embodiments, $A^1$ is of formula:

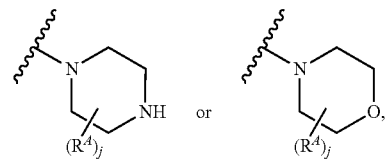

wherein j is 0-4.

In certain embodiments, is optionally substituted pyrimidinyl. In certain embodiments, $A^1$ is optionally substituted pyrazinyl. In certain embodiments, $A^1$ is of formula:

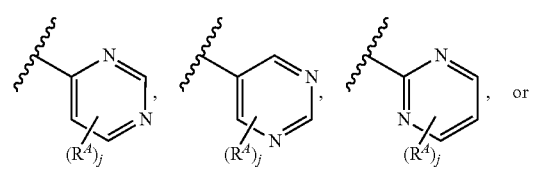

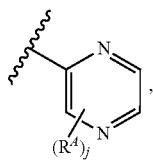

wherein j is 0-3. In certain embodiments, A¹ is optionally substituted pyridinyl. In certain embodiments, A¹ is of formula:

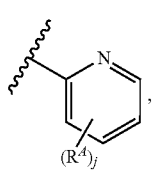, 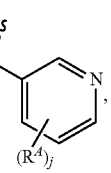 or 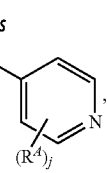, wherein j is 0-4. In certain embodiments, A¹ is of formula:

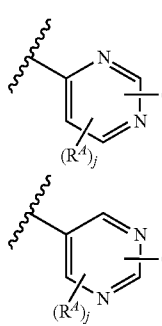

wherein j is 0-2. In certain embodiments, A¹ is of formula:

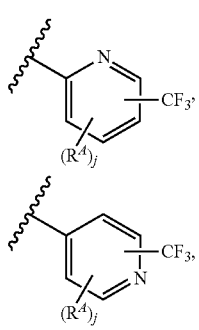

wherein j is 0-3.

In certain embodiments, A¹ is optionally substituted phenyl. In certain embodiments, A¹ is of formula:

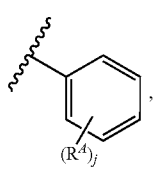, wherein j is 0-5. In certain embodiments, A¹ is of formula:

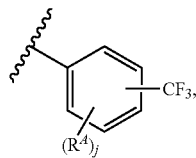

wherein j is 0-4. In certain embodiments, A¹ is of formula:

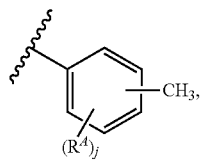

wherein j is 0-4. In certain embodiments, A¹ is of formula:

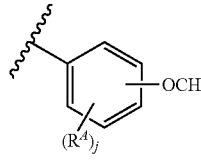

wherein j is 0-4.

In certain embodiments, group A¹ is selected from a group listed in Table 1.

TABLE 1

Examples of group A¹.

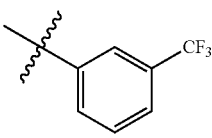 [SMILES: *c1cccc(C(F)(F)F)c1]

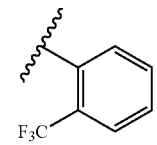

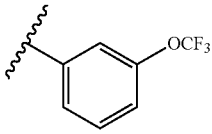 [SMILES: *c1cccc(OC(F)(F)F)c1]

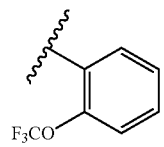

TABLE 1-continued
Examples of group A¹.
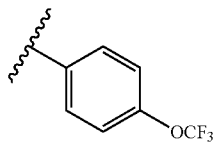 [SMILES: *c1ccc(OC(F)(F)F)cc1]
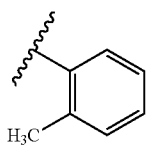
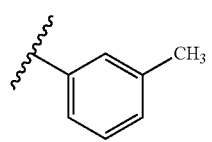 [SMILES: *c1cccc(C)c1]
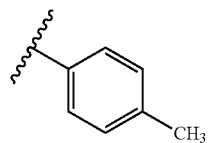 [SMILES: *c1ccc(C)cc1]
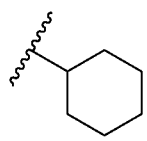 [SMILES: *C1CCCCC1]
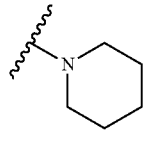 [SMILES: *N1CCCCC1]
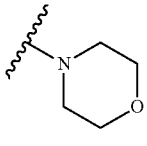 [SMILES: *N1CCOCC1]
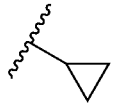 [SMILES: *C1CC1]
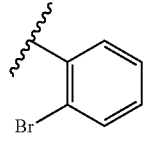
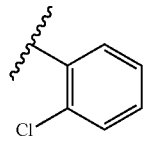 [SMILES: *c1ccccc1Cl]
TABLE 1-continued
Examples of group A¹.
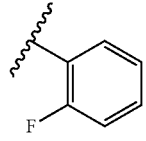 [SMILES: *c1ccccc1F]
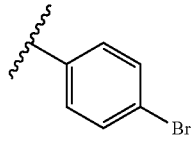
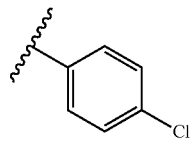 [SMILES: *c1ccc(Cl)cc1]
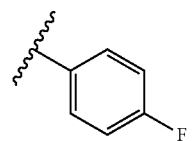 [SMILES: *c1ccc(F)cc1]
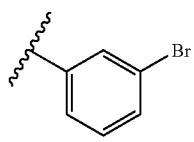
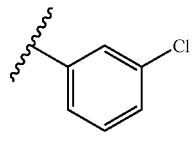 [SMILES: *c1cccc(Cl)c1]
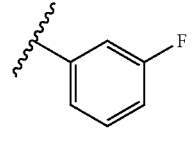 [SMILES: *c1cccc(F)c1]
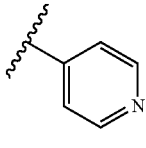 [SMILES: *c1ccncc1]
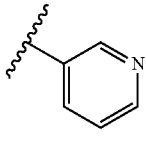 [SMILES: *c1cccnc1]
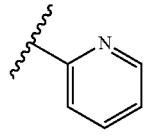 [SMILES: *c1ccccn1]

TABLE 1-continued
Examples of group A[1].
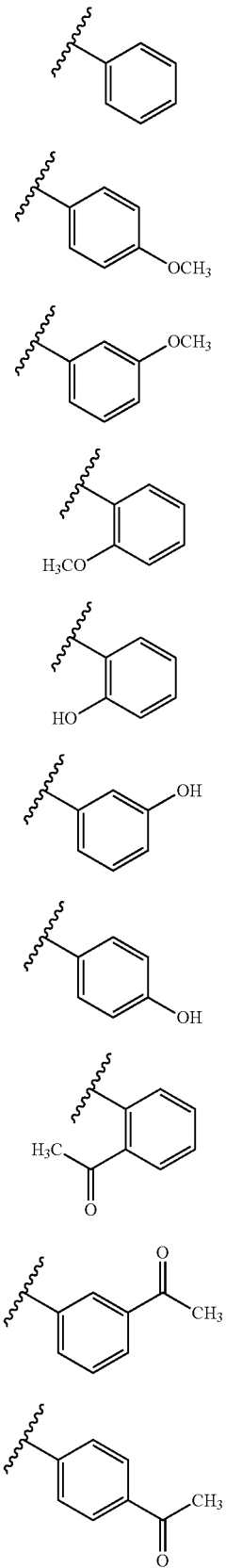
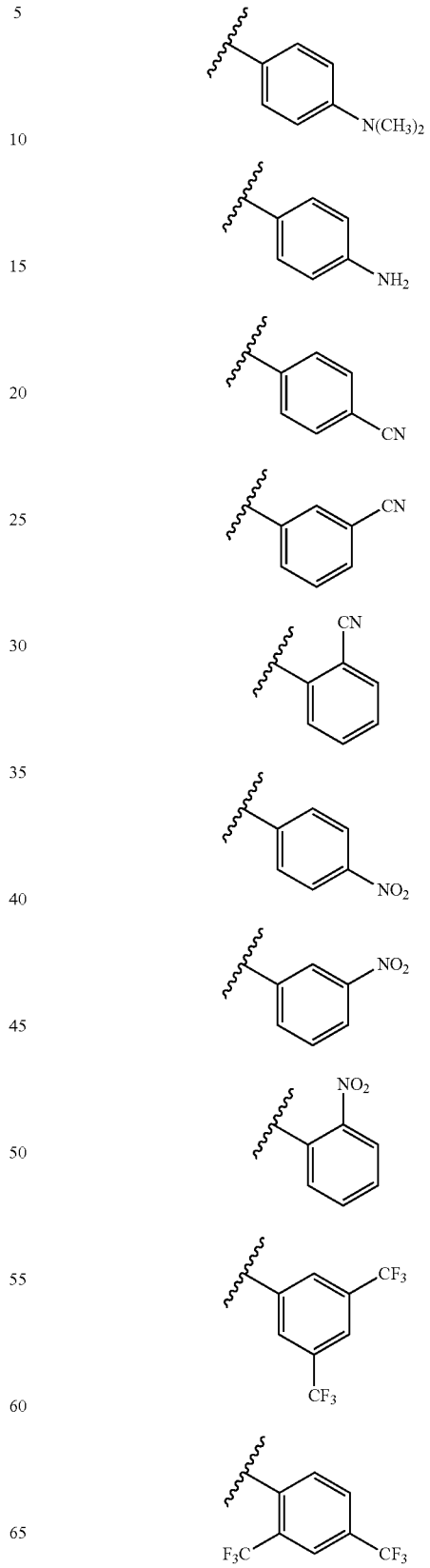

TABLE 1-continued
Examples of group A¹.
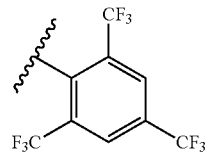
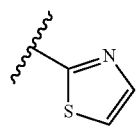 [SMILES: *c1nccs1]
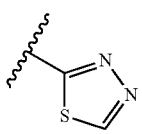 [SMILES: *c1nncs1]
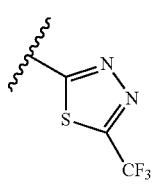
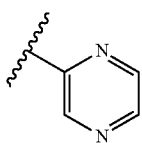 [SMILES: *c1cnccn1]
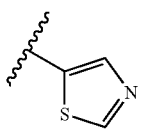 [SMILES: *c1cncs1]
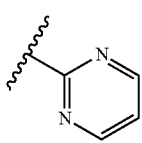
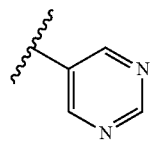
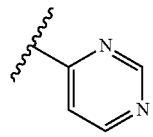 [SMILES: *c1ccncn1]
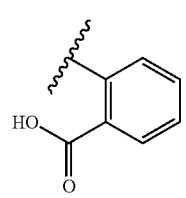
TABLE 1-continued
Examples of group A¹.
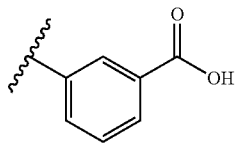 [SMILES: *c1cccc(C(=O)O)c1]
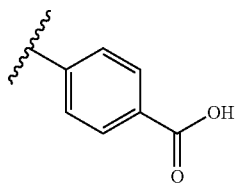 [SMILES: *c1ccc(C(=O)O)cc1]
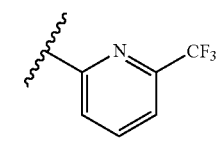 [SMILES: *c1cccc(C(F)(F)F)n1]
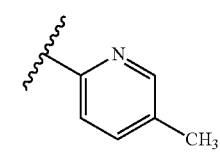
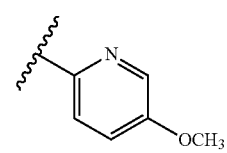
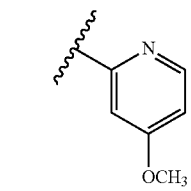
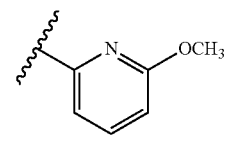 [SMILES: *c1cccc(OC)n1]
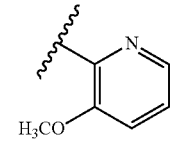
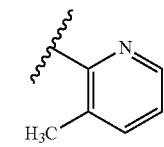

TABLE 1-continued
Examples of group A$^1$.
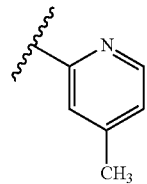
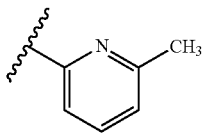 [SMILES: *c1cccc(C)n1]
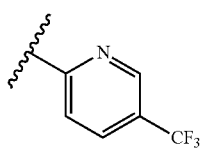 [SMILES: *c1ccc(C(F)(F)F)cn1]
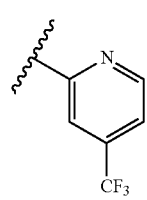 [SMILES: *c1cc(C(F)(F)F)ccn1]
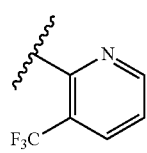
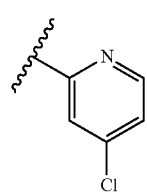 [SMILES: *c1cc(Cl)ccn1]
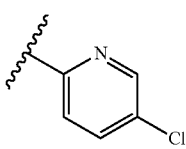 [SMILES: *c1ccc(Cl)cn1]
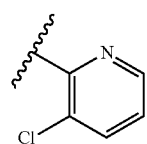 [SMILES: *c1ncccc1Cl]
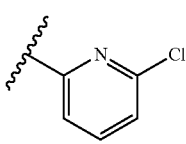 [SMILES: *c1cccc(Cl)n1]
TABLE 1-continued
Examples of group A$^1$.
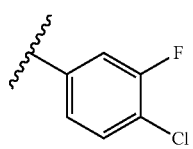 [SMILES: *c1ccc(Cl)c(F)c1]
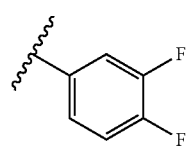 [SMILES: *c1ccc(F)c(F)c1]
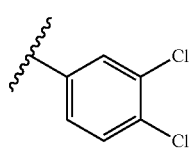
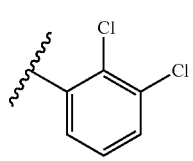 [SMILES: *c1cccc(Cl)c1Cl]
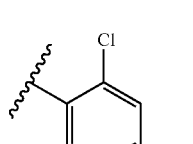
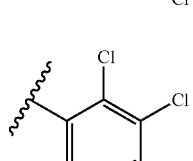
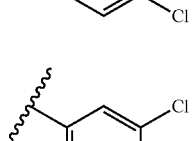
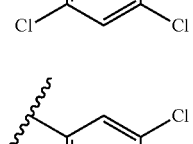
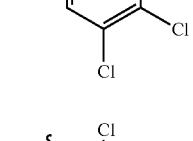
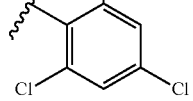

TABLE 1-continued
Examples of group A¹.
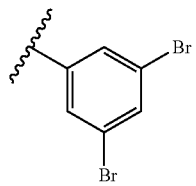 [SMILES: *c1cc(Br)cc(Br)c1]
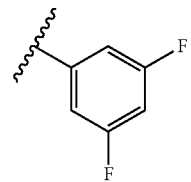 [SMILES: *c1cc(F)cc(F)c1]
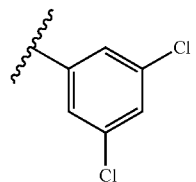 [SMILES: *c1cc(Cl)cc(Cl)c1]
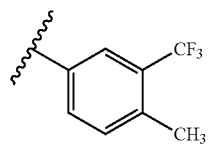
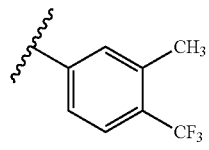
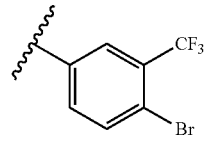 [SMILES: *c1ccc(Br)c(C(F)(F)F)c1]
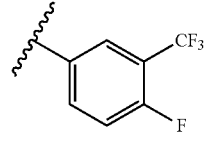 [SMILES: *c1ccc(F)c(C(F)(F)F)c1]
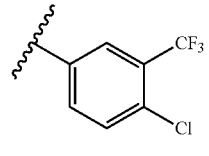
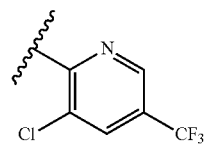
TABLE 1-continued
Examples of group A¹.
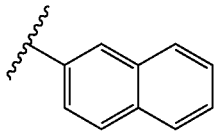
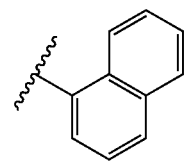 [SMILES: *c1cccc2ccccc12]
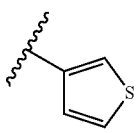 [SMILES: *c1ccsc1]
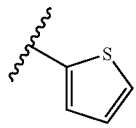 [SMILES: *c1cccs1]
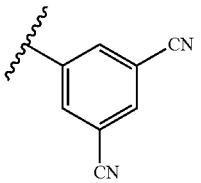 [SMILES: *c1cc(C#N)cc(C#N)c1]
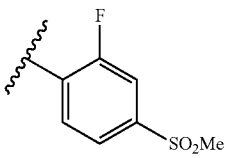 [SMILES: *c1ccc(S(C)(=O)=O)cc1F]
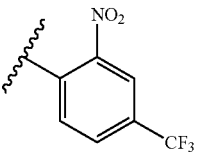 [SMILES: *c1ccc(C(F)(F)F)cc1[N+](=O)[O-]]
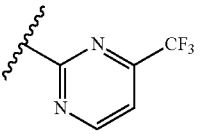 [SMILES: *c1nccc(C(F)(F)F)n1]
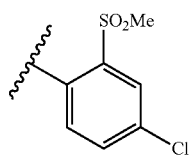 [SMILES: *c1ccc(Cl)cc1S(C)(=O)=O]
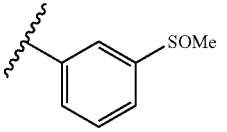

TABLE 1-continued
Examples of group A¹.
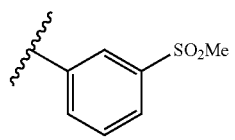 [SMILES: *c1cccc(S(C)(=O)=O)c1]
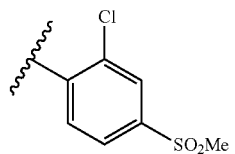 [SMILES: *c1ccc(S(C)(=O)=O)cc1Cl]
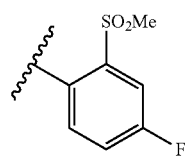 [SMILES: *c1ccc(F)cc1S(C)(=O)=O]
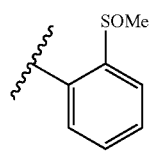
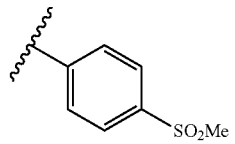
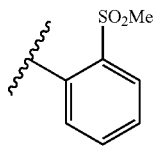
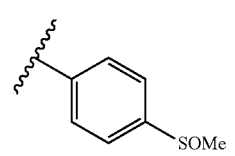
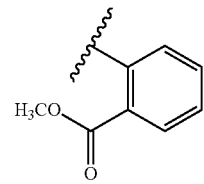 [SMILES: *c1ccccc1C(=O)OC]
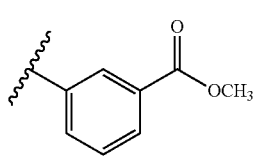 [SMILES: *c1cccc(C(=O)OC)c1]
TABLE 1-continued
Examples of group A¹.
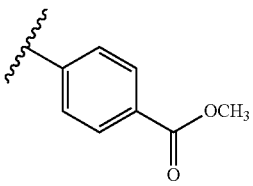 [SMILES: *c1ccc(C(=O)OC)cc1]
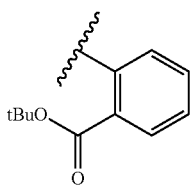 [SMILES: *c1ccccc1C(=O)OC(C)(C)C]
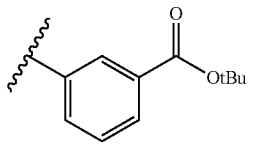 [SMILES: *c1cccc(C(=O)OC(C)(C)C)c1]
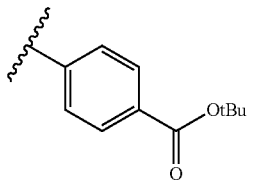 [SMILES: *c1ccc(C(=O)OC(C)(C)C)cc1]
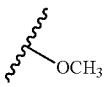
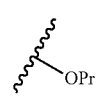
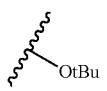
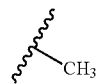
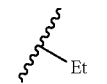
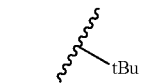
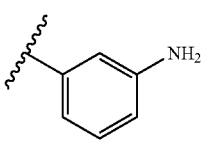 [SMILES: *c1cccc(N)c1]

TABLE 1-continued
Examples of group A[1].
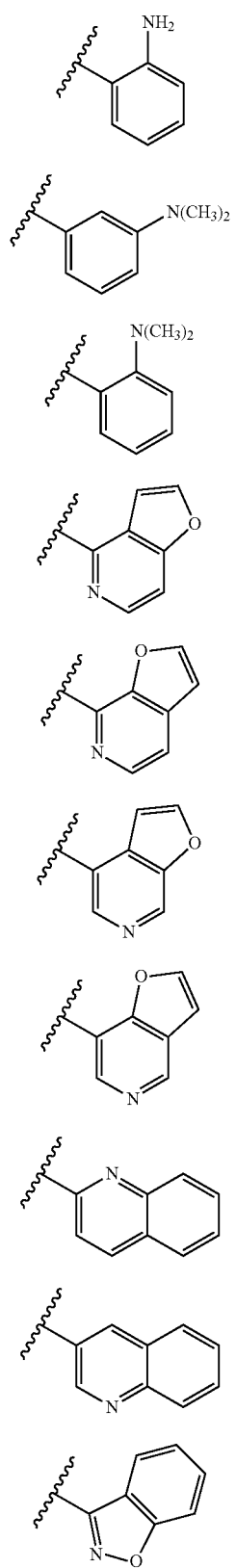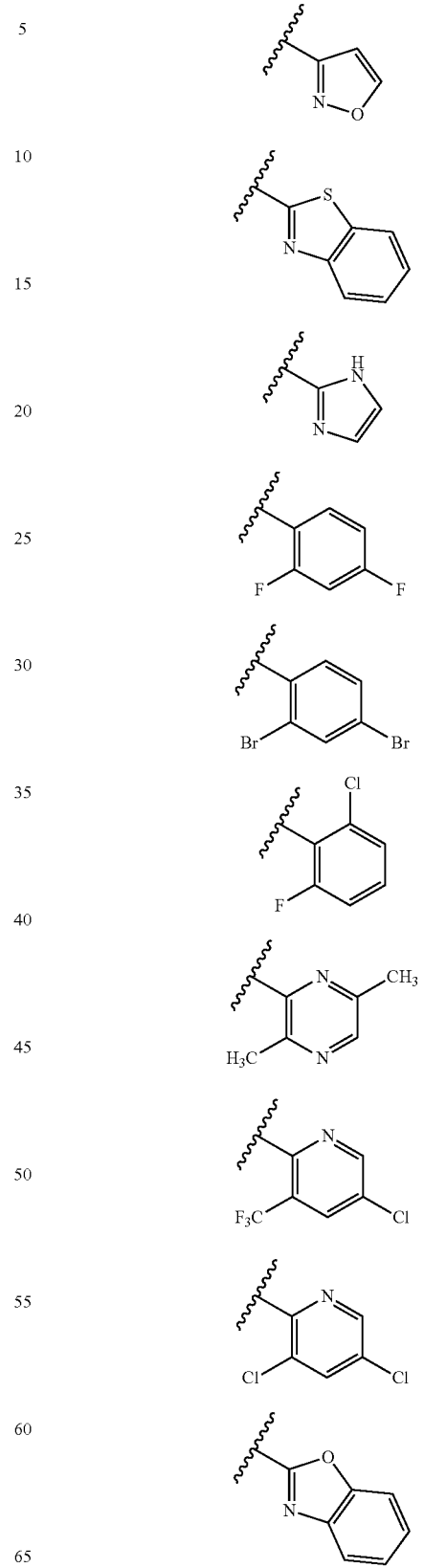

TABLE 1-continued
Examples of group A¹.
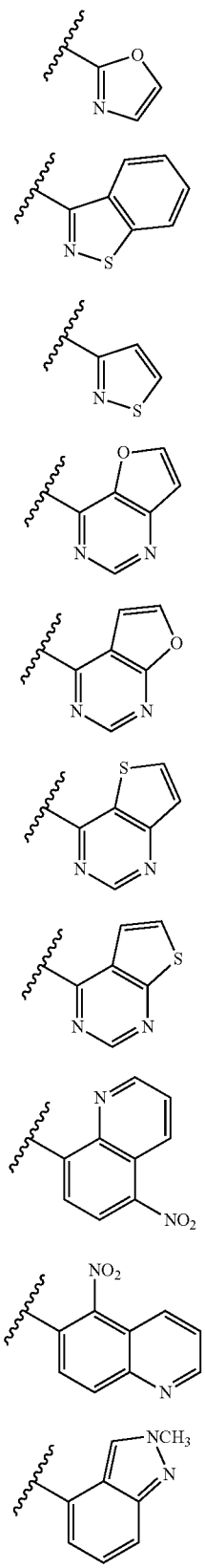
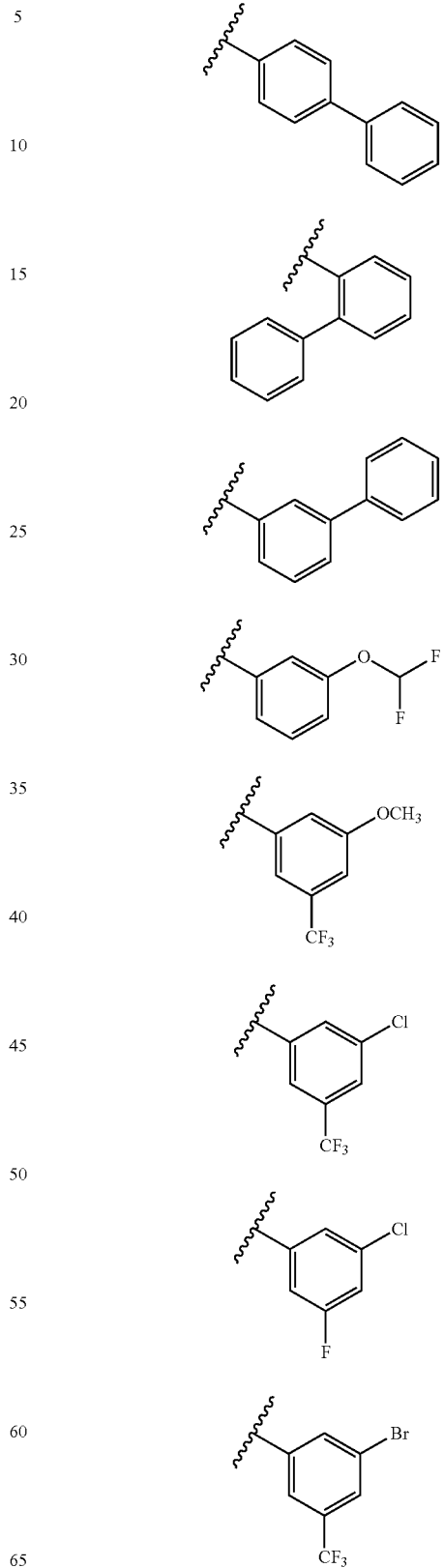

TABLE 1-continued
Examples of group A¹.
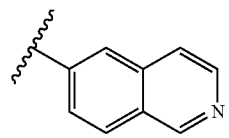 [SMILES: *c1ccc2cnccc2c1]
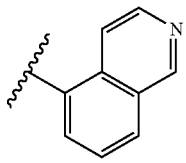 [SMILES: *c1cccc2cnccc12]
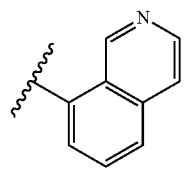 [SMILES: *c1cccc2ccncc12]
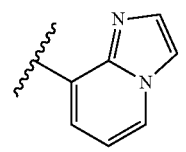
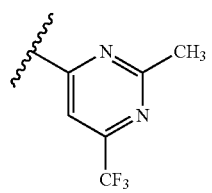 [SMILES: *c1cc(C(F)(F)F)nc(C)n1]
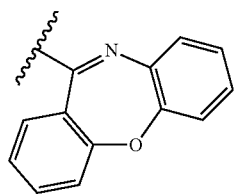 [SMILES: *C1=Nc2ccccc2Oc2ccccc21]
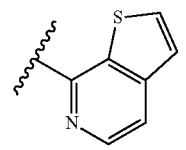 [SMILES: *c1nccc2ccsc12]
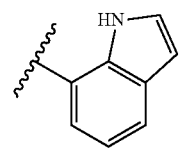 [SMILES: *c1cccc2cc[nH]c12]
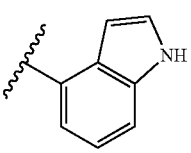 [SMILES: *c1cccc2[nH]ccc12]
TABLE 1-continued
Examples of group A¹.
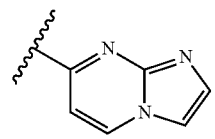 [SMILES: *c1ccn2ccnc2c1]
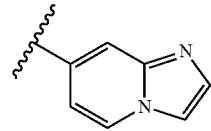 [SMILES: *c1ccn2ccnc2c1]
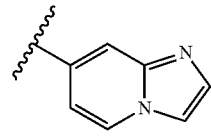
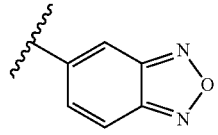
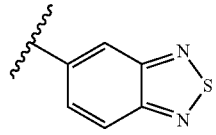 [SMILES: *c1ccc2nsnc2c1]
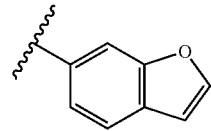
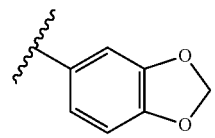 [SMILES: *c1ccc2c(c1)OCO2]
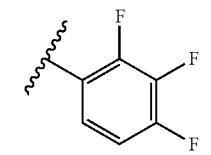 [SMILES: *c1ccc(F)c(F)c1F]
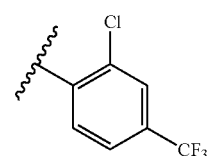
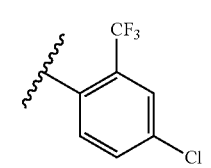 [SMILES: *c1ccc(Cl)cc1C(F)(F)F]

TABLE 1-continued

Examples of group $A^1$.

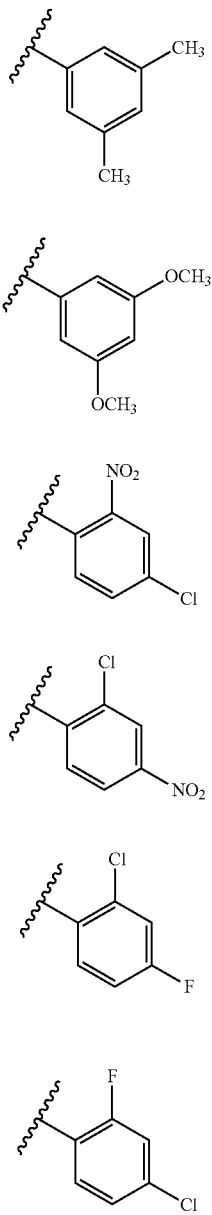

In another aspect, the present invention provides compounds of Formula (II):

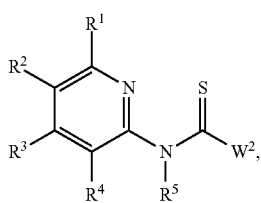

or pharmaceutically acceptable salts, solvates, hydrates, polymorphs, co-crystals, tautomers, stereoisomers, isotopically labeled derivatives, pro-drugs, and pharmaceutical compositions thereof, wherein:

$W^2$ is of formula:

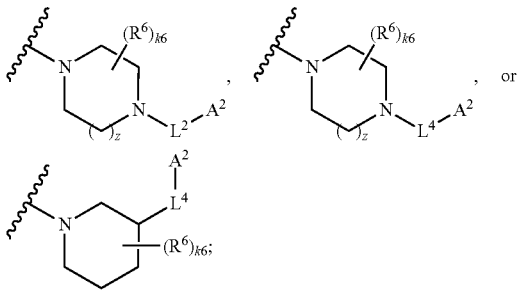

$L^2$ is optionally substituted alkylene, optionally substituted alkenylene, optionally substituted alkynylene, —C(═O)—, —C(═O)O—, —C(═O)NR$^a$—, —S(═O)—, —S(═O)O—, —S(═O)NR$^a$—, —S(═O)$_2$—, —S(═O)$_2$O—, or —S(═O)$_2$NR$^a$—;

$L^4$ is an optionally substituted alkylene, optionally substituted alkenylene, optionally substituted alkynylene, —NR$^a$—, —O—, —S—, —C(═O)—, —C(═O)O—, —C(═O)NR$^a$—, —OC(═O)—, —NR$^a$C(═O)—, —OC(═O)O—, —NR$^a$C(═O)NR$^a$—, —NR$^a$C(═O)O—, —OC(═O)NR$^a$, —S(═O)—, —S(═O)O—, —S(═O)NR$^a$—, —O(S═O)—, —NR$^a$S(═O)—, —S(═O)$_2$—, —S(═O)$_2$O—, —S(═O)$_2$NR$^a$—, —OS(═O)$_2$—, or —NR$^a$S(═O)$_2$—;

$A^2$ is optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^1$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —SCN, —NCS, —N$_3$, —NO$_2$, —OR$^b$, —NR$^c$R$^d$, —NR$^c$(OR$^b$), —SR$^e$, —SSR$^e$, —C(═O)R$^f$, —C(═O)OR$^b$, —C(═O)NR$^c$R$^d$, —C(═NR$^c$)R$^f$, —C(═NR$^c$)OR$^b$, —C(═NR$^c$)NR$^c$R$^d$, —OC(═O)R$^f$, —OC(═O)OR$^b$, —OC(═O)NR$^c$R$^d$, —OC(═NR$^c$)R$^f$, —OC(═NR$^c$)OR$^b$, —OC(═NR$^c$)NR$^c$R$^d$, —NR$^c$C(═O)R$^f$, —NR$^e$C(═O)OR$^b$, —NR$^c$C(═O)NR$^c$R$^d$, —NR$^c$C(═NR$^c$)R$^f$, —NR$^c$C(═NR$^e$)OR$^b$, —NR$^c$C(═NR$^c$)NR$^c$R$^d$, —C(═S)R$^f$, —C(═S)OR$^b$, —C(═O)SR$^e$, —C(═S)NR$^c$R$^d$, —NR$^c$C(═S)NR$^c$R$^d$, —Si(R$^f$)$_3$, —OSi(R$^f$)$_3$, —S(═O)R$^f$, —S(═O)OR$^b$, —S(═O)NR$^c$R$^d$, —S(═O)$_2$R$^f$, —S(═O)$_2$OR$^b$, or —S(═O)$_2$NR$^c$R$^d$;

$R^2$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —SCN, —NCS, —N$_3$, —NO$_2$, —OR$^b$, —NR$^c$R$^d$, —NR$^c$(OR$^b$), —SR$^e$, —SSR$^e$, —C(═O)R$^f$, —C(═O)OR$^b$, —C(═O)NR$^c$R$^d$, —C(═NR$^c$)R$^f$, —C(═NR$^c$)OR$^b$, —C(═NR$^c$)NR$^c$R$^d$, —OC(═O)R$^f$, —OC(═O)OR$^b$, —OC(═O)NR$^c$R$^d$, —OC(═NR$^c$)R$^f$, —OC(═NR$^c$)OR$^b$, —OC(═NR$^c$)NR$^c$R$^d$, —NR$^c$C(═O)R$^f$, —NR$^e$C (=O)OR$^b$, —NR$^c$C(=O)NR$^c$R$^d$, —NR$^c$C(=NR$^e$)R$^f$, —NR$^c$C(=NR$^e$)OR$^b$, —NR$^e$C(=NR$^e$)NR$^c$R$^d$, —C(=S)R$^f$, —C(=S)OR$^b$, —C(=O)SR$^e$, —C(=S)NR$^c$R$^d$, —NR$^c$C(=S)NR$^c$R$^d$, —Si(R$^f$)$_3$, —OSi(R$^f$)$_3$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

R$^3$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —SCN, —NCS, —N$_3$, —NO$_2$, —OR$^b$, —NR$^c$R$^d$, —NR$^c$(OR$^b$), —SR$^e$, —SSR$^e$, —C(=O)R$^f$, —C(=O)OR$^b$, —C(=O)NR$^c$R$^d$, —C(=NR$^e$)R$^f$, —C(=NR$^e$)OR$^b$, —C(=NR$^e$)NR$^c$R$^d$, —OC(=O)R$^f$, —OC(=O)OR$^b$, —OC(=O)NR$^c$R$^d$, —OC(=NR$^e$)R$^f$, —OC(=NR$^e$)OR$^b$, —OC(=NR$^e$)NR$^c$R$^d$, —NR$^c$C(=O)R$^f$, —NR$^c$C(=O)OR$^b$, —NR$^c$C(=O)NR$^c$R$^d$, —NR$^c$C(=NR$^e$)R$^f$, —NR$^c$C(=NR$^e$)OR$^b$, —NR$^c$C(=NR$^e$)NR$^c$R$^d$, —C(=S)R$^f$, —C(=S)OR$^b$, —C(=O)SR$^e$, —C(=S)NR$^c$R$^d$, —NR$^c$C(=S)NR$^c$R$^d$, —Si(R$^f$)$_3$, —OSi(R$^f$)$_3$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

R$^4$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —SCN, —NCS, —N$_3$, —NO$_2$, —OR$^b$, —NR$^c$R$^d$, —NR$^c$(OR$^b$), —SR$^e$, —SSR$^e$, —C(=O)R$^f$, —C(=O)OR$^b$, —C(=O)NR$^c$R$^d$, —C(=NR$^e$)R$^f$, —C(=NR$^e$)OR$^b$, —C(=NR$^e$)NR$^c$R$^d$, —OC(=O)R$^f$, —OC(=O)OR$^b$, —OC(=O)NR$^c$R$^d$, —OC(=NR$^e$)R$^f$, —OC(=NR$^e$)OR$^b$, —OC(=NR$^e$)NR$^c$R$^d$, —NR$^c$C(=O)R$^f$, —NR$^c$C(=O)OR$^b$, —NR$^c$C(=O)NR$^c$R$^d$, —NR$^c$C(=NR$^e$)R$^f$, —NR$^c$C(=NR$^e$)OR$^b$, —NR$^c$C(=NR$^e$)NR$^c$R$^d$, —C(=S)R$^f$, —C(=S)OR$^b$, —C(=O)SR$^e$, —C(=S)NR$^c$R$^d$, —NR$^c$C(=S)NR$^c$R$^d$, —Si(R$^f$)$_3$, —OSi(R$^f$)$_3$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

R$^5$ is hydrogen, optionally substituted C$_1$-C$_6$ alkyl, or a nitrogen protecting group;

each R$^6$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^b$, —NR$^c$R$^d$, —SR$^e$, —C(=O)R$^f$, —C(=O)OR$^b$, or —C(=O)NR$^c$R$^d$;

each R$^a$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each R$^b$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each of R$^c$ and R$^d$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or R$^c$ and R$^d$ are joined to form an optionally substituted heterocyclic or optionally substituted heteroaryl ring;

each R$^e$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a sulfur protecting group;

each R$^f$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

k6 is 0, 1,2,3, or 4; and z is 1 or 2;

provided:

A$^2$ is not substituted or unsubstituted pyridazinyl, and the compound is not:

N-(4,6-dimethylpyridin-2-yl)-4-(3-(trifluoromethyl)benzyl)piperazine-1-carbothioamide;

N-(4-methylpyridin-2-yl)-4-((3-(trifluoromethyl)phenyl)amino)piperidine-1-carbothioamide;

N-(4,6-dimethylpyridin-2-yl)-4-(3-(trifluoromethyl)phenyl)sulfonyl)piperazine-1-carbothioamide; or N-(pyridin-2-yl)-4-(tert-butoxycarbonyl)piperazine-1-carbothioamide.

In certain embodiments, the invention provides compounds of Formula (II) or pharmaceutically acceptable salts thereof. In certain embodiments, the invention provides compounds of Formula (II) or pharmaceutically acceptable salts thereof, or pharmaceutical compositions thereof.

Compounds not included in Formula (II) are:

N-(4,6-dimethylpyridin-2-yl)-4-(3-(trifluoromethyl)benzyl)piperazine-1-carbothioamide:

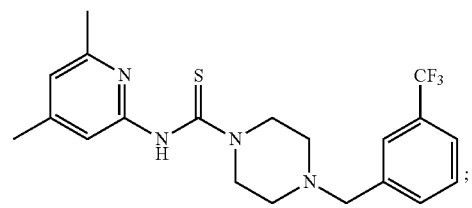 [SMILES: Cc1cc(C)nc(NC(=S)N2CCN(Cc3cccc(C(F)(F)F)c3)CC2)c1]

N-(4-methylpyridin-2-yl)-4-((3-(trifluoromethyl)phenyl)amino)piperidine-1-carbothioamide,

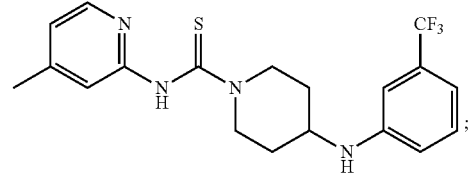 [SMILES: Cc1ccnc(NC(=S)N2CCC(Nc3cccc(C(F)(F)F)c3)CC2)c1]

N-(4,6-dimethylpyridin-2-yl)-4-(3-(trifluoromethyl)phenyl) sulfonyl)piperazine-1-carbothioamide:

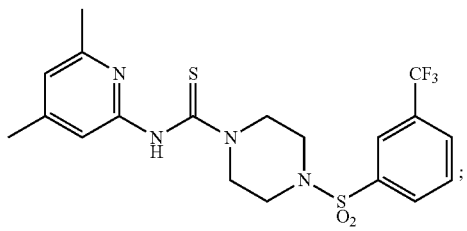 [SMILES: Cc1cc(C)nc(NC(=S)N2CCN(S(=O)(=O)c3cccc(C(F)(F)F)c3)CC2)c1]

N-(pyridin-2-yl)-4-(?err-butoxycarbonyl)piperazine-1-carbothioamide:

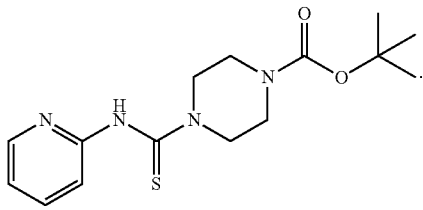 [SMILES: CC(C)(C)OC(=O)N1CCN(C(=S)Nc2ccccn2)CC1]

Compounds of Formula (II) do not include compounds, wherein $A^2$ is an optionally substituted ring of formula:

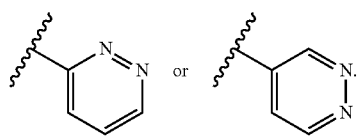 [SMILES: *c1cccnn1 ; *c1ccnnc1]

In certain embodiments, the compound of Formula (II) is of Formula (II-A):

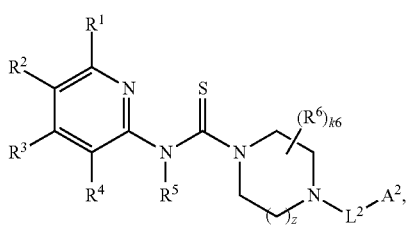

wherein $L^2$, $A^2$, $R^1$-$R^6$, $R^a$-$R^f$, k6, and z are as defined for compounds of Formula (II).

In certain embodiments, the compound of Formula (II) is of Formula (II-B):

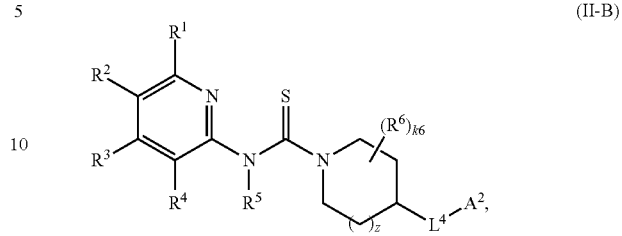

wherein $L^4$, $A^2$, $R^1$-$R^6$, $R^a$-$R^f$, k6, and z are as defined for compounds of Formula (II)

In certain embodiments, the compound of Formula (II) is of Formula (II-C):

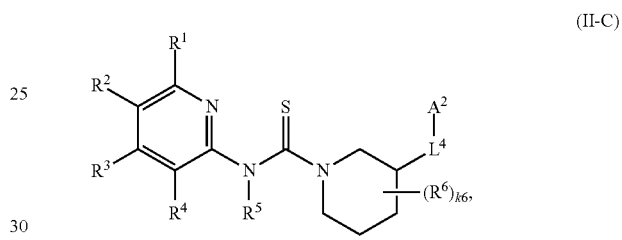

wherein $L^4$, $A^2$, $R^1$-$R^6$, $R^a$-$R^f$, k6, and z are as defined for compounds of Formula (II).

In another aspect, the compound of Formula (II) is of Formula (II'):

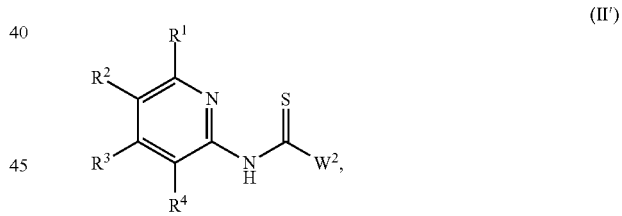

wherein:

$W^2$ is:

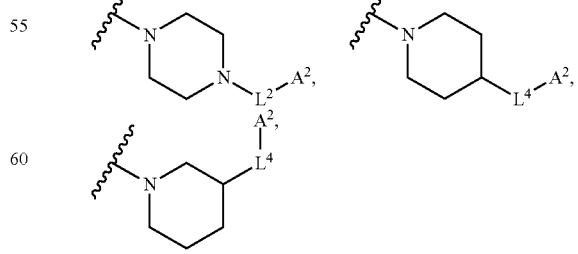

and $L^2$, $A^2$, $R^1$-$R^4$, and $R^a$-$R^f$ are as defined for compounds of Formula (II).

In certain embodiments, the compound of Formula (II') is of Formula (II'-A):

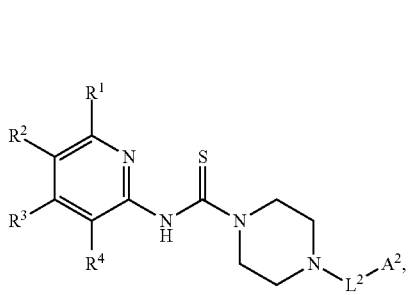

(II'-A)

wherein L², A², R¹-R⁴, and Rᵃ-Rᶠ are as defined for compounds of Formula (II).

In certain embodiments, the compound of Formula (II') is of Formula (II'-B):

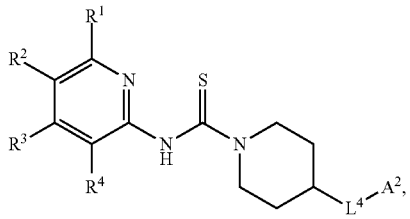

(II'-B)

wherein L⁴, A², R¹-R⁴, and Rᵃ-Rᶠ are as defined for compounds of Formula (II).

In certain embodiments, the compound of Formula (II') is of Formula (II'-C):

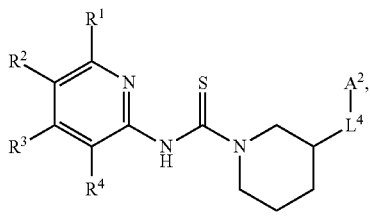

(II'-C)

wherein L⁴, A², R¹-R⁴, and Rᵃ-Rᶠ are as defined for compounds of Formula (II).

Compounds of Formula (I) include group W². In certain embodiments, W² is of formula:

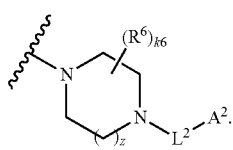

In certain embodiments, W² is of formula:

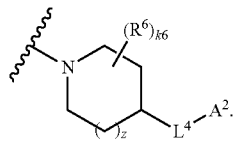

certain embodiments, W² is of formula:

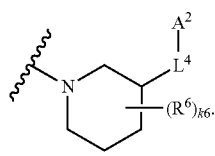

In certain embodiments, W is of formula:

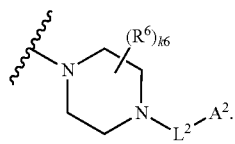

In certain embodiments, W² is of formula:

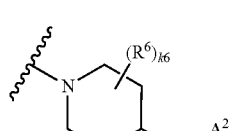

In certain embodiments, W² is of formula:

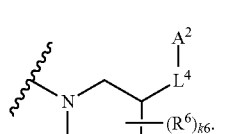

In certain embodiments, W² is of formula:

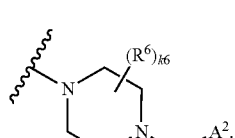

In certain embodiments, W² is of formula:

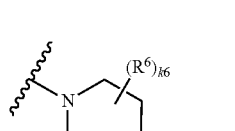

In certain embodiments, W² is of formula:

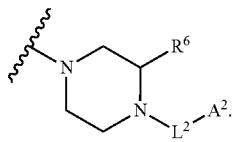

In certain embodiments, W² is of formula:

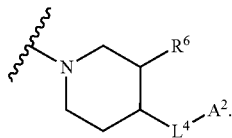

In certain embodiments, W² is of formula:

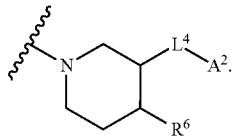

In certain embodiments, W² is of formula:

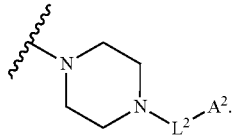

In certain embodiments, W² is of formula:

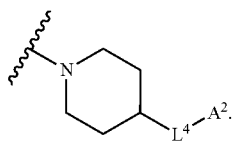

In certain embodiments, W² is of formula:

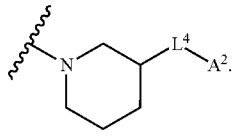

In certain embodiments, W² is of formula:

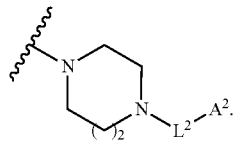

In certain embodiments, W² is of formula:

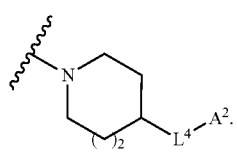

Compounds of Formula (II) include linker $L^2$. In certain embodiments, $L^2$ is optionally substituted alkylene, —C(=O)—, —C(=O)O—, or —C(=O)NR$^a$—. In certain embodiments, $L^2$ is optionally substituted alkylene. In certain embodiments, $L^2$ is optionally substituted $C_1$-$C_6$ alkylene. In certain embodiments, $L^2$ is alkylene. In certain embodiments, $L^2$ is $C_1$-$C_6$ alkylene. In certain embodiments, $L^2$ is methylene. In certain embodiments, $L^2$ is ethylene. In certain embodiments, $L^2$ is propylene. In certain embodiments, $L^2$ is butylene. In certain embodiments, $L^2$ is optionally substituted alkenylene. In certain embodiments, $L^2$ is optionally substituted alkynylene.

In certain embodiments, $L^2$ is —C(=O)—. In certain embodiments, $L^2$ is —C(=O)O—. In certain embodiments, $L^2$ is —C(=O)NR$^a$—. In certain embodiments, $L^2$ is —S(=O)—. In certain embodiments, $L^2$ is —S(=O)O—. In certain embodiments, $L^2$ is —S(=O)NR$^a$—. In certain embodiments, $L^2$ is —S(=O)$_2$—. In certain embodiments, $L^2$ is —S(=O)$_2$O—. In certain embodiments, $L^2$ is —S(=O)$_2$NR$^a$—. In certain embodiments, $L^2$ is —C(=O)NH—. In certain embodiments, $L^2$ is —S(=O)NH—. In certain embodiments, $L^2$ is —S(=O)$_2$NH—.

Compounds of Formula (II) include linker $L^4$. In certain embodiments, $L^4$ is optionally substituted alkylene, —NR$^a$—, —O—, —S—, —C(=O)—, —C(=O)O—, —C(=O)NR$^a$—, —OC(=O)—, or —NR$^a$C(=O)—. In certain embodiments, $L^4$ is optionally substituted alkylene. In certain embodiments, $L^4$ is optionally substituted $C_1$-$C_6$ alkylene. In certain embodiments, $L^4$ is alkylene. In certain embodiments, $L^4$ is $C_1$-$C_6$ alkylene. In certain embodiments, L is methylene. In certain embodiments, $L^4$ is ethylene. In certain embodiments, L is propylene. In certain embodiments, $L^4$ is butylene. In certain embodiments, L is optionally substituted alkenylene. In certain embodiments, $L^4$ is optionally substituted alkynylene.

In certain embodiments, $L^4$ is —NR$^a$—. In certain embodiments, $L^4$ is —NH—. In certain embodiments, $L^4$ is —O—. In certain embodiments, $L^4$ is —S—. In certain embodiments, $L^4$ is —C(=O)—. In certain embodiments, $L^4$ is —C(=O)O—. In certain embodiments, $L^4$ is —C(=O)NR$^a$—. In certain embodiments, $L^4$ is —OC(=O)—. In certain embodiments, $L^4$ is —NR$^a$C(=O)—. In certain embodiments, $L^4$ is —OC(=O)—. In certain embodiments, L is —NR$^a$C(=O)NR$^a$—. In certain embodiments, $L^4$ is —NR$^a$C(=O)O—. In certain embodiments, $L^4$ is —OC(=O)NR$^a$—. In certain embodiments, $L^4$ is —S(=O)—. In certain embodiments, $L^4$ is —S(=O)O—.

In certain embodiments, $L^4$ is —S(=O)$NR^a$—. In certain embodiments, $L^4$ is —OS(=O)—. In certain embodiments, $L^4$ is —$NR^a$S(=O)—. In certain embodiments, $L^4$ is —S(=O)$_2$—. In certain embodiments, $L^4$ is —S(=O)$_2$O—. In certain embodiments, $L^4$ is —S(=O)$_2NR^a$—. In certain embodiments, $L^4$ is —OS(=O)$_2$—. In certain embodiments, $L^4$ is —$NR^a$S(=O)$_2$—. In certain embodiments, $L^4$ is —C(=O)NH—. In certain embodiments, $L^4$ is —S(=O)NH—. In certain embodiments, $L^4$ is —S(=O)$_2$NH—. In certain embodiments, $L^4$ is —NHC(=O)—. In certain embodiments, $L^4$ is —NHS(=O)—. In certain embodiments, $L^4$ is —NHS(=O)$_2$—. In certain embodiments, $L^4$ is —OC(=O)NH—. In certain embodiments, $L^4$ is —NHC(=O)O—. In certain embodiments, $L^4$ is —NHC(=O)NH—.

Compounds of Formula (II) may contain one or more independent groups $R^A$ within certain embodiments of group $A^2$. In such embodiments, $A^2$ are rings of formula:

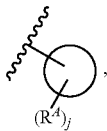

wherein the circle indicates a ring, and $R^A$ is an optional substituent. The ring may contain one or more heteroatoms at any position, heteroatoms are independently selected from N, O, and S, and may be monocyclic or polycyclic. Each $R^A$ is independently halogen, nitrile, nitro, optionally substituted alkyl, optionally substituted alkenyl, optionally substituted carbocyclyl, optionally substituted heterocyclyl, optionally substituted aryl, optionally substituted heteroaryl, —$OR^b$, —$NR^cR^d$, —$SR^e$, —C(=O)$R^f$, —C(=O)$OR^b$, —C(=O)$NR^cR^d$, —S(=O)$R^f$, —S(=O)$OR^b$, —S(=O)$NR^cR^d$, —S(=O)$_2R^f$, —S(=O)$_2OR^b$, or —S(=O)$_2NR^cR^d$. The number of independently selected substituents is defined by j, which may be 0, 1, 2, 3, 4, 5, 6, 7, or 8, contingent on ring size and available valency.

Compounds of Formula (II) include group $A^2$. In certain embodiments, $A^2$ is optionally substituted alkyl, optionally substituted carbocyclyl, optionally substituted heterocyclyl, optionally substituted aryl, or optionally substituted heteroaryl. In certain embodiments, $A^2$ is optionally substituted alkyl. In certain embodiments, $A^2$ is optionally substituted alkenyl. In certain embodiments, $A^2$ is optionally substituted alkynyl. In certain embodiments, $A^2$ is optionally substituted carbocyclyl. In certain embodiments, $A^2$ is optionally substituted heterocyclyl. In certain embodiments, $A^2$ is optionally substituted aryl. In certain embodiments, $A^2$ is optionally substituted heteroaryl.

In certain embodiments, $A^2$ is optionally substituted cyclohexyl. In certain embodiments, $A^2$ is optionally substituted piperidinyl. In certain embodiments, $A^2$ is optionally substituted piperizinyl. In certain embodiments, $A^2$ is optionally substituted morpholinyl. In certain embodiments, $A^2$ is of formula:

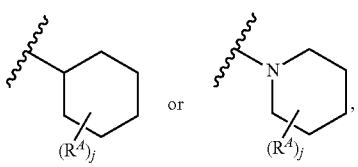

wherein j is 0.5 In certain embodiments, $A^2$ is of formula:

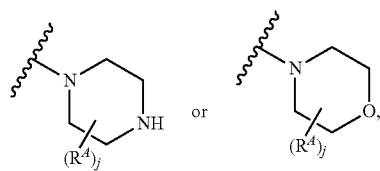

wherein j is 0-4.

In certain embodiments, is optionally substituted pyrimidinyl. In certain embodiments, $A^2$ is optionally substituted pyrazinyl. In certain embodiments, $A^2$ is of formula:

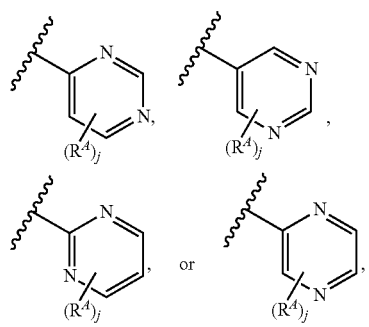

wherein j is 0-3. In certain embodiments, $A^2$ is optionally substituted pyridinyl. In certain embodiments, $A^2$ is of formula:

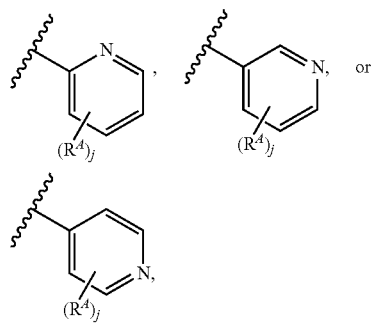

wherein j is 0-4. In certain embodiments, $A^2$ is of formula:

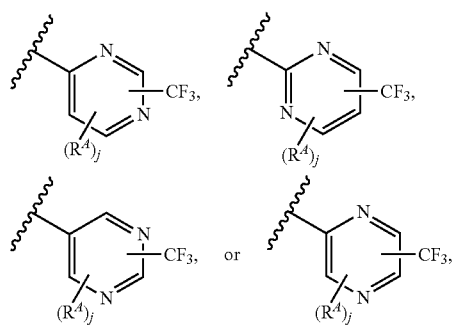

wherein j is 0-2. In certain embodiments, A² is of formula:

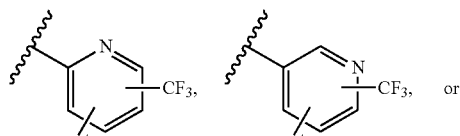

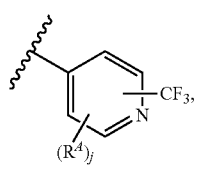

In certain embodiments, A² is optionally substituted phenyl. In certain embodiments, A² is of formula:

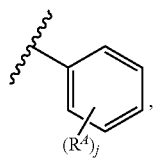

wherein j is 0-5. In certain embodiments, A² is of formula:

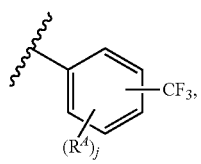

wherein j is 0-4. In certain embodiments. A² is of formula:

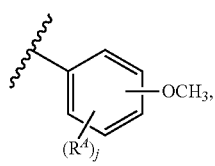

wherein j is 0-4. In certain embodiments, A² is of formula:

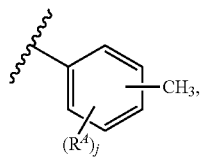

wherein j is 0-4.

In certain embodiments, group A² is selected from a group listed in Table 2.

TABLE 2

Examples of group A².

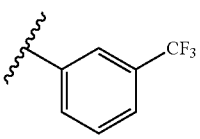

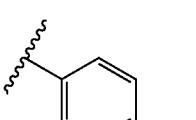

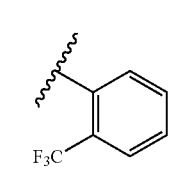

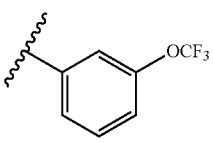 [SMILES: *c1cccc(OC(F)(F)F)c1]

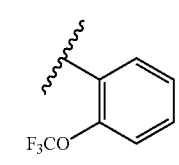

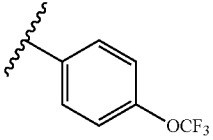

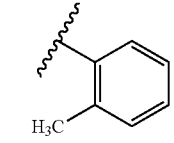 [SMILES: *c1ccccc1C]

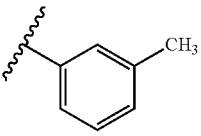 [SMILES: *c1cccc(C)c1]

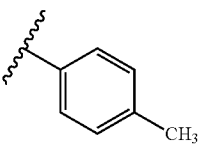

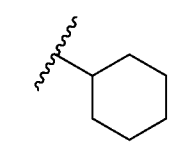 [SMILES: *C1CCCCC1]

TABLE 2-continued
Examples of group $A^2$.
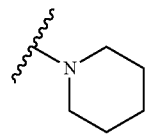 [SMILES: *N1CCCCC1]
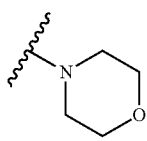
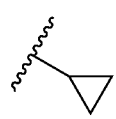
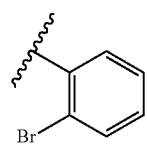
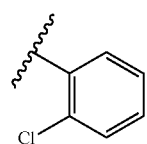 [SMILES: *c1ccccc1Cl]
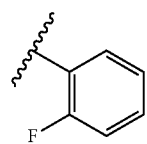 [SMILES: *c1ccccc1F]
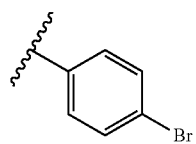 [SMILES: *c1ccc(Br)cc1]
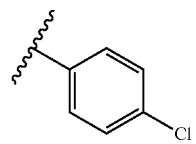 [SMILES: *c1ccc(Cl)cc1]
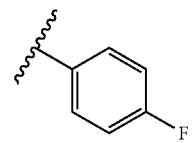 [SMILES: *c1ccc(F)cc1]
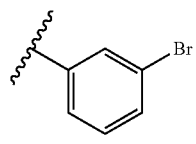 [SMILES: *c1cccc(Br)c1]
TABLE 2-continued
Examples of group $A^2$.
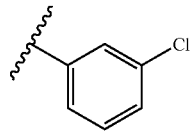
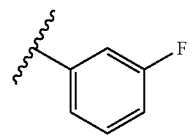
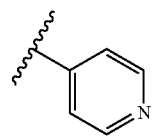 [SMILES: *c1ccncc1]
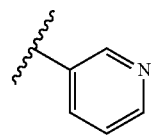 [SMILES: *c1cccnc1]
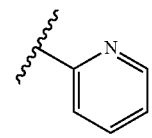
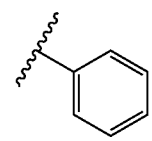 [SMILES: *c1ccccc1]
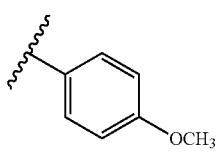 [SMILES: *c1ccc(OC)cc1]
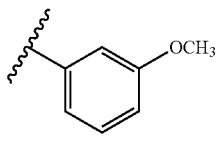 [SMILES: *c1cccc(OC)c1]
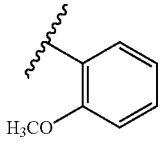
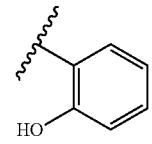 [SMILES: *c1ccccc1O]

TABLE 2-continued
Examples of group A².
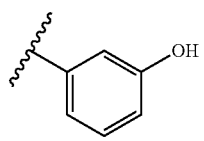 [SMILES: *c1cccc(O)c1]
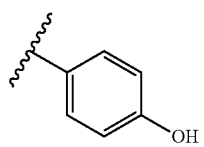 [SMILES: *c1ccc(O)cc1]
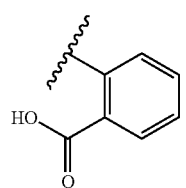
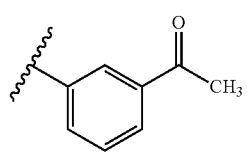 [SMILES: *c1cccc(C(C)=O)c1]
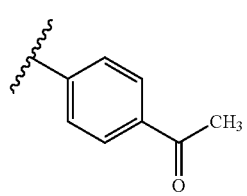 [SMILES: *c1ccc(C(C)=O)cc1]
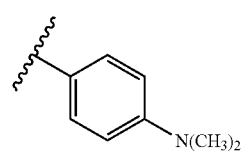
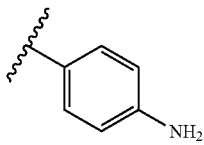
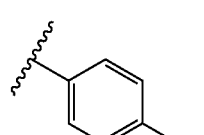
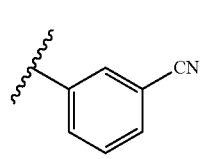 [SMILES: *c1cccc(C#N)c1]
TABLE 2-continued
Examples of group A².
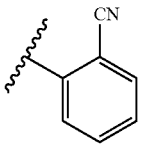 [SMILES: *c1ccccc1C#N]
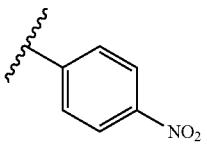 [SMILES: *c1ccc([N+](=O)[O-])cc1]
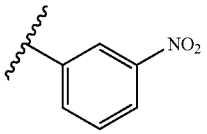 [SMILES: *c1cccc([N+](=O)[O-])c1]
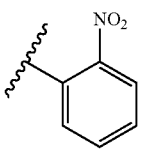 [SMILES: *c1ccccc1[N+](=O)[O-]]
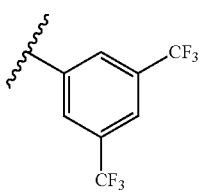 [SMILES: *c1cc(C(F)(F)F)cc(C(F)(F)F)c1]
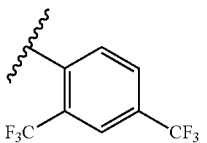
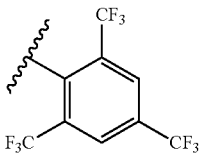
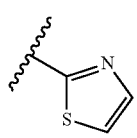 [SMILES: *c1nccs1]
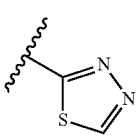 [SMILES: *c1nncs1]
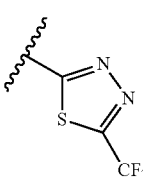

TABLE 2-continued
Examples of group A².
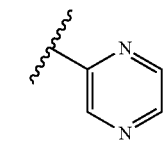
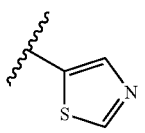
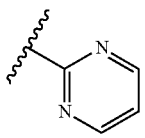 [SMILES: *c1ncccn1]
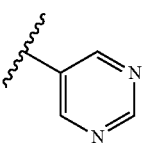
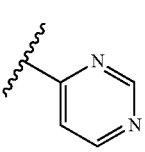 [SMILES: *c1ccncn1]
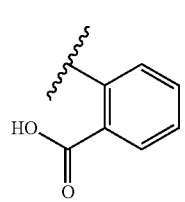 [SMILES: *c1ccccc1C(=O)O]
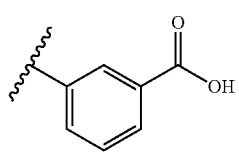 [SMILES: *c1cccc(C(=O)O)c1]
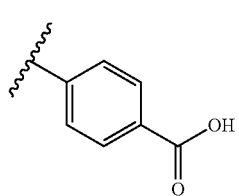 [SMILES: *c1ccc(C(=O)O)cc1]
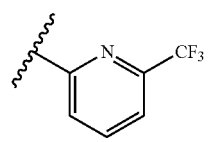 [SMILES: *c1cccc(C(F)(F)F)n1]
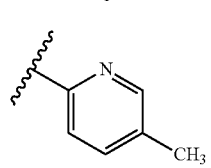
TABLE 2-continued
Examples of group A².
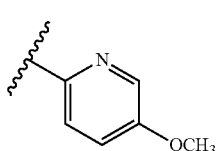
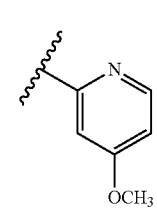 [SMILES: *c1cc(OC)ccn1]
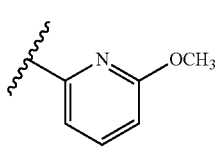 [SMILES: *c1cccc(OC)n1]
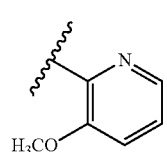
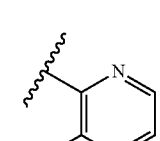
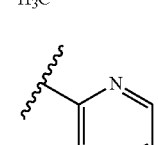
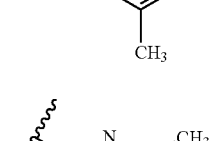
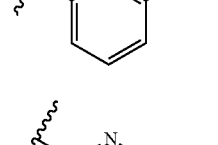
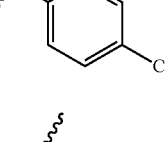
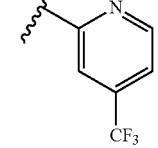

TABLE 2-continued
Examples of group A².
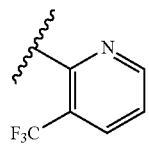
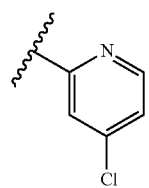 [SMILES: *c1cc(Cl)ccn1]
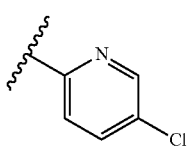 [SMILES: *c1ccc(Cl)cn1]
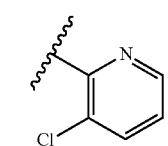
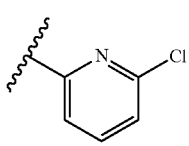 [SMILES: *c1cccc(Cl)n1]
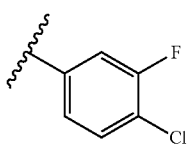 [SMILES: *c1ccc(Cl)c(F)c1]
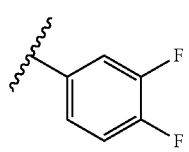 [SMILES: *c1ccc(F)c(F)c1]
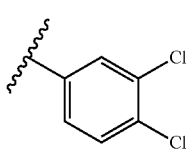 [SMILES: *c1ccc(Cl)c(Cl)c1]
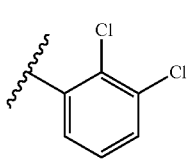 [SMILES: *c1cccc(Cl)c1Cl]
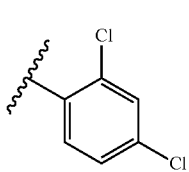 [SMILES: *c1ccc(Cl)cc1Cl]
TABLE 2-continued
Examples of group A².
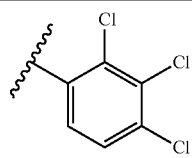
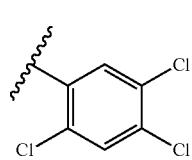 [SMILES: *c1cc(Cl)c(Cl)cc1Cl]
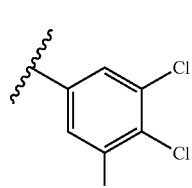
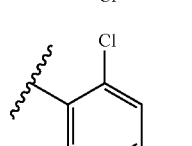
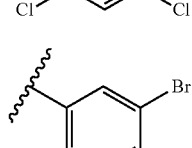
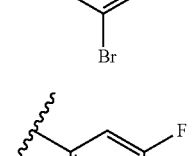
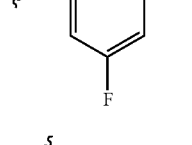
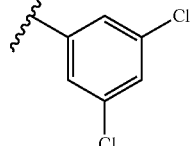
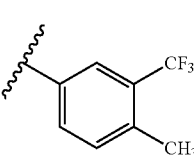
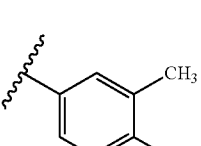

TABLE 2-continued
Examples of group $A^2$.
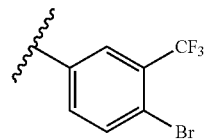
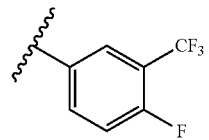
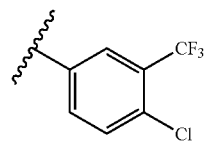 [SMILES: *c1ccc(Cl)c(C(F)(F)F)c1]
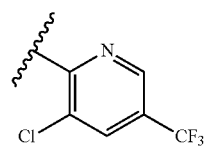
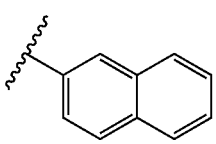 [SMILES: *c1ccc2ccccc2c1]
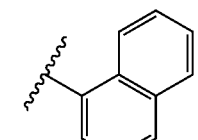
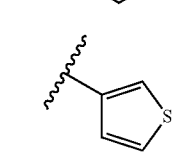
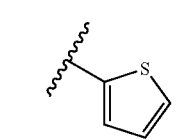 [SMILES: *c1cccs1]
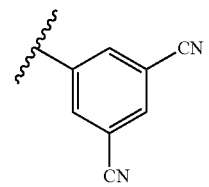 [SMILES: *c1cc(C#N)cc(C#N)c1]
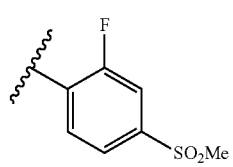 [SMILES: *c1ccc(S(C)(=O)=O)cc1F]
TABLE 2-continued
Examples of group $A^2$.
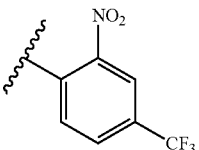
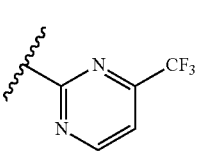
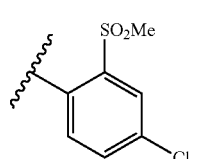
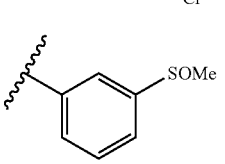
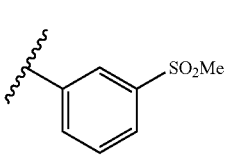 [SMILES: *c1cccc(S(C)(=O)=O)c1]
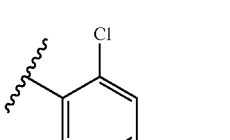
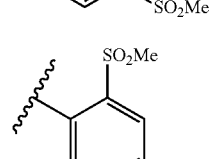
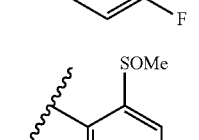
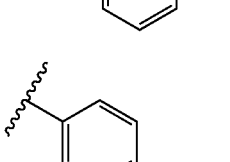
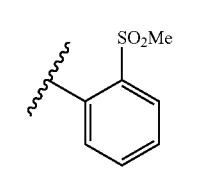 [SMILES: *c1ccccc1S(C)(=O)=O]

TABLE 2-continued
Examples of group A².
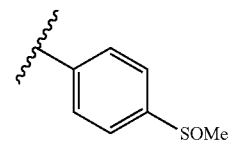
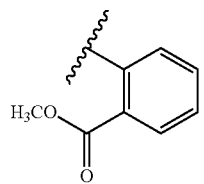 [SMILES: *c1ccccc1C(=O)OC]
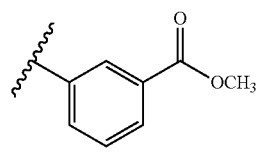 [SMILES: *c1cccc(C(=O)OC)c1]
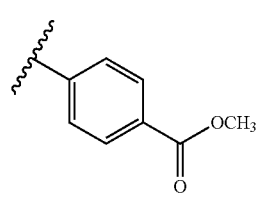 [SMILES: *c1ccc(C(=O)OC)cc1]
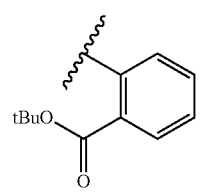 [SMILES: *c1ccccc1C(=O)OC(C)(C)C]
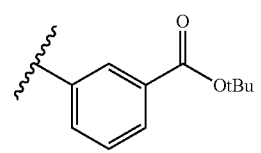 [SMILES: *c1cccc(C(=O)OC(C)(C)C)c1]
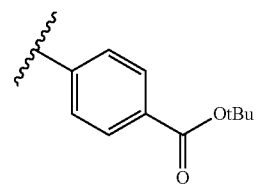 [SMILES: *c1ccc(C(=O)OC(C)(C)C)cc1]
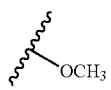
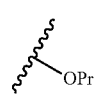
TABLE 2-continued
Examples of group A².
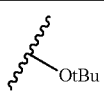
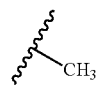
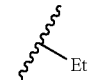
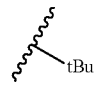
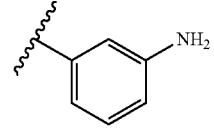 [SMILES: *c1cccc(N)c1]
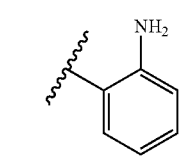 [SMILES: *c1ccccc1N]
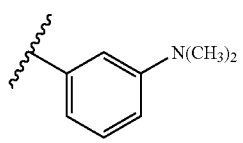 [SMILES: *c1cccc(N(C)C)c1]
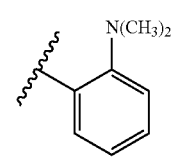 [SMILES: *c1ccccc1N(C)C]
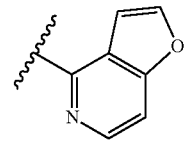
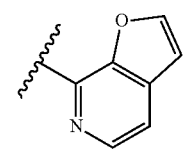
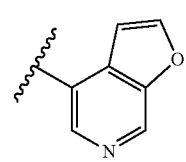

TABLE 2-continued
Examples of group A².
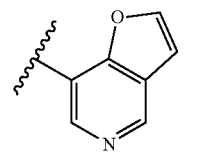 [SMILES: *c1cncc2ccoc12]
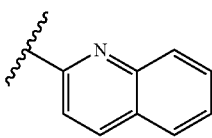 [SMILES: *c1ccc2ccccc2n1]
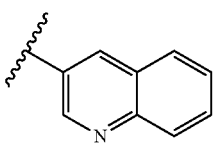 [SMILES: *c1cnc2ccccc2c1]
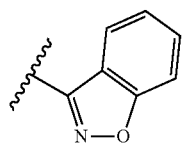 [SMILES: *c1noc2ccccc12]
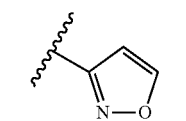 [SMILES: *c1ccon1]
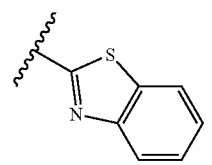 [SMILES: *c1nc2ccccc2s1]
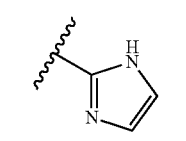
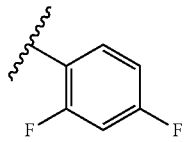 [SMILES: *c1ccc(F)cc1F]
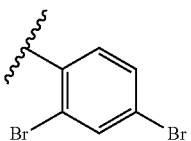 [SMILES: *c1ccc(Br)cc1Br]
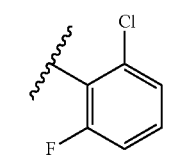 [SMILES: *c1c(F)cccc1Cl]
TABLE 2-continued
Examples of group A².
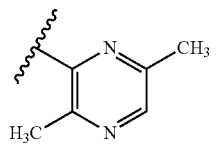
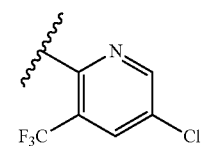
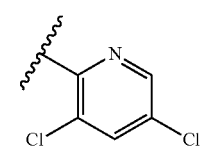
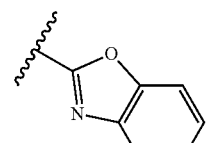
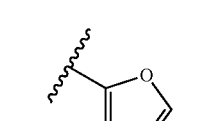
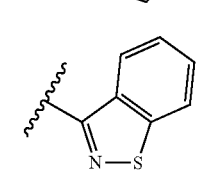
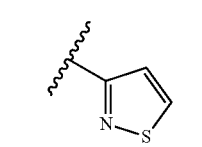 [SMILES: *c1ccsn1]
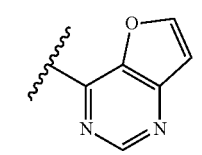 [SMILES: *c1ncnc2ccoc12]
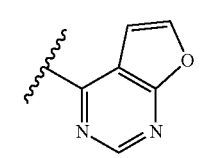
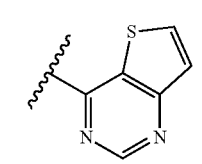 [SMILES: *c1ncnc2ccsc12]

TABLE 2-continued
Examples of group A².
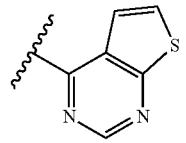 [SMILES: *c1ncnc2sccc12]
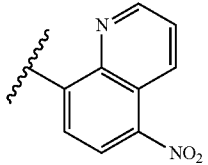 [SMILES: *c1ccc([N+](=O)[O-])c2cccnc12]
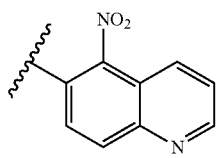 [SMILES: *c1ccc2ncccc2c1[N+](=O)[O-]]
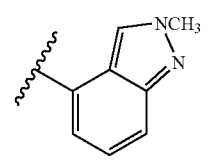 [SMILES: *c1cccc2nn(C)cc12]
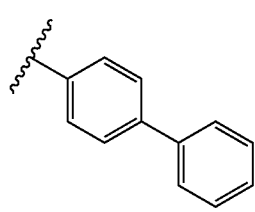 [SMILES: *c1ccc(-c2ccccc2)cc1]
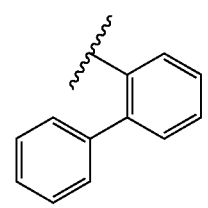 [SMILES: *c1ccccc1-c1ccccc1]
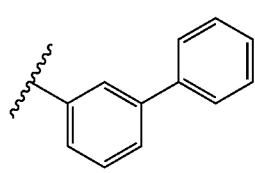 [SMILES: *c1cccc(-c2ccccc2)c1]
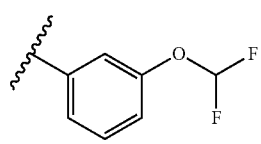 [SMILES: *c1cccc(OC(F)F)c1]
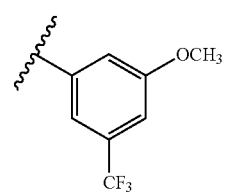 [SMILES: *c1cc(OC)cc(C(F)(F)F)c1]
TABLE 2-continued
Examples of group A².
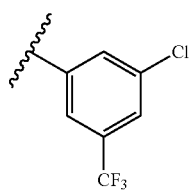
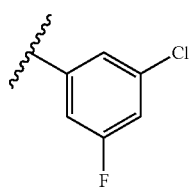 [SMILES: *c1cc(F)cc(Cl)c1]
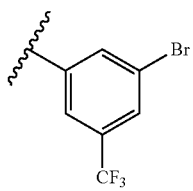
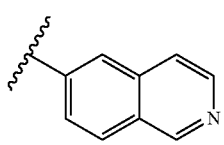 [SMILES: *c1ccc2cnccc2c1]
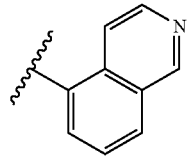 [SMILES: *c1cccc2cnccc12]
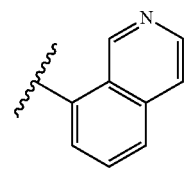 [SMILES: *c1cccc2ccncc12]
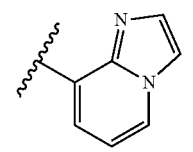 [SMILES: *c1cccn2ccnc12]
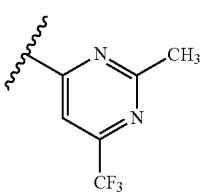 [SMILES: *c1cc(C(F)(F)F)nc(C)n1]

TABLE 2-continued
Examples of group A².
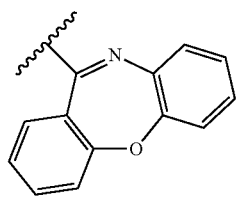 [SMILES: *C1=Nc2ccccc2Oc2ccccc21]
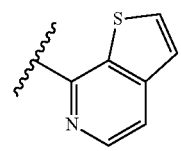 [SMILES: *c1nccc2ccsc12]
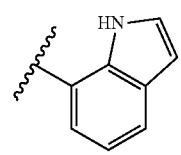 [SMILES: *c1cccc2cc[nH]c12]
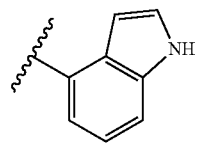 [SMILES: *c1cccc2[nH]ccc12]
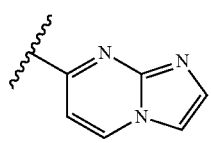 [SMILES: *c1ccn2ccnc2n1]
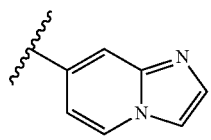
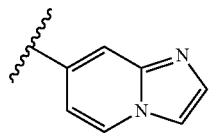 [SMILES: *c1ccn2ccnc2c1]
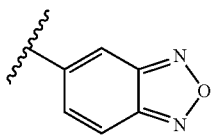 [SMILES: *c1ccc2nonc2c1]
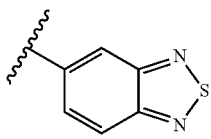
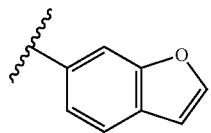 [SMILES: *c1ccc2ccoc2c1]
TABLE 2-continued
Examples of group A².
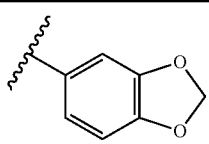
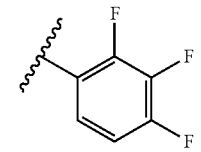 [SMILES: *c1ccc(F)c(F)c1F]
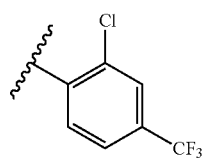 [SMILES: *c1ccc(C(F)(F)F)cc1Cl]
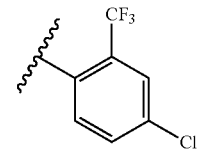
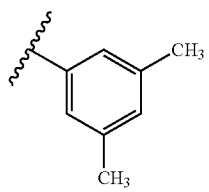
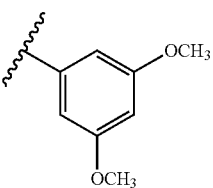
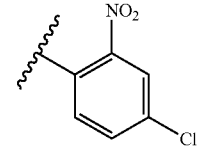 [SMILES: *c1ccc(Cl)cc1[N+](=O)[O-]]
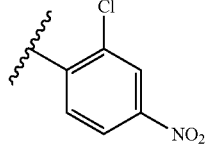 [SMILES: *c1ccc([N+](=O)[O-])cc1Cl]
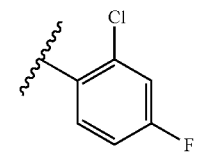 [SMILES: *c1ccc(F)cc1Cl]

TABLE 2-continued

Examples of group $A^2$.

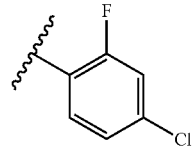 [SMILES: *c1ccc(Cl)cc1F]

Compounds of Formula (I), (II), or (III) include group $R^A$. $R^A$ may be halogen, nitrile, nitro, optionally substituted alkyl, —$OR^b$, —$NR^cR^d$, —$SR^e$, —C(=O)$R^f$, —C(=O)$OR^b$, —C(=O)$NR^cR^d$, —S(=O)$R^f$, —S(=O)$OR^b$, —S(=O)$NR^cR^d$, —S(=O)$_2R^f$, —S(=O)$_2OR^b$, or —S(=O)$_2NR^cR^d$. In certain embodiments, $R^A$ is halogen, optionally substituted alkyl, —$OR^b$, —$NR^cR^d$, —$SR^e$, —C(=O)$R^f$, —C(=O)$OR^b$, or —C(=O)$NR^cR^d$. In certain embodiments, $R^A$ is halogen. In certain embodiments, $R^A$ is optionally substituted alkyl. In certain embodiments, $R^A$ is optionally substituted alkenyl. In certain embodiments, $R^A$ is optionally substituted alkynyl. In certain embodiments, $R^A$ is optionally substituted carbocyclyl. In certain embodiments, $R^A$ is optionally substituted heterocyclyl. In certain embodiments, $R^A$ is optionally substituted aryl. In certain embodiments, $R^A$ is optionally substituted heteroaryl. In certain embodiments, $R^A$ is phenyl. In certain embodiments, $R^A$ is pyridyl.

In certain embodiments, $R^A$ is —F. In certain embodiments, $R^A$ is —Cl, —Br, or —I. In certain embodiments, $R^A$ is optionally substituted alkyl. In certain embodiments, $R^A$ is optionally substituted Ch-Ce alkyl. In certain embodiments, $R^A$ is alkyl. In certain embodiments, $R^A$ is $C_1$-$C_6$ alkyl. In certain embodiments, $R^A$ is —OR. In certain embodiments, $R^A$ is —$NR^cR^d$. In certain embodiments, $R^A$ is —$SR^e$. In certain embodiments, $R^A$ is —C(=O)$R^f$. In certain embodiments, $R^A$ is —C(=O)$OR^b$. In certain embodiments, $R^A$ is —C(=O)$NR^cR^d$. In certain embodiments, $R^A$ is —S(=O)$R^f$. In certain embodiments, $R^A$ is —S(=O)$OR^b$. In certain embodiments, $R^A$ is —S(=O)$NR^cR^d$. In certain embodiments, $R^A$ is —S(=O)$_2R^f$. In certain embodiments, $R^A$ is —S(=O)$_2OR^b$. In certain embodiments, $R^A$ is —S(=O)$_2NR^cR^d$.

In certain embodiments, $R^A$ is methyl. In certain embodiments, $R^A$ is ethyl. In certain embodiments, $R^A$ is propyl. In certain embodiments, $R^A$ is —$CF_3$. In certain embodiments, $R^A$ is —OH. In certain embodiments, $R^A$ is methoxy. In certain embodiments, $R^A$ is —$OCF_3$. In certain embodiments, $R^A$ is —$NH_2$. In certain embodiments, $R^A$ is —NHMe. In certain embodiments, $R^A$ is —$NMe_2$. In certain embodiments, $R^A$ is —C(=O)H. In certain embodiments, $R^A$ is —C(=O)Me. In certain embodiments, $R^A$ is —C(=O)OH. In certain embodiments, $R^A$ is —C(=O)OMe. In certain embodiments, $R^A$ is —C(=O)OEt. In certain embodiments, $R^A$ is —C(=O)OtBu. In certain embodiments, $R^A$ is —C(=O)$NH_2$. In certain embodiments, $R^A$ is —C(=O)NHMe. In certain embodiments, $R^A$ is —C(=O)$NMe_2$. In certain embodiments, $R^A$ is —CN. In certain embodiments, $R^A$ is —$NO_2$. In certain embodiments, $R^A$ is —S(=O)$CH_3$. In certain embodiments, $R^A$ is —S(=O)$_2CH_3$.

In certain embodiments, j is 0. In certain embodiments, j is 1. In certain embodiments, j is 2. In certain embodiments, j is 3. In certain embodiments, j is 4. In certain embodiments, j is 5. In certain embodiments, j is 6. In certain embodiments, j is 7. In certain embodiments, j is 8.

Compounds of Formula (I), (II), or (III) include group $R^1$. In certain embodiments, $R^1$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^b$, —$NR^cR^d$, —$SR^e$, —C(=O)$R^f$, —C(=O)$OR^b$, —C(=O)$NR^cR^d$, —S(=O)$R^f$, —S(=O)$OR^b$, —S(=O)$NR^cR^d$, —S(=O)$_2R^f$, —S(=O)$_2OR^b$, or —S(=O)$_2NR^cR^d$. In certain embodiments, $R^1$ is halogen, optionally substituted alkyl, —$OR^b$, —$NR^cR^d$, —$SR^e$, —C(=O)$R^f$, —C(=O)$OR^b$, or —C(=O)$NR^cR^d$. In certain embodiments, $R^1$ is halogen. In certain embodiments, $R^1$ is optionally substituted alkyl. In certain embodiments, $R^1$ is optionally substituted alkenyl. In certain embodiments, $R^1$ is optionally substituted alkynyl. In certain embodiments, $R^1$ is optionally substituted carbocyclyl. In certain embodiments, $R^1$ is optionally substituted heterocyclyl. In certain embodiments, $R^1$ is optionally substituted aryl. In certain embodiments, $R^1$ is optionally substituted heteroaryl. In certain embodiments, $R^1$ is phenyl. In certain embodiments, $R^1$ is pyridyl.

In certain embodiments, $R^1$ is —F. In certain embodiments, $R^1$ is —Cl, —Br, or —I. In certain embodiments, $R^1$ is optionally substituted alkyl. In certain embodiments, R is optionally substituted $C_1$-$C_6$ alkyl. In certain embodiments, $R^1$ is alkyl. In certain embodiments, $R^1$ is $C_1$-$C_6$ alkyl. In certain embodiments, $R^1$ is —$OR^b$. In certain embodiments, $R^1$ is —$NR^cR^d$. In certain embodiments, $R^1$ is —$SR^e$. In certain embodiments, $R^1$ is —C(=O)$R^f$. In certain embodiments, $R^1$ is —C(=O)$OR^b$. In certain embodiments, $R^1$ is —C(=O)$NR^cR^d$. In certain embodiments, $R^1$ is —S(=O)$R^f$. In certain embodiments, $R^1$ is —S(=O)$OR^b$. In certain embodiments, $R^1$ is —S(=O)$NR^cR^d$. In certain embodiments, $R^1$ is —S(=O)$_2R^f$. In certain embodiments, $R^1$ is —S(=O)$_2OR^b$. In certain embodiments, $R^1$ is —S(=O)$_2NR^cR^d$.

In certain embodiments, $R^1$ is hydrogen. In certain embodiments, $R^1$ is methyl. In certain embodiments, $R^1$ is ethyl. In certain embodiments, $R^1$ is propyl. In certain embodiments, $R^1$ is —$CF_3$. In certain embodiments, $R^1$ is —OH. In certain embodiments, $R^1$ is methoxy. In certain embodiments, $R^1$ is —$OCF_3$. In certain embodiments, $R^1$ is —$NH_2$. In certain embodiments, $R^1$ is —NHMe. In certain embodiments, $R^1$ is —$NMe_2$. In certain embodiments, $R^1$ is —C(=O)H. In certain embodiments, $R^1$ is —C(=O)Me. In certain embodiments, $R^1$ is —C(=O)OH. In certain embodiments, $R^1$ is —C(=O)OMe. In certain embodiments, $R^1$ is —C(=O)OEt. In certain embodiments, $R^1$ is —C(=O)OtBu. In certain embodiments, $R^1$ is —C(=O)$NH_2$. In certain embodiments, $R^1$ is —C(=O)NHMe. In certain embodiments, $R^1$ is —C(=O)$NMe_2$. In certain embodiments, $R^1$ is —S(=O)$CH_3$. In certain embodiments, $R^1$ is —S(=O)$_2CH_3$. In certain embodiments $R^1$ is —CN. In certain embodiments $R^1$ is —SCN. In certain embodiments $R^1$ is —$NO_2$.

Compounds of Formula (I), (II), or (III) include group $R^2$. In certain embodiments, $R^2$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^b$, —$NR^cR^d$, —$SR^e$, —C(=O)$R^f$, —C(=O)$OR^b$, —C(=O)$NR^cR^d$, —S(=O)$R^f$, —S(=O)$OR^b$, —S(=O)$NR^cR^d$, —S(=O)$_2R^f$, —S(=O)$_2OR^b$, or —S(=O)$_2NR^cR^d$. In certain embodiments, $R^2$ is halogen, optionally substituted alkyl, —$OR^b$, —$NR^cR^d$, —$SR^e$, —C(=O)$R^f$, —C(=O)$OR^b$, or —C(=O)$NR^cR^d$. In certain embodiments, $R^2$ is halogen. In certain embodiments, $R^2$ is optionally substituted alkyl. In certain embodiments, $R^2$ is optionally substituted alkenyl. In certain embodiments, $R^2$ is optionally substituted alkynyl. In certain embodiments, $R^2$ is optionally substituted carbocyclyl. In certain embodiments, $R^2$ is optionally substituted heterocyclyl. In certain embodiments, $R^2$ is optionally substituted aryl. In certain embodiments, $R^2$ is optionally substituted heteroaryl. In certain embodiments, $R^2$ is phenyl. In certain embodiments, $R^2$ is pyridyl.

In certain embodiments, $R^2$ is —F. In certain embodiments, $R^2$ is —Cl, —Br, or —I. In certain embodiments, $R^2$ is optionally substituted alkyl. In certain embodiments, $R^2$ is optionally substituted $C_1$-$C_6$ alkyl. In certain embodiments, $R^2$ is alkyl. In certain embodiments, $R^2$ is $C_1$-$C_6$ alkyl. In certain embodiments, $R^2$ is —$OR^b$. In certain embodiments, $R^2$ is —$NR^cR^d$. In certain embodiments, $R^2$ is —$SR^e$. In certain embodiments, $R^2$ is —$C(=O)R^f$. In certain embodiments, $R^2$ is —$C(=O)OR^b$. In certain embodiments, $R^2$ is —$C(=O)NR^cR^d$. In certain embodiments, $R^2$ is —$S(=O)R^f$. In certain embodiments, $R^2$ is —$S(=O)OR^b$. In certain embodiments, $R^2$ is —$S(=O)NR^cR^d$. In certain embodiments, $R^2$ is —$S(=O)_2R^f$. In certain embodiments, $R^2$ is —$S(=O)_2OR^b$. In certain embodiments, $R^2$ is —$S(=O)_2NR^cR^d$.

In certain embodiments, $R^2$ is hydrogen. In certain embodiments, $R^2$ is methyl. In certain embodiments, $R^2$ is ethyl. In certain embodiments, $R^2$ is propyl. In certain embodiments, $R^2$ is —$CF_3$. In certain embodiments, $R^2$ is —OH. In certain embodiments, $R^2$ is methoxy. In certain embodiments, $R^2$ is —$OCF_3$. In certain embodiments, $R^2$ is —$NH_2$. In certain embodiments, $R^2$ is —NHMe. In certain embodiments, $R^2$ is —$NMe_2$. In certain embodiments, $R^2$ is —C(=O)H. In certain embodiments, $R^2$ is —C(=O)Me. In certain embodiments, $R^2$ is —C(=O)OH. In certain embodiments, $R^2$ is —C(=O)OMe. In certain embodiments, $R^2$ is —C(=O)OEt. In certain embodiments, $R^2$ is —C(=O)OtBu. In certain embodiments, $R^2$ is —C(=O)$NH_2$. In certain embodiments, $R^2$ is —C(=O)NHMe. In certain embodiments, $R^2$ is —C(=O)$NMe_2$. In certain embodiments, $R^2$ is —S(=O)$CH_3$. In certain embodiments, $R^2$ is —$S(=O)_2CH_3$. In certain embodiments $R^2$ is —CN. In certain embodiments $R^2$ is —SCN. In certain embodiments $R^2$ is —$NO_2$.

Compounds of Formula (I), (II), or (III) include group $R^3$. In certain embodiments, $R^3$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^b$, —$NR^cR^d$, —$SR^e$, —$C(=O)R^f$, —$C(=O)OR^b$, —$C(=O)NR^cR^d$, —$S(=O)R^f$, —$S(=O)OR^b$, —$S(=O)NR^cR^d$, —$S(=O)_2R^f$, —$S(=O)_2OR^b$, or —$S(=O)_2NR^cR^d$. In certain embodiments, $R^3$ is halogen, optionally substituted alkyl, —$OR^b$, —$NR^cR^d$, —$SR^e$, —$C(=O)R^f$, —$C(=O)OR^b$, or —$C(=O)NR^cR^d$. In certain embodiments, $R^3$ is halogen. In certain embodiments, $R^3$ is optionally substituted alkyl. In certain embodiments, $R^3$ is optionally substituted alkenyl. In certain embodiments, $R^3$ is optionally substituted alkynyl. In certain embodiments, $R^3$ is optionally substituted carbocyclyl. In certain embodiments, $R^3$ is optionally substituted heterocyclyl. In certain embodiments, $R^3$ is optionally substituted aryl. In certain embodiments, $R^3$ is optionally substituted heteroaryl. In certain embodiments, $R^3$ is phenyl. In certain embodiments, $R^3$ is pyridyl.

In certain embodiments, $R^3$ is —F. In certain embodiments, $R^3$ is —Cl, —Br, or —I. In certain embodiments, $R^3$ is optionally substituted alkyl. In certain embodiments, $R^3$ is optionally substituted $C_1$-$C_6$ alkyl. In certain embodiments, $R^3$ is alkyl. In certain embodiments, $R^3$ is $C_1$-$C_6$ alkyl. In certain embodiments, $R^3$ is —$OR^b$. In certain embodiments, $R^3$ is —$NR^cR^d$. In certain embodiments, $R^3$ is —$SR^e$. In certain embodiments, $R^3$ is —$C(=O)R^f$. In certain embodiments, $R^3$ is —$C(=O)OR^b$. In certain embodiments, $R^3$ is —$C(=O)NR^cR^d$. In certain embodiments, $R^3$ is —$S(=O)R^f$. In certain embodiments, $R^3$ is —$S(=O)OR^b$. In certain embodiments, $R^3$ is —$S(=O)NR^cR^d$. In certain embodiments, $R^3$ is —$S(=O)_2R^f$. In certain embodiments, $R^3$ is —$S(=O)_2OR^b$. In certain embodiments, $R^3$ is —$S(=O)_2NR^cR^d$.

In certain embodiments, $R^3$ is hydrogen. In certain embodiments, $R^3$ is methyl. In certain embodiments, $R^3$ is ethyl. In certain embodiments, $R^3$ is propyl. In certain embodiments, $R^3$ is —$CF_3$. In certain embodiments, $R^3$ is —OH. In certain embodiments, $R^3$ is methoxy. In certain embodiments, $R^3$ is —$OCF_3$. In certain embodiments, $R^3$ is —$NH_2$. In certain embodiments, $R^3$ is —NHMe. In certain embodiments, $R^3$ is —$NMe_2$. In certain embodiments, $R^3$ is —C(=O)H. In certain embodiments, $R^3$ is —C(=O)Me. In certain embodiments, $R^3$ is —C(=O)OH. In certain embodiments, $R^3$ is —C(=O)OMe. In certain embodiments, $R^3$ is —C(=O)OEt. In certain embodiments, $R^3$ is —C(=O)OtBu. In certain embodiments, $R^3$ is —C(=O)$NH_2$. In certain embodiments, $R^3$ is —C(=O)NHMe. In certain embodiments, $R^3$ is —C(=O)$NMe_2$. In certain embodiments, $R^3$ is —S(=O)$CH_3$. In certain embodiments, $R^3$ is —$S(=O)_2CH_3$. In certain embodiments $R^3$ is —CN. In certain embodiments $R^3$ is —SCN. In certain embodiments $R^3$ is —$NO_2$.

Compounds of Formula (I), (II), or (III) include group $R^4$. In certain embodiments, $R^4$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^b$, —$NR^cR^d$, —$SR^e$, —$C(=O)R^f$, —$C(=O)OR^b$, —$C(=O)NR^cR^d$, —$S(=O)R^f$, —$S(=O)OR^b$, —$S(=O)NR^cR^d$, —$S(=O)_2R^f$, —$S(=O)_2OR^b$, or —$S(=O)_2NR^cR^d$. In certain embodiments, $R^4$ is halogen, optionally substituted alkyl, —$OR^b$, —$NR^cR^d$, —$SR^e$, —$C(=O)R^f$, —$C(=O)OR^b$, or —$C(=O)NR^cR^d$. In certain embodiments, $R^4$ is halogen. In certain embodiments, $R^4$ is optionally substituted alkyl. In certain embodiments, $R^4$ is optionally substituted alkenyl. In certain embodiments, $R^4$ is optionally substituted alkynyl. In certain embodiments, $R^4$ is optionally substituted carbocyclyl. In certain embodiments, $R^4$ is optionally substituted heterocyclyl. In certain embodiments, $R^4$ is optionally substituted aryl. In certain embodiments, $R^4$ is optionally substituted heteroaryl. In certain embodiments, $R^4$ is phenyl. In certain embodiments, $R^4$ is pyridyl.

In certain embodiments, $R^4$ is —F. In certain embodiments, $R^4$ is —Cl, —Br, or —I. In certain embodiments, $R^4$ is optionally substituted alkyl. In certain embodiments, $R^4$ is optionally substituted $C_4$-$C_6$ alkyl. In certain embodiments, $R^4$ is alkyl. In certain embodiments, $R^4$ is $C_4$-$C_6$ alkyl. In certain embodiments, $R^4$ is —$OR^b$. In certain embodiments, $R^4$ is —$NR^cR^d$. In certain embodiments, $R^4$ is —$SR^e$. In certain embodiments, $R^4$ is —$C(=O)R^f$. In certain embodiments, $R^4$ is —$C(=O)OR^b$. In certain embodiments, $R^4$ is —$C(=O)NR^cR^d$. In certain embodiments, $R^4$ is —$S(=O)R^f$. In certain embodiments, $R^4$ is —$S(=O)OR^b$. In certain embodiments, $R^4$ is —$S(=O)NR^cR^d$. In certain embodiments, $R^4$ is —$S(=O)_2R^f$. In certain embodiments, $R^4$ is —$S(=O)_2OR^b$. In certain embodiments, $R^4$ is —$S(=O)_2NR^cR^d$.

In certain embodiments, $R^4$ is hydrogen. In certain embodiments, $R^4$ is methyl. In certain embodiments, $R^4$ is ethyl. In certain embodiments, $R^4$ is propyl. In certain embodiments, $R^4$ is —$CF_3$. In certain embodiments, $R^4$ is —OH. In certain embodiments, $R^4$ is methoxy. In certain embodiments, $R^4$ is —$OCF_3$. In certain embodiments, $R^4$ is —$NH_2$. In certain embodiments, $R^4$ is —NHMe. In certain embodiments, $R^4$ is —$NMe_2$. In certain embodiments, $R^4$ is —C(=O)H. In certain embodiments, $R^4$ is —C(=O)Me. In certain embodiments, $R^4$ is —C(=O)OH. In certain embodiments, $R^4$ is —C(=O)OMe. In certain embodiments, $R^4$ is —C(=O)OEt. In certain embodiments, $R^4$ is —C(=O)OtBu. In certain embodiments, $R^4$ is —C(=O)$NH_2$. In certain embodiments, $R^4$ is —C(=O)NHMe. In certain embodiments, $R^4$ is —C(=O)$NMe_2$. In certain embodiments, $R^4$ is —S(=O)$CH_3$. In certain embodiments, $R^4$ is —S(=O)$_2CH_3$. In certain embodiments $R^4$ is —CN. In certain embodiments $R^4$ is —SCN. In certain embodiments $R^4$ is —$NO_2$.

In compounds of Formula (I), (II), or (III), the substituents $R^1$, $R^2$, $R^3$, and $R^4$ are attached to a pyridine ring (attached to one nitrogen of the thiourea) of formula:

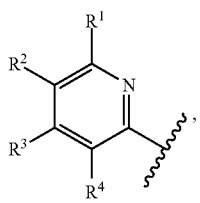

hereinafter referred to as Ring Z. In certain embodiments, Ring Z is of formula:

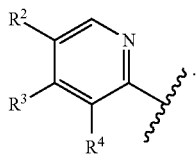

In certain embodiments, Ring Z is of formula:

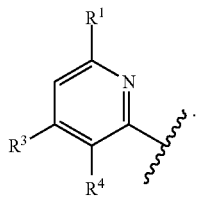

In certain embodiments, Ring Z is of formula:

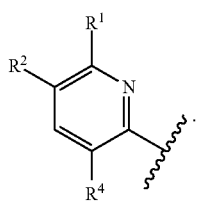

In certain embodiments, Ring Z is of formula:

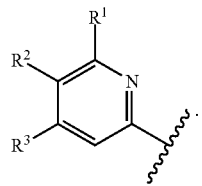

In certain embodiments, Ring Z is of formula:

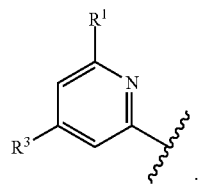

In certain embodiments, Ring Z is of formula:

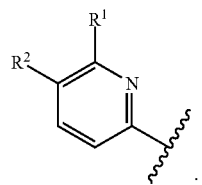

In certain embodiments, Ring Z is of formula:

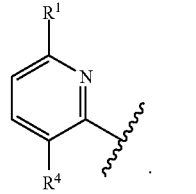

In certain embodiments, Ring Z is of formula:

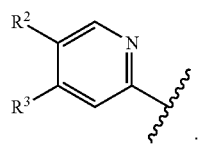

In certain embodiments, Ring Z is of formula:

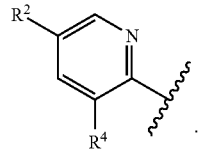

In certain embodiments, Ring Z is of formula:

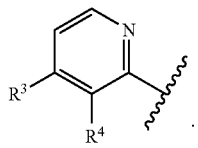

In certain embodiments, Ring Z is of formula:

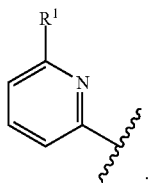

In certain embodiments, Ring Z is of formula:

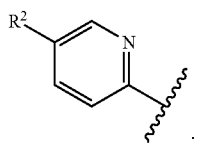

In certain embodiments, Ring Z is of formula:

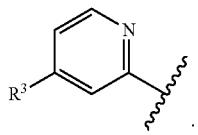

In certain embodiments, Ring Z is of formula:

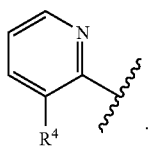

In certain embodiments, Ring Z is of formula:

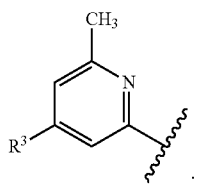

In certain embodiments, Ring Z is of formula:

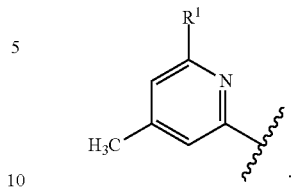

In certain embodiments, Ring Z is of formula:

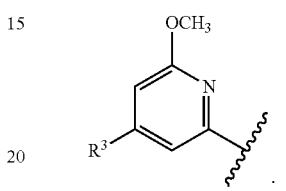

In certain embodiments, Ring Z is of formula:

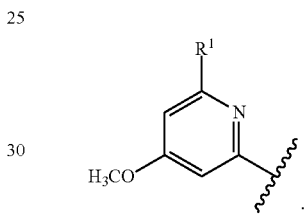

In certain embodiments, Ring Z is of formula:

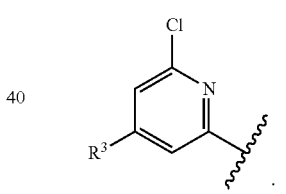

In certain embodiments, Ring Z is of formula:

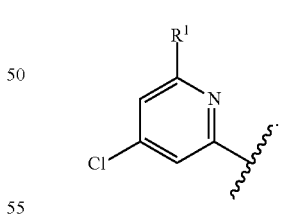

In certain embodiments, Ring Z is of formula:

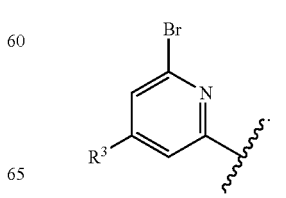

In certain embodiments, Ring Z is of formula:

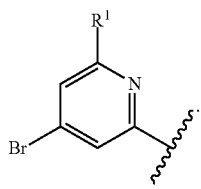

In certain embodiments, Ring Z is of formula:

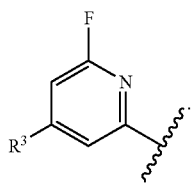

In certain embodiments, Ring Z is of formula:

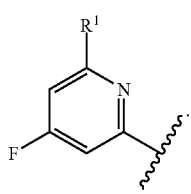

In certain embodiments, Ring Z is of formula:

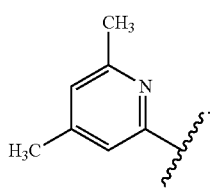

In certain embodiments, Ring Z is of formula:

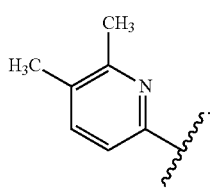

In certain embodiments, Ring Z is of formula:

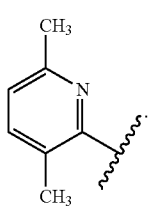

In certain embodiments, Ring Z is of formula:

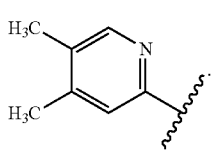

In certain embodiments, Ring Z is of formula:

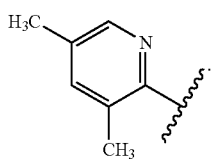

In certain embodiments, Ring Z is of formula:

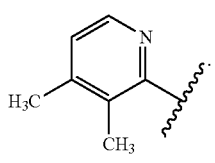

In certain embodiments, Ring Z is of formula:

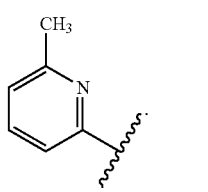

In certain embodiments, Ring Z is of formula:

In certain embodiments, Ring Z is of formula:

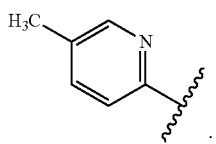

In certain embodiments, Ring Z is of formula:

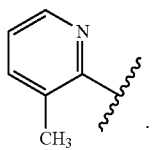

In certain embodiments, Ring Z is of formula:

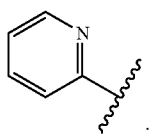

In certain embodiments, Ring Z is of formula:

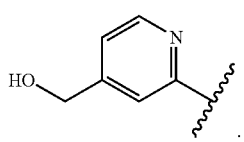 [SMILES: *c1cc(CO)ccn1]

In certain embodiments, Ring Z is of formula:

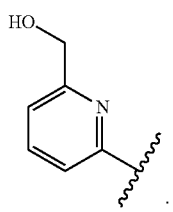

In certain embodiments, Ring Z is of formula:

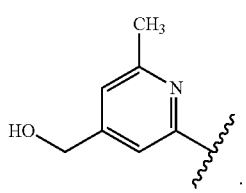 [SMILES: *c1cc(CO)cc(C)n1]

In certain embodiments, Ring Z is of formula:

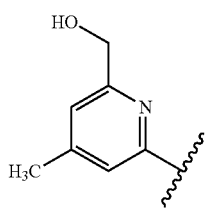

In certain embodiments, Ring Z is of formula:

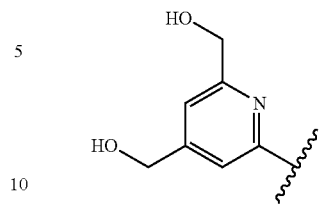

In certain embodiments, Ring Z is of formula:

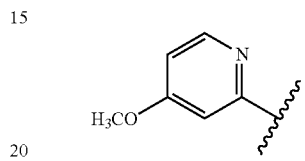

In certain embodiments, Ring Z is of formula:

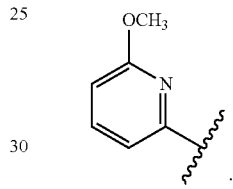

In certain embodiments, Ring Z is of formula:

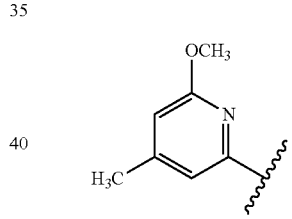

In certain embodiments, Ring Z is of formula:

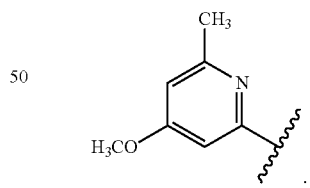

In certain embodiments, Ring Z is of formula:

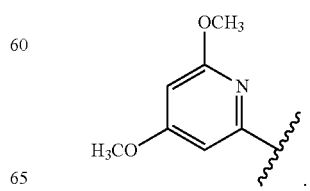

In certain embodiments, Ring Z is of formula:

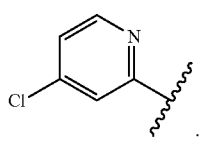

In certain embodiments, Ring Z is of formula:

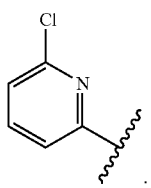 [SMILES: *c1cccc(Cl)n1]

In certain embodiments, Ring Z is of formula:

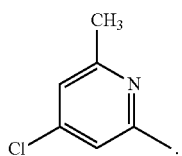

In certain embodiments, Ring Z is of formula:

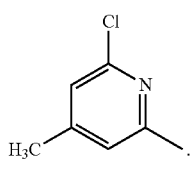

In certain embodiments, Ring Z is of formula:

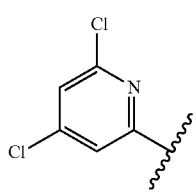

In certain embodiments, Ring Z is of formula:

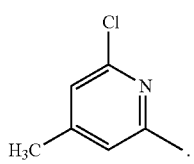

In certain embodiments, Ring Z is of formula:

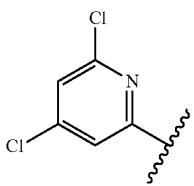

In certain embodiments, Ring Z is of formula:

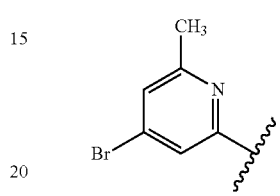

In certain embodiments, Ring Z is of formula:

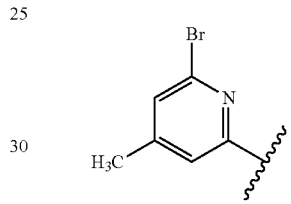

In certain embodiments, Ring Z is of formula:

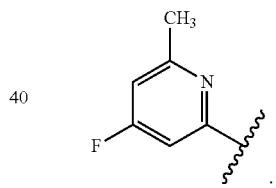

In certain embodiments, Ring Z is of formula:

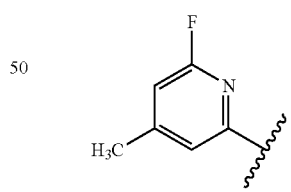

In certain embodiments, Ring Z is of formula:

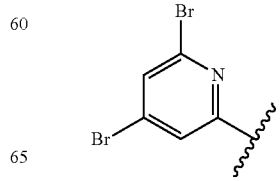

In certain embodiments, Ring Z is of formula:

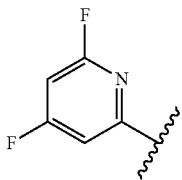

In certain embodiments, Ring Z is of formula:

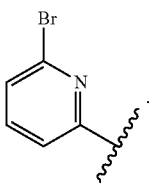 [SMILES: *c1cccc(Br)n1]

In certain embodiments, Ring Z is of formula:

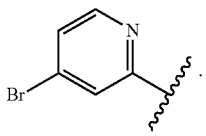

In certain embodiments, Ring Z is of formula:

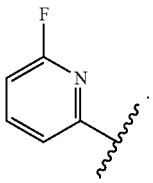

In certain embodiments, Ring Z is of formula:

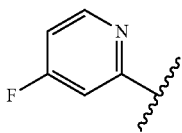

In certain embodiments, Ring Z is of formula:

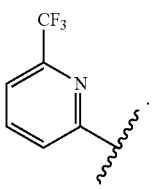

In certain embodiments, Ring Z is of formula:

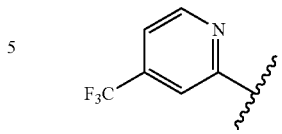

In certain embodiments, Ring Z is of formula:

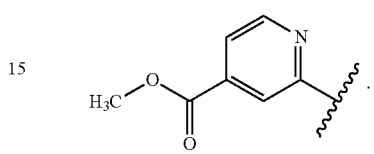

Compounds of Formula (I), (II), or (III) include group $R^5$. In certain embodiments, $R^5$ is hydrogen. In certain embodiments, $R^5$ is optionally substituted $C_1$-$C_6$ alkyl. In certain embodiments, $R^5$ is $C_1$-$C_6$ alkyl. In certain embodiments, $R^5$ is a nitrogen protecting group. In certain embodiments, $R^5$ is methyl. In certain embodiments, $R^5$ is ethyl. In certain embodiments, $R^5$ is propyl.

Compounds of Formula (I), (II), or (III) may include one or more independent $R^6$ groups. In certain embodiments, each $R^6$ is independently halogen, optionally substituted alkyl, optionally substituted carbocyclyl, optionally substituted heterocyclyl, optionally substituted aryl, optionally substituted heteroaryl, —OR$^b$, —NR$^c$R$^d$, —SR$^e$, —C(=O)R$^f$, —C(=O)OR$^b$, or —C(=O)NR$^c$R$^d$. In certain embodiments, $R^6$ is halogen, optionally substituted alkyl, —OR$^b$, —NR$^c$R$^d$, —SR$^e$, —C(=O)R$^f$, —C(=O)OR$^b$, or —C(=O)NR$^c$R$^d$. In certain embodiments, $R^6$ is halogen. In certain embodiments, $R^6$ is optionally substituted alkyl. In certain embodiments, $R^6$ is optionally substituted alkenyl. In certain embodiments, $R^6$ is optionally substituted alkynyl. In certain embodiments, $R^6$ is optionally substituted carbocyclyl. In certain embodiments, $R^6$ is optionally substituted heterocyclyl. In certain embodiments, $R^6$ is optionally substituted aryl. In certain embodiments, $R^6$ is optionally substituted heteroaryl. In certain embodiments, $R^6$ is phenyl. In certain embodiments, $R^6$ is pyridyl.

In certain embodiments, $R^6$ is —F. In certain embodiments, $R^6$ is —Cl, —Br, or —I. In certain embodiments, $R^6$ is optionally substituted alkyl. In certain embodiments, $R^6$ is optionally substituted $C_1$-$C_6$ alkyl. In certain embodiments, $R^6$ is alkyl. In certain embodiments, $R^6$ is $C_1$-$C_6$ alkyl. In certain embodiments, $R^6$ is —OR$^b$. In certain embodiments, $R^6$ is —NR$^c$R$^d$. In certain embodiments, $R^6$ is —SR$^e$. In certain embodiments, $R^6$ is —C(=O)R$^f$. In certain embodiments, $R^6$ is —C(=O)OR$^b$. In certain embodiments, $R^6$ is —C(=O)NR$^c$R$^d$.

In certain embodiments, $R^6$ is hydrogen. In certain embodiments, $R^6$ is methyl. In certain embodiments, $R^6$ is ethyl. In certain embodiments, $R^6$ is propyl. In certain embodiments, $R^6$ is —CF$_3$. In certain embodiments, $R^6$ is —OH. In certain embodiments, $R^6$ is methoxy. In certain embodiments, $R^6$ is —OCF3. In certain embodiments, $R^6$ is —NH$_2$. In certain embodiments, $R^6$ is —NHMe. In certain embodiments, $R^6$ is —NMe$_2$. In certain embodiments, $R^6$ is —C(=O)H. In certain embodiments, $R^6$ is —C(=O)Me. In certain embodiments, $R^6$ is —C(=O)OH. In certain embodiments, $R^6$ is —C(=O)OMe. In certain embodiments, $R^6$ is —C(=O)OEt. In certain embodiments, $R^6$ is —C(=O)OtBu. In certain embodiments, $R^6$ is —C(=O)NH$_2$. In certain embodiments, $R^6$ is —C(=O)NHMe. In certain embodiments, $R^6$ is —C(=O)NMe$_2$.

Compounds of Formula (I), (II), or (III) may include one or more independent $R^a$ groups. In certain embodiments, $R^a$ is hydrogen. In certain embodiments, $R^a$ is optionally substituted alkyl. In certain embodiments, $R^a$ is optionally substituted alkenyl. In certain embodiments, $R^a$ is optionally substituted alkynyl. In certain embodiments, $R^a$ is optionally substituted carbocyclyl. In certain embodiments, $R^a$ is optionally substituted heterocyclyl. In certain embodiments, $R^a$ is optionally substituted aryl. In certain embodiments, $R^a$ is optionally substituted heteroaryl. In certain embodiments, $R^a$ is a nitrogen protecting group.

In certain embodiments, $R^a$ is optionally substituted $C_1$-$C_6$ alkyl. In certain embodiments, $R^a$ is alkyl. In certain embodiments, $R^a$ is $C_1$-$C_6$ alkyl. In certain embodiments, $R^a$ is methyl. In certain embodiments, $R^a$ is ethyl. In certain embodiments, $R^a$ is propyl. In certain embodiments, $R^a$ is —CF$_3$. In certain embodiments, $R^a$ is optionally substituted cyclohexyl. In certain embodiments, $R^a$ is cyclohexyl. In certain embodiments, $R^a$ is optionally substituted phenyl. In certain embodiments, $R^a$ is phenyl. In certain embodiments, $R^a$ is optionally substituted pyridyl. In certain embodiments, $R^a$ is pyridyl.

Compounds of Formula (I), (II), or (III) may include one or more independent $R^b$ groups. In certain embodiments, $R^b$ is hydrogen. In certain embodiments, $R^b$ is optionally substituted alkyl. In certain embodiments, $R^b$ is optionally substituted alkenyl. In certain embodiments, $R^b$ is optionally substituted alkynyl. In certain embodiments, $R^b$ is optionally substituted carbocyclyl. In certain embodiments, $R^b$ is optionally substituted heterocyclyl. In certain embodiments, $R^b$ is optionally substituted aryl. In certain embodiments, $R^b$ is optionally substituted heteroaryl. In certain embodiments, $R^b$ is an oxygen protecting group.

In certain embodiments, $R^b$ is optionally substituted $C_1$-$C_6$ alkyl. In certain embodiments, $R^b$ is alkyl. In certain embodiments, $R^b$ is $C_1$-$C_6$ alkyl. In certain embodiments, $R^b$ is methyl. In certain embodiments, $R^b$ is ethyl. In certain embodiments, $R^b$ is propyl. In certain embodiments, $R^b$ is —CF$_3$. In certain embodiments, $R^b$ is optionally substituted cyclohexyl. In certain embodiments, $R^b$ is cyclohexyl. In certain embodiments, $R^b$ is optionally substituted phenyl. In certain embodiments, $R^b$ is phenyl. In certain embodiments, $R^b$ is optionally substituted pyridyl. In certain embodiments, $R^b$ is pyridyl.

Compounds of Formula (I), (II), or (III) may include one or more independent $R^c$ groups. In certain embodiments, $R^c$ is hydrogen. In certain embodiments, $R^c$ is optionally substituted alkyl. In certain embodiments, $R^c$ is optionally substituted alkenyl. In certain embodiments, $R^c$ is optionally substituted alkynyl. In certain embodiments, $R^c$ is optionally substituted carbocyclyl. In certain embodiments, $R^c$ is optionally substituted heterocyclyl. In certain embodiments, $R^c$ is optionally substituted aryl. In certain embodiments, $R^c$ is optionally substituted heteroaryl. In certain embodiments, $R^c$ is a nitrogen protecting group.

In certain embodiments, $R^c$ is optionally substituted Q-Ce alkyl. In certain embodiments, $R^c$ is alkyl. In certain embodiments, $R^c$ is $C_1$-$C_6$ alkyl. In certain embodiments, $R^c$ is methyl. In certain embodiments, $R^c$ is ethyl. In certain embodiments, $R^c$ is propyl. In certain embodiments, $R^c$ is —CF$_3$. In certain embodiments, $R^c$ is optionally substituted cyclohexyl. In certain embodiments, $R^c$ is cyclohexyl. In certain embodiments, $R^c$ is optionally substituted phenyl. In certain embodiments, $R^c$ is phenyl. In certain embodiments, $R^c$ is optionally substituted pyridyl. In certain embodiments, $R^c$ is pyridyl.

Compounds of Formula (I), (II), or (III) may include one or more independent $R^d$ groups. In certain embodiments, $R^d$ is hydrogen. In certain embodiments, $R^d$ is optionally substituted alkyl. In certain embodiments, $R^d$ is optionally substituted alkenyl. In certain embodiments, $R^d$ is optionally substituted alkynyl. In certain embodiments, $R^d$ is optionally substituted carbocyclyl. In certain embodiments, $R^d$ is optionally substituted heterocyclyl. In certain embodiments, $R^d$ is optionally substituted aryl. In certain embodiments, $R^d$ is optionally substituted heteroaryl. In certain embodiments, $R^d$ is a nitrogen protecting group.

In certain embodiments, $R^d$ is optionally substituted $C_1$-$C_6$ alkyl. In certain embodiments, $R^d$ is alkyl. In certain embodiments, $R^d$ is $C_1$-$C_6$ alkyl. In certain embodiments, $R^d$ is methyl. In certain embodiments, $R^d$ is ethyl. In certain embodiments, $R^d$ is propyl. In certain embodiments, $R^d$ is —CF$_3$. In certain embodiments, $R^d$ is optionally substituted cyclohexyl. In certain embodiments, $R^d$ is cyclohexyl. In certain embodiments, $R^d$ is optionally substituted phenyl. In certain embodiments, $R^d$ is phenyl. In certain embodiments, $R^d$ is optionally substituted pyridyl. In certain embodiments, $R^d$ is pyridyl.

In certain embodiments, $R^c$ and $R^d$ are joined to form a heterocyclic ring. In certain embodiments, $R^c$ and $R^d$ are joined to form a heteroaryl ring. In certain embodiments, $R^c$ and $R^d$ are joined to form an optionally substituted piperidinyl ring. In certain embodiments, $R^c$ and $R^d$ are joined to form an optionally substituted piperizinyl ring. In certain embodiments, $R^c$ and $R^d$ are joined to form an optionally substituted morpholinyl ring.

Compounds of Formula (I), (II), or (III) may include one or more independent $R^e$ groups. In certain embodiments, $R^e$ is hydrogen. In certain embodiments, $R^e$ is optionally substituted alkyl. In certain embodiments, $R^e$ is optionally substituted alkenyl. In certain embodiments, $R^e$ is optionally substituted alkynyl. In certain embodiments, $R^e$ is optionally substituted carbocyclyl. In certain embodiments, $R^e$ is optionally substituted heterocyclyl. In certain embodiments, $R^e$ is optionally substituted aryl. In certain embodiments, $R^e$ is optionally substituted heteroaryl. In certain embodiments, $R^e$ is a sulfur protecting group.

In certain embodiments, $R^e$ is optionally substituted $C_1$-$C_6$ alkyl. In certain embodiments, $R^e$ is alkyl. In certain embodiments, $R^e$ is $C_1$-$C_6$ alkyl. In certain embodiments, $R^e$ is methyl. In certain embodiments, $R^e$ is ethyl. In certain embodiments, $R^e$ is propyl. In certain embodiments, $R^e$ is —CF$_3$. In certain embodiments, $R^e$ is optionally substituted cyclohexyl. In certain embodiments, $R^e$ is cyclohexyl. In certain embodiments, $R^e$ is optionally substituted phenyl. In certain embodiments, $R^e$ is phenyl. In certain embodiments, $R^e$ is optionally substituted pyridyl. In certain embodiments, $R^e$ is pyridyl.

Compounds of Formula (I), (II), or (III) may include one or more independent $R^f$ groups. In certain embodiments, $R^f$ is hydrogen. In certain embodiments, $R^f$ is optionally substituted alkyl. In certain embodiments, $R^f$ is optionally substituted alkenyl. In certain embodiments, $R^f$ is optionally substituted alkynyl. In certain embodiments, $R^f$ is optionally substituted carbocyclyl. In certain embodiments, $R^f$ is optionally substituted heterocyclyl. In certain embodiments, $R^f$ is optionally substituted aryl. In certain embodiments, $R^f$ is optionally substituted heteroaryl.

In certain embodiments, $R^f$ is optionally substituted $C_1$-$C_6$ alkyl. In certain embodiments, $R^f$ is alkyl. In certain embodiments, $R^f$ is $C_1$-$C_6$ alkyl. In certain embodiments, $R^f$ is methyl. In certain embodiments, $R^f$ is ethyl. In certain embodiments, $R^f$ is propyl. In certain embodiments, $R^f$ is —$CF_3$. In certain embodiments, $R^f$ is optionally substituted cyclohexyl. In certain embodiments, $R^f$ is cyclohexyl. In certain embodiments, $R^f$ is optionally substituted phenyl. In certain embodiments, $R^f$ is phenyl. In certain embodiments, $R^f$ is optionally substituted pyridyl. In certain embodiments, $R^f$ is pyridyl.

In certain embodiments, the compound is a compound listed in Table 3. In Table 3 mass-to-charge ratios (m/z) are from positive ion HRMS and correspond to the (M+H)$^+$ ion, unless otherwise indicated.

TABLE 3

| | Exemplary compounds. | | |
|---|---|---|---|
| Cmpd. No. | Structure | m/z | Calc. m/z |
| 2 | | | |
| 4 | | | |
| 5 | | | |
| 6 | | | |
| 7 | | | |

TABLE 3-continued

Exemplary compounds.

| Cmpd. No. | Structure | m/z | Calc. m/z |
|---|---|---|---|
| 8 | 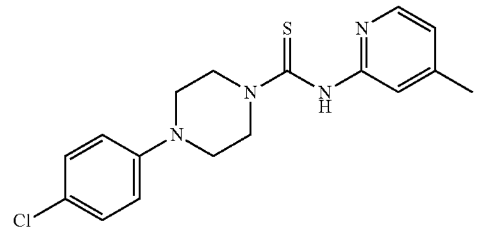 [SMILES: Cc1ccnc(NC(=S)N2CCN(c3ccc(Cl)cc3)CC2)c1] | | |
| 9 | 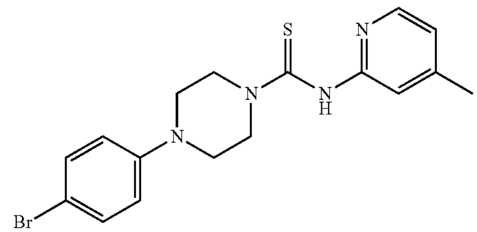 | | |
| 10 | 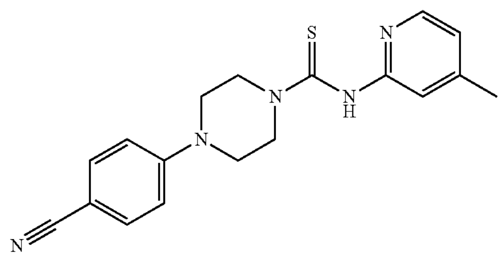 [SMILES: Cc1ccnc(NC(=S)N2CCN(c3ccc(C#N)cc3)CC2)c1] | | |
| 11 | 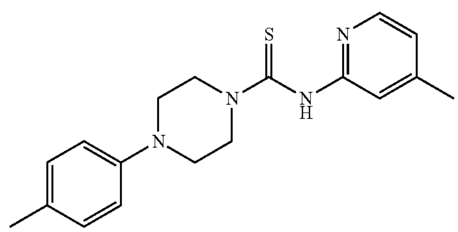 | | |
| 12 | 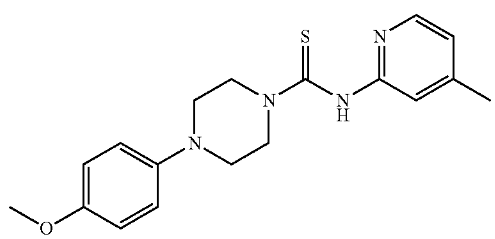 | | |
| 13 | 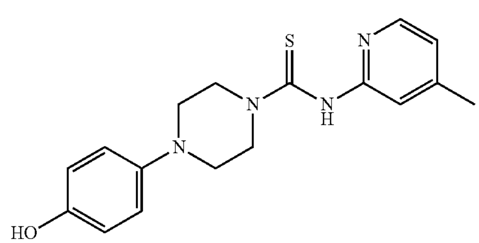 [SMILES: Cc1ccnc(NC(=S)N2CCN(c3ccc(O)cc3)CC2)c1] | | |

TABLE 3-continued

Exemplary compounds.

| Cmpd. No. | Structure | m/z | Calc. m/z |
|---|---|---|---|
| 14 | ![structure] | | |
| 16 | ![structure] | | |
| 17 | ![structure] | | |
| 18 | ![structure] | | |
| 20 | ![structure] | | |
| 24 | ![structure] | | |

TABLE 3-continued

Exemplary compounds.

| Cmpd. No. | Structure | m/z | Calc. m/z |
|---|---|---|---|
| 25 | 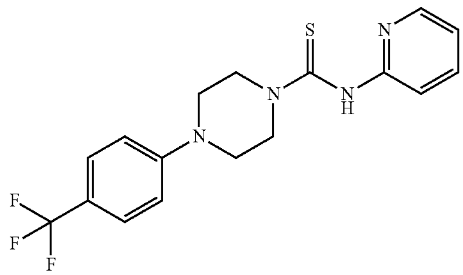 [SMILES: FC(F)(F)c1ccc(N2CCN(C(=S)Nc3ccccn3)CC2)cc1] | | |
| 26 | 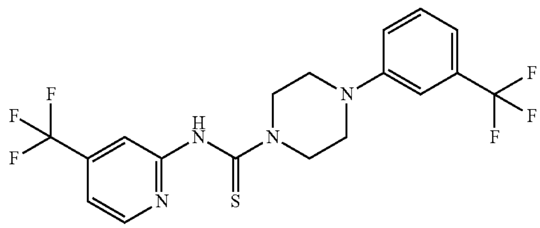 [SMILES: FC(F)(F)c1cccc(N2CCN(C(=S)Nc3cc(C(F)(F)F)ccn3)CC2)c1] | | |
| 27 | 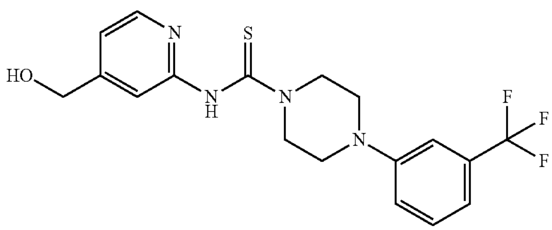 [SMILES: OCc1ccnc(NC(=S)N2CCN(c3cccc(C(F)(F)F)c3)CC2)c1] | | |
| 28 | 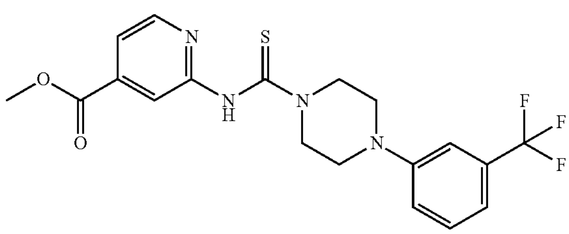 [SMILES: COC(=O)c1ccnc(NC(=S)N2CCN(c3cccc(C(F)(F)F)c3)CC2)c1] | | |
| 35 | 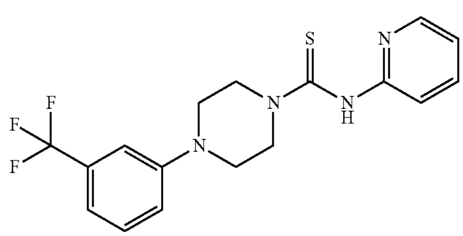 [SMILES: FC(F)(F)c1cccc(N2CCN(C(=S)Nc3ccccn3)CC2)c1] | | |
| 36 | 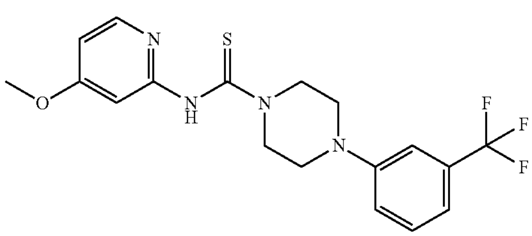 [SMILES: COc1ccnc(NC(=S)N2CCN(c3cccc(C(F)(F)F)c3)CC2)c1] | | |

TABLE 3-continued

Exemplary compounds.

| Cmpd. No. | Structure | m/z | Calc. m/z |
|---|---|---|---|
| 37 | 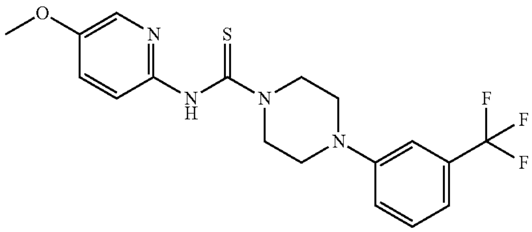 [SMILES: COc1ccc(NC(=S)N2CCN(c3cccc(C(F)(F)F)c3)CC2)nc1] | | |
| 38 | 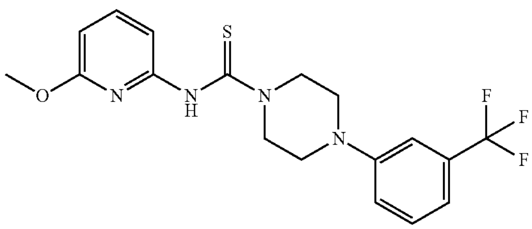 [SMILES: COc1cccc(NC(=S)N2CCN(c3cccc(C(F)(F)F)c3)CC2)n1] | | |
| 39 | 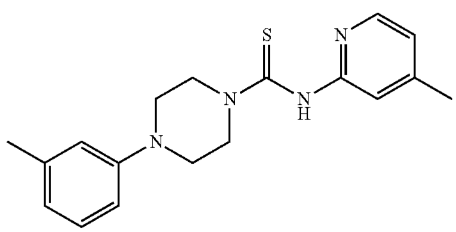 | | |
| 41 | 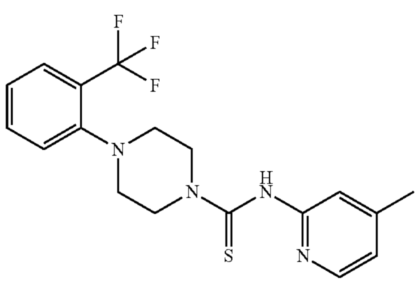 [SMILES: Cc1ccnc(NC(=S)N2CCN(c3ccccc3C(F)(F)F)CC2)c1] | | |
| 48 | 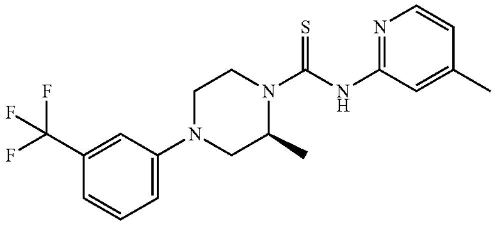 [SMILES: Cc1ccnc(NC(=S)N2CCN(c3cccc(C(F)(F)F)c3)C[C@@H]2C)c1] | | |
| 52 | 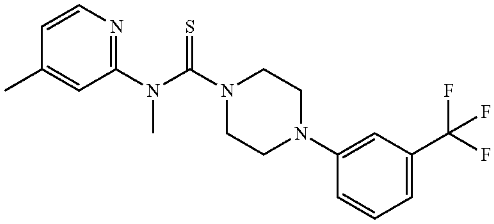 [SMILES: Cc1ccnc(N(C)C(=S)N2CCN(c3cccc(C(F)(F)F)c3)CC2)c1] | | |

TABLE 3-continued

Exemplary compounds.

| Cmpd. No. | Structure | m/z | Calc. m/z |
|---|---|---|---|
| 56 | 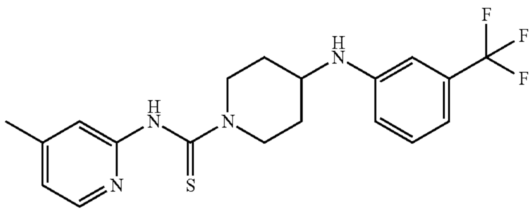 [SMILES: Cc1ccnc(NC(=S)N2CCC(Nc3cccc(C(F)(F)F)c3)CC2)c1] | | |
| 57 | 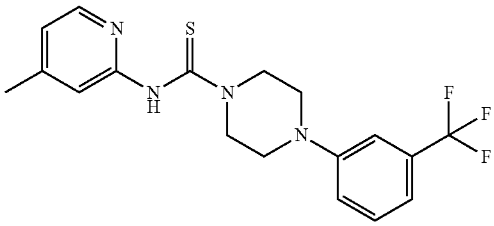 [SMILES: Cc1ccnc(NC(=S)N2CCN(c3cccc(C(F)(F)F)c3)CC2)c1] | | |
| 58 | 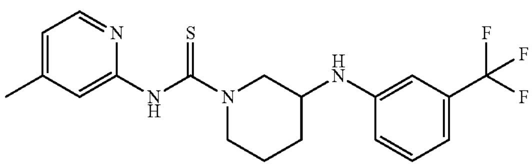 [SMILES: Cc1ccnc(NC(=S)N2CCCC(Nc3cccc(C(F)(F)F)c3)C2)c1] | | |
| 62 | 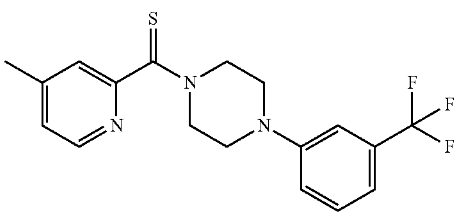 [SMILES: Cc1ccnc(C(=S)N2CCN(c3cccc(C(F)(F)F)c3)CC2)c1] | | |
| 63 | 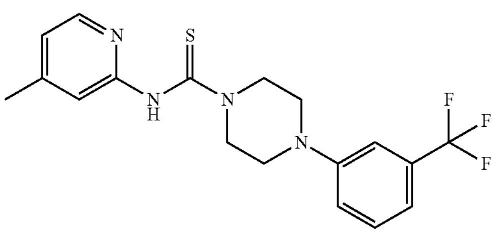 [SMILES: Cc1ccnc(NC(=S)N2CCN(c3cccc(C(F)(F)F)c3)CC2)c1] | | |
| 64 | 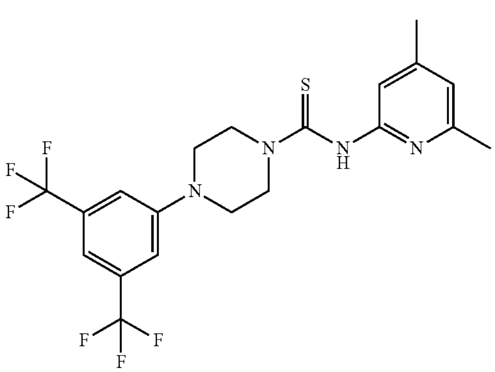 [SMILES: Cc1cc(C)nc(NC(=S)N2CCN(c3cc(C(F)(F)F)cc(C(F)(F)F)c3)CC2)c1] | | |

TABLE 3-continued
Exemplary compounds.
| Cmpd. No. | Structure | m/z | Calc. m/z |
|---|---|---|---|
| 65 | 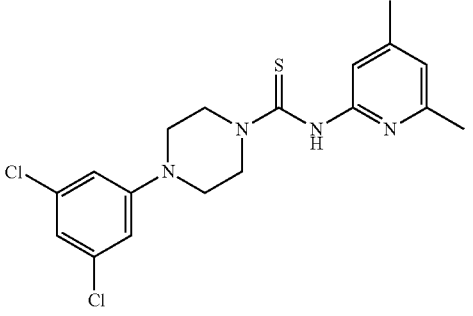 [SMILES: Cc1cc(C)nc(NC(=S)N2CCN(c3cc(Cl)cc(Cl)c3)CC2)c1] | | |
| 66 | 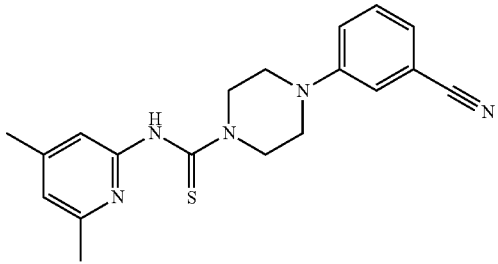 [SMILES: Cc1cc(C)nc(NC(=S)N2CCN(c3cccc(C#N)c3)CC2)c1] | | |
| 67 | 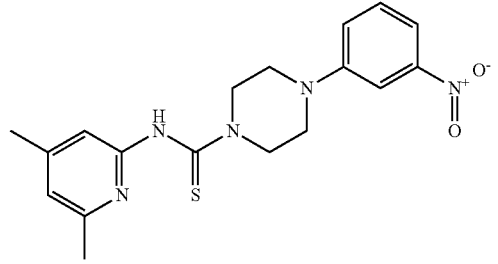 | | |
| 68 | 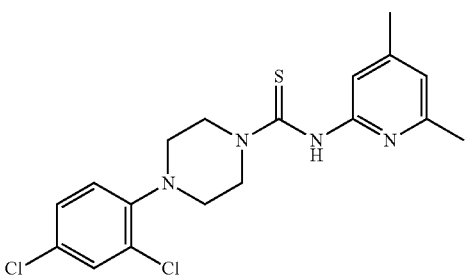 [SMILES: Cc1cc(C)nc(NC(=S)N2CCN(c3ccc(Cl)cc3Cl)CC2)c1] | | |

TABLE 3-continued

Exemplary compounds.

| Cmpd. No. | Structure | m/z | Calc. m/z |
|---|---|---|---|
| 69 | 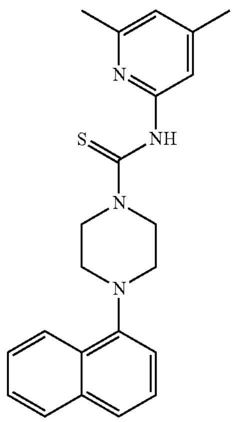 [SMILES: Cc1cc(C)nc(NC(=S)N2CCN(c3cccc4ccccc34)CC2)c1] | | |
| 70 | 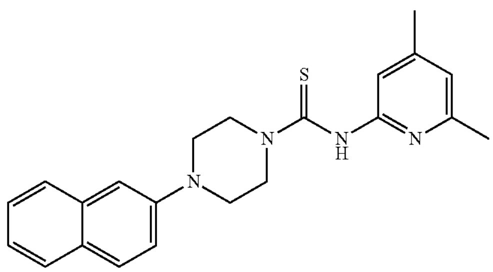 [SMILES: Cc1cc(C)nc(NC(=S)N2CCN(c3ccc4ccccc4c3)CC2)c1] | | |
| 71 | (NCGC00242266) | | |
| 72 | (NCT-502) | | |

TABLE 3-continued

Exemplary compounds.

| Cmpd. No. | Structure | m/z | Calc. m/z |
|---|---|---|---|
| 77 | 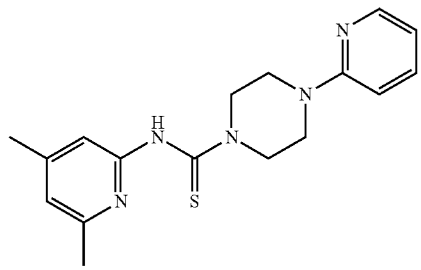 [SMILES: Cc1cc(C)nc(NC(=S)N2CCN(c3ccccn3)CC2)c1] | | |
| 79 | 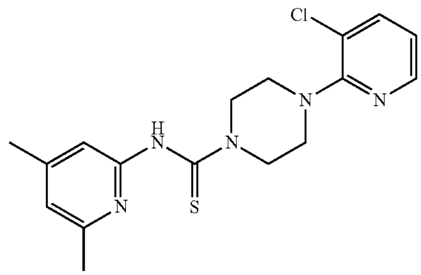 [SMILES: Cc1cc(C)nc(NC(=S)N2CCN(c3ncccc3Cl)CC2)c1] | | |
| 80 | 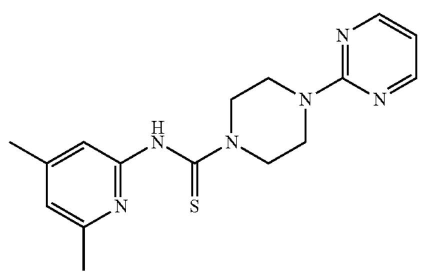 [SMILES: Cc1cc(C)nc(NC(=S)N2CCN(c3ncccn3)CC2)c1] | | |
| 81 | 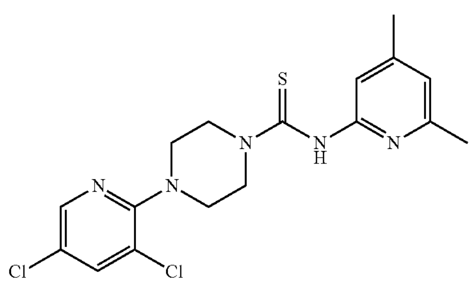 [SMILES: Cc1cc(C)nc(NC(=S)N2CCN(c3ncc(Cl)cc3Cl)CC2)c1] | | |
| 83 | 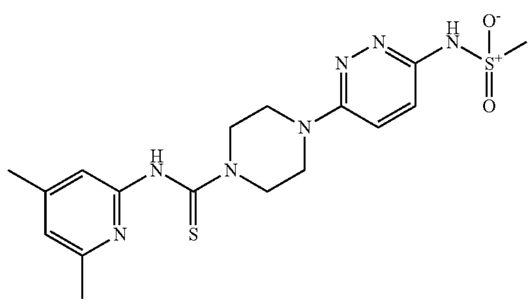 | | |

TABLE 3-continued

Exemplary compounds.

| Cmpd. No. | Structure | m/z | Calc. m/z |
|---|---|---|---|
| 84 | 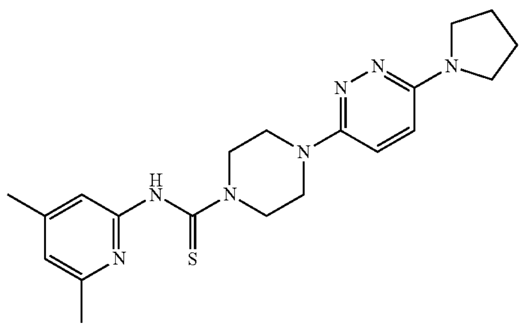 [SMILES: Cc1cc(C)nc(NC(=S)N2CCN(c3ccc(N4CCCC4)nn3)CC2)c1] | | |
| 85 | 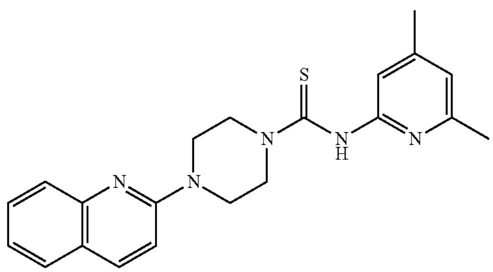 [SMILES: Cc1cc(C)nc(NC(=S)N2CCN(c3ccc4ccccc4n3)CC2)c1] | | |
| 86 | 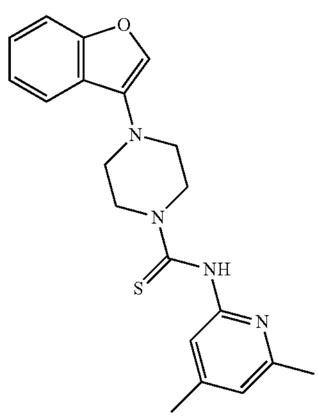 [SMILES: Cc1cc(C)nc(NC(=S)N2CCN(c3coc4ccccc34)CC2)c1] | | |
| 87 | 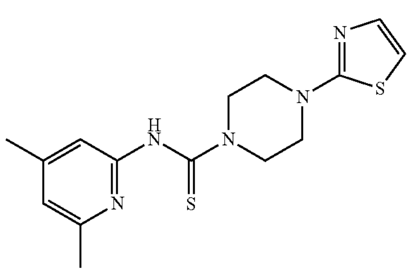 [SMILES: Cc1cc(C)nc(NC(=S)N2CCN(c3nccs3)CC2)c1] | | |

TABLE 3-continued

Exemplary compounds.

| Cmpd. No. | Structure | m/z | Calc. m/z |
|---|---|---|---|
| 89 | 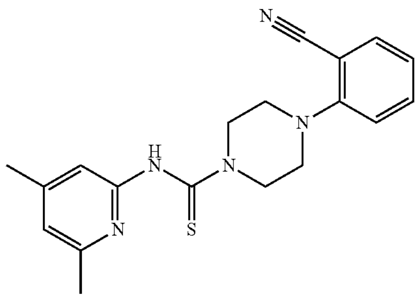 [SMILES: Cc1cc(C)nc(NC(=S)N2CCN(c3ccccc3C#N)CC2)c1] | | |
| 90 | 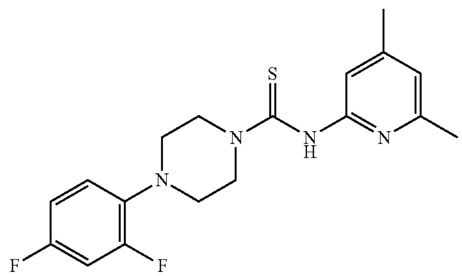 [SMILES: Cc1cc(C)nc(NC(=S)N2CCN(c3ccc(F)cc3F)CC2)c1] | | |
| 92 | 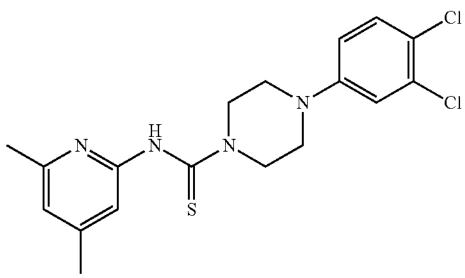 | | |
| 93 | 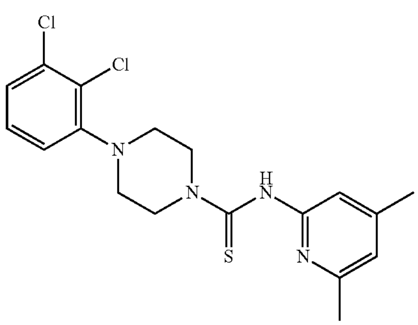 [SMILES: Cc1cc(C)nc(NC(=S)N2CCN(c3cccc(Cl)c3Cl)CC2)c1] | | |
| 94 | 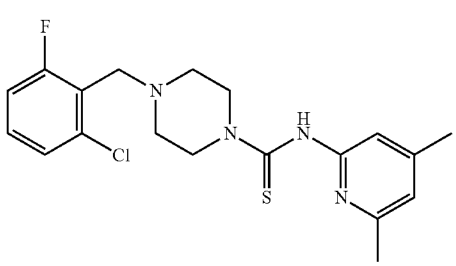 [SMILES: Cc1cc(C)nc(NC(=S)N2CCN(Cc3c(F)cccc3Cl)CC2)c1] | | |

TABLE 3-continued

Exemplary compounds.

| Cmpd. No. | Structure | m/z | Calc. m/z |
|---|---|---|---|
| 97 | 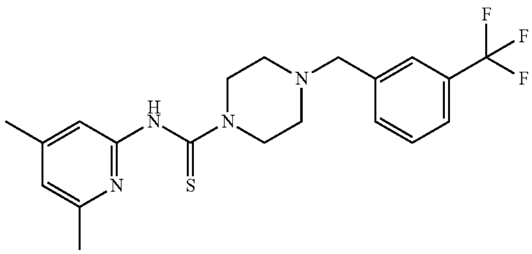 [SMILES: Cc1cc(C)nc(NC(=S)N2CCN(Cc3cccc(C(F)(F)F)c3)CC2)c1] | | |
| 100 | 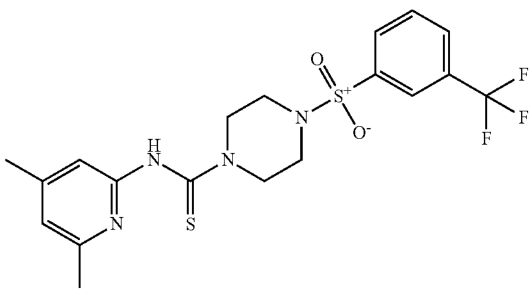 [SMILES: Cc1cc(C)nc(NC(=S)N2CCN([S+](=O)([O-])c3cccc(C(F)(F)F)c3)CC2)c1] | | |
| 101 | 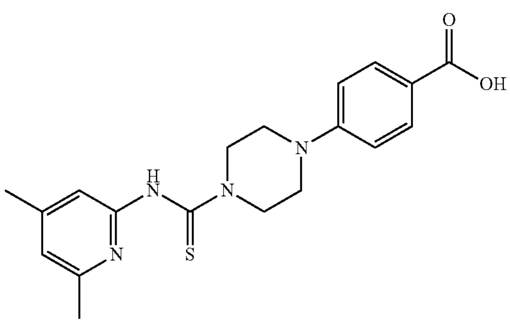 [SMILES: Cc1cc(C)nc(NC(=S)N2CCN(c3ccc(C(=O)O)cc3)CC2)c1] | | |
| 102 | 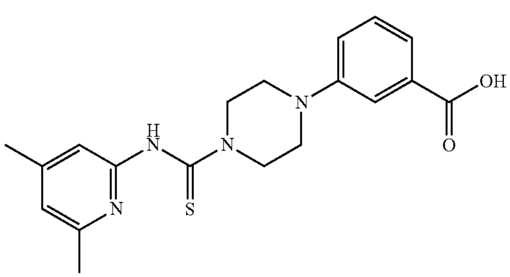 [SMILES: Cc1cc(C)nc(NC(=S)N2CCN(c3cccc(C(=O)O)c3)CC2)c1] | | |

TABLE 3-continued

Exemplary compounds.

| Cmpd. No. | Structure | m/z | Calc. m/z |
|---|---|---|---|
| 103 | 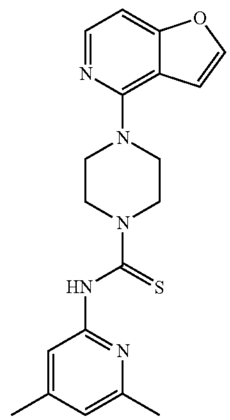 [SMILES: Cc1cc(C)nc(NC(=S)N2CCN(c3nccc4occc34)CC2)c1] | | |
| 104 | 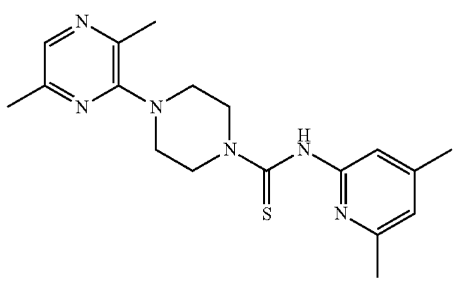 | | |
| 105 | 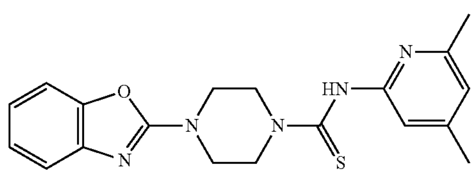 [SMILES: Cc1cc(C)nc(NC(=S)N2CCN(c3nc4ccccc4o3)CC2)c1] | | |
| 106 | 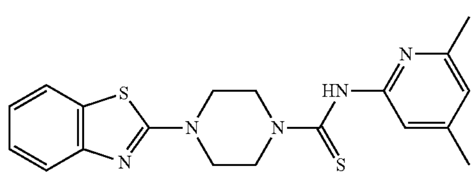 | | |
| 107 | 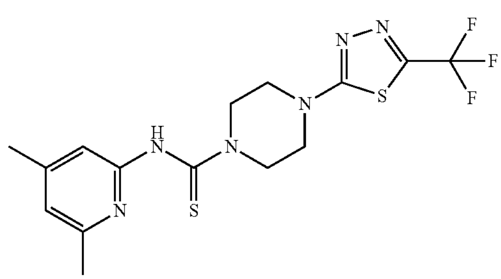 [SMILES: Cc1cc(C)nc(NC(=S)N2CCN(c3nnc(C(F)(F)F)s3)CC2)c1] | | |

TABLE 3-continued

Exemplary compounds.

| Cmpd. No. | Structure | m/z | Calc. m/z |
|---|---|---|---|
| 108 | 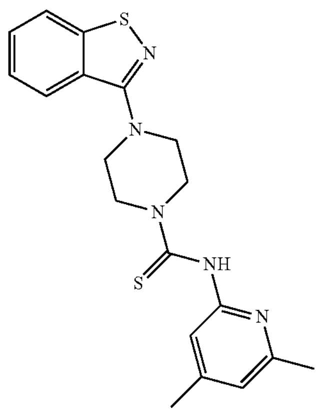 [SMILES: Cc1cc(C)nc(NC(=S)N2CCN(c3nsc4ccccc34)CC2)c1] | | |
| 109 | 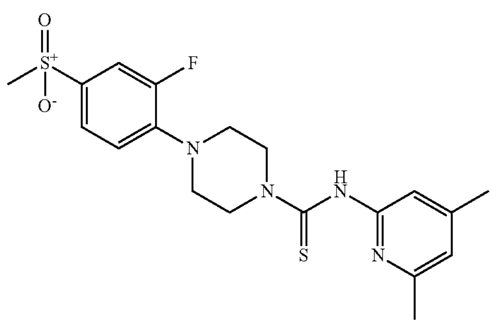 | | |
| 110 | 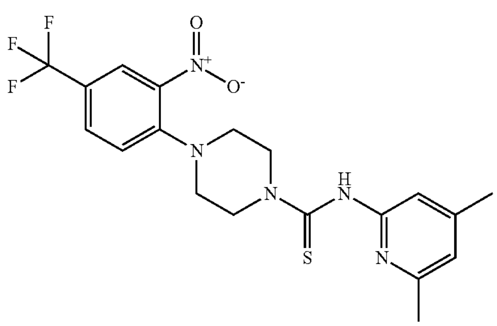 [SMILES: Cc1cc(C)nc(NC(=S)N2CCN(c3ccc(C(F)(F)F)cc3[N+](=O)[O-])CC2)c1] | | |
| 111 | 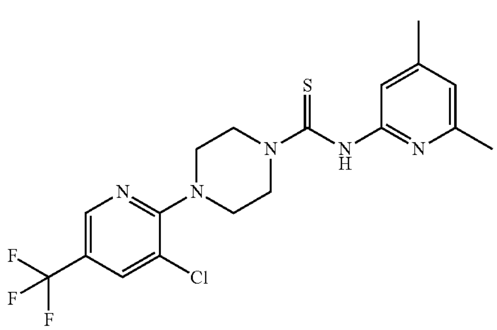 [SMILES: Cc1cc(C)nc(NC(=S)N2CCN(c3ncc(C(F)(F)F)cc3Cl)CC2)c1] | | |

TABLE 3-continued

Exemplary compounds.

| Cmpd. No. | Structure | m/z | Calc. m/z |
|---|---|---|---|
| 113 | 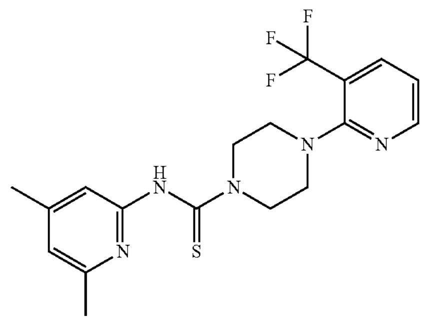 [SMILES: Cc1cc(C)nc(NC(=S)N2CCN(c3ncccc3C(F)(F)F)CC2)c1] | | |
| 115 | 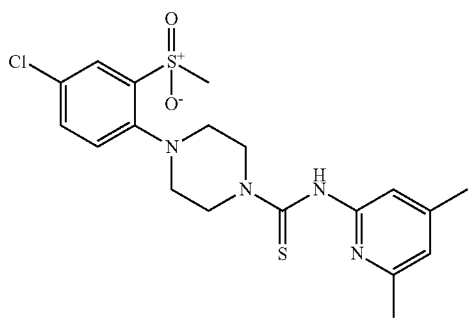 [SMILES: Cc1cc(C)nc(NC(=S)N2CCN(c3ccc(Cl)cc3[S+](C)(=O)[O-])CC2)c1] | | |
| 116 | 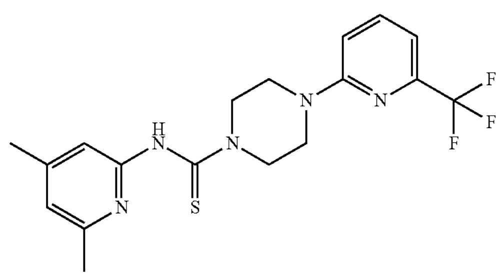 [SMILES: Cc1cc(C)nc(NC(=S)N2CCN(c3cccc(C(F)(F)F)n3)CC2)c1] | | |
| 117 | 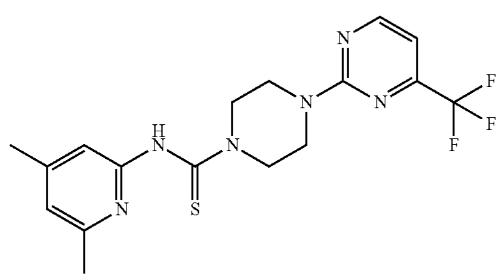 [SMILES: Cc1cc(C)nc(NC(=S)N2CCN(c3nccc(C(F)(F)F)n3)CC2)c1] | | |
| 118 | 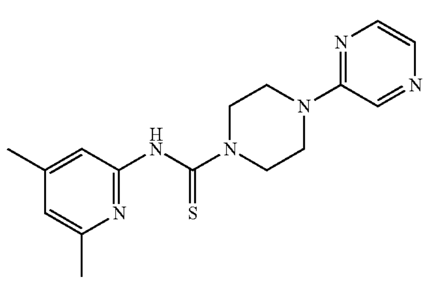 [SMILES: Cc1cc(C)nc(NC(=S)N2CCN(c3cnccn3)CC2)c1] | | |

TABLE 3-continued

Exemplary compounds.

| Cmpd. No. | Structure | m/z | Calc. m/z |
|---|---|---|---|
| 120 | 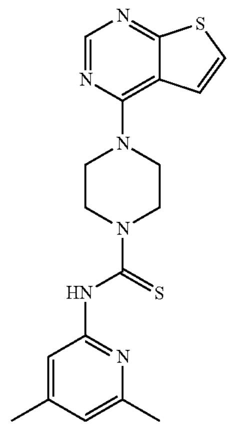 [SMILES: Cc1cc(C)nc(NC(=S)N2CCN(c3ncnc4sccc34)CC2)c1] | | |
| 121 | 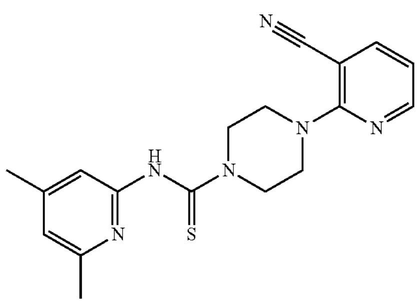 [SMILES: Cc1cc(C)nc(NC(=S)N2CCN(c3ncccc3C#N)CC2)c1] | | |
| 122 | 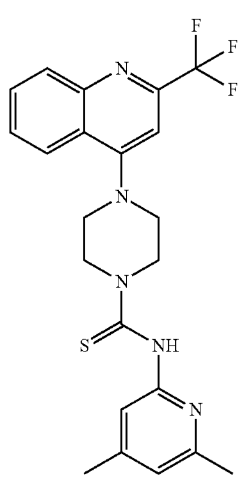 [SMILES: Cc1cc(C)nc(NC(=S)N2CCN(c3cc(C(F)(F)F)nc4ccccc34)CC2)c1] | | |

TABLE 3-continued

Exemplary compounds.

| Cmpd. No. | Structure | m/z | Calc. m/z |
|---|---|---|---|
| 123 | 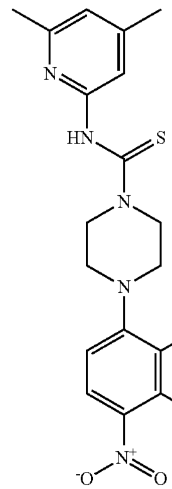 | | |
| 124 | 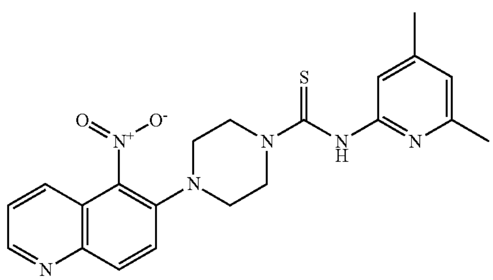 [SMILES: Cc1cc(C)nc(NC(=S)N2CCN(c3ccc4ncccc4c3[N+](=O)[O-])CC2)c1] | | |
| 129 | 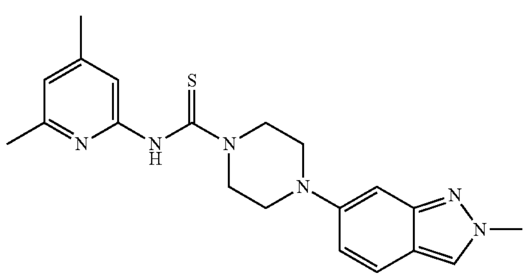 | | |
| 131 | 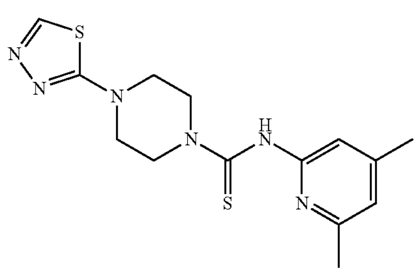 [SMILES: Cc1cc(C)nc(NC(=S)N2CCN(c3nncs3)CC2)c1] | | |

TABLE 3-continued

Exemplary compounds.

| Cmpd. No. | Structure | m/z | Calc. m/z |
|---|---|---|---|
| 133 | 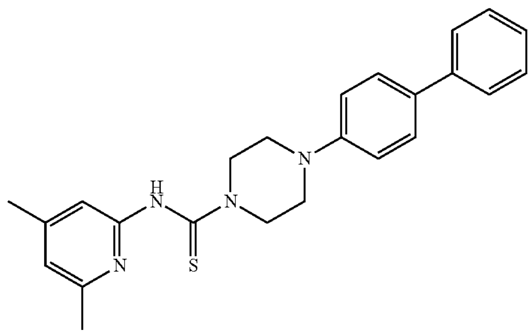 [SMILES: Cc1cc(C)nc(NC(=S)N2CCN(c3ccc(-c4ccccc4)cc3)CC2)c1] | | |
| 134 | 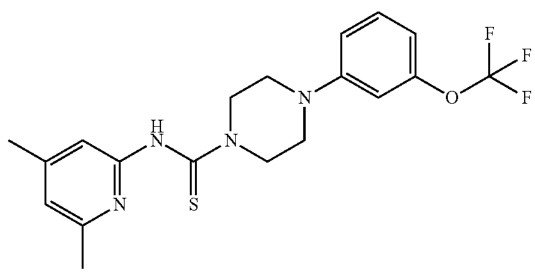 [SMILES: Cc1cc(C)nc(NC(=S)N2CCN(c3cccc(OC(F)(F)F)c3)CC2)c1] | | |
| 135 | 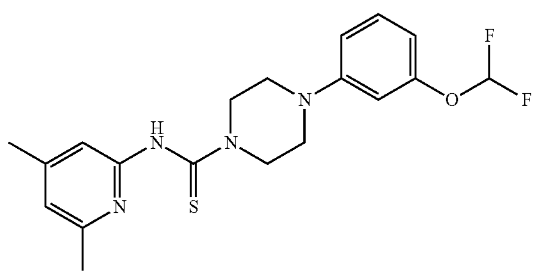 [SMILES: Cc1cc(C)nc(NC(=S)N2CCN(c3cccc(OC(F)F)c3)CC2)c1] | | |
| 136 | 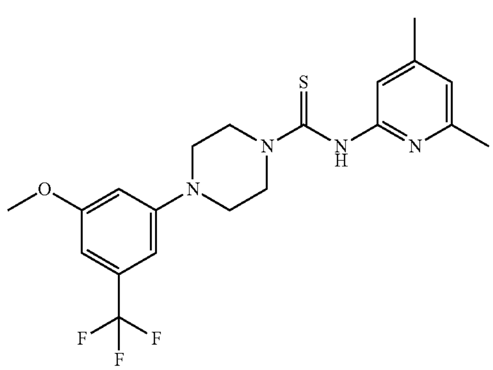 | | |

TABLE 3-continued

Exemplary compounds.

| Cmpd. No. | Structure | m/z | Calc. m/z |
|---|---|---|---|
| 137 | 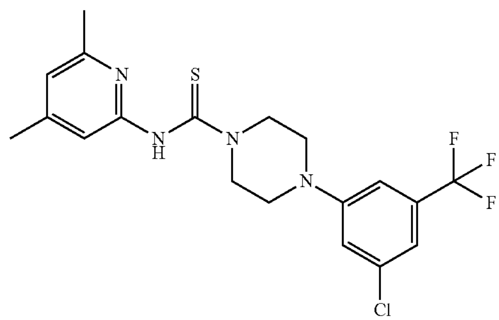 [SMILES: Cc1cc(C)nc(NC(=S)N2CCN(c3cc(Cl)cc(C(F)(F)F)c3)CC2)c1] | | |
| 139 | 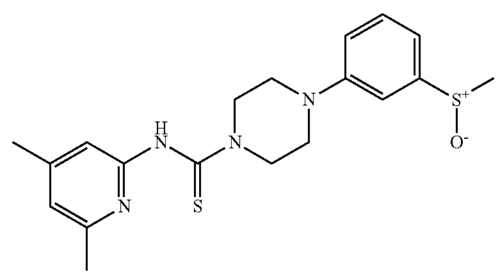 | | |
| 140 | 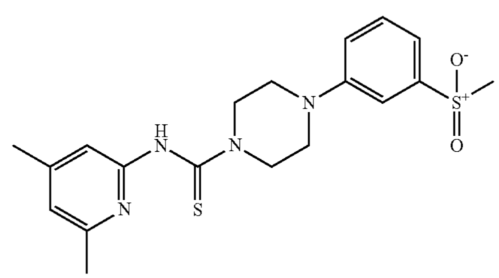 | | |
| 141 | 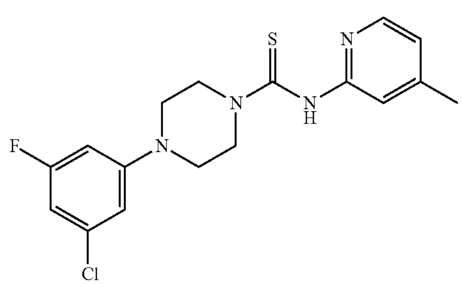 [SMILES: Cc1ccnc(NC(=S)N2CCN(c3cc(F)cc(Cl)c3)CC2)c1] | | |
| 142 | 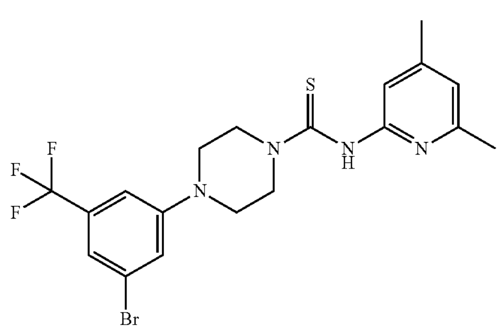 [SMILES: Cc1cc(C)nc(NC(=S)N2CCN(c3cc(Br)cc(C(F)(F)F)c3)CC2)c1] | | |

TABLE 3-continued

Exemplary compounds.

| Cmpd. No. | Structure | m/z | Calc. m/z |
|---|---|---|---|
| 145 | 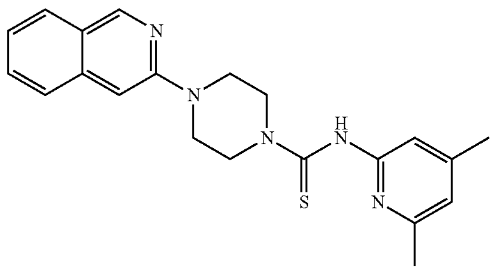 [SMILES: Cc1cc(C)nc(NC(=S)N2CCN(c3cc4ccccc4cn3)CC2)c1] | | |
| 147 | 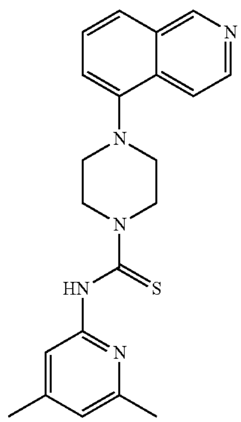 [SMILES: Cc1cc(C)nc(NC(=S)N2CCN(c3cccc4cnccc34)CC2)c1] | | |
| 148 | 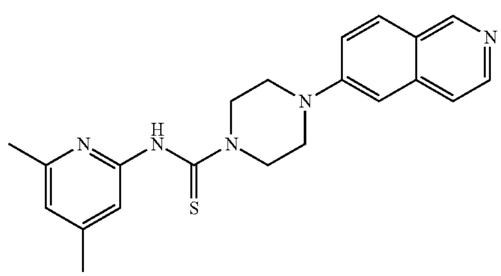 [SMILES: Cc1cc(C)nc(NC(=S)N2CCN(c3ccc4cnccc4c3)CC2)c1] | | |
| 149 | 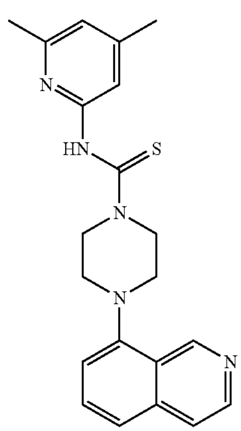 [SMILES: Cc1cc(C)nc(NC(=S)N2CCN(c3cccc4ccncc34)CC2)c1] | | |

TABLE 3-continued

Exemplary compounds.

| Cmpd. No. | Structure | m/z | Calc. m/z |
|---|---|---|---|
| 150 | 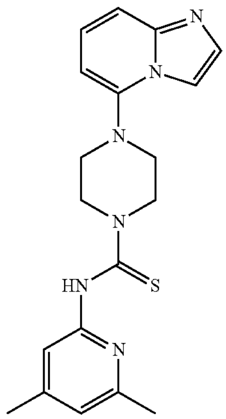 [SMILES: Cc1cc(C)nc(NC(=S)N2CCN(c3cccc4nccn34)CC2)c1] | | |
| 151 | 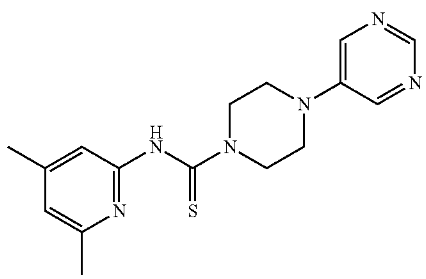 [SMILES: Cc1cc(C)nc(NC(=S)N2CCN(c3cncnc3)CC2)c1] | | |
| 152 | 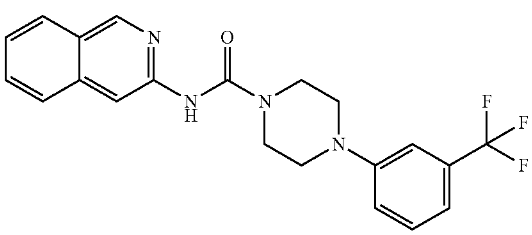 [SMILES: O=C(Nc1cc2ccccc2cn1)N1CCN(c2cccc(C(F)(F)F)c2)CC1] | | |
| 153 | 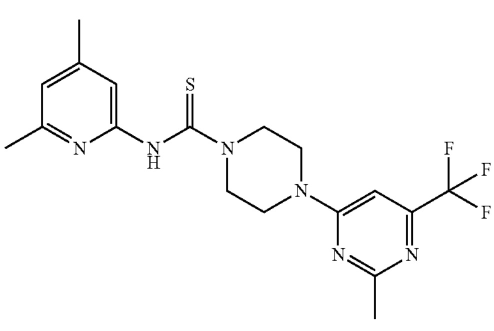 [SMILES: Cc1cc(C)nc(NC(=S)N2CCN(c3cc(C(F)(F)F)nc(C)n3)CC2)c1] | | |

TABLE 3-continued

Exemplary compounds.

| Cmpd. No. | Structure | m/z | Calc. m/z |
|---|---|---|---|
| 154 | 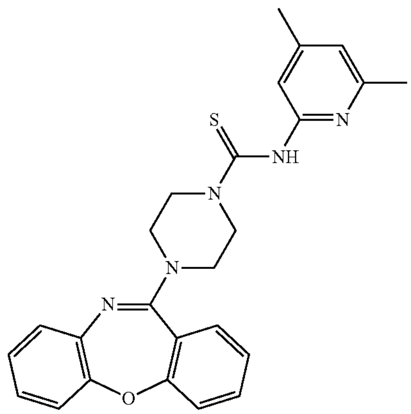 [SMILES: Cc1cc(C)nc(NC(=S)N2CCN(C3=Nc4ccccc4Oc4ccccc43)CC2)c1] | | |
| 155 | 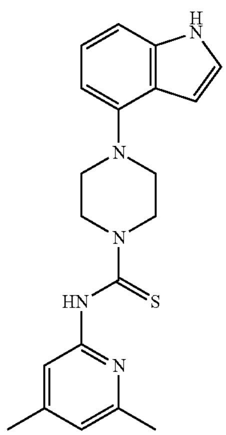 [SMILES: Cc1cc(C)nc(NC(=S)N2CCN(c3cccc4[nH]ccc34)CC2)c1] | | |
| 156 | 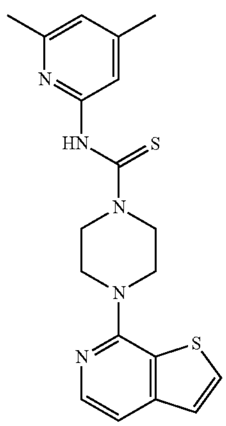 [SMILES: Cc1cc(C)nc(NC(=S)N2CCN(c3nccc4ccsc34)CC2)c1] | | |
| 157 | 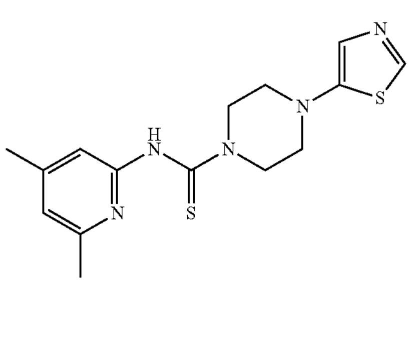 [SMILES: Cc1cc(C)nc(NC(=S)N2CCN(c3cncs3)CC2)c1] | | |

TABLE 3-continued
Exemplary compounds.
| Cmpd. No. | Structure | m/z | Calc. m/z |
|---|---|---|---|
| 159 | 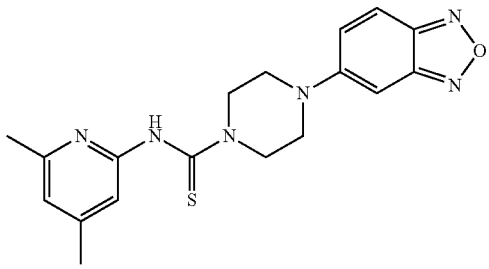 [SMILES: Cc1cc(C)nc(NC(=S)N2CCN(c3ccc4nonc4c3)CC2)c1] | | |
| 160 | 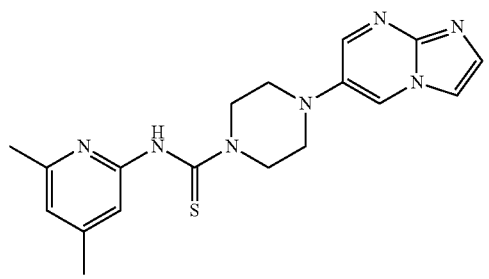 [SMILES: Cc1cc(C)nc(NC(=S)N2CCN(c3cnc4nccn4c3)CC2)c1] | | |
| 161 | 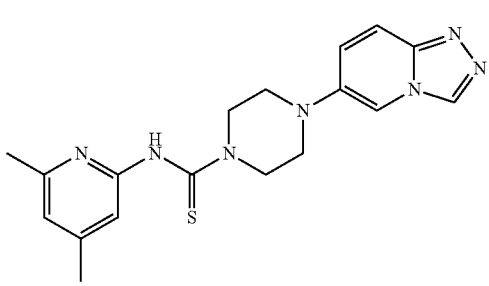 [SMILES: Cc1cc(C)nc(NC(=S)N2CCN(c3ccc4nncn4c3)CC2)c1] | | |
| 162 | 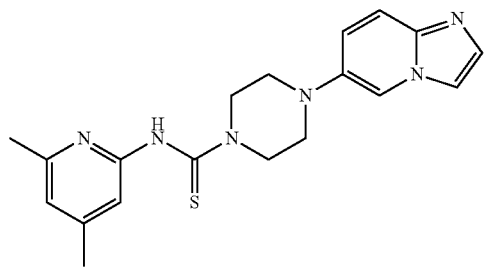 [SMILES: Cc1cc(C)nc(NC(=S)N2CCN(c3ccc4nccn4c3)CC2)c1] | | |
| 163 | 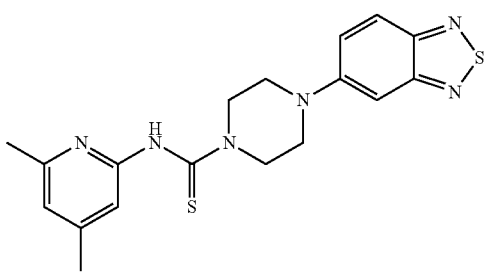 [SMILES: Cc1cc(C)nc(NC(=S)N2CCN(c3ccc4nsnc4c3)CC2)c1] | | |

TABLE 3-continued

Exemplary compounds.

| Cmpd. No. | Structure | m/z | Calc. m/z |
|---|---|---|---|
| 164 | 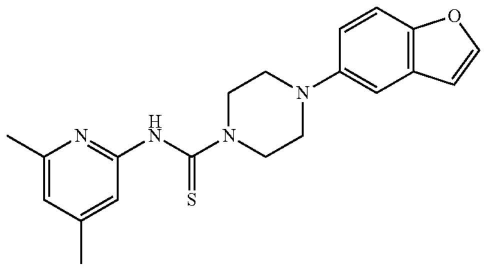 [SMILES: Cc1cc(C)nc(NC(=S)N2CCN(c3ccc4occc4c3)CC2)c1] | | |
| 165 | 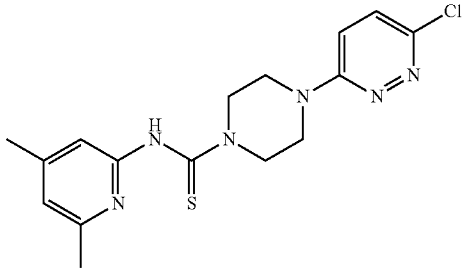 [SMILES: Cc1cc(C)nc(NC(=S)N2CCN(c3ccc(Cl)nn3)CC2)c1] | | |
| 166 | 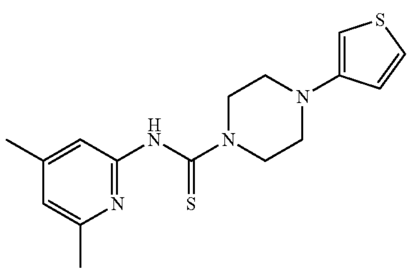 [SMILES: Cc1cc(C)nc(NC(=S)N2CCN(c3ccsc3)CC2)c1] | | |
| 167 | 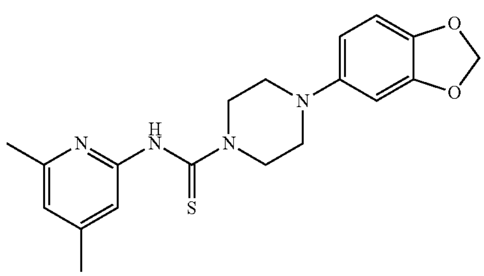 [SMILES: Cc1cc(C)nc(NC(=S)N2CCN(c3ccc4c(c3)OCO4)CC2)c1] | | |
| 168 | 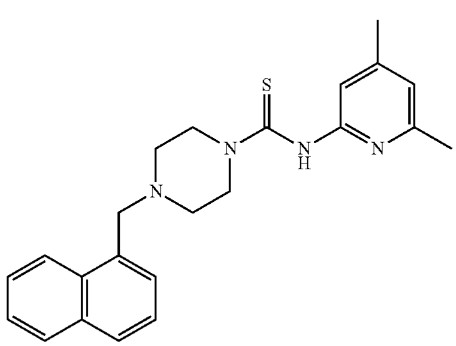 [SMILES: Cc1cc(C)nc(NC(=S)N2CCN(Cc3cccc4ccccc34)CC2)c1] | | |

TABLE 3-continued

Exemplary compounds.

| Cmpd. No. | Structure | m/z | Calc. m/z |
|---|---|---|---|
| 169 | 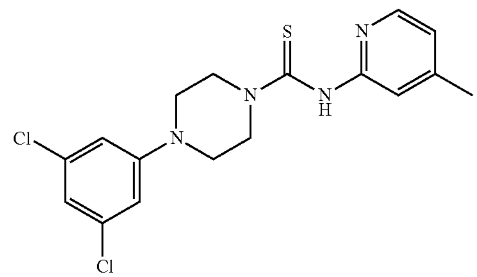 [SMILES: Cc1ccnc(NC(=S)N2CCN(c3cc(Cl)cc(Cl)c3)CC2)c1] | | |
| 170 | 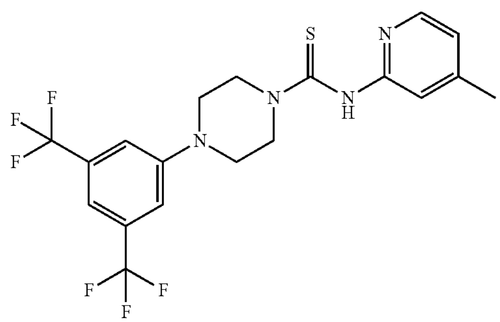 [SMILES: Cc1ccnc(NC(=S)N2CCN(c3cc(C(F)(F)F)cc(C(F)(F)F)c3)CC2)c1] | | |
| 171 | 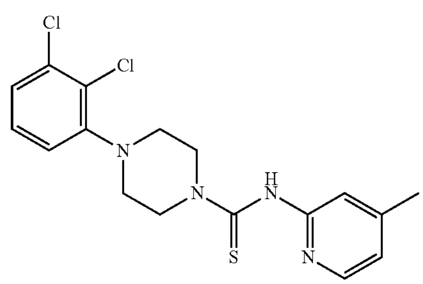 [SMILES: Cc1ccnc(NC(=S)N2CCN(c3cccc(Cl)c3Cl)CC2)c1] | | |
| 172 | 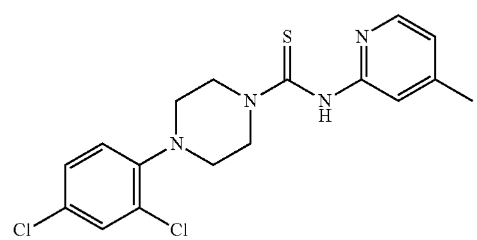 [SMILES: Cc1ccnc(NC(=S)N2CCN(c3ccc(Cl)cc3Cl)CC2)c1] | | |
| 173 | 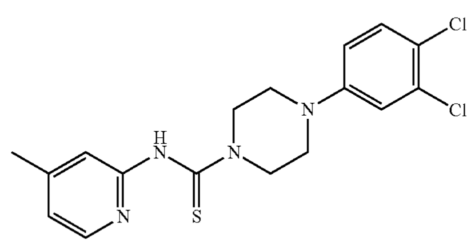 [SMILES: Cc1ccnc(NC(=S)N2CCN(c3ccc(Cl)c(Cl)c3)CC2)c1] | | |

TABLE 3-continued

Exemplary compounds.

| Cmpd. No. | Structure | m/z | Calc. m/z |
|---|---|---|---|
| 174 | 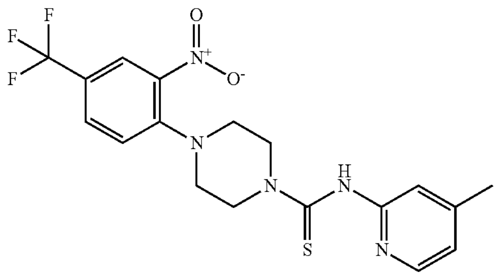 [SMILES: Cc1ccnc(NC(=S)N2CCN(c3ccc(C(F)(F)F)cc3[N+](=O)[O-])CC2)c1] | | |
| 175 | 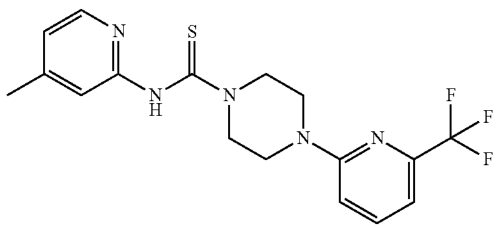 [SMILES: Cc1ccnc(NC(=S)N2CCN(c3cccc(C(F)(F)F)n3)CC2)c1] | | |
| 176 | 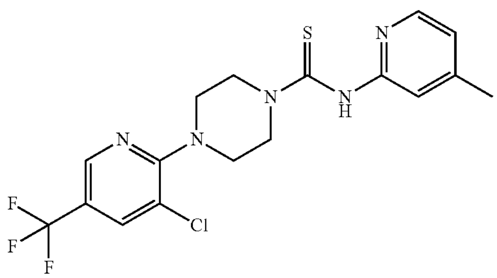 [SMILES: Cc1ccnc(NC(=S)N2CCN(c3ncc(C(F)(F)F)cc3Cl)CC2)c1] | | |
| 177 | 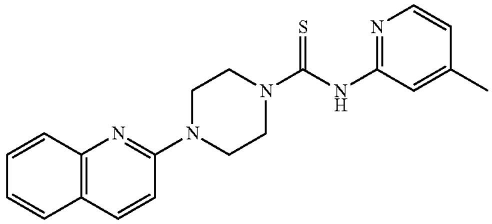 [SMILES: Cc1ccnc(NC(=S)N2CCN(c3ccc4ccccc4n3)CC2)c1] | | |
| 178 | 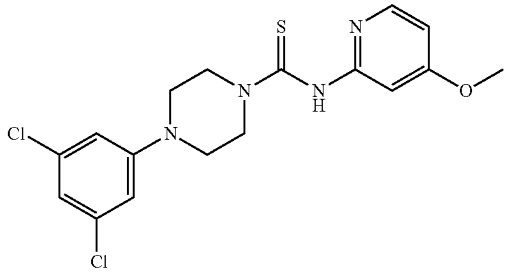 [SMILES: COc1ccnc(NC(=S)N2CCN(c3cc(Cl)cc(Cl)c3)CC2)c1] | | |

TABLE 3-continued

Exemplary compounds.

| Cmpd. No. | Structure | m/z | Calc. m/z |
|---|---|---|---|
| 179 | 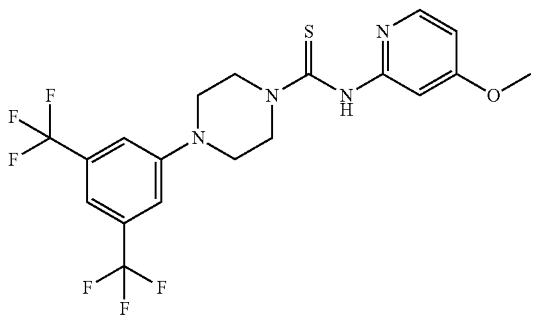 [SMILES: COc1ccnc(NC(=S)N2CCN(c3cc(C(F)(F)F)cc(C(F)(F)F)c3)CC2)c1] | | |
| 180 | 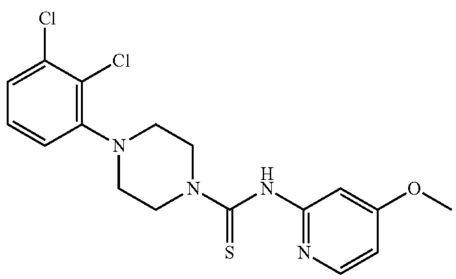 [SMILES: COc1ccnc(NC(=S)N2CCN(c3cccc(Cl)c3Cl)CC2)c1] | | |
| 181 | 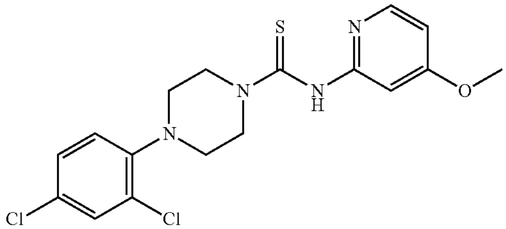 [SMILES: COc1ccnc(NC(=S)N2CCN(c3ccc(Cl)cc3Cl)CC2)c1] | | |
| 182 | 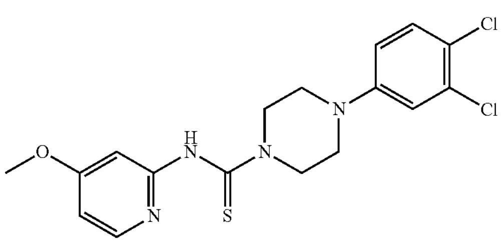 [SMILES: COc1ccnc(NC(=S)N2CCN(c3ccc(Cl)c(Cl)c3)CC2)c1] | | |
| 183 | 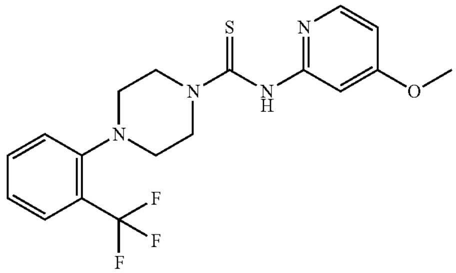 [SMILES: COc1ccnc(NC(=S)N2CCN(c3ccccc3C(F)(F)F)CC2)c1] | | |

TABLE 3-continued

Exemplary compounds.

| Cmpd. No. | Structure | m/z | Calc. m/z |
|---|---|---|---|
| 184 | 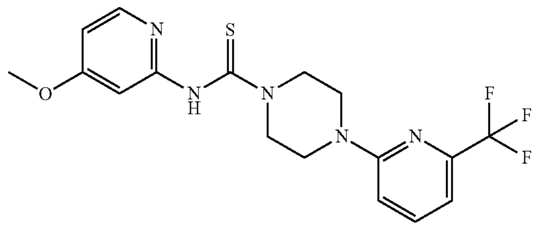 [SMILES: COc1ccnc(NC(=S)N2CCN(c3cccc(C(F)(F)F)n3)CC2)c1] | | |
| 185 | 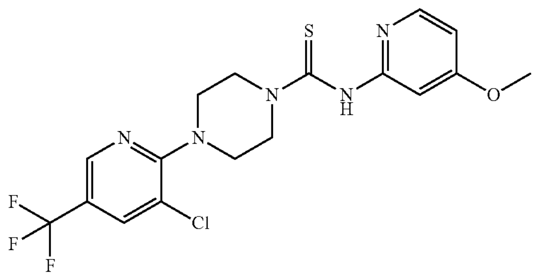 [SMILES: COc1ccnc(NC(=S)N2CCN(c3ncc(C(F)(F)F)cc3Cl)CC2)c1] | | |
| 186 | 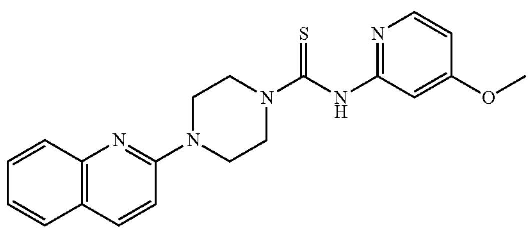 [SMILES: COc1ccnc(NC(=S)N2CCN(c3ccc4ccccc4n3)CC2)c1] | | |
| 187 | 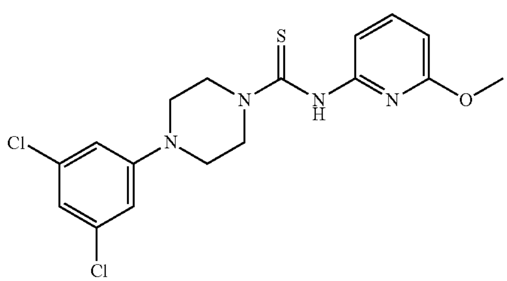 [SMILES: COc1cccc(NC(=S)N2CCN(c3cc(Cl)cc(Cl)c3)CC2)n1] | | |
| 188 | 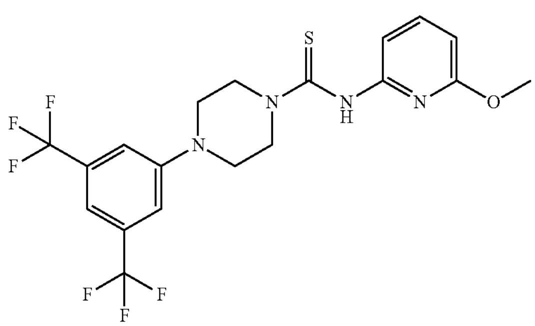 [SMILES: COc1cccc(NC(=S)N2CCN(c3cc(C(F)(F)F)cc(C(F)(F)F)c3)CC2)n1] | | |

TABLE 3-continued

Exemplary compounds.

| Cmpd. No. | Structure | m/z | Calc. m/z |
|---|---|---|---|
| 189 | 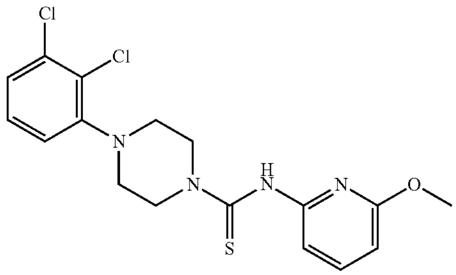 [SMILES: COc1cccc(NC(=S)N2CCN(c3cccc(Cl)c3Cl)CC2)n1] | | |
| 190 | 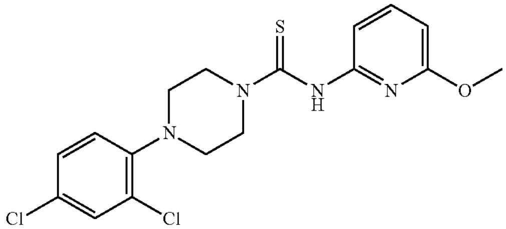 [SMILES: COc1cccc(NC(=S)N2CCN(c3ccc(Cl)cc3Cl)CC2)n1] | | |
| 191 | 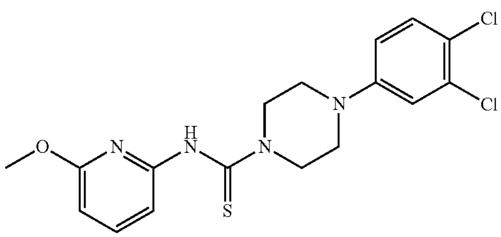 [SMILES: COc1cccc(NC(=S)N2CCN(c3ccc(Cl)c(Cl)c3)CC2)n1] | | |
| 192 | 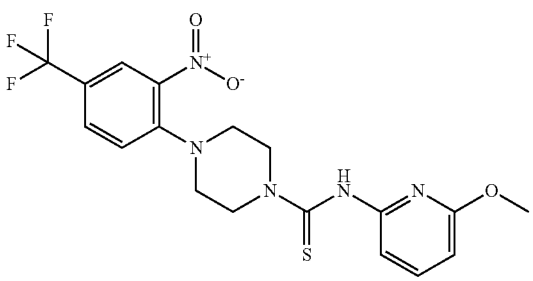 [SMILES: COc1cccc(NC(=S)N2CCN(c3ccc(C(F)(F)F)cc3[N+](=O)[O-])CC2)n1] | | |
| 193 | 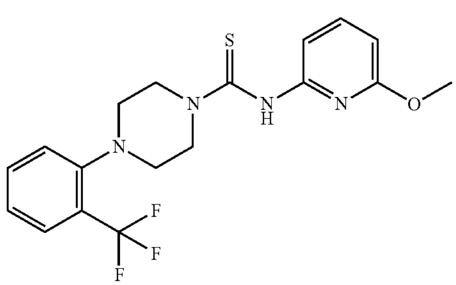 [SMILES: COc1cccc(NC(=S)N2CCN(c3ccccc3C(F)(F)F)CC2)n1] | | |
| 194 | 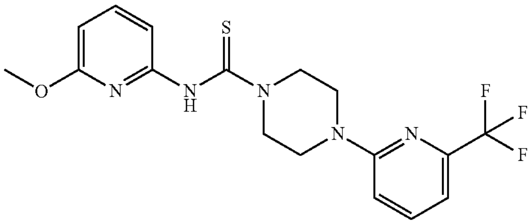 [SMILES: COc1cccc(NC(=S)N2CCN(c3cccc(C(F)(F)F)n3)CC2)n1] | | |

TABLE 3-continued

Exemplary compounds.

| Cmpd. No. | Structure | m/z | Calc. m/z |
|---|---|---|---|
| 195 | 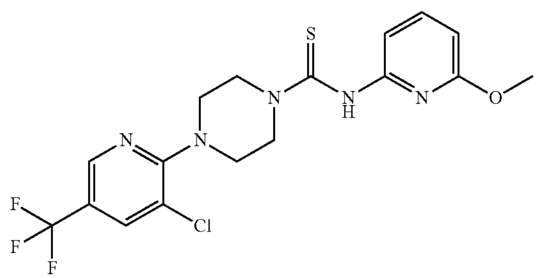 [SMILES: COc1cccc(NC(=S)N2CCN(c3ncc(C(F)(F)F)cc3Cl)CC2)n1] | | |
| 196 | 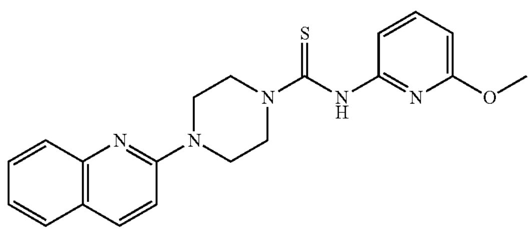 [SMILES: COc1cccc(NC(=S)N2CCN(c3ccc4ccccc4n3)CC2)n1] | | |
| 197 | 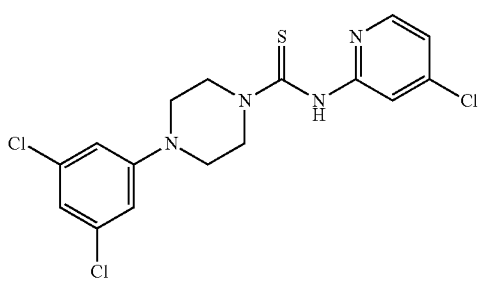 [SMILES: S=C(Nc1cc(Cl)ccn1)N1CCN(c2cc(Cl)cc(Cl)c2)CC1] | | |
| 198 | 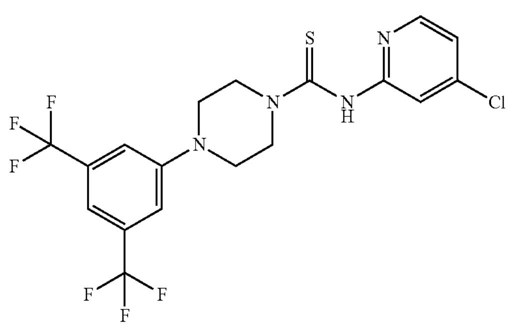 [SMILES: FC(F)(F)c1cc(N2CCN(C(=S)Nc3cc(Cl)ccn3)CC2)cc(C(F)(F)F)c1] | | |
| 199 | 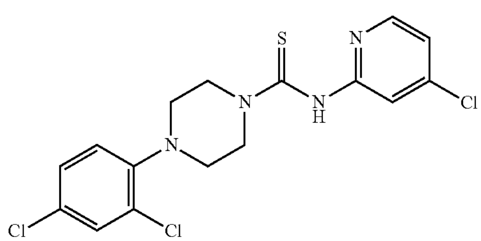 [SMILES: S=C(Nc1cc(Cl)ccn1)N1CCN(c2ccc(Cl)cc2Cl)CC1] | | |

TABLE 3-continued

Exemplary compounds.

| Cmpd. No. | Structure | m/z | Calc. m/z |
|---|---|---|---|
| 200 | 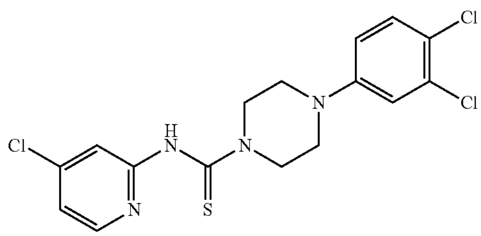 [SMILES: S=C(Nc1cc(Cl)ccn1)N1CCN(c2ccc(Cl)c(Cl)c2)CC1] | | |
| 201 | 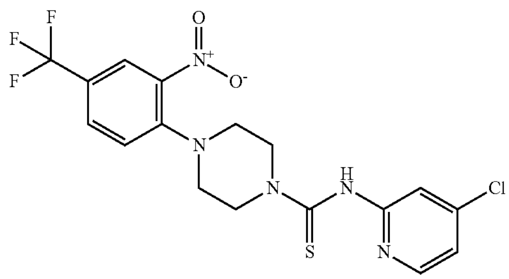 [SMILES: O=[N+]([O-])c1cc(C(F)(F)F)ccc1N1CCN(C(=S)Nc2cc(Cl)ccn2)CC1] | | |
| 202 | 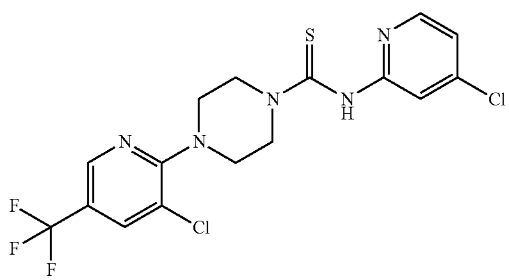 [SMILES: FC(F)(F)c1cnc(N2CCN(C(=S)Nc3cc(Cl)ccn3)CC2)c(Cl)c1] | | |
| 203 | 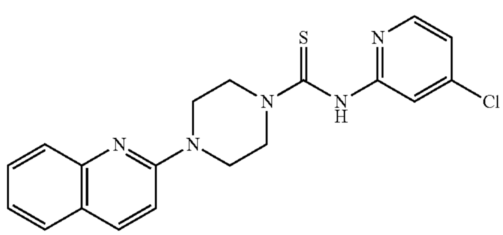 [SMILES: S=C(Nc1cc(Cl)ccn1)N1CCN(c2ccc3ccccc3n2)CC1] | | |
| 205 | 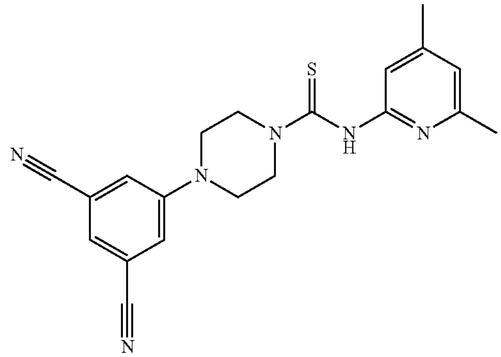 [SMILES: Cc1cc(C)nc(NC(=S)N2CCN(c3cc(C#N)cc(C#N)c3)CC2)c1] | | |

TABLE 3-continued

Exemplary compounds.

| Cmpd. No. | Structure | m/z | Calc. m/z |
|---|---|---|---|
| 206 | 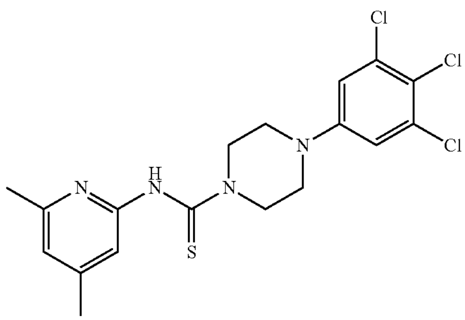 [SMILES: Cc1cc(C)nc(NC(=S)N2CCN(c3cc(Cl)c(Cl)c(Cl)c3)CC2)c1] | | |
| 207 | 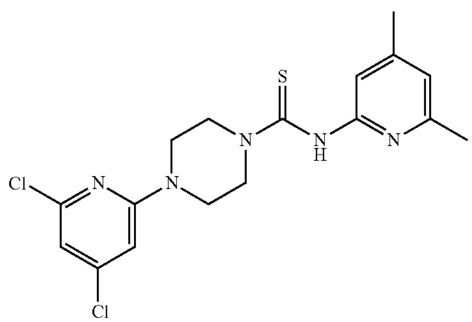 [SMILES: Cc1cc(C)nc(NC(=S)N2CCN(c3cc(Cl)cc(Cl)n3)CC2)c1] | | |
| 208 | 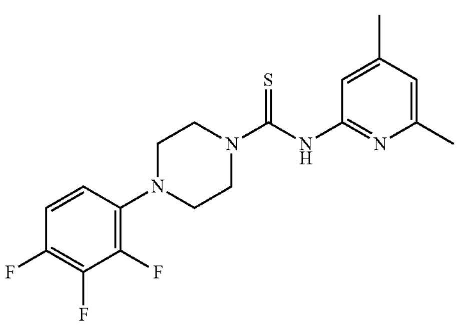 [SMILES: Cc1cc(C)nc(NC(=S)N2CCN(c3ccc(F)c(F)c3F)CC2)c1] | | |
| 209 | 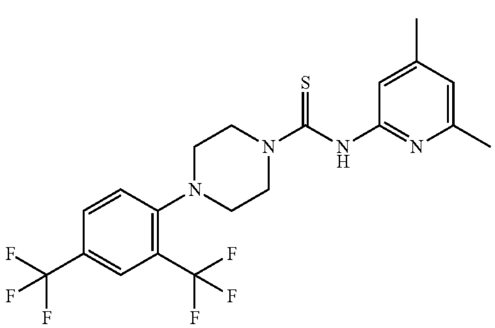 [SMILES: Cc1cc(C)nc(NC(=S)N2CCN(c3ccc(C(F)(F)F)cc3C(F)(F)F)CC2)c1] | | |

TABLE 3-continued

Exemplary compounds.

| Cmpd. No. | Structure | m/z | Calc. m/z |
|---|---|---|---|
| 210 | 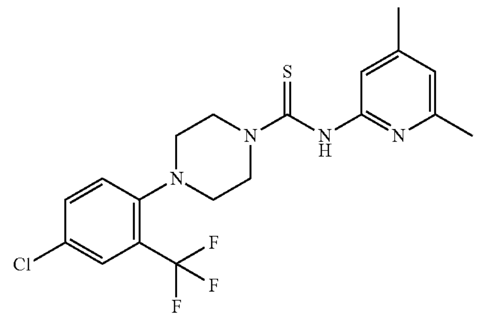 [SMILES: Cc1cc(C)nc(NC(=S)N2CCN(c3ccc(Cl)cc3C(F)(F)F)CC2)c1] | | |
| 211 | 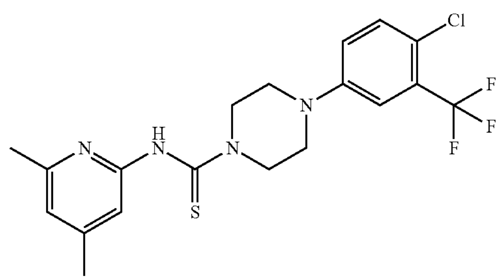 [SMILES: Cc1cc(C)nc(NC(=S)N2CCN(c3ccc(Cl)c(C(F)(F)F)c3)CC2)c1] | | |
| 212 | 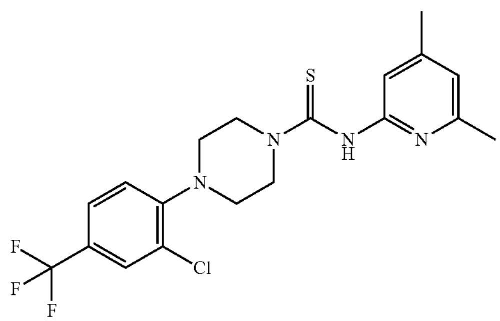 [SMILES: Cc1cc(C)nc(NC(=S)N2CCN(c3ccc(C(F)(F)F)cc3Cl)CC2)c1] | | |
| 213 | 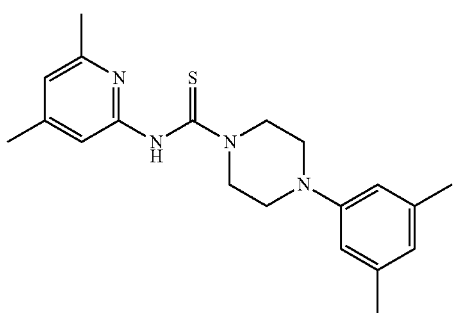 | | |
| 214 | 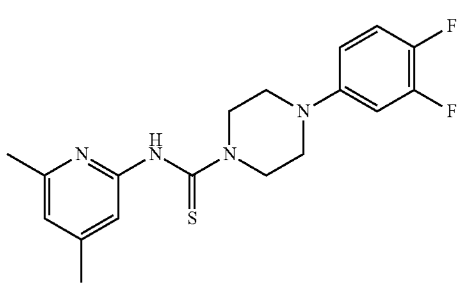 [SMILES: Cc1cc(C)nc(NC(=S)N2CCN(c3ccc(F)c(F)c3)CC2)c1] | | |

TABLE 3-continued

Exemplary compounds.

| Cmpd. No. | Structure | m/z | Calc. m/z |
|---|---|---|---|
| 215 | 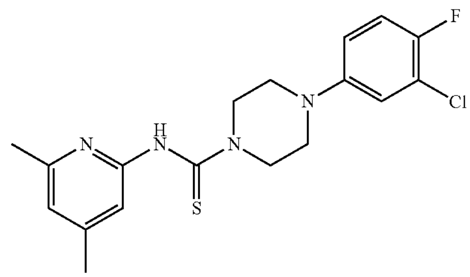 [SMILES: Cc1cc(C)nc(NC(=S)N2CCN(c3ccc(F)c(Cl)c3)CC2)c1] | | |
| 216 | 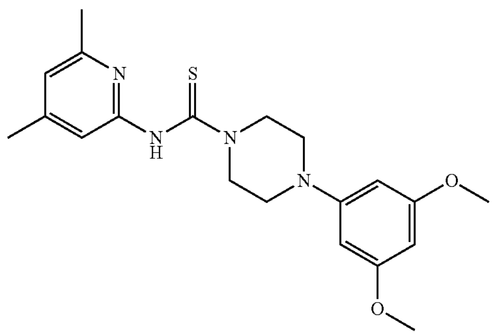 | | |
| 217 | 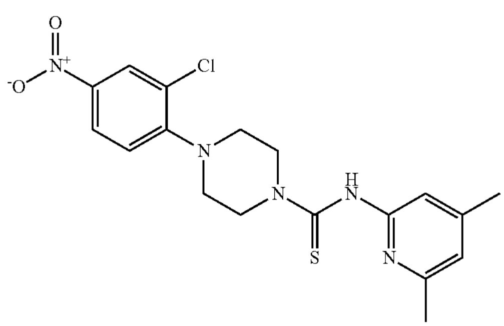 | | |
| 218 | 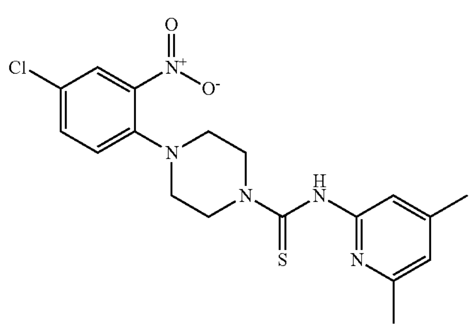 [SMILES: Cc1cc(C)nc(NC(=S)N2CCN(c3ccc(Cl)cc3[N+](=O)[O-])CC2)c1] | | |
| 219 | 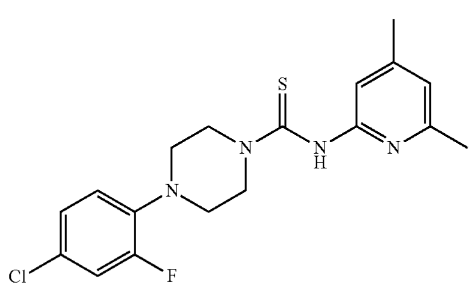 [SMILES: Cc1cc(C)nc(NC(=S)N2CCN(c3ccc(Cl)cc3F)CC2)c1] | | |

TABLE 3-continued

Exemplary compounds.

| Cmpd. No. | Structure | m/z | Calc. m/z |
|---|---|---|---|
| 220 | 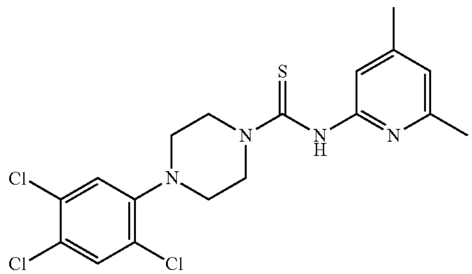 [SMILES: Cc1cc(C)nc(NC(=S)N2CCN(c3cc(Cl)c(Cl)cc3Cl)CC2)c1] | | |
| 221 | 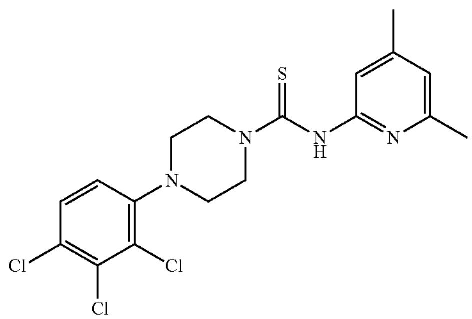 [SMILES: Cc1cc(C)nc(NC(=S)N2CCN(c3ccc(Cl)c(Cl)c3Cl)CC2)c1] | | |
| 226 | 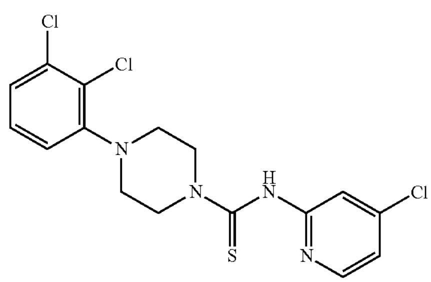 [SMILES: S=C(Nc1cc(Cl)ccn1)N1CCN(c2cccc(Cl)c2Cl)CC1] | | |
| 250 | (NCGC00351759) | 409.1682 | 409.1668 |
| 251 | 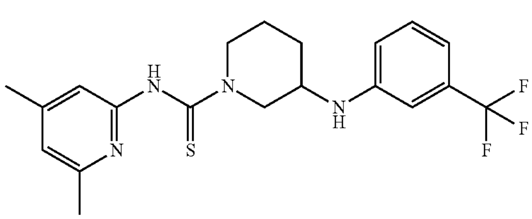 [SMILES: Cc1cc(C)nc(NC(=S)N2CCCC(Nc3cccc(C(F)(F)F)c3)C2)c1] | 409.1677 | 409.1668 |

TABLE 3-continued

Exemplary compounds.

| Cmpd. No. | Structure | m/z | Calc. m/z |
|---|---|---|---|
| 252 | 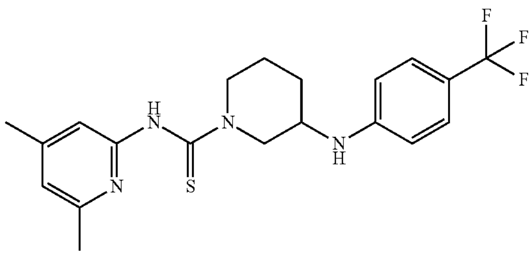 [SMILES: Cc1cc(C)nc(NC(=S)N2CCCC(Nc3ccc(C(F)(F)F)cc3)C2)c1] | 409.1660 | 409.1668 |
| 253 | 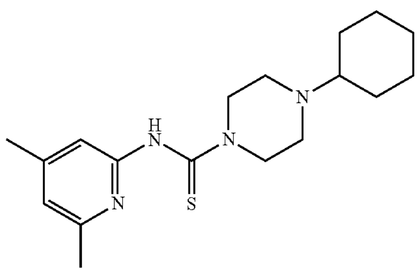 [SMILES: Cc1cc(C)nc(NC(=S)N2CCN(C3CCCCC3)CC2)c1] | 333.2101 | 333.2107 |
| 254 | 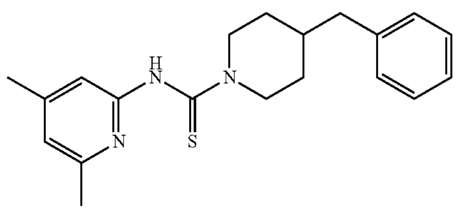 | 340.1855 | 340.1842 |
| 255 | 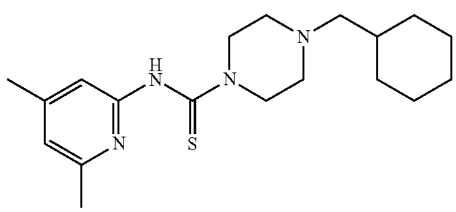 [SMILES: Cc1cc(C)nc(NC(=S)N2CCN(CC3CCCCC3)CC2)c1] | 347.2274 | 347.2264 |
| 256 | 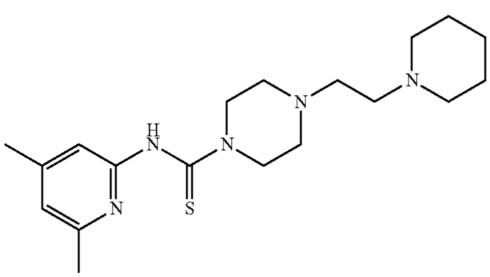 [SMILES: Cc1cc(C)nc(NC(=S)N2CCN(CCN3CCCCC3)CC2)c1] | 362.2369 | 362.2373 |
| 257 | 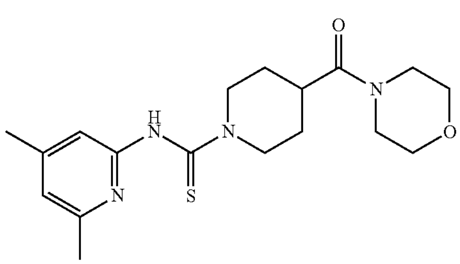 [SMILES: Cc1cc(C)nc(NC(=S)N2CCC(C(=O)N3CCOCC3)CC2)c1] | 363.1861 | 363.1849 |

TABLE 3-continued

Exemplary compounds.

| Cmpd. No. | Structure | m/z | Calc. m/z |
|---|---|---|---|
| 258 | 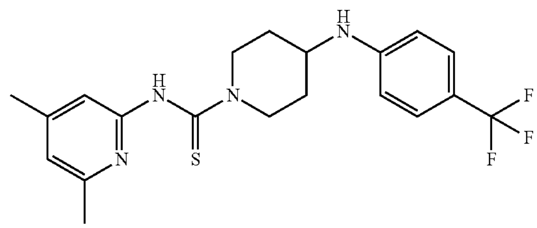 [SMILES: Cc1cc(C)nc(NC(=S)N2CCC(Nc3ccc(C(F)(F)F)cc3)CC2)c1] | 409.1686 | 409.1668 |
| 259 | 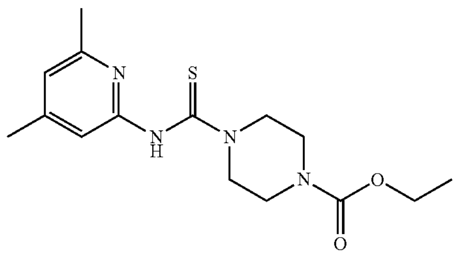 [SMILES: CCOC(=O)N1CCN(C(=S)Nc2cc(C)cc(C)n2)CC1] | 323.1531 | 323.1536 |
| 260 | 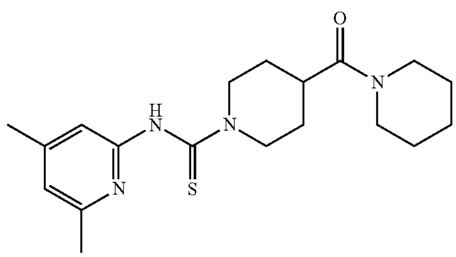 [SMILES: Cc1cc(C)nc(NC(=S)N2CCC(C(=O)N3CCCCC3)CC2)c1] | 361.2058 | 361.2057 |
| 261 | 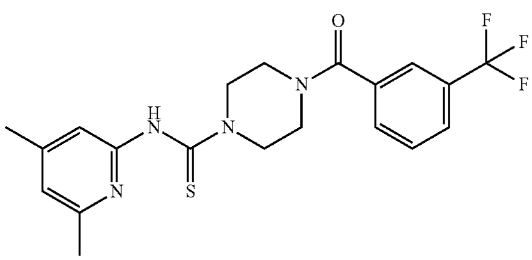 [SMILES: Cc1cc(C)nc(NC(=S)N2CCN(C(=O)c3cccc(C(F)(F)F)c3)CC2)c1] | 423.1471 | 423.1461 |
| 262 | 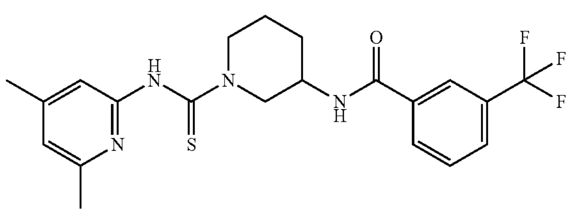 [SMILES: Cc1cc(C)nc(NC(=S)N2CCCC(NC(=O)c3cccc(C(F)(F)F)c3)C2)c1] | 437.1631 | 437.1617 |
| 263 | 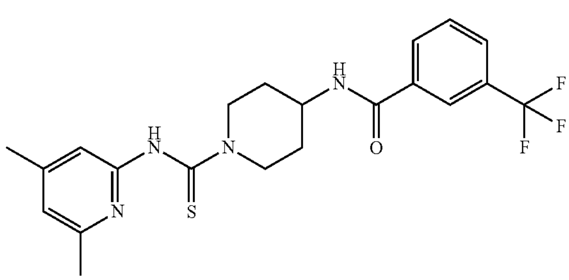 [SMILES: Cc1cc(C)nc(NC(=S)N2CCC(NC(=O)c3cccc(C(F)(F)F)c3)CC2)c1] | 437.1636 | 437.1617 |

TABLE 3-continued

Exemplary compounds.

| Cmpd. No. | Structure | m/z | Calc. m/z |
|---|---|---|---|
| 264 | 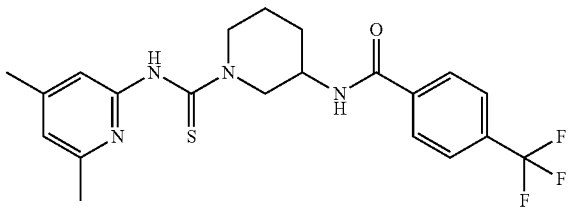 [SMILES: Cc1cc(C)nc(NC(=S)N2CCCC(NC(=O)c3ccc(C(F)(F)F)cc3)C2)c1] | 437.1622 | 437.1617 |
| 265 | (NCGC00351951) | 423.1464 | 423.1461 |
| 266 | 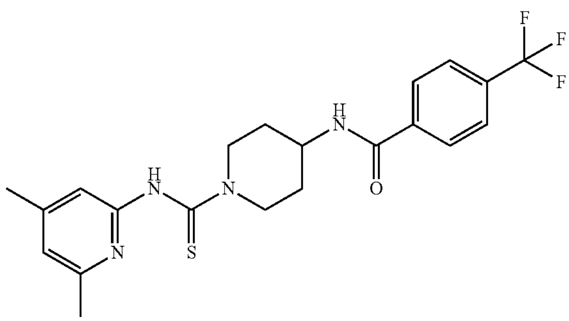 [SMILES: Cc1cc(C)nc(NC(=S)N2CCC(NC(=O)c3ccc(C(F)(F)F)cc3)CC2)c1] | 437.1609 | 437.1617 |
| 267 | (NCT-503) | 409.1671 | 409.1668 |
| 269 | 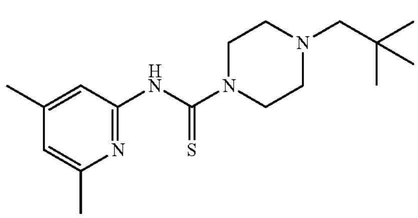 [SMILES: Cc1cc(C)nc(NC(=S)N2CCN(CC(C)(C)C)CC2)c1] | 321.2118 | 321.2107 |
| 270 | 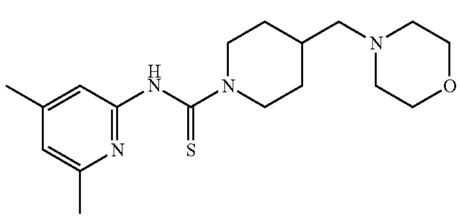 [SMILES: Cc1cc(C)nc(NC(=S)N2CCC(CN3CCOCC3)CC2)c1] | 349.2046 | 349.2057 |

TABLE 3-continued

Exemplary compounds.

| Cmpd. No. | Structure | m/z | Calc. m/z |
|---|---|---|---|
| 271 | 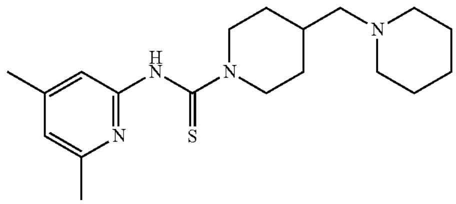 [SMILES: Cc1cc(C)nc(NC(=S)N2CCC(CN3CCCCC3)CC2)c1] | 347.2264 | 347.2264 |
| 272 | 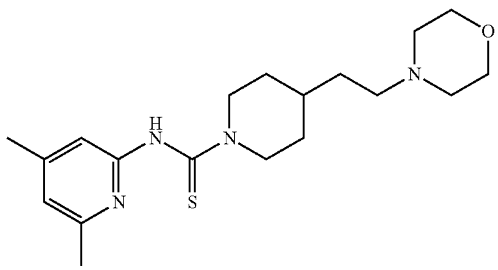 [SMILES: Cc1cc(C)nc(NC(=S)N2CCC(CCN3CCOCC3)CC2)c1] | 364.2183 | 364.2166 |
| 273 | (NCGC00356258) | 485.1974 | 485.1981 |
| 274 | 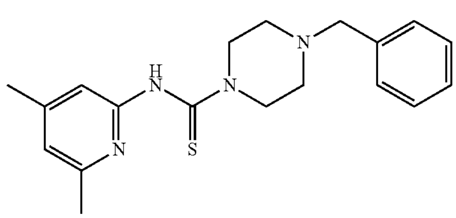 [SMILES: Cc1cc(C)nc(NC(=S)N2CCN(Cc3ccccc3)CC2)c1] | 341.1796 | 341.1794 |
| 275 | (NCGC00356356) | 423.1842 | 423.1825 |

TABLE 3-continued
Exemplary compounds.
| Cmpd. No. | Structure | m/z | Calc. m/z |
|---|---|---|---|
| 276 | 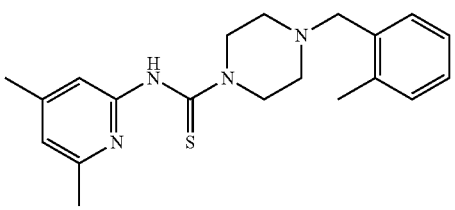 | 355.1950 | 355.1951 |
| 277 | 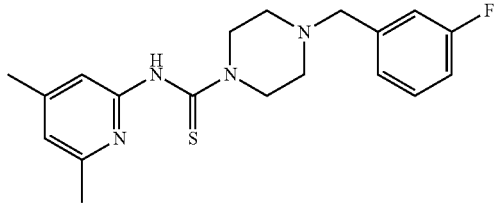 [SMILES: Cc1cc(C)nc(NC(=S)N2CCN(Cc3cccc(F)c3)CC2)c1] | 359.1683 | 359.1700 |
| 278 | 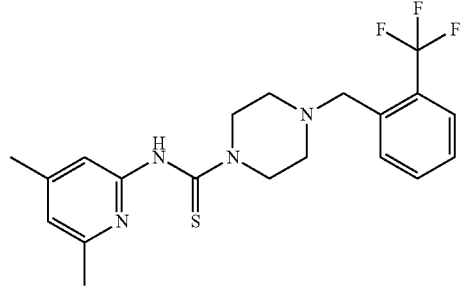 [SMILES: Cc1cc(C)nc(NC(=S)N2CCN(Cc3ccccc3C(F)(F)F)CC2)c1] | 409.1665 | 409.1668 |
| 279 | 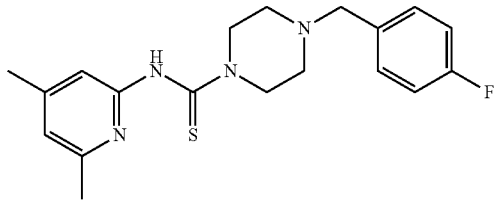 [SMILES: Cc1cc(C)nc(NC(=S)N2CCN(Cc3ccc(F)cc3)CC2)c1] | 359.1716 | 359.1700 |
| 280 | 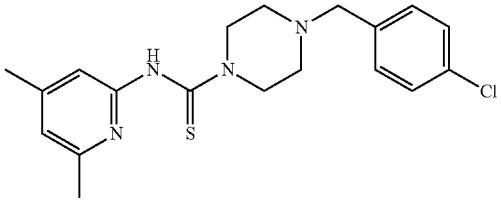 [SMILES: Cc1cc(C)nc(NC(=S)N2CCN(Cc3ccc(Cl)cc3)CC2)c1] | 375.1418 | 375.1405 |
| 281 | 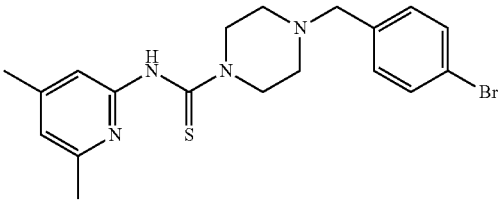 [SMILES: Cc1cc(C)nc(NC(=S)N2CCN(Cc3ccc(Br)cc3)CC2)c1] | 419.0893 | 419.0900 |

TABLE 3-continued
Exemplary compounds.
| Cmpd. No. | Structure | m/z | Calc. m/z |
|---|---|---|---|
| 282 | 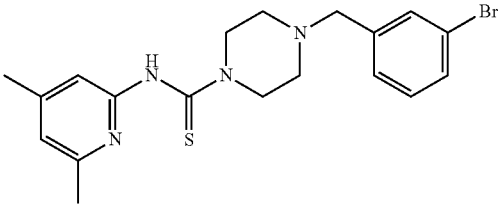 [SMILES: Cc1cc(C)nc(NC(=S)N2CCN(Cc3cccc(Br)c3)CC2)c1] | 419.0886 | 419.0900 |
| 283 | 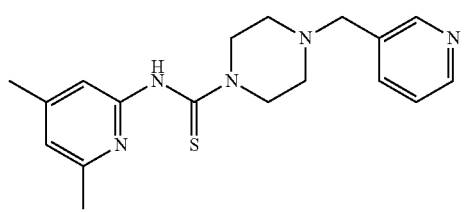 [SMILES: Cc1cc(C)nc(NC(=S)N2CCN(Cc3cccnc3)CC2)c1] | 342.1744 | 342.1747 |
| 284 | 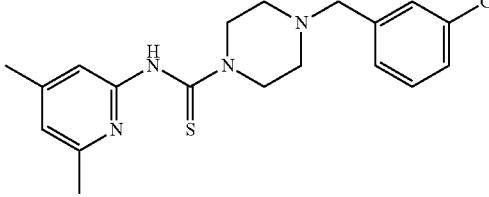 | 375.1407 | 375.1405 |
| 285 | 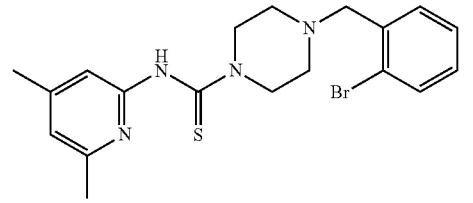 | 419.0893 | 419.0900 |
| 286 | 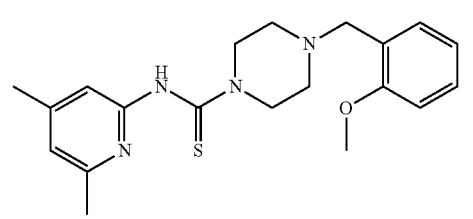 [SMILES: COc1ccccc1CN1CCN(C(=S)Nc2cc(C)cc(C)n2)CC1] | 371.1898 | 371.1900 |
| 287 | 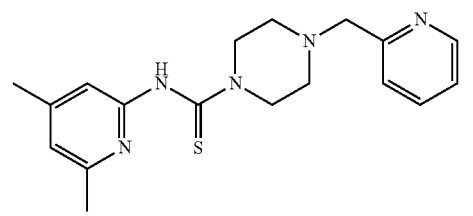 [SMILES: Cc1cc(C)nc(NC(=S)N2CCN(Cc3ccccn3)CC2)c1] | 342.1744 | 342.1747 |
| 288 | 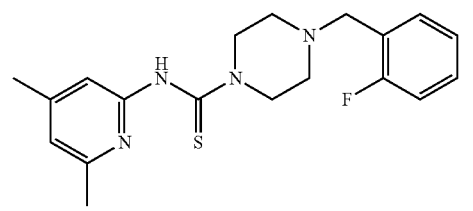 [SMILES: Cc1cc(C)nc(NC(=S)N2CCN(Cc3ccccc3Cl)CC2)c1] | 359.1695 | 359.1700 |

TABLE 3-continued

Exemplary compounds.

| Cmpd. No. | Structure | m/z | Calc. m/z |
|---|---|---|---|
| 289 | 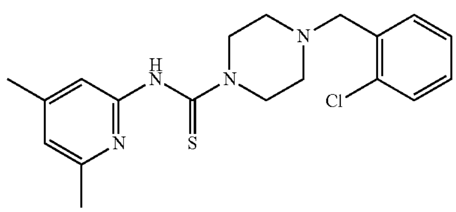 | 375.1413 | 375.1405 |
| 290 | 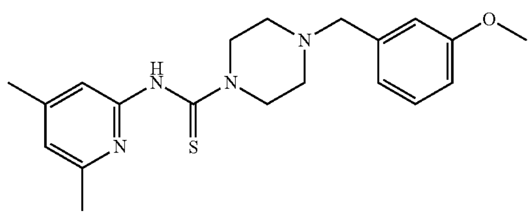 | 371.1912 | 371.1900 |
| 291 | 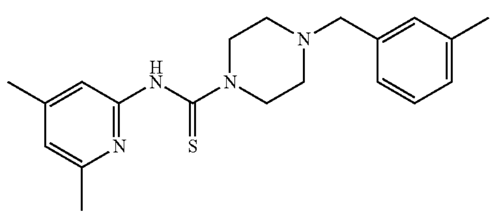 | 355.1951 | 355.1951 |
| 292 | 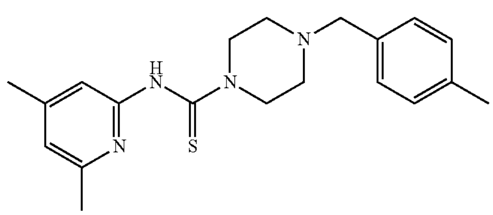 | 355.1949 | 355.1951 |
| 293 | 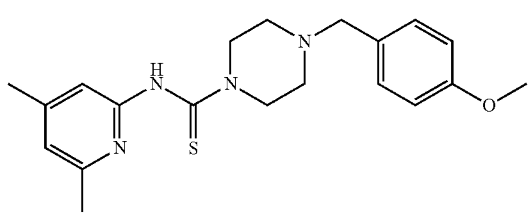 | 371.1 (LRMS) | 371.2 |
| 294 | 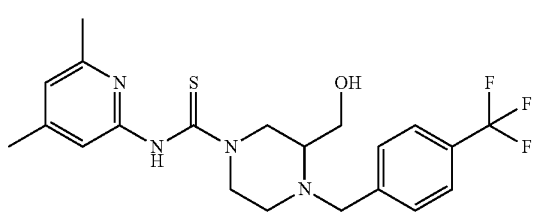 [SMILES: Cc1cc(C)nc(NC(=S)N2CCN(Cc3ccc(C(F)(F)F)cc3)C(CO)C2)c1] | 439.1754 | 439.1774 |

TABLE 3-continued

Exemplary compounds.

| Cmpd. No. | Structure | m/z | Calc. m/z |
|---|---|---|---|
| 295 | 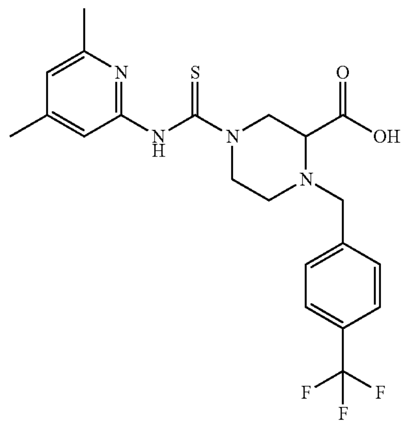 [SMILES: Cc1cc(C)nc(NC(=S)N2CCN(Cc3ccc(C(F)(F)F)cc3)C(C(=O)O)C2)c1] | 453.1584 | 453.1567 |
| 296 | (NCGC00356789) | 425.1637 | 425.1617 |
| 297 | (NCGC00356784) | 423.1835 | 423.1825 |
| 298 | (NCGC00356785) | 423.1818 | 423.1825 |
| 299 | 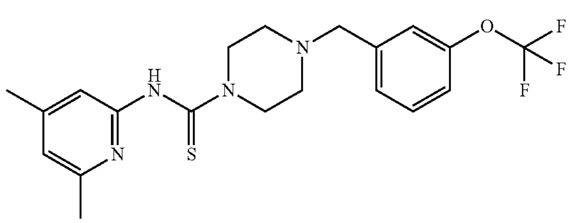 [SMILES: Cc1cc(C)nc(NC(=S)N2CCN(Cc3cccc(OC(F)(F)F)c3)CC2)c1] | 425.1627 | 425.1617 |

TABLE 3-continued

Exemplary compounds.

| Cmpd. No. | Structure | m/z | Calc. m/z |
|---|---|---|---|
| 300 | (NCGC00356790) | 443.1282 | 443.1279 |
| 301 | 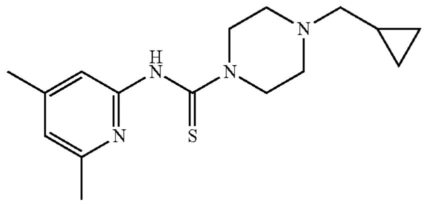 | 305.1792 | 305.1794 |
| 302 | (NCGC00356793) | 423.1841 | 423.1825 |

In certain embodiments, the compound is a compound listed in Table 4. In Table 4 mass-to-charge ratios (m/z) are from positive ion HRMS and correspond to the (M+H)⁺ ion, unless otherwise indicated.

TABLE 4

Exemplary compounds.

| 3 | |
| 15 | |
| 19 | |

TABLE 4-continued
Exemplary compounds.
21 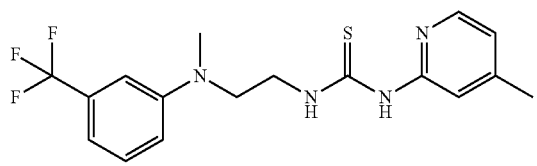 [SMILES: Cc1ccnc(NC(=S)NCCN(C)c2cccc(C(F)(F)F)c2)c1]
22 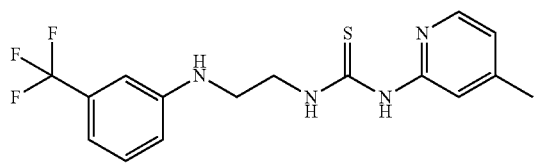 [SMILES: Cc1ccnc(NC(=S)NCCNc2cccc(C(F)(F)F)c2)c1]
23 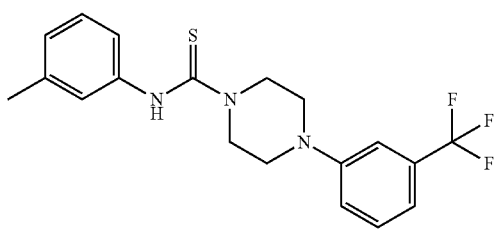
29 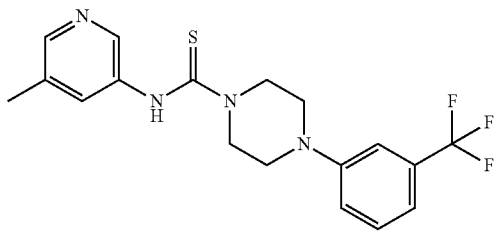 [SMILES: Cc1cncc(NC(=S)N2CCN(c3cccc(C(F)(F)F)c3)CC2)c1]
30 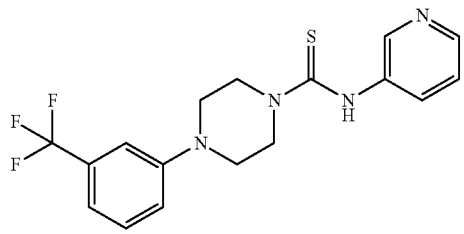 [SMILES: FC(F)(F)c1cccc(N2CCN(C(=S)Nc3cccnc3)CC2)c1]
31 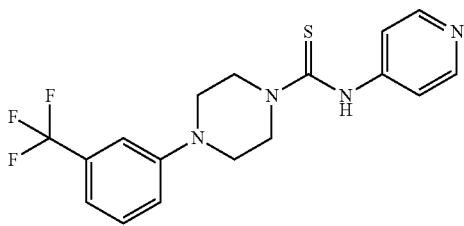 [SMILES: FC(F)(F)c1cccc(N2CCN(C(=S)Nc3ccncc3)CC2)c1]
32 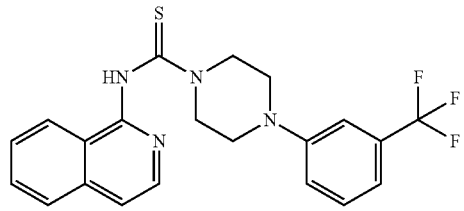 [SMILES: FC(F)(F)c1cccc(N2CCN(C(=S)Nc3nccc4ccccc34)CC2)c1]

TABLE 4-continued
Exemplary compounds.
34
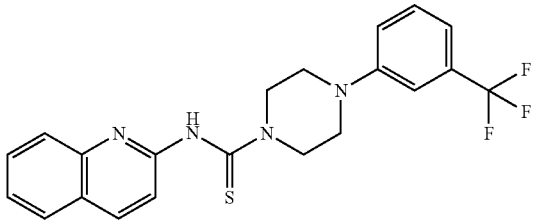 [SMILES: FC(F)(F)c1cccc(N2CCN(C(=S)Nc3ccc4ccccc4n3)CC2)c1]
42
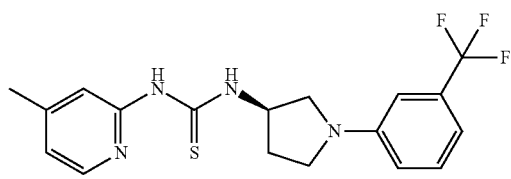 [SMILES: Cc1ccnc(NC(=S)N[C@@H]2CCN(c3cccc(C(F)(F)F)c3)C2)c1]
43
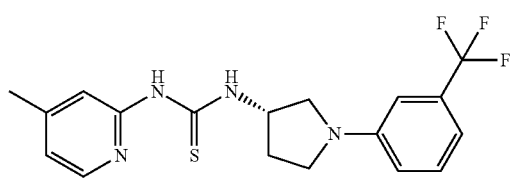 [SMILES: Cc1ccnc(NC(=S)N[C@H]2CCN(c3cccc(C(F)(F)F)c3)C2)c1]
44
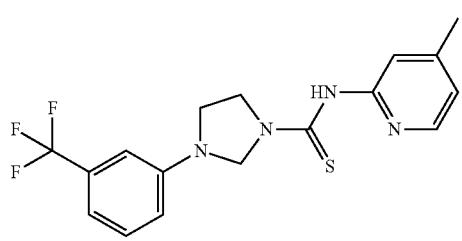 [SMILES: Cc1ccnc(NC(=S)N2CCN(c3cccc(C(F)(F)F)c3)C2)c1]
45
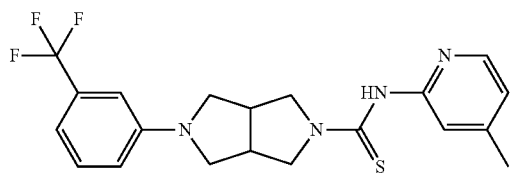 [SMILES: Cc1ccnc(NC(=S)N2CC3CN(c4cccc(C(F)(F)F)c4)CC3C2)c1]
46
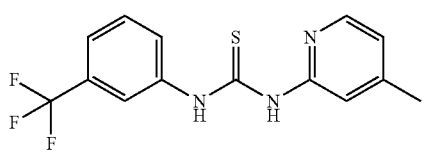 [SMILES: Cc1ccnc(NC(=S)Nc2cccc(C(F)(F)F)c2)c1]
47
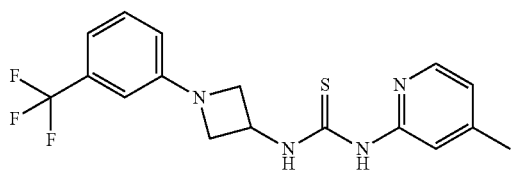 [SMILES: Cc1ccnc(NC(=S)NC2CN(c3cccc(C(F)(F)F)c3)C2)c1]
49
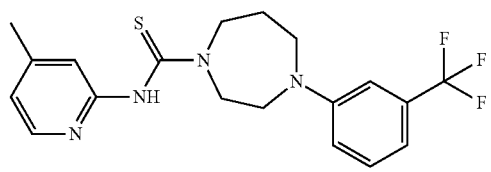 [SMILES: Cc1ccnc(NC(=S)N2CCCN(c3cccc(C(F)(F)F)c3)CC2)c1]

TABLE 4-continued
Exemplary compounds.
50 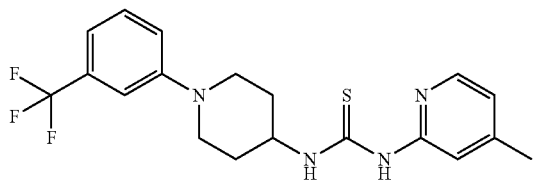 [SMILES: Cc1ccnc(NC(=S)NC2CCN(c3cccc(C(F)(F)F)c3)CC2)c1]
51 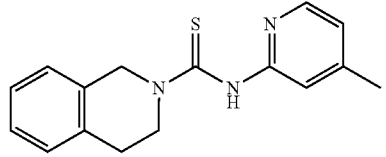 [SMILES: Cc1ccnc(NC(=S)N2CCc3ccccc3C2)c1]
53 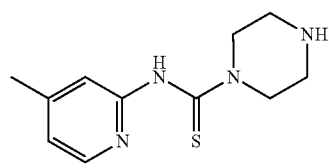 [SMILES: Cc1ccnc(NC(=S)N2CCNCC2)c1]
54 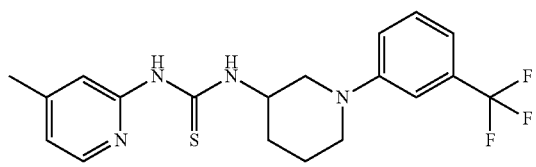 [SMILES: Cc1ccnc(NC(=S)NC2CCCN(c3cccc(C(F)(F)F)c3)C2)c1]
55 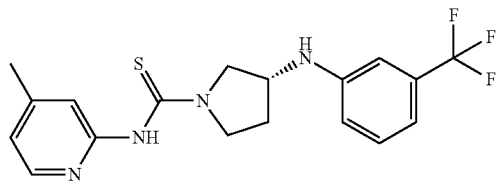 [SMILES: Cc1ccnc(NC(=S)N2CC[C@@H](Nc3cccc(C(F)(F)F)c3)C2)c1]
59 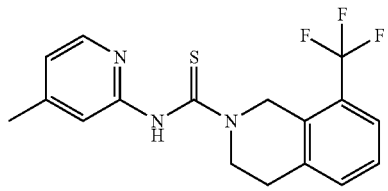 [SMILES: Cc1ccnc(NC(=S)N2CCc3cccc(C(F)(F)F)c3C2)c1]
60 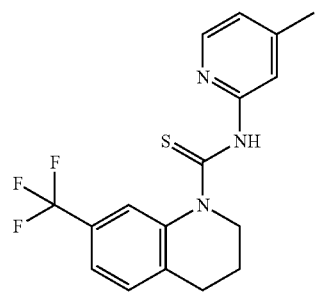 [SMILES: Cc1ccnc(NC(=S)N2CCCc3ccc(C(F)(F)F)cc32)c1]
61 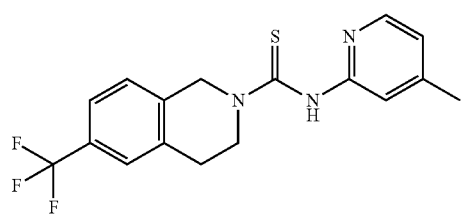 [SMILES: Cc1ccnc(NC(=S)N2CCc3cc(C(F)(F)F)ccc3C2)c1]

TABLE 4-continued
Exemplary compounds.
95 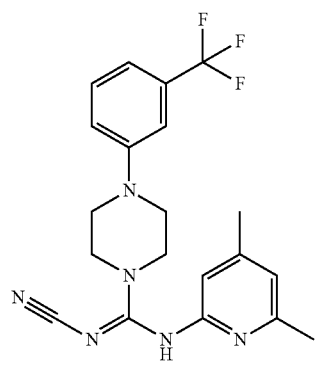 [SMILES: Cc1cc(C)nc(N/C(=N/C#N)N2CCN(c3cccc(C(F)(F)F)c3)CC2)c1]
96 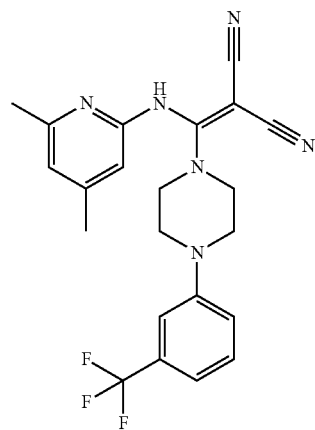 [SMILES: Cc1cc(C)nc(NC(=C(C#N)C#N)N2CCN(c3cccc(C(F)(F)F)c3)CC2)c1]
125 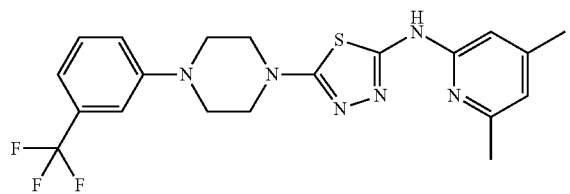 [SMILES: Cc1cc(C)nc(Nc2nnc(N3CCN(c4cccc(C(F)(F)F)c4)CC3)s2)c1]
126 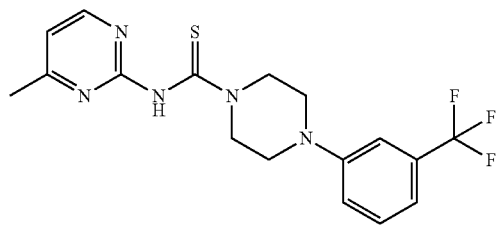
127 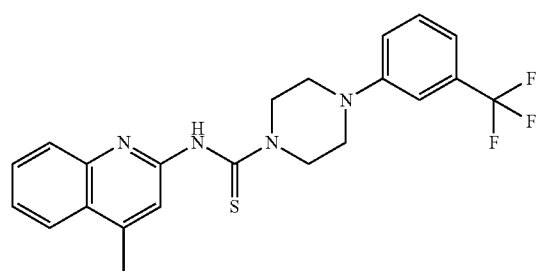 [SMILES: Cc1cc(NC(=S)N2CCN(c3cccc(C(F)(F)F)c3)CC2)nc2ccccc12]

TABLE 4-continued
Exemplary compounds.
128
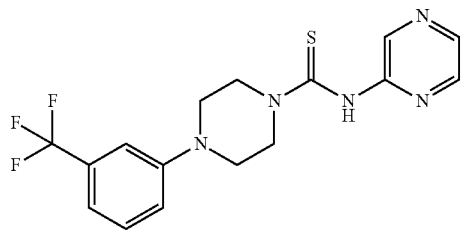 [SMILES: FC(F)(F)c1cccc(N2CCN(C(=S)Nc3cnccn3)CC2)c1]
130
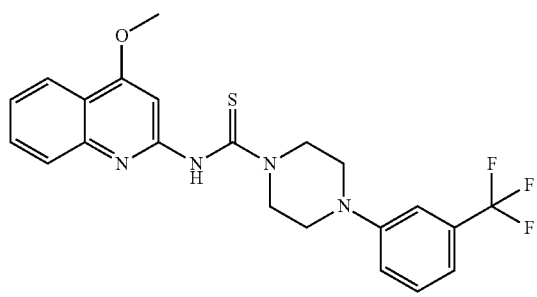 [SMILES: COc1cc(NC(=S)N2CCN(c3cccc(C(F)(F)F)c3)CC2)nc2ccccc12]
132
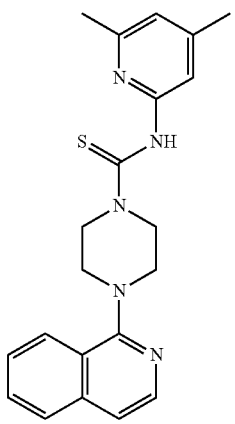 [SMILES: Cc1cc(C)nc(NC(=S)N2CCN(c3nccc4ccccc34)CC2)c1]
143
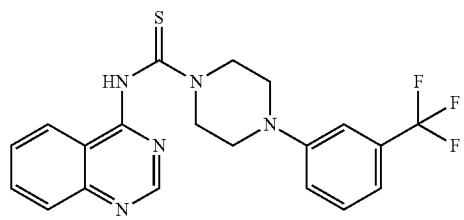 [SMILES: FC(F)(F)c1cccc(N2CCN(C(=S)Nc3ncnc4ccccc34)CC2)c1]
144
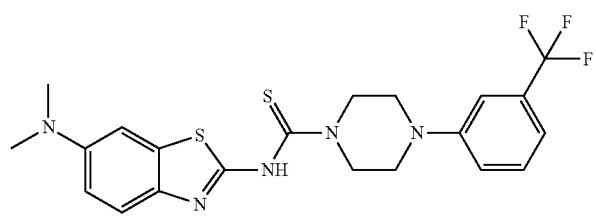 [SMILES: CN(C)c1ccc2nc(NC(=S)N3CCN(c4cccc(C(F)(F)F)c4)CC3)sc2c1]

TABLE 4-continued
Exemplary compounds.
146 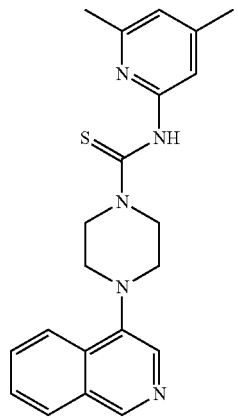 [SMILES: Cc1cc(C)nc(NC(=S)N2CCN(c3cncc4ccccc34)CC2)c1]
151 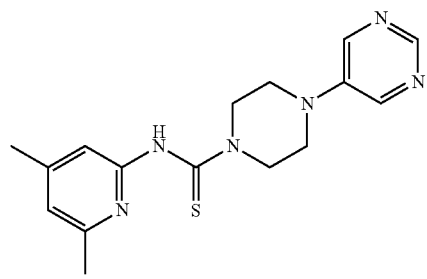 [SMILES: Cc1cc(C)nc(NC(=S)N2CCN(c3cncnc3)CC2)c1]
158 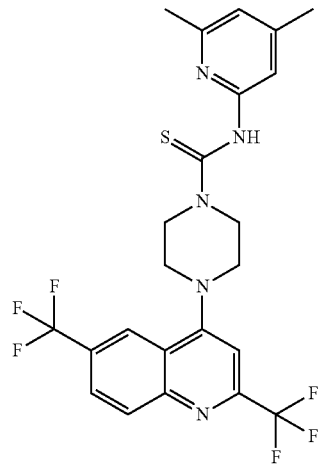 [SMILES: Cc1cc(C)nc(NC(=S)N2CCN(c3cc(C(F)(F)F)nc4ccc(C(F)(F)F)cc34)CC2)c1]
204 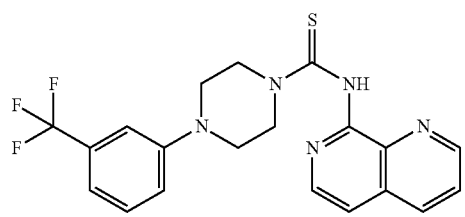 [SMILES: FC(F)(F)c1cccc(N2CCN(C(=S)Nc3nccc4cccnc34)CC2)c1]

TABLE 4-continued
Exemplary compounds.
222 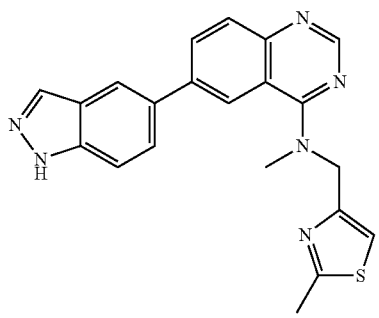 [SMILES: Cc1nc(CN(C)c2ncnc3ccc(-c4ccc5[nH]ncc5c4)cc23)cs1]
223 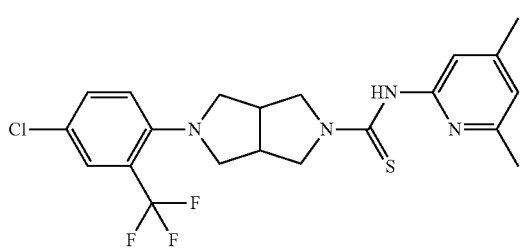 [SMILES: Cc1cc(C)nc(NC(=S)N2CC3CN(c4ccc(Cl)cc4C(F)(F)F)CC3C2)c1]
224 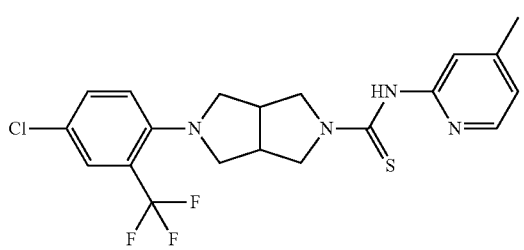 [SMILES: Cc1ccnc(NC(=S)N2CC3CN(c4ccc(Cl)cc4C(F)(F)F)CC3C2)c1]
225 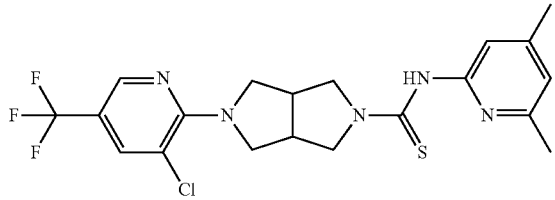 [SMILES: Cc1cc(C)nc(NC(=S)N2CC3CN(c4ncc(C(F)(F)F)cc4Cl)CC3C2)c1]
227 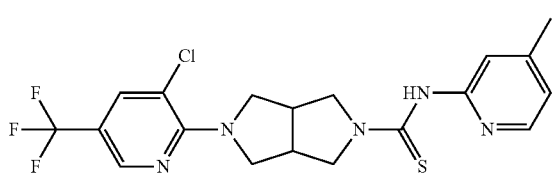 [SMILES: Cc1ccnc(NC(=S)N2CC3CN(c4ncc(C(F)(F)F)cc4Cl)CC3C2)c1]
228 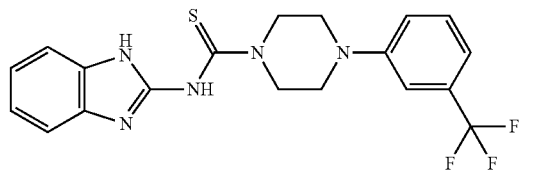 [SMILES: FC(F)(F)c1cccc(N2CCN(C(=S)Nc3nc4ccccc4[nH]3)CC2)c1] 406.1327 406.1308
229 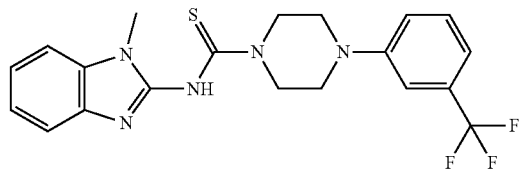 [SMILES: Cn1c(NC(=S)N2CCN(c3cccc(C(F)(F)F)c3)CC2)nc2ccccc21] 420.1465 420.1464

TABLE 4-continued

Exemplary compounds.

| | | | |
|---|---|---|---|
| 230 | [structure] | 454.1303 | 454.1284 (M + Na)+ |
| 231 | [structure] | 372.1217 | 372.1213 |
| 232 | [structure] | 381.1373 | 381.1355 |
| 233 | [structure] | 357.1107 | 357.1104 |
| 234 | [structure] | 357.1109 | 357.1104 |
| 235 | [structure] | 357.1089 | 357.1104 |
| 236 | [structure] | 356.1141 | 356.1151 |

TABLE 4-continued
Exemplary compounds.
| 237 | 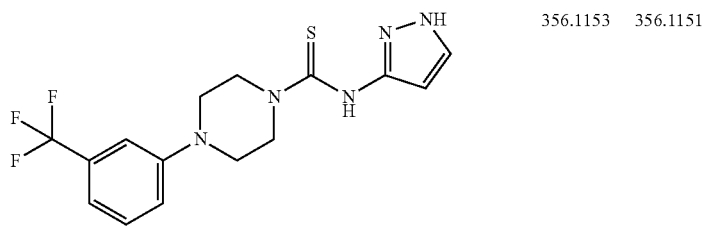 | 356.1153 | 356.1151 |
| 238 | 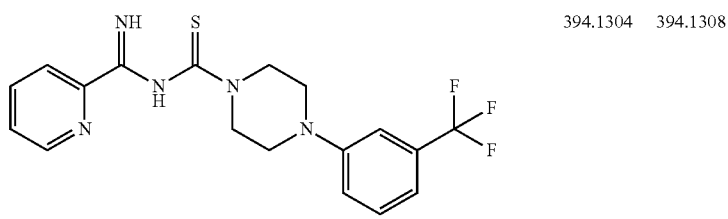 | 394.1304 | 394.1308 |
| 239 | 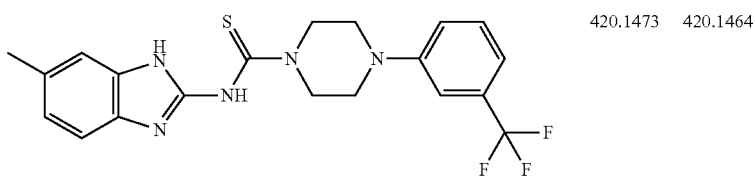 | 420.1473 | 420.1464 |
| 240 | 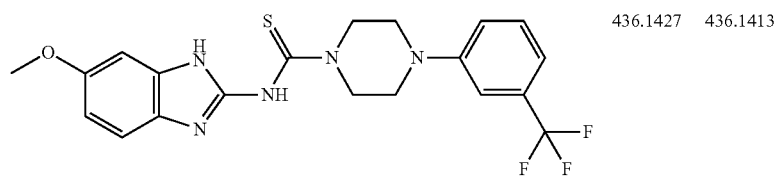 | 436.1427 | 436.1413 |
| 241 | 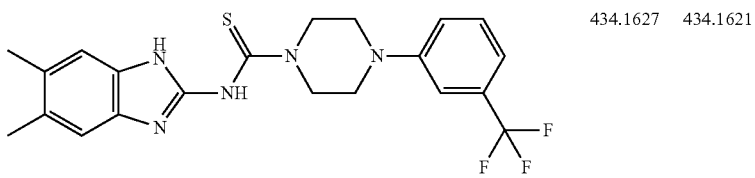 | 434.1627 | 434.1621 |
| 242 | 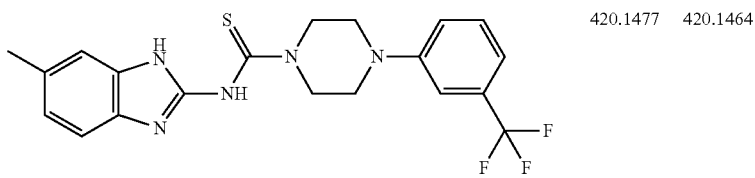 | 420.1477 | 420.1464 |
| 243 | 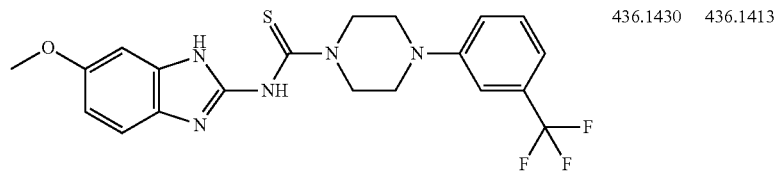 | 436.1430 | 436.1413 |
| 244 | 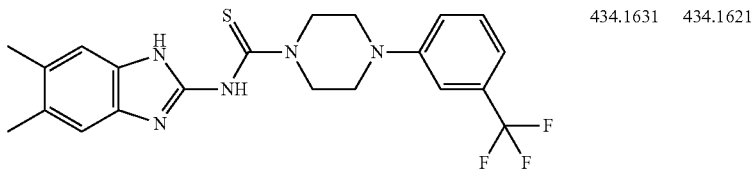 | 434.1631 | 434.1621 |

TABLE 4-continued

Exemplary compounds.

245 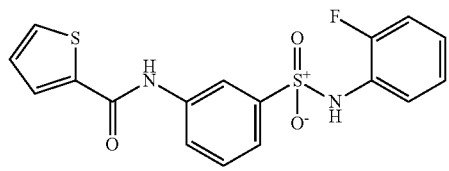 [SMILES: O=C(Nc1cccc([S+](=O)([O-])Nc2ccccc2F)c1)c1cccs1]

246 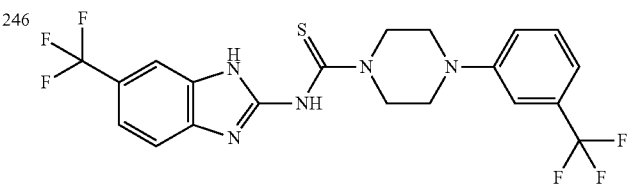  474.1194  474.1182

247 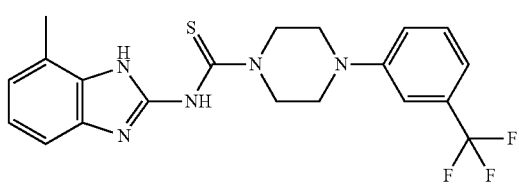 [SMILES: Cc1cccc2nc(NC(=S)N3CCN(c4cccc(C(F)(F)F)c4)CC3)[nH]c12]  420.1472  420.1464

248 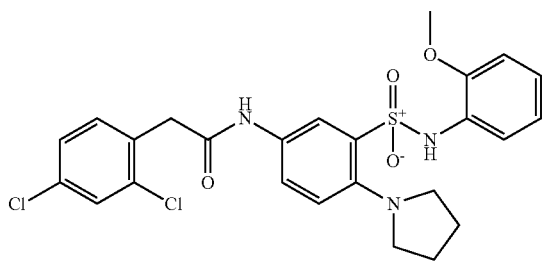 [SMILES: COc1ccccc1N[S+](=O)([O-])c1cc(NC(=O)Cc2ccc(Cl)cc2Cl)ccc1N1CCCC1]

249 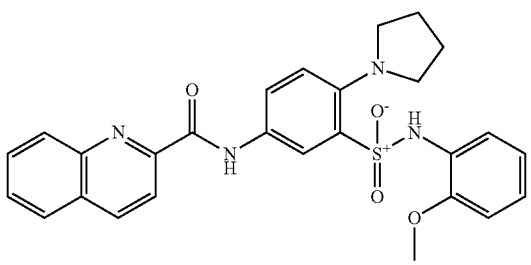 [SMILES: COc1ccccc1N[S+](=O)([O-])c1cc(NC(=O)c2ccc3ccccc3n2)ccc1N1CCCC1]

Compounds of the invention may be synthesized according to the schemes described below. The reagents and conditions described are intended to be exemplary and not limiting. As one of skill in the art would appreciate, various analogs may be prepared by modifying the synthetic reactions such as using different starting materials, different reagents, and different reaction conditions (e.g., temperature, solvent, concentration, etc.)

In one aspect, the present invention provides methods for the synthesis of compounds of Formula (II) and intermediates thereto. In some embodiments, such methods are as shown in Scheme 1 or Scheme 2.

Scheme 1.

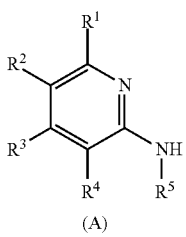

(A)

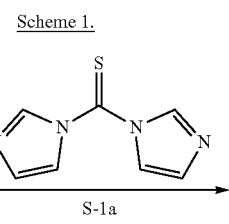

S-1a

227
-continued

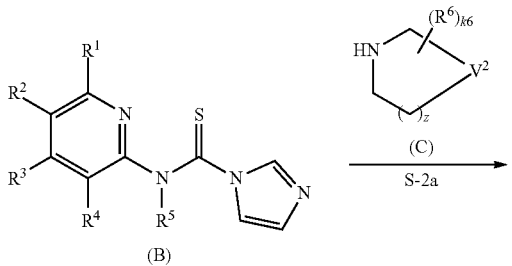

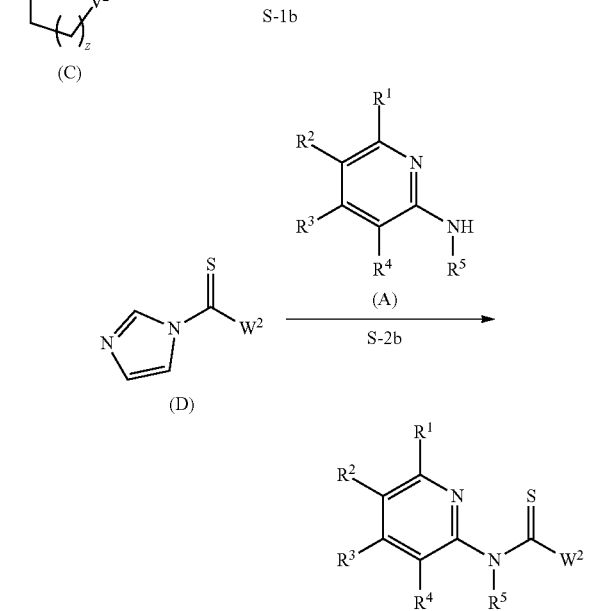

Wherein, for Scheme 1 and Scheme 2:
V² is of formula:

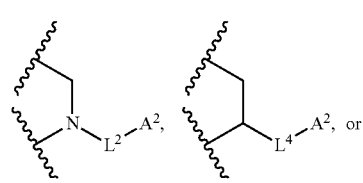

228
-continued

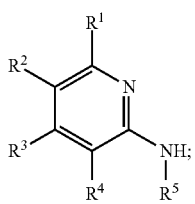

and $R^1$-$R^6$, $W^2$, $L^2$, $L^4$, $A^2$, $k^6$, and z are as defined for compounds of Formula (II).

In step S-1a, an aminopyridine of formula (A) is reacted with N,N'-thiocarbonyldiimidazole to form a thiourea of formula (B). Suitable reagents for step S-1a include a base such as triethylamine. In step S-2a, a thiourea of formula (B) is reacted with a piperazine, piperidine, diazepane, or azepane of formula (C) to give a compound of Formula (II). Suitable reagents for step S-2a include a base such as triethylamine.

In step S-1b, a piperazine, piperidine, diazepane, or azepane of formula (C) is reacted with N,N'-thiocarbonyldiimidazole to form a thiourea of formula (D). Suitable reagents for step S-1b include a base such as triethylamine. In step S-2b, a thiourea of formula (D) is reacted with an aminopyridine of formula (A) to give a compound of Formula (II). Suitable reagents for step S-2b include a base such as triethylamine.

In certain embodiments, the method for preparation of a compound of Formula (II) comprises the steps of:

(a) providing an aminopyridine of formula (A):

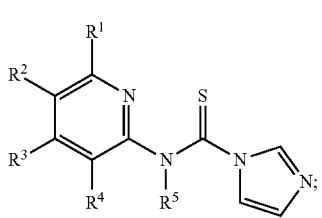

(b) reacting the compound of formula (A) with N,N'-thiocarbonyldiimidazole to form a thiourea of formula (B):

(c) reacting the compound of formula (B) with a piperazine, piperidine, diazepane, or azepane of formula (C):

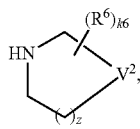
(C)

wherein $V^2$ is of formula:

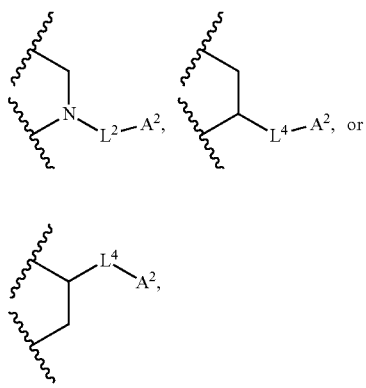

to form a compound of Formula (II).

In certain embodiments, the method for preparation of a compound of Formula (II) comprises the steps of:

(a) providing a piperazine, piperidine, diazepane, or azepane of formula (C):

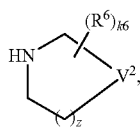
(C)

$V^2$ is of formula:

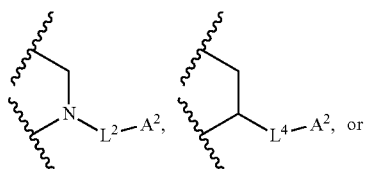

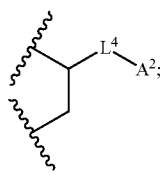

(b) reacting the compound of formula (C) with N,N'-thiocarbonyldiimidazole to form a thiourea of formula (D):

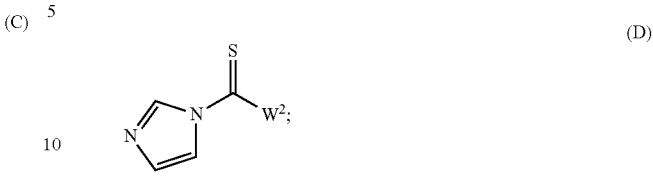
(D)

and (c) reacting the compound of formula (D) with an aminopyridine of formula (A):

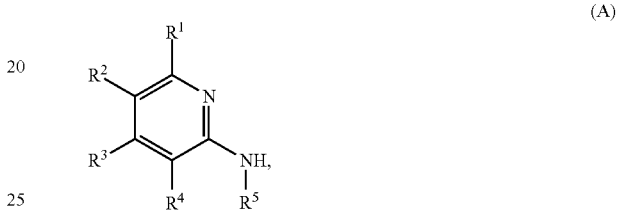
(A)

to form a compound of Formula (II).

In certain embodiments, each of the aforementioned synthetic steps may be performed sequentially with isolation of each intermediate performed after each step. Alternatively, each of steps S-1a, S-2a, S-1b, S-2b as depicted in Scheme 1 and Scheme 2 above, may be performed in a manner whereby no isolation of one or more intermediates (B) or (D) is performed.

In certain embodiments, all the steps of the aforementioned synthesis may be performed to prepare the desired final product. In other embodiments, two, three, four, five, or more sequential steps may be performed to prepare an intermediate or the desired final product.

In certain embodiments, all the steps of the aforementioned synthesis may be performed using solution phase or solid phase synthetic techniques, or a combination thereof. In some embodiments, robotic techniques may be employed. In certain embodiments, automatic liquid handling reaction stations may be used. In some embodiments, parallel synthesis may be used. In some embodiments, high-throughput synthesis may be used. In some embodiments, one-by-one synthesis may be used.

In another aspect, the present invention provides methods for the synthesis of compounds of Formula (I) or (III) and intermediates thereto. In some embodiments, such methods are as shown in Scheme 3. or Scheme 4.

Scheme 3.

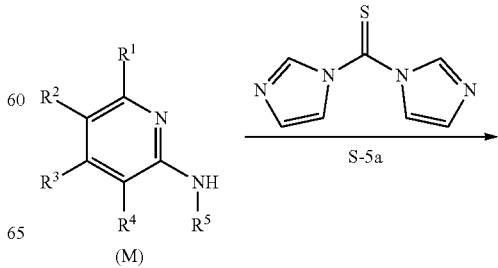

-continued

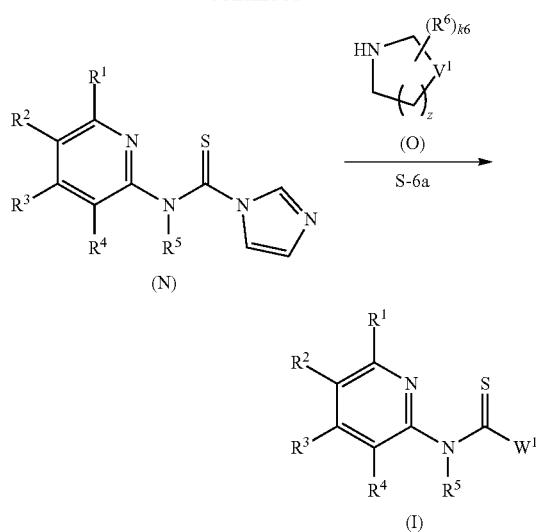

(N)

(I)

Scheme 4.

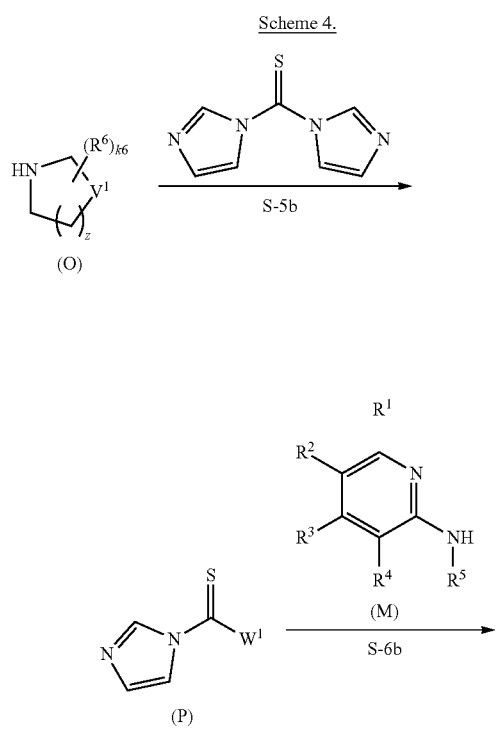

(P)

(I)

Wherein, for Scheme 1 and Scheme 2:
$V^1$ is of formula:

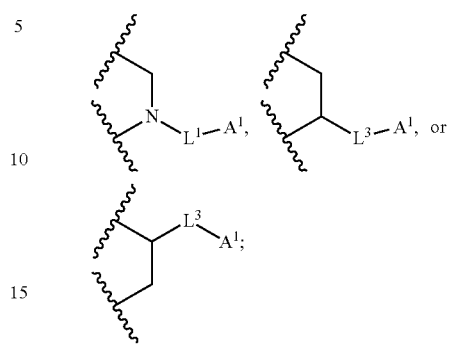

$R^1$-$R^6$, $W^2$, $L^1$, $L^3$, $A^1$, $k^6$, and z are as defined for compounds of Formula (I).

In step S-5a, an aminopyridine of formula (M) is reacted with N,N'-thiocarbonyldiimidazole to form a thiourea of formula (N). Suitable reagents for step S-5a include a base such as triethylamine. In step S-6a, a thiourea of formula (N) is reacted with a piperazine, piperidine, diazepane, or azepane of formula (O) to give a compound of Formula (I). Suitable reagents for step S-6a include a base such as triethylamine.

In step S-5b, a piperazine, piperidine, diazepane, or azepane of formula (O) is reacted with N,N'-thiocarbonyldiimidazole to form a thiourea of formula (P). Suitable reagents for step S-5b include a base such as triethylamine. In step S-6b, a thiourea of formula (P) is reacted with an aminopyridine of formula (M) to give a compound of Formula (I). Suitable reagents for step S-6b include a base such as triethylamine.

In certain embodiments, the method for preparation of a compound of Formula (I) comprises the steps of:

(a) providing an aminopyridine of formula (M):

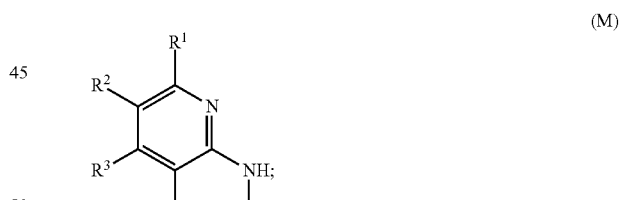

(b) reacting the compound of formula (M) with N,N'-thiocarbonyldiimidazole to form a thiourea of formula (N):

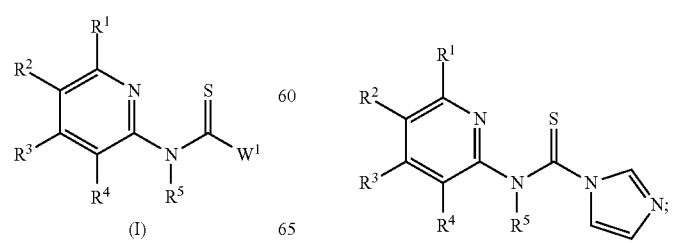

(c) reacting the compound of formula (N) with a piperazine, piperidine, diazepane, or azepane of formula (O):

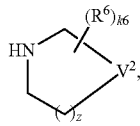
(O)

wherein $V^1$ is of formula:

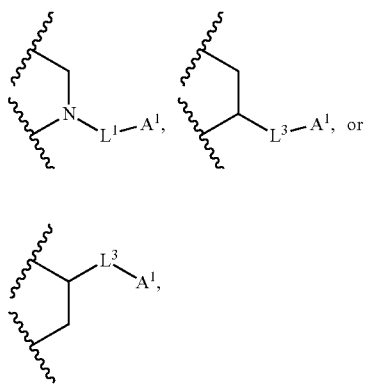

to form a compound of Formula (I).

In certain embodiments, the method for preparation of a compound of Formula (I) comprises the steps of:

(a) providing a piperazine, piperidine, diazepane, or azepane of formula (O):

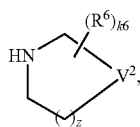
(O)

$V^2$ is of formula:

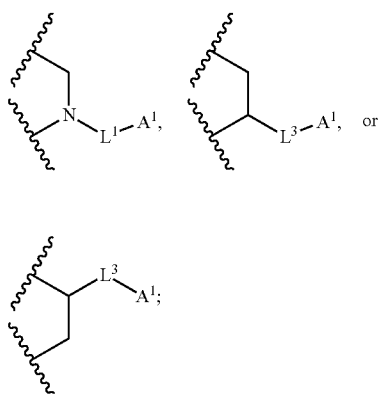

(b) reacting the compound of formula (O) with N,N'-thiocarbonyldiimidazole to form a thiourea of formula (P):

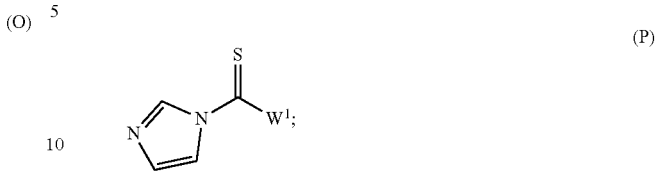
(P)

and (c) reacting the compound of formula (P) with an aminopyridine of formula (M):

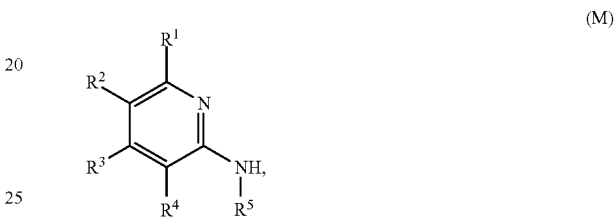
(M)

to form a compound of Formula (II).

In embodiments in which $L^1$ or $L^3$ are a bond the methods for preparing a compound of Formula (I) will provide compounds of Formula (III).

In certain embodiments, each of the aforementioned synthetic steps may be performed sequentially with isolation of each intermediate performed after each step. Alternatively, each of steps S-5a, S-6a, S-5b, S-6b as depicted in Scheme 1 and Scheme 2 above, may be performed in a manner whereby no isolation of one or more intermediates (N) or (P) is performed.

In certain embodiments, all the steps of the aforementioned synthesis may be performed to prepare the desired final product. In other embodiments, two, three, four, five, or more sequential steps may be performed to prepare an intermediate or the desired final product.

In certain embodiments, all the steps of the aforementioned synthesis may be performed using solution phase or solid phase synthetic techniques, or a combination thereof. In some embodiments, robotic techniques may be employed. In certain embodiments, automatic liquid handling reaction stations may be used. In some embodiments, parallel synthesis may be used. In some embodiments, high-throughput synthesis may be used. In some embodiments, one-by-one synthesis may be used.

Pharmaceutical Compositions, Kits, and Administration

The present invention also provides pharmaceutical compositions comprising a compound of Formula (I), (II), or (III), or of a sub-formula thereof, or a pharmaceutically acceptable salt, solvate, hydrate, polymorph, co-crystals, tautomer, stereoisomer, isotopically labeled derivative, or pro-drug thereof, and optionally a pharmaceutically acceptable excipient.

In certain embodiments, the compound of Formula (I), (II), or (III), or of a sub-formula thereof, or a pharmaceutically acceptable salt, solvate, hydrate, polymorph, co-crystal, tautomer, stereoisomer, isotopically labeled derivative, or pro-drug thereof, is provided in an effective amount in the pharmaceutical composition. In certain embodiments, the effective amount is a therapeutically effective amount. In certain embodiments, the effective amount is a therapeutically effective amount for the treatment of a proliferative disease (e.g., cancer (e.g., breast cancer, ER negative breast cancer, melanoma, cervical cancer), benign neoplasms, diseases associated with angiogenesis, inflammatory diseases, autoinflammatory diseases, autoimmune diseases). In certain embodiments, the effective amount is a therapeutically effective amount for the treatment of a fibrotic disease (e.g., idiopathic pulmonary fibrosis, nephrogenic systemic fibrosis, scleroderma). In certain embodiments, the effective amount is a prophylactically effective amount. In certain embodiments, the effective amount is a prophylactically effective amount for the prevention of a proliferative disesase (e.g., cancer (e.g., breast cancer, ER negative breast cancer, melanoma, cervical cancer), benign neoplasms, diseases associated with angiogenesis, inflammatory diseases, autoinflammatory diseases, autoimmune diseases). In certain embodiments, the effective amount is a prophylactically effective amount for the prevention of a fibrotic disease (e.g., idiopathic pulmonary fibrosis, nephrogenic systemic fibrosis, scleroderma). In certain embodiments, the effective amount is an amount useful for treating or preventing (or both) a disease associated with over-expression of phosphoglycerate dehydrogenase (PHGDH) in a subject in need thereof. In certain embodiments, the effective amount is an amount useful for treating or preventing (or both) a disease associated with increased activity of phosphoglycerate dehydrogenase (PHGDH) in a subject in need thereof. In certain embodiments, the effective amount is an amount useful for treating or preventing (or both) a disease associated with abnormal serine production (e.g., increased serine biosynthetic pathway flux) in a subject in need thereof. In certain embodiments, the effective amount is an amount useful for inhibiting the activity of phosphoglycerate dehydrogenase (PHGDH) in a subject in need thereof. In certain embodiments, the effective amount is an amount useful for modulating (e.g., reducing) serine production in a subject in need thereof.

The effective amount of the compound in the composition may be useful for treating or preventing (or both) a disease associated with the over-expression of PHGDH, treating or preventing (or both) a disease associated with aberrant activity (e.g., increased activity) of PHGDH, treating or preventing (or both) a disease associated with abnormal production of serine (e.g., increased serine production), inhibiting PHGDH activity, and/or modulating (e.g., inhibiting) serine production as a single agent or in combination with one or more additional pharmaceutical agents.

An effective amount of a compound may vary from about 0.001 mg/kg to about 1000 mg/kg in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

Pharmaceutical compositions described herein can be prepared by any method known in the art of pharmacology. In general, such preparatory methods include the steps of bringing the compound of Formula (I), (II), or (III), or of a sub-formula thereof (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, poly aery lie acid, acrylic acid polymer, and carboxy vinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, camauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (I) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier or excipient and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid vaccines to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds described herein may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity in treating or preventing (or both) a disease associated with over-expression of PHGDH, treating or preventing (or both) a disease associated with increased activity of PHGDH, treating or preventing (or both) a disease associated with abnormal serine production (e.g., increased serine biosynthetic pathway flux), attenuating PHGDH activity, and/or modulating serine production in a subject in need thereof), bioavailability, reduce and/or modify their metabolism, inhibit their excretion, and/or modify their distribution within the body of a subject. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agent(s) and/or the desired therapeutic and/or prophylactic effect to be achieved. In general, it is expected that the additional pharmaceutical agent(s) utilized in combination be utilized at levels that do not exceed the levels at which they are utilized individually. In some embodiments, the levels utilized in combination will be lower than those utilized individually.

Additional pharmaceutical agents include, but are not limited to, anti-proliferative agents (e.g., anti-cancer agents), anti-diabetic agents, anti-inflammatory agents, immunosuppressant agents, antifungal agents, antiprotozoan agents, anti-bacterial agents, anti-viral agents, anti-inflammatory agents, anti-allergic agents, and pain-relieving agents. In certain embodiments, the additional pharmaceutical agent is a PHGDH modulator. In certain embodiments, the additional pharmaceutical agent is a PHGDH inhibitor. In certain embodiments, the additional pharmaceutical agent is an inhibitor of PSAT1 or PSPH. In certain embodiments, the additional pharmaceutical agent is a modulator of the serine biosynthetic pathway. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agents are pharmaceutical agents useful for treating or preventing (or both) Parkinson's disease, such as such as 1-dopa, dopa decarboxylase inhibitors (such as carbidopa, levodopa, benserazide, combination preparations of carbidopa/levodopa (e.g., SENEMET, PARCOPA), benserazide/levodopa (e.g., MADOPAR)), carbidopa/levodopa/entacapone (STALEVO), COMT inhibitors (such as entacapone (COMTAN) and tolcapone (TASMAR)), dopamine agonists (such as bromocriptine (PARLODEL), pergolide (PERMA), pramipexole (MIRAPE), rotigotine transdermal (NEUPRO), ropinirole (REQUIP), cabergoline, apomorphine (APOKYN), and lisuride), dopamine agonists, MAO-B inhibitors (such as rasagiline (AZILECT), selegiline (ELDEPRYL, CARBEX, DEPRENYL), benzotropine mesylate (COGENTIN), metabolites of selegiline (L-amphetamine and L-methamphetamine), amantadine (SYMMETREL) and trihexyphenyl (ARTANE)). In certain embodiments, the additional pharmaceutical agents are pharmaceutical agents useful for treating or preventing (or both) Alzheimer's disease, such as cholinesterase inhibitors (e.g., ARICEPT, rivastigmine (EXELON), galantamine (REMINYL, now RAZADYNE)), NMDA antagonists (such as memantine (NAMENDA) and PDE4 inhibitors such as cilomilast (ARIFLO)), nonsteroidal anti-inflammatory drugs (NSAIDs) (such as R-flurbiprofen (FLURIZAN)), cholesterol-lowering statin drugs (such as pravastatin, simvastatin, and atorvastatin), anti-amyloid and anti-$\Delta\beta$ immune therapy, compounds which inhibit the aggregation of $\alpha\beta$ (such as scylloinositol and clioquinol), compounds which inhibit or modify $\alpha\beta$ production or processing (such as y-secretase inhibitors, β-secretase inhibitors, γ-secretase modulators, AP modulators, and GSK-3 inhibitors), compounds which regulate αβ turnover (such as PAI-1 inhibitors), compounds which regulate tau phosphorylation (such as GSK-3 and CDK-5 inhibitors), PPARy agonists (such as rosiglitazone), compounds which regulate tau or phosphor-tau turnover or oligomerization (such as HSP90 inhibitors, HD AC inhibitors and anti-tau immune therapy), compounds which stabilize or bind to microtubules (such as taxane derivatives and epothilone derivatives), and compounds which regulate mitochondria function (such as latrepirdine).

In one aspect, the additional pharmaceutical agent is an anti-cancer agent. Anti-cancer agents encompass biotherapeutic anti-cancer agents as well as chemotherapeutic agents.

Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)).

Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), *vinca* alkaloids (e.g. vincristine, vinblastine, vindesine, and vinorelbine), taxoids (e.g. paclitaxel or a paclitaxel equivalent such as nanoparticle albumin-bound paclitaxel (Abraxane), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated pro-drug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonuclotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. l-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In certain embodiments, the additional pharmaceutical agent is an anti-cancer agent for breast cancer. Exemplary anti-cancer agents for the treatment or prevention (or both) of breast cancer include, but are not limited: ABITREXATE® (Methotrexate), ABRAXANE® (Paclitaxel Albumin-stabilized Nanoparticle Formulation), AC, AC-T, ADRIAMYCIN PFS® (Doxorubicin Hydrochloride), ADRIAMYCIN RDF® (Doxorubicin Hydrochloride), ADRUCIL® (Fluorouracil), AFINITOR® (Everolimus), AFINITOR DISPERZ® (Everolimus), AREDIA® (Pamidronate Disodium), ARIMIDEX® (Anastrozole), AROMASIN® (Exemestane), CAF, CLAFEN® (Cyclophosphamide), CMF, CYTOXAN® (Cyclophosphamide), Doxorubicin Hydrochloride, EFUDEX® (Fluorouracil), ELLENCE® (Epirubicin Hydrochloride), FARESTON® (Toremifene), FASLODEX® (Fulvestrant), FEC, FEMARA® (Letrozole), Fluoroplex® (Fluorouracil), FOLEX® (Methotrexate), FOLEX PFS® (Methotrexate), GEMZAR® (Gemcitabine Hydrochloride), HERCEPTIN® (Trastuzumab), IXEMPRA® (Ixabepilone), KADCYLA® (Ado-Trastuzumab Emtansine), MEGACE® (Megestrol Acetate), METHOTREXATE LPF® (Methotrexate), MEXATE® (Methotrexate), MEXATE-AQ® (Methotrexate), NEOSAR® (Cyclophosphamide), NOLVADEX® (Tamoxifen Citrate), PERJETA® (Pertuzumab), TAC, TAXOL® (Paclitaxel), TAXOTERE® (Docetaxel), TYKERB® (Lapatinib Ditosylate), XELODA® (Capecitabine), and ZOLADEX® (Goserelin Acetate).

In certain embodiments, the additional pharmaceutical agent is an anti-cancer agent for cervical cancer. Exemplary anti-cancer agents for the treatment or prevention (or both)

of cervical cancer include, but are not limited: CERVARIX® (Recombinant HPV Bivalent Vaccine), GARDASIL® (Recombinant HPV Quadrivalent Vaccine), AVASTIN® (Bevacizumab), BLENOXANE® (Bleomycin), Gemcitabine-Cisplatin, HYCAMTIN® (Topotecan Hydrochloride), PLATINOL® (Cisplatin), and PLATINOL-AQ® (Cisplatin).

In certain embodiments, the additional pharmaceutical agent is an anti-cancer agent for melanoma. Exemplary anti-cancer agents for the treatment or prevention (or both) of melanoma include, but are not limited: DTIC-DOME® (Dacarbazine), INTRON A® (Recombinant Interferon Alfa-2b), KEYTRUDA® (Pembrolizumab), MEKINIST® (Trametinib), PROLEUKIN® (Aldesleukin), SYLATRON® (Peginterferon Alfa-2b), PEG-INTRON® (Peginterferon Alfa-2b), TAFINLAR® (Dabrafenib), YERVOY® (Ipilimumab), and ZELBORAF® (Vemurafenib).

Also encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the first container and the second container are combined to form one unit dosage form. In some embodiments, the inventive pharmaceutical composition or compound is provided in multiple unit dosages for a course of treatement.

Thus, in one aspect, provided are kits including a first container comprising a compound of Formula (I), (II), or (III), or of a sub-formula thereof, or a pharmaceutically acceptable salt, solvate, hydrate, polymorph, co-crystal, tautomer, stereoisomer, isotopically labeled derivative, or pro-drug thereof, or a pharmaceutical composition thereof. In certain embodiments, the kits described herein are useful for preventing or treating (or both) a proliferative disease (e.g., cancer (e.g., breast cancer, ER negative breast cancer, melanoma, cervical cancer), benign neoplasms, diseases associated with angiogenesis, inflammatory diseases, autoinflammatory diseases, autoimmune diseases). In certain embodiments, the kits described herein are useful for preventing or treating (or both) a fibrotic disease (e.g., idiopathic pulmonary fibrosis, nephrogenic systemic fibrosis, scleroderma). In certain embodiments, the kits described herein are useful for treating or preventing (or both) a disease associated with over-expression of phosphoglycerate dehydrogenase (PHGDH) in a subject in need thereof. In certain embodiments, the kits described herein are useful for treating or preventing (or both) a disease associated with aberrant activity (e.g., increased activity) of phosphoglycerate dehydrogenase (PHGDH) in a subject in need thereof. In certain embodiments, the kits described herein are useful for treating or preventing (or both) a disease associated with abnormal serine production (e.g., increased serine biosynthetic pathway flux) in a subject in need thereof. In certain embodiments, the kits described herein are useful for attenuating phosphoglycerate dehydrogenase (PHGDH) activity in a subject in need thereof. In certain embodiments, the kits described herein are useful for modulating serine production in a subject in need thereof.

In certain embodiments, the kits include one or more devices (e.g., syringe and/or needle, suppository, dropper, inhaler, sprayer) for administering the composition or compound. In certain embodiments, the kits further include instructions for administering the compound, or a pharmaceutically acceptable salt, solvate, hydrate, polymorph, co-crystal, tautomer, stereoisomer, isotopically labeled derivative, or pro-drug, or a pharmaceutical composition thereof. A kit described herein may also include information as required by a regulatory agency such as the U.S. Food and Drug Administration (FDA). In certain embodiments, the information included in the kits is prescribing information. In certain embodiments, the kits and instructions provide for treating a proliferative disease (e.g., cancer (e.g., breast cancer, ER negative breast cancer, melanoma, cervical cancer), benign neoplasms, diseases associated with angiogenesis, inflammatory diseases, autoinflammatory diseases, and autoimmune diseases) in a subject in need thereof or preventing a proliferative disease (e.g., cancer (e.g., breast cancer, ER negative breast cancer, melanoma, cervical cancer), benign neoplasms, diseases associated with angiogenesis, inflammatory diseases, autoinflammatory diseases, autoimmune diseases) in a subject in need thereof. The kit of the invention may include one or more additional pharmaceutical agents described herein as a separate composition.

Methods of Treatment and Uses

The present invention also provides methods for the treatment or prevention of a disease. In certain embodiments, the disease is a proliferative disease (e.g., cancer (e.g., breast cancer, ER negative breast cancer, melanoma, cervical cancer), benign neoplasms, diseases associated with angiogenesis, inflammatory diseases, autoinflammatory diseases, autoimmune diseases). In certain embodiments, the disease is a fibrotic disease (e.g., idiopathic pulmonary fibrosis, nephrogenic systemic fibrosis, scleroderma).

The compounds of Formula (I), (II), or (III), or of a sub-formula thereof, may exhibit dehydrogenase inhibitory activity, exhibit the ability to inhibit phosphoglycerate dehydrogenase (PHGDH), exhibit a therapeutic effect or preventative effect (or both) in the treatment of cancers, exhibit a therapeutic effect or preventative effect (or both) in the treatment of cancers associated with PHGDH over-expression, exhibit a therapeutic effect or preventative effect (or both) in the treatment of cancers, exhibit a therapeutic effect or preventative effect (or both) in the treatment of cancers associated with PHGDH-dependent cells, and/or exhibit a therapeutic profile (e.g., optimum safety and curative effect) that is superior to existing chemotherapeutic agents.

The present invention provides methods for the treatment of disease by administering a compound of Formula (I), (II), or (III), or of a sub-formula thereof. In certain embodiments, the present invention provides methods for the treatment of disease by administering a compound of Formula (I). In certain embodiments, the present invention provides methods for the treatment of disease by administering a compound of Formula (II), or of a sub-formula thereof. In certain embodiments, the present invention provides methods for the treatment of disease by administering a compound of Formula (III), or of a sub-formula thereof. In certain embodiments, the compound may be administered as a pharmaceutically acceptable salt of the compound. In certain embodiments, the compound may be administered as a pharmaceutically acceptable salt solvate, hydrate, polymorph, co-crystal, tautomer, stereoisomer, isotopically labeled derivative, or pro-drug of the compound. In certain embodiments, the compound may be administered as a component of a pharmaceutical composition.

The present invention also provides uses of the inventive compounds, and pharmaceutically acceptable salts, solvates, hydrates, polymorphs, co-crystals, tautomers, stereoisomers, isotopically labeled derivatives, pro-drugs, and pharmaceutical compositions and formulations thereof, in the manufacture of medicaments for the treatment and prevention of diseases. In certain embodiments, the disease is associated with the over-expression or aberrant activity (e.g., increased activity), or both, of phosphoglycerate dehydrogenase (PHGDH). In certain embodiments, the use of the inventive compounds, salts, or compositions thereof, is for the treatment or prevention (or both) of a proliferative disease (e.g., cancer (e.g., breast cancer, ER negative breast cancer, melanoma, cervical cancer), benign neoplasms, diseases associated with angiogenesis, inflammatory diseases, autoinflammatory diseases, autoimmune diseases). In certain embodiments, the use of the inventive compounds, salts, or compositions thereof, is for the treatment or prevention (or both) of a fibrotic disease (e.g., idiopathic pulmonary fibrosis, nephrogenic systemic fibrosis, scleroderma)

In certain embodiments, the methods of the invention include administering to the subject an effective amount of a compound of Formula (I), (II), or (III), or of a sub-formula thereof, or a pharmaceutically acceptable salt thereof, or a pharmaceutical composition thereof. In certain embodiments, the effective amount is a therapeutically effective amount.

In another aspect, the present invention provides methods for treatment of a disease by administering a therapeutically effective amount of a compound of Formula (I), (II), or (III), or of a sub-formula thereof, or a pharmaceutically acceptable salt thereof, or pharmaceutical composition thereof. In certain embodiments, the disease is a proliferative disease. In certain embodiments, the disease is benign neoplasm. In certain embodiments, the disease is a disease associated with angiogenesis. In certain embodiments, the disease is an inflammatory disease. In certain embodiments, the disease is an autoinflammatory disease. In certain embodiments, the disease is an autoimmune disease. In certain embodiments, the proliferative disease is cancer. All types of cancers disclosed herein or known in the art are contemplated as being within the scope of the invention. In certain embodiments, the proliferative disease is breast cancer. In certain embodiments, the proliferative disease is adenocarcinoma of the breast, papillary carcinoma of the breast, mammary cancer, or medullary carcinoma of the breast. In certain embodiments, the proliferative disease is triple-negative breast cancer (TNBC), ER positive breast cancer, ER negative breast cancer, PR positive breast cancer, PR negative breast cancer, ER/PR positive breast cancer, ER/PR negative breast cancer, HER2 positive breast cancer, or HER2 negative breast cancer. In certain embodiments, the disease is ER negative breast cancer. In certain embodiments, the proliferative disease is cervical cancer. In certain embodiments, the proliferative disease is cervical adenocarcinoma or squamous cell carcinoma of the cervix. In certain embodiments, the proliferative disease is bone cancer. In certain embodiments, the proliferative disease is osteosarcoma. In certain embodiments, the proliferative disease is lung cancer. In certain embodiments, the proliferative disease is colorectal cancer. In certain embodiments, the proliferative disease is leukemia. In certain embodiments, the proliferative disease is lymphoma. In certain embodiments, the proliferative disease is melanoma. In certain embodiments, the disease is a fibrotic disease. In certain embodiments, the disease is idiopathic pulmonary fibrosis. In certain embodiments, the disease is nephrogenic systemic fibrosis. In certain embodiments, the disease is scleroderma.

In certain embodiments, the disease is a cancer selected from: acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast, triple negative breast cancer (TNBC), ER positive breast cancer, ER negative breast cancer, PR positive breast cancer, PR negative breast cancer, ER/PR positive breast cancer, ER/PR negative breast cancer, HER2 positive breast cancer, HER2 negative breast cancer); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma, squamous cell carcinoma of the cervix); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; kidney cancer (e.g., nephroblastoma a.ka. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

In certain embodiments, the disease is a fibrotic disease selected from: pulmonary fibrosis, idiopathic pulmonary fibrosis, cystic fibrosis, cirrhosis, endomyocardial fibrosis, atrial fibrosis, mediastinal fibrosis, myelofibrosis, retroperitoneal fibrosis, progressive massive fibrosis, nephrogenic systemic fibrosis, Crohn's disease, chronic kidney disease, keloid, scleroderma, systemic sclerosis, arthrofibrosis, Peyronie's disease, Dupuytren's contracture, asthma, and adhesive capsulitis.

In certain embodiments, the proliferative disease is a disease associated with over-expression of PHGDH. In certain embodiments, the proliferative disease is a disease associated with aberrant activity of PHGDH. Aberrant activity of PHGDH may be an elevated or an inappropriate activity (or both) of the PHGDH. In certain embodiments, PHGDH is not over-expressed, and the activity of PHGDH is not elevated or inappropriate (or not both). In certain other embodiments, PHGDH is over-expressed, and the activity of PHGDH is elevated or inappropriate (or both). In certain embodiments, the proliferative disease is a disease associated with abnormal serine production (e.g., increased serine biosynthetic pathway flux). In certain embodiments, the proliferative disease is a disease associated with increased serine production.

In another aspect, the present invention provides methods of inhibiting the activity of PHGDH in a subject in need thereof, by administering to the subject a compound of Formula (I), (II), or (III), or of a sub-formula thereof, or a pharmaceutically acceptable salt thereof, or a pharmaceutical composition thereof.

In another aspect, the present invention provides methods of inhibiting the activity of PHGDH in a biological sample (e.g., cells, tissues, biopsied tissues, blood, tumors), by contacting the sample with a compound of Formula (I), (II), or (III), or of a sub-formula thereof, or a pharmaceutically acceptable salt thereof, or a pharmaceutical composition thereof.

In another aspect, the present invention provides methods of inhibiting the serine biosynthetic pathway in a subject in need thereof, by administering to the subject a compound of Formula (I), (II), or (III), or of a sub-formula thereof, or a pharmaceutically acceptable salt thereof, or a pharmaceutical composition thereof.

In another aspect, the present invention provides methods of inhibiting the serine biosynthetic pathway in a biological sample (e.g., cells, tissues, biopsied tissues, blood, tumors), by contacting the sample with a compound of Formula (I), (II), or (III), or of a sub-formula thereof, or a pharmaceutically acceptable salt thereof, or a pharmaceutical composition thereof.

In another aspect, the present invention provides methods of inhibiting cell growth in a subject in need thereof, by administering to the subject a compound of Formula (I), (II), or (III), or of a sub-formula thereof, or a pharmaceutically acceptable salt thereof, or a pharmaceutical composition thereof. In certain embodiments, the method of inhibiting cell growth is for PHGDH-dependent cells. In certain embodiments, the method of inhibiting cell growth is selective for PHGDH-dependent cells.

In another aspect, the present invention provides methods of inhibiting cell growth in a biological sample (e.g., cells, tissues, biopsied tissues, blood, tumors), by contacting the sample with a compound of Formula (I), (II), or (III), or of a sub-formula thereof, or a pharmaceutically acceptable salt thereof, or a pharmaceutical composition thereof. In certain embodiments, the method of inhibiting cell growth is for PHGDH-dependent cells. In certain embodiments, the method of inhibiting cell growth is selective for PHGDH-dependent cells.

In another aspect, the present invention provides methods of inducing cell death in a subject in need thereof, by administering to the subject a compound of Formula (I), (II), or (III), or of a sub-formula thereof, or a pharmaceutically acceptable salt thereof, or a pharmaceutical composition thereof. In certain embodiments, the method of inducing cell death is for PHGDH-dependent cells. In certain embodiments, the method of inducing cell death is selective for PHGDH-dependent cells.

In another aspect, the present invention provides methods of inducing cell death in a biological sample (e.g., cells, tissues, biopsied tissues, blood, tumors), by contacting the sample with a compound of Formula (I), (II), or (III), or of a sub-formula thereof, or a pharmaceutically acceptable salt thereof, or a pharmaceutical composition thereof. In certain embodiments, the method of inducing cell death is for PHGDH-dependent cells. In certain embodiments, the method of inducing cell death is selective for PHGDH-dependent cells.

The invention also provides methods of using the compounds of Formula (I), (II), or (III), or sub-formula thereof, or pharmaceutically acceptable salts, solvates, hydrates, polymorphs, co-crystals, tautomers, stereoisomers, isotopically labeled derivatives, pro-drugs, and pharmaceutical compositions thereof, are in research studies in the Field of disease pathology, biochemistry, cell biology, oncology, and other fields associated with proliferative diseases. The compounds of the invention can be used to study the roles of biomolecules (e.g., PHGDH, serine). The compounds of the invention can be used to study biological pathways (e.g., PHGDH expression, serine biosynthetic pathway, TCA cycle, PSAT1 expression, PSPH expression). The compounds of the invention can be used to study aspects of proliferative diseases (e.g., tumorigenesis, cell proliferation, cell growth, cell death). In certain embodiments, the method uses the compounds or compositions thereof to inhibit PHGDH. In certain embodiments, the method comprises determining the concentration of a biomolecule in a biological sample.

In certain embodiments, the method comprises determining the concentration of PHGDH in a biological sample. In certain embodiments, the method comprises determining the concentration of serine in a biological sample. In certain embodiments, the method comprises determining the concentration of NAD+, NADP+, NADH, NADPH, or α-ketoglutarate in a biological sample. In certain embodiments, the method comprises determining the concentration of PSAT1 or PSPH in a biological sample. In certain embodiments, the method comprises determining the concentration of 3-phospho-D-glycerate, 3-phophonooxypyruvate, 2-hydroxyglutarate, or 2-oxogluturate in a biological sample. In certain embodiments, the method comprises determining the concentration of a biomolecule of the serine biosynthetic pathway in a biological sample. In certain embodiments, the method comprises determining the concentration of a metabolite of the serine biosynthetic pathway in a biological sample. In certain embodiments, the method comprises determining the concentration of an amino acid in a biological sample.

In certain embodiments, the method comprises determining the activity of an enzyme in a biological sample. In certain embodiments, the method comprises determining the activity of PHGDH in a biological sample. In certain embodiments, the method comprises determining the activity of PSAT1 or PSPH in a biological sample. In certain embodiments, the method comprises determining the serine biosynthetic pathway flux in a biological sample.

The invention provides methods for determining if a cancer over-expresses PHGDH, for determining if cancer cells have one or more extra copies of the PHGDH gene, or for a diagnostic test for determining if a subject has cancer that over-expresses PHGDH. In certain embodiments, the method comprises determining if a cancer over-expresses PHGDH. In certain embodiments, the method comprises measuring PHGDH mRNA in a sample obtained from the cancer. In certain embodiments, the method comprises measuring PHGDH protein in a sample obtained from the cancer. In certain embodiments, the method comprises an immunohistochemistry stain. In certain embodiments, the method comprises performing an immunohistochemistry stain with an antibody that binds PHGDH and comparing the level of staining in cancer cells with a control level (e.g., cells from non-cancerous tissue). In certain embodiments, the method comprises fluorescent in situ hybridization or genetic sequencing. These methods and diagnostic tests may allow identification or selection of subjects for treatment with PHGDH inhibitors.

In one aspect, the method of treating a proliferative disease comprises the steps of determining if a cancer in a subject over-expresses PHGDH, and treating the subject with a compound of Formula (I), (II), or (III), or composition thereof. In certain embodiments, the method of treating a proliferative disease comprises the steps of determining if cancer cells from a subject have one or more extra copies of the PHGDH gene, and treating the subject with a compound of Formula (I), (II), or (III), or composition thereof. In certain embodiments, the method of treating a proliferative disease comprises the steps of performing a diagnostic test to determining if cancer in a subject over-expresses PHGDH, and treating the subject with a compound of Formula (I), (II), or (III), or composition thereof. In certain embodiments, the method comprises measuring PHGDH mRNA in a sample obtained from the cancer. In certain embodiments, the method comprises measuring PHGDH protein in a sample obtained from the cancer. In certain embodiments, the method comprises performing an immunohistochemistry stain with an antibody that binds PHGDH and comparing the level of staining in cancer cells with a control level (e.g., cells from non-cancerous tissue). In certain embodiments, the method comprises fluorescent in situ hybridization or genetic sequencing.

In certain embodiments, the subject described herein is a human. In certain embodiments, the subject is an animal. The animal may be of either sex and may be at any stage of development. In certain embodiments, the subject is a mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

In certain embodiments, the biological sample described herein is one or more cells. In certain embodiments, the biological sample described herein is one or more cancer cells. In certain embodiments, a cell described herein is in vitro. In certain embodiments, a cell described herein is ex vivo. In certain embodiments, a cell described herein is in vivo. In certain embodiments, a cell described herein is a malignant cell. In certain embodiments, a cell In certain embodiments, the biological sample described herein is blood, bone, or tissue. In certain embodiments, the biological sample described herein is bone marrow or lymph node. In certain embodiments, the biological sample described herein is biopsied tissue. In certain embodiments, the biological sample described herein is a tumor.

In another aspect, the present invention provides methods of treating or preventing (or both) a disease associated with PHGDH expression or activity in a subject in need thereof. In certain embodiments, the diseases is associated with over-expression of PHGDH. In certain embodiments the disease is associated with aberrant activity of PHGDH. In certain embodiments the disease is associated with increased activity of PHGDH. In certain embodiments the disease is associated with abnormal serine production (e.g., increased serine biosynthetic pathway flux). In certain embodiments the disease is associated with increased serine production.

Another aspect of the present invention relates to methods of treating or preventing (or both) a proliferative disease in a subject in need thereof. In certain embodiments the disease is cancer. In certain embodiments, the proliferative disease that may be treated or prevented (or both) by the inventive methods include, but are not limited to, breast cancer, adenocarcinoma of the breast, papillary carcinoma of the breast, mammary cancer, medullary carcinoma of the breast, triple-negative breast cancer (TNBC), ER positive breast cancer, ER negative breast cancer, PR positive breast cancer, PR negative breast cancer, ER/PR positive breast cancer, ER/PR negative breast cancer, HER2 positive breast cancer, HER2 negative breast cancer, cervical cancer, cervical adenocarcinoma, squamous cell carcinoma of the cervix, bone cancer, osteosarcoma, leukemia, lymphoma, melanoma, colorectal cancer or lung cancer.

Certain methods described herein, may comprise administering one or more additional pharmaceutical agent in combination with the compounds described herein. In certain embodiments, the additional pharmaceutical agent may be an anti-proliferative agent. In certain embodiments, the additional pharmaceutical agent is an anti-cancer agent. The additional pharmaceutical agent may also be an inhibitor. In certain embodiments, the additional pharmaceutical agent is an inhibitor of PHGDH. In certain embodiments, the additional pharmaceutical agent is an inhibitor of PSAT1 or PSPH. In certain embodiments, the additional pharmaceutical agent is a modulator of the serine biosynthesitic pathway. In certain embodiments, the additional pharmaceutical agent is an inhibitor of serine production.

In one aspect, the additional pharmaceutical agent is an anti-cancer agent. Anti-cancer agents encompass biotherapeutic anti-cancer agents as well as chemotherapeutic agents.

Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)).

Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (Abraxane), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated pro-drug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonuclotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. l-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In certain embodiments, the additional pharmaceutical agent is an anti-cancer agent for breast cancer. Exemplary anti-cancer agents for the treatment or prevention (or both) of breast cancer include, but are not limited: ABITREXATE® (Methotrexate), ABRAXANE® (Paclitaxel Albumin-stabilized Nanoparticle Formulation), AC, AC-T, ADRIAMYCIN PFS® (Doxorubicin Hydrochloride), ADRIAMYCIN RDF® (Doxorubicin Hydrochloride), ADRUCIL® (Fluorouracil), AFINITOR® (Everolimus), AFINITOR DISPERZ® (Everolimus), AREDIA® (Pamidronate Disodium), ARIMIDEX® (Anastrozole), AROMASIN® (Exemestane), CAF, CLAFEN® (Cyclophosphamide), CMF, CYTOXAN® (Cyclophosphamide), Doxorubicin Hydrochloride, EFUDEX® (Fluorouracil), ELLENCE® (Epirubicin Hydrochloride), FARESTON® (Toremifene), FASLODEX® (Fulvestrant), FEC, FEMARA® (Letrozole), Fluoroplex® (Fluorouracil), FOLEX® (Methotrexate), FOLEX PFS® (Methotrexate), GEMZAR® (Gemcitabine Hydrochloride), HERCEPTIN® (Trastuzumab), IXEMPRA® (Ixabepilone), KADCYLA® (Ado-Trastuzumab Emtansine), MEGACE® (Megestrol Acetate), METHOTREXATE LPF® (Methotrexate), MEXATE® (Methotrexate), MEXATE-AQ® (Methotrexate), NEOSAR® (Cyclophosphamide), NOLVADEX® (Tamoxifen Citrate), PERJETA® (Pertuzumab), TAC, TAXOL® (Paclitaxel), TAXOTERE® (Docetaxel), TYKERB® (Lapatinib Ditosylate), XELODA® (Capecitabine), and ZOLADEX® (Goserelin Acetate).

In certain embodiments, the additional pharmaceutical agent is an anti-cancer agent for cervical cancer. Exemplary anti-cancer agents for the treatment or prevention (or both) of cervical cancer include, but are not limited: CERVARIX® (Recombinant HPV Bivalent Vaccine), GARDASIL® (Recombinant HPV Quadrivalent Vaccine), AVASTIN® (Bevacizumab), BLENOXANE® (Bleomycin), Gemcitabine-Cisplatin, HYCAMTIN® (Topotecan Hydrochloride), PLATINOL® (Cisplatin), and PLATINOL-AQ® (Cisplatin).

In certain embodiments, the additional pharmaceutical agent is an anti-cancer agent for melanoma. Exemplary anti-cancer agents for the treatment or prevention (or both) of melanoma include, but are not limited: DTIC-DOME® (Dacarbazine), INTRON A® (Recombinant Interferon Alfa-2b), KEYTRUDA® (Pembrolizumab), MEKINIST® (Trametinib), PROLEUKIN® (Aldesleukin), SYLATRON® (Peginterferon Alfa-2b), PEG-INTRON® (Peginterferon Alfa-2b), TAFINLAR® (Dabrafenib), YERVOY® (Ipilimumab), and ZELBORAF® (Vemurafenib).

The compounds of Formula (I), (II), or (III), or subformula thereof, may be selective inhibitors of PHGDH. In certain embodiments, the activity of PHGDH is selectively inhibited by administration of the compound, compared to activity of a different protein. In certain embodiments, the activity of PHGDH is non-selectively inhibited by administration of the compound.

The compounds of Formula (I), (II), or (III), or subformula thereof, may be selectively cytotoxic for cells over-expressing PHGDH. In certain embodiments, the cytotoxicity of the compounds may be greater in cells over-expressing PHGDH compared to cytotoxicity in other cells. In certain embodiments, the cytotoxicity of the compounds may be 1 to 5 times greater in cells over-expressing PHGDH compared to cytotoxicity in other cells. In certain embodiments, the cytotoxicity of the compounds may be 5 to 10 times greater in cells over-expressing PHGDH compared to cytotoxicity in other cells. In certain embodiments, the cytotoxicity of the compounds may be 10 to 100 times greater in cells over-expressing PHGDH compared to cytotoxicity in other cells. In certain embodiments, the cytotoxicity of the compounds may be 100 to 1000 times greater in cells over-expressing PHGDH compared to cytotoxicity in other cells. In certain embodiments, the cytotoxicity of the compounds may be 1000 to 10000 times greater in cells over-expressing PHGDH compared to cytotoxicity in other cells. In certain embodiments, the cytotoxicity of the compounds may be 10000 to 100000 times greater in cells over-expressing PHGDH compared to cytotoxicity in other cells. In certain embodiments, the cytotoxicity of the compounds may be more than 100000 times greater in cells over-expressing PHGDH compared to cytotoxicity in other cells. In certain embodiments, the compounds are non-selectively cytotoxic for cells over-expressing PHGDH inhibited by administration of the compound.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

General Synthetic Methods

All air- or moisture-sensitive reactions were performed under positive pressure of nitrogen with oven-dried glassware. Anhydrous solvents or reagents such as dichloromethane, N,N-dimethylformamide (DMF), acetonitrile, methanol, and triethylamine were purchased from Sigma-Aldrich. Preparative purification was performed on a Waters semi-preparative HPLC system. The column used was a Phenomenex Luna C18 (5 micron, 30×75 mm) at a flow rate of 45 mL/min. The mobile phase consisted of acetonitrile and water (each containing 0.1% trifluoroacetic acid). A gradient of 10% to 50% acetonitrile over 8 minutes was used during the purification. Fraction collection was triggered by UV detection (220 nM). Analytical analysis was performed on an Agilent LC/MS (Agilent Technologies, Santa Clara, Calif.). Purity analysis was determined using a 7 minute gradient of 4% to 100% acetonitrile (containing 0.025% trifluoroacetic acid) and water (containing 0.05% trifluoroacetic acid) with an 8 minute run time at a flow rate of 1 mL/min. A Phenomenex Luna C18 column (3 micron, 3×75 mm) was used at a temperature of 50° C. using an Agilent Diode Array Detector. Mass determination was performed using an Agilent 6130 mass spectrometer with electrospray ionization in the positive mode. $^1$H NMR spectra were recorded on Varian 400 MHz spectrometers. Chemical shifts are reported in ppm with non-deuterated solvent (DMSO-$d_6$ at 2.50 ppm) as internal standard for DMSO-$d_6$ solutions. All of the analogs tested in the biological assays have a purity greater than 95% based on LCMS analysis. High resolution mass spectrometry was recorded on Agilent 6210 Time-of-Flight LC/MS system. A gradient of 4% to 100% acetonitrile (containing 0.025% trifluoroacetic acid) and water (containing 0.05% trifluoroacetic acid) with a 4.5 minute run time at a flow rate of 1 mL/min was used. An Agilent Extend-C18 column (3.5 micron, 4.6×100 mm) was used at a temperature of 50° C. using an Agilent Diode Array Detector. Confirmation of molecular formulae was accomplished using electrospray ionization in the positive mode with the Agilent Masshunter software.

Syntheses

Example 1. N-(1-(((4,6-dimethylpyridin-2-yl)carbamothioyl)piperidin-3-yl)-3-(trifluoromethyl)benzamide (Compound 262)

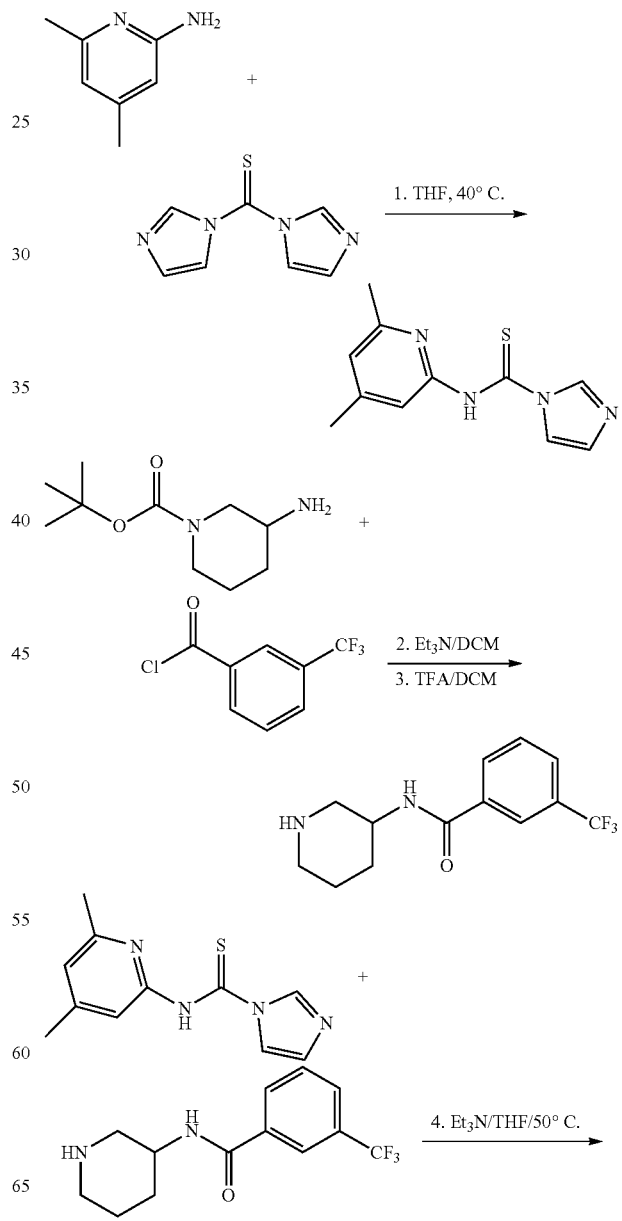

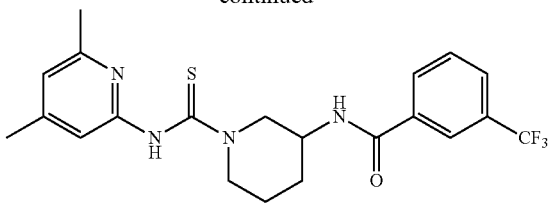

Step 1. N-(4,6-dimethylpyridin-2-yl)-1H-imidazole-1-carbothioamide

A mixture of 4,6-dimethylpyridin-2-amine (0.28 g, 2.292 mmol) and di(1H-imidazol-1-yl)methanethione (0.408 g, 2.292 mmol) in THF (12 ml) was stirred at 40° C. for 30 min. The product (suspension) was used in the next reaction.

Step 2. tert-butyl 3-(3-(trifluoromethyl)benzamido)piperidine-1-carboxylate

To a solution of tert-butyl 3-aminopiperidine-1-carboxylate (0.5 g, 2.497 mmol) and TEA (1.740 ml, 12.48 mmol) in DCM (5 ml) was added 3-(trifluoromethyl)benzoyl chloride (0.376 ml, 2.497 mmol). The mixture was stirred at r.t. for overnight. To the reaction mixture, a Sat. NaHCO₃ solution was added and the solution was extracted with DCM. The organic layer was dried over MgSO₄ and concentrated. The crude product was used in the next reaction without further purification.

Step 3. N-(piperidin-3-yl)-3-(trifluoromethyl)benzamide

To a solution of tert-butyl 3-(3-(trifluoromethyl)benzamido)piperidine-1-carboxylate (0.9 g, 2.417 mmol) in DCM (5 ml) was added TFA (1 ml). The mixture was stirred at r.t. for overnight. The solvent was removed. The crude product was used in the next reaction without further purification.

Step 4. N-(1-((4,6-dimethylpyridin-2-yl)carbamothioyl)piperidin-3-yl)-3-(trifluoromethyl)benzamide (Compound 262)

To a solution of N-(piperidin-3-yl)-3-(trifluoromethyl)benzamide (0.1 g, 0.367 mmol) and TEA (0.205 ml, 1.469 mmol) in THF (1 ml) was added a solution of N-(4,6-dimethylpyridin-2-yl)-1H-imidazole-1-carbothioamide (0.085 g, 0.367 mmol) in THF (2 ml). The mixture was stirred at 50° C. for 1 hr. The solvent was removed. The crude product was purified by reverse phase purification system in basic condition to afford Compound 262.

¹H NMR (400 MHz, DMSO-d6) δ ppm 9.61 (s, 1H), 8.59 (d, J=7.4 Hz, 1H), 8.19-8.10 (m, 2H), 7.91 (ddd, J=7.7, 1.9, 1.0 Hz, 1H), 7.72 (tt, J=7.8, 0.7 Hz, 1H), 7.15 (s, 1H), 6.72 (s, 1H), 4.53 (s, 1H), 4.38 (d, J=13.0 Hz, 1H), 3.96 (s, 1H), 3.31 (s, 2H), 2.34 (d, J=0.6 Hz, 3H), 2.19 (t, J=0.7 Hz, 3H), 2.06-1.94 (m, 1H), 1.90-1.78 (m, 1H), 1.65 (dt, J=27.5, 14.3 Hz, 2H); HRMS: m/z (M+H)⁺=437.1626 (Calculated for C₂₁H₂F₃N₄OS=437.1617); retention time: 2.755 min.

Example 2. N-(1-((4,6-dimethylpyridin-2-yl)carbamothioyl)piperidin-3-yl)-4-(trifluoromethyl)benzamide. (Compound 264)

Scheme E2.

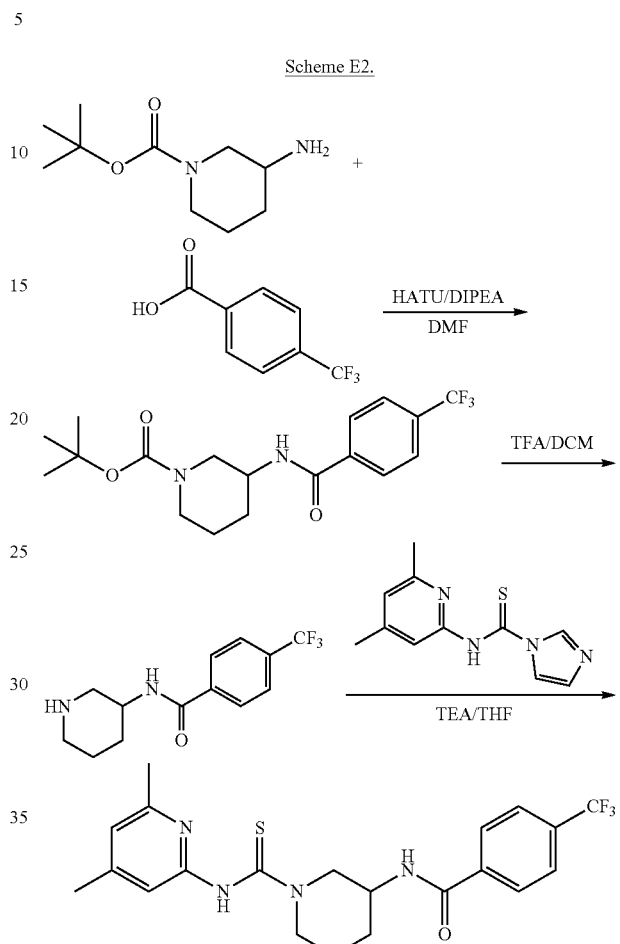

Step 1. tert-butyl 3-(4-(trifluoromethyl)benzamido)piperidine-1-carboxylate

To a solution of 4-(trifluoromethyl)benzoic acid (431 mg, 2.27 mmol), HATU (949 mg, 2.497 mmol) and DIPEA (1.19 ml, 6.81 mmol) in DMF (5 ml) was added tert-butyl 3-aminopiperidine-1-carboxylate (500 mg, 2.497 mmol). The mixture was stirred at r.t. for 2 hrs. Water (60 ml) was added to the mixture. The solid was filtered and washed with water, and dried. The crude product was used in the next reaction without further purification (0.8 g, 95%).

Step 2. N-(piperidin-3-yl)-4-(trifluoromethyl)benzamide

N-(piperidin-3-yl)-4-(trifluoromethyl)benzamide was prepared according to the method described in Example 1, Step 3, substituting tert-butyl 3-(4-(trifluoromethyl)benzamido)piperidine-1-carboxylate for tert-butyl 3-(3-(trifluoromethyl)benzamido)piperidine-1-carboxylate.

Step 3. N-(1-((4,6-dimethylpyridin-2-yl)carbamothioyl)piperidin-3-yl)-4-(trifluoromethyl)benzamide. (Compound 264)

Compound 264 was prepared according to the method described in Example 1, Step 4, substituting N-(piperidin- 3-yl)-4-(trifluoromethyl)benzamide for N-(piperidin-3-yl)-3-(trifluoromethyl)benzamide. HRMS: m/z (M+Na)⁺=459.1459 (Calculated for $C_{21}H_{23}F_3N_4NaOS$=459.1437); retention time: 2.751 min.

Example 3. N-(4,6-dimethylpyridin-2-yl)-4-(4-(trifluoromethyl)benzyl)piperazine-1-carbothioamide (Compound 267)

Scheme E3.

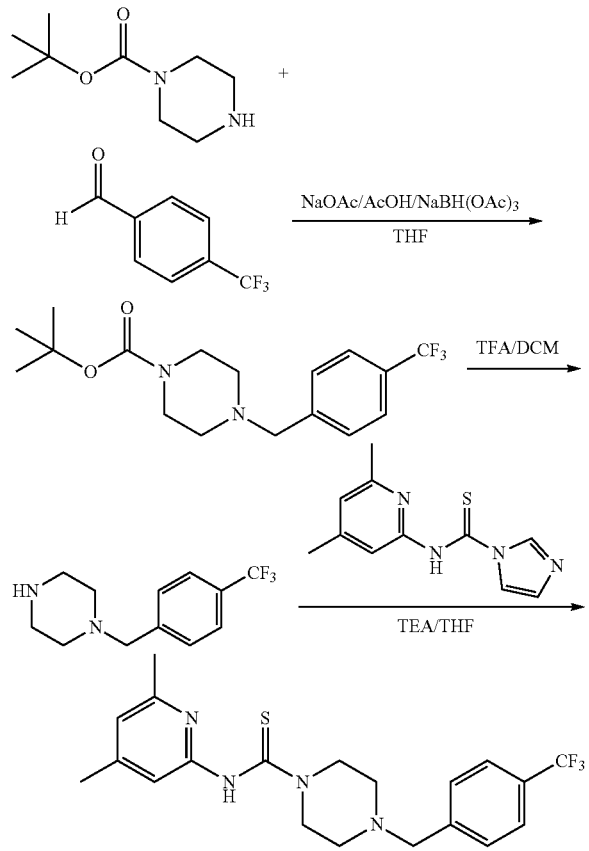

Step 1. tert-butyl 4-(4-(trifluoromethyl)benzyl)piperazine-1-carboxylate

To a mixture of tert-butyl piperazine-1-carboxylate (0.2 g, 1.074 mmol), sodium acetate (0.115 g, 1.396 mmol) and acetic acid (0.086 ml, 1.503 mmol) in THF (5 ml) was added 4-(trifluoromethyl)benzaldehyde (0.147 ml, 1.074 mmol). The mixture was stirred at r.t. for 4 hrs. Sodium triacetoxyborohydride (0.341 g, 1.611 mmol) was added to the mixture. The reaction mixture was stirred at r.t. overnight. Water was added to the mixture and extracted with EtOAc (2 times). The organic layer was washed with Sat. NaHCO₃ (3 times) and brine, and dried over MgSO₄, and concentrated (0.36 g, 97%).

Step 2. 1-(4-(trifluoromethyl)benzyl)piperazine 1-(4-(trifluoromethyl)benzyl)piperazine was prepared according to the method described in Example 1, Step 3, substituting tert-butyl 4-(4-(trifluoromethyl)benzyl)piperazine-1-carboxylate for tert-butyl 3-(3-(trifluoromethyl)benzamido)piperidine-1-carboxylate.

Step 3. N-(4,6-dimethylpyridin-2-yl)-4-(4-(trifluoromethyl)benzyl)piperazine-1-carbothioamide (Compound 267 (NCT-503))

Compound 267 (NCT-503) was prepared according to the method described in Example 1, Step 4, substituting 1-(4-(trifluoromethyl)benzyl)piperazine for N-(piperidin-3-yl)-3-(trifluoromethyl)benzamide. HRMS: m/z (M+H)⁺=409.1686 (Calculated for $C_{20}H_{24}F_3N_4S$=409.1668); retention time: 2.473 min.

Scheme E3-1. Alternate Procedure for the Synthesis of Compound 267 (NCT-503)

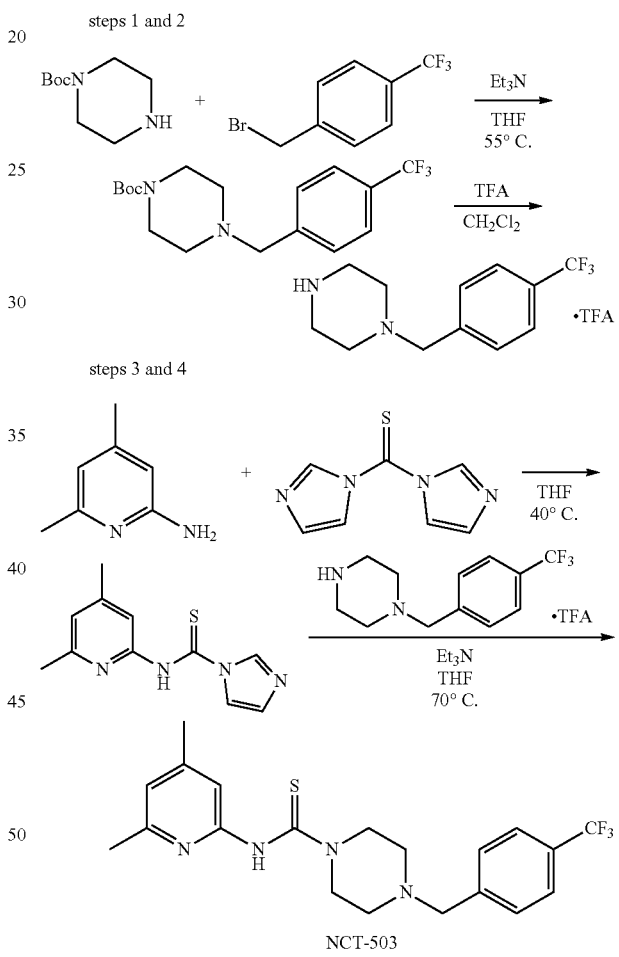

Steps 1 and 2: To a solution of tert-butyl piperazine-1-carboxylate (1.31 g, 7.05 mmol) and triethylamine (1.2 mL, 8.5 mmol) in THF (30 ml) was added 1-(bromomethyl)-4-(trifluoromethyl)benzene (1.69 g, 7.05 mmol). The reaction mixture was heated with stirring at 55° C. overnight. The reaction mixture was diluted with water and DCM. The layers were separated and the aqueous layer was re-extracted with DCM. The combined organic layers were dried with MgSO₄ and concentrated in vacuo to afford tert-butyl 4-(4-(trifluoromethyl)benzyl)piperazine-1-carboxylate. This material was taken up in DCM (20 mL) and treated with TFA (2 mL). After standing at rt for 1 hr, an additional aliquot of TFA (3 mL) was added. Upon standing at rt for an additional 2 hr, the reaction was determined to be complete by LCMS (LCMS: m/z (M+H)$^+$=245.1). The reaction mixture was concentrated in vacuo, rediluted with ~50 mL of DCM, and reconcentrated in vacuo to yield a partially crystalline, faint tan solid which was used without further purification.

Steps 3 and 4: To a solution of di(1H-imidzazol-1-yl) methanethione (1.26 g, 7.05 mmol) in THF (30 mL) was added 4,6-dimethylpyridine-2-amine (0.861 g, 7.05 mmol). The resulting reaction mixture was heated at 40° C. for 35 min. During the reaction, the mixture was sonicated in order to produce a homogeneous yellow slurry. This slurry was transferred to another vial containing a slurry comprised of the TFA salt of 1-(4-(trifluoromethyl)benzyl)piperazine (from step 2), THF (10 mL), and triethylamine (1 mL, 7.05 mmol). An additional aliquot of THF (5 mL) was used to complete the transfer. The resulting reaction mixture was heated with stirring at 70° C. for 1.25 hr. The reaction mixture was diluted with water and DCM. The layers were separated and the aqueous layer was re-extracted with DCM. The combined organic layers were dried with MgSO$_4$ and concentrated in vacuo. The resulting residue was taken up in DMSO and purified via reversed phase column chromatography (10 to 50% acetonitrile/water 0.1% TFA). The pure fractions were combined and most of the organic portion removed in vacuo. To the resulting mixture was added DCM as well as saturated aqueous sodium bicarbonate solution, in order to free base the product. The layers were separated and the aqueous layer was re-extracted with DCM three additional times. The combined organic layers were dried with MgSO$_4$ and concentrated in vacuo to afford N-(4,6-dimethylpyridin-2-yl)-4-(4-(trifluoromethyl)benzyl)piperazine-1-carbothioamide (NCT-503, 0.809 g, 28% over 3 steps) as a colorless foam. HRMS: m/z (M+H)$^+$=409.1686 (Calculated for C$_{20}$H$_{24}$F$_3$N$_4$S=409.1668), Retention time: 2.473 min; $^1$H NMR (400 MHz, DMSO-d$_6$) δ 9.59 (br s, 1H), 7.72-7.64 (m, 2H), 7.58-7.48 (m, 2H), 7.13 (s, 1H), 6.70 (s, 1H), 3.91-3.79 (m, 4H), 3.60 (s, 2H), 2.44-2.38 (m, 4H), 2.32 (s, 3H), 2.20 (s, 3H); $^{13}$C NMR (101 MHz, DMSO-d$_6$) δ 181.44, 154.04, 143.35 (m), 129.92, 128.85, 128.13 (q, J$_{C-F}$=31.31 Hz), 126.15, 125.55 (q, J$_{C-F}$=4.04 Hz), 123.44, 119.17 (br), 115.62, 61.26, 52.67, 48.88, 23.56 (br), 21.03.

Example 4. N-(4,6-dimethylpyridin-2-yl)-4-(pyridin-2-ylmethyl)piperazine-1-carbothioamide (Compound 287)

Scheme E4.

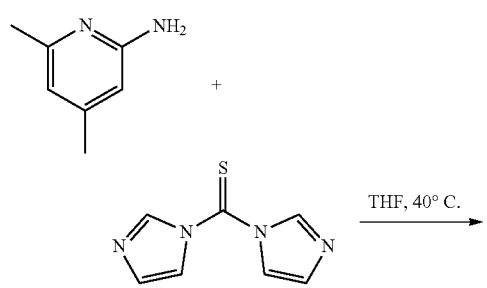

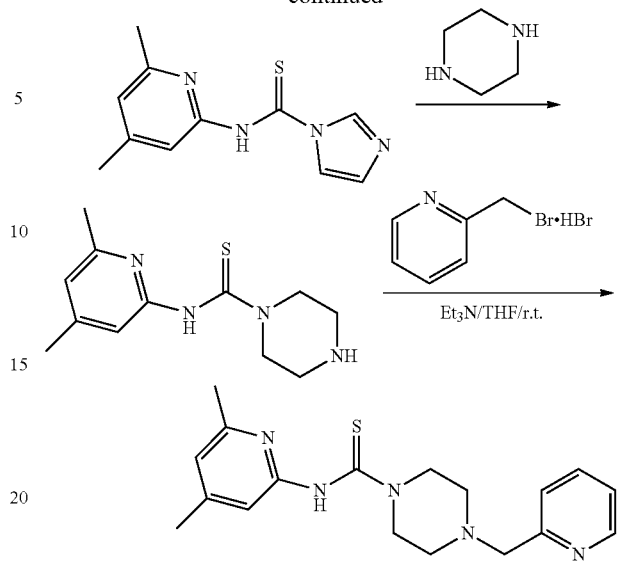

Step 1. N-(4,6-dimethylpyridin-2-yl)-1H-imidazole-1-carbothioamide

N-(4,6-dimethylpyridin-2-yl)-1H-imidazole-1-carbothioamide was prepared according to the method used to prepare compound described in Example 1, Step 1.

Step 2. N-(4,6-dimethylpyridin-2-yl)piperazine-1-carbothioamide

To a solution of N-(4,6-dimethylpyridin-2-yl)-1H-imidazole-1-carbothioamide (0.57 g, 3.20 mmol) in THF (32 ml) was added piperazine (0.275 g, 3.20 mmol) and the mixture stirred at 70° C. for 1.5 hr. The reaction mixture was used in the next reaction.

Step 3. N-(4,6-dimethylpyridin-2-yl)-4-(pyridin-2-ylmethyl)piperazine-1-carbothioamide (Compound 287)

To the mixture of N-(4,6-dimethylpyridin-2-yl)piperazine-1-carbothioamide (50 mg, 0.200 mmol) in THF (2 ml) were added 2-(bromomethyl)pyridine hydrobromide (50.5 mg, 0.200 mmol) and TEA (0.028 ml, 0.200 mmol). The reaction mixture was stirred at r.t. overnight. The solvent was removed. The crude product was purified by reverse phase purification system in basic condition to afford Compound 287. HRMS: m/z (M+H)$^+$=342.1748 (Calculated for C$_{18}$H$_{24}$N$_5$S=342.1747); retention time: 1.996 min.

Example 5. N-(pyridin-2-ylmethyl)-4-(3-(trifluoromethyl)phenyl)piperazine-1-carbothioamide (Compound 232)

Scheme E5.

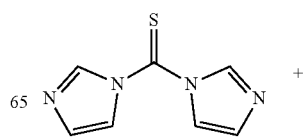

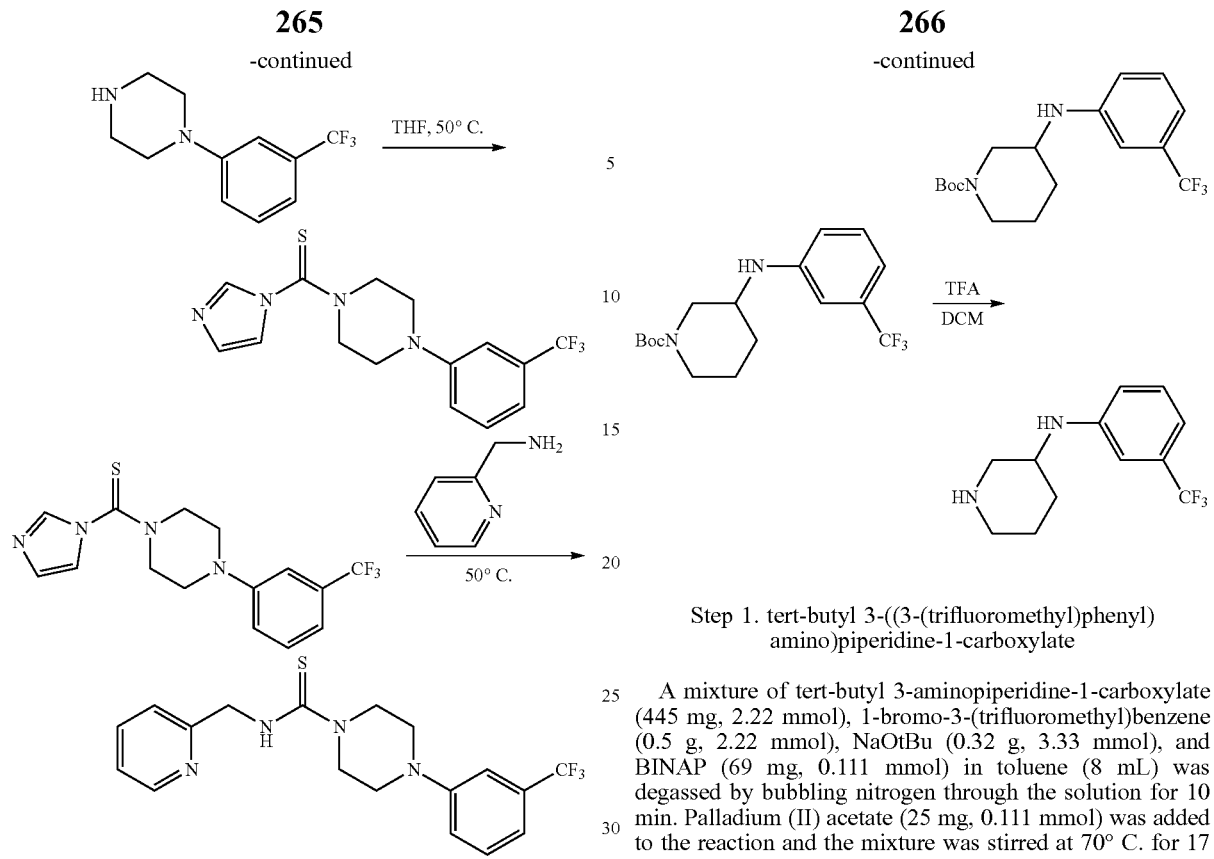

Step 1. (1H-imidazol-1-yl)(4-(3-(trifluoromethyl)phenyl)piperazin-1-yl)methanethione A mixture of 1-(3-(trifluoromethyl)phenyl)piperazine (50 mg, 0.217 mmol) and di(1H-imidazol-1-yl)methanethione (39 mg, 0.217 mmol) in THF (2 ml) was stirred at 50° C. for 60 min. The product was used in the next reaction.

Step 2. N-(pyridin-2-ylmethyl)-4-(3-(trifluoromethyl)phenyl)piperazine-1-carbothioamide (Compound 232)

Pyridin-2-ylmethanamine (24 mg, 0.217 mmol) was added to the above reaction mixture and heating continued at 50° C. for 1 hr. The solvent was removed. The crude product was purified by reverse phase purification system to afford Compound 232. HRMS: m/z (M+H)$^+$=381.1373 (Calculated for $C_{18}H_{20}F_3N_4S$=381.1355); retention time: 2.71 min.

Example 6.
N-(3-(trifluoromethyl)phenyl)piperidin-3-amine

Scheme E6.

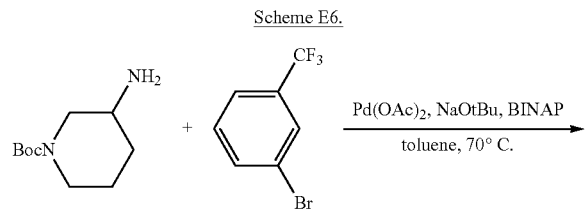

Step 1. tert-butyl 3-((3-(trifluoromethyl)phenyl)amino)piperidine-1-carboxylate A mixture of tert-butyl 3-aminopiperidine-1-carboxylate (445 mg, 2.22 mmol), 1-bromo-3-(trifluoromethyl)benzene (0.5 g, 2.22 mmol), NaOtBu (0.32 g, 3.33 mmol), and BINAP (69 mg, 0.111 mmol) in toluene (8 mL) was degassed by bubbling nitrogen through the solution for 10 min. Palladium (II) acetate (25 mg, 0.111 mmol) was added to the reaction and the mixture was stirred at 70° C. for 17 h. The reaction mixture was concentrated under a stream of air and dry loaded on silica gel using a mixture of dichloromethane and methanol. Chromatographic purification (5 to 25% EtOAc/hexanes) yielded the desired coupling product, tert-butyl 3-((3-(trifluoromethyl)phenyl)amino)piperidine-1-carboxylate, which was used in the following step.

Step 2.
N-(3-(trifluoromethyl)phenyl)piperidin-3-amine

Deprotection of tert-butyl 3-((3-(trifluoromethyl)phenyl)amino)piperidine-1-carboxylate was conducted by dilution of the starting material with DCM (20 ml) and subsequent addition of TFA (~2 mL). The solution was allowed to stand at rt for 2.5 h and was subsequently concentrated to yield N-(3-(trifluoromethyl)phenyl)piperidin-3-amine as a light yellow solid. LCMS: m/z (M+H)$^+$=245.0.

Example 7.
2-methyl-1-(4-(trifluoromethyl)benzyl)piperazine

Scheme E7.

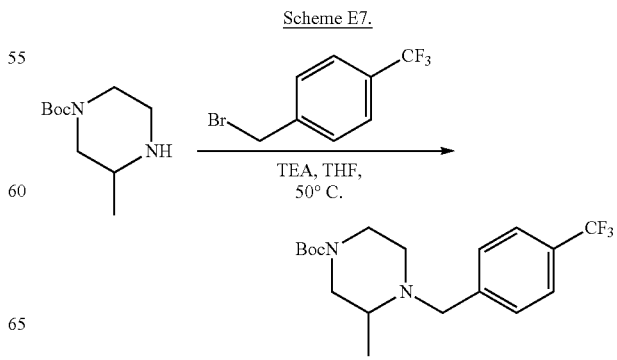

267

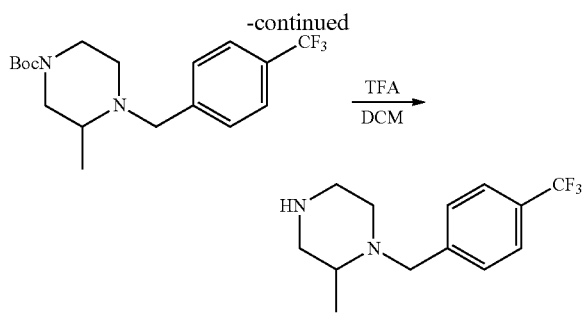

Step 1. tert-butyl 3-methyl-4-(4-(trifluoromethyl)benzyl)piperazine-1-carboxylate 1-(Bromomethyl)-4-(triflluromethyl)benzene (75 mg, 0.315 mmol) was added to a mixture of tert-butyl 3-methylpiperazine-1-carboxylate (63 mg, 0.315 mmol) and TEA (53 μl, 0.378 mmol) in THF (2 ml) was stirred at 50° C. for 17 h. The reaction mixture was concentrated under a stream of air. The product was used in the next reaction.

Step 2. 2-methyl-1-(4-(trifluoromethyl)benzyl)piperazine

De-protection of the Boc group was effected in a manner similar to that indicated in Example 6, Step 2, to afford 2-methyl-1-(4-(trifluoromethyl)benzyl)piperazine. LCMS: m/z (M+H)$^+$=259.1.

Example 8. 4-((4,6-dimethylpyridin-2-yl)carbamothioyl)-1-(4-(trifluoromethyl)benzyl)piperazine-2-carboxylic acid (Compound 295)

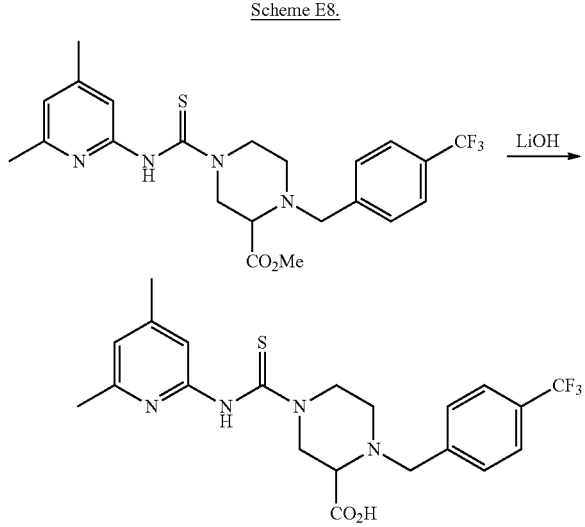

Step 1. Methyl 4-((4,6-dimethylpyridin-2-yl)carbamothioyl)-1-(4-(trifluoromethyl)benzyl)piperazine-2-carboxylate Methyl 4-((4,6-dimethylpyridin-2-yl)carbamothioyl)-1-(4-(trifluoromethyl)benzyl)piperazine-2-carboxylate was prepared according to the methods analogous to those described in Example 3, Steps 1 and 2.

Step 2. 4-((4,6-dimethylpyridin-2-yl)carbamothioyl)-1-(4-(trifluoromethyl)benzyl)piperazine-2-carboxylic acid (Compound 295)

Hydrolysis was conducted in a 3:2:1 mixture of THF/MeOH/water (4 mL) along with lithium hydroxide (66 mg, 9 eq relative to 0.300 mmol of the ester starting material used). The reaction was heated at 50° C. for 2.5 hr, concentrated under a stream of air, acidified with AcOH, and purified via reverse phase chromatography to afford Compound 295. HRMS: m/z (M+H)$^+$=453.1584 (Calculated for $C_{21}H_{24}F_3N_4O_2S$=453.1567); retention time: 2.506 min.

Example 9. N-(4,6-dimethylpyridin-2-yl)-4-(5-(trifluoromethyl)pyridin-2-yl)piperazine-1-carbothioamide (NCT-502 (Compound 72))

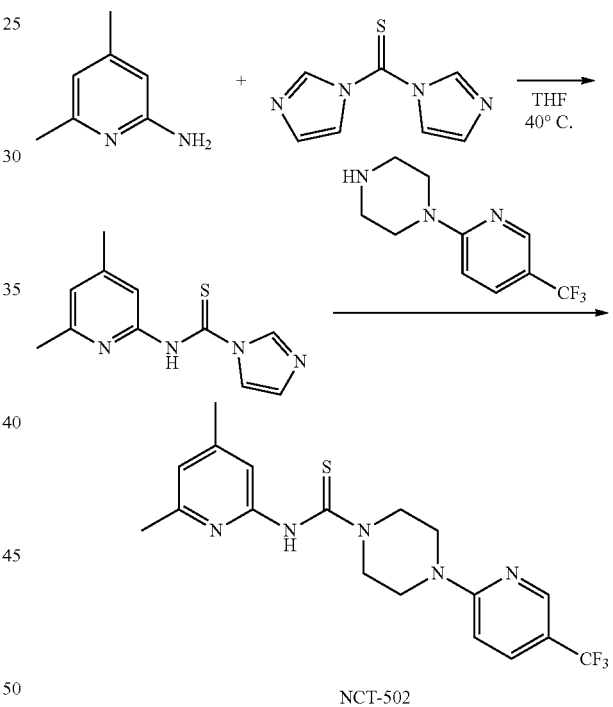

To a solution of di(1H-imidzazol-1-yl)methanethione (0.60 g, 3.4 mmol) in THF (15 mL) was added 4,6-dimethylpyridine-2-amine (0.41 g, 3.4 mmol). The resulting reaction mixture was heated with stirring at 40° C. for 30 min. During the reaction, the mixture was sonicated in order to produce a homogeneous yellow slurry. To the resulting mixture was added 1-(5-(trifluoromethyl)pyridin-2-yl)piperazine (0.78 g, 3.4 mmol). The resulting reaction mixture was heated with stirring at 50° C. for 1 hr. The reaction mixture was concentrated under a stream of air. The resulting residue was taken up in DMSO and purified via reverse phase column chromatography (acetonitrile/water 0.1% HCl). Combined fractions were partially concentrated in vacuo, neutralized with saturated aqueous sodium bicarbonate solution, and filtered to remove the solid. The solid was taken up in DMSO and repurified via reverse phase column chromatography (5 to 100% acetonitrile/water 0.1% TFA). Combined fractions were partially concentrated in vacuo (to remove organics) and filtered to provide the desired product, N-(4,6-dimethylpyridin-2-yl)-4-(5-(trifluoromethyl)pyridin-2-yl)piperazine-1-carbothioamide trifluoroacetate salt (NCT-502, 0.44 g, 26%), as a solid. HRMS: m/z (M+H)$^+$=396.1474 (Calculated for $C_{18}H_{21}F_3N_5S$=396.1464), Retention time: 2.4979 min; $^1$H NMR (400 MHz, DMSO-$d_6$) δ 10.02 (br s, 1H), 8.42 (m, 1H), 7.82 (dd, J=9.2, 2.6 Hz, 1H), 7.27 (s, 1H), 6.97-6.90 (m, 2H), 4.06-3.99 (m, 4H), 3.80-3.72 (m, 4H), 2.41 (s, 3H), 2.30 (s, 3H); $^{13}$C NMR (101 MHz, DMSO-$d_6$) δ 181.34, 160.18, 158.81, 158.46, 145.68 (q, $J_{C-F}$=5.05 Hz), 135.06 (q, $J_{C-F}$=3.03 Hz), 126.65, 123.97, 120.6 (br), 116.93, 113.91 (q, $J_{C-F}$=32.32 Hz), 106.72, 48.21, 43.81, 22.05, 21.37.

Example 10. N-(4,6-dimethylpyridin-2-yl)-4-(pyridin-4-yl)piperazine-1-carbothioamide (NCGC00242266 (Compound 71))

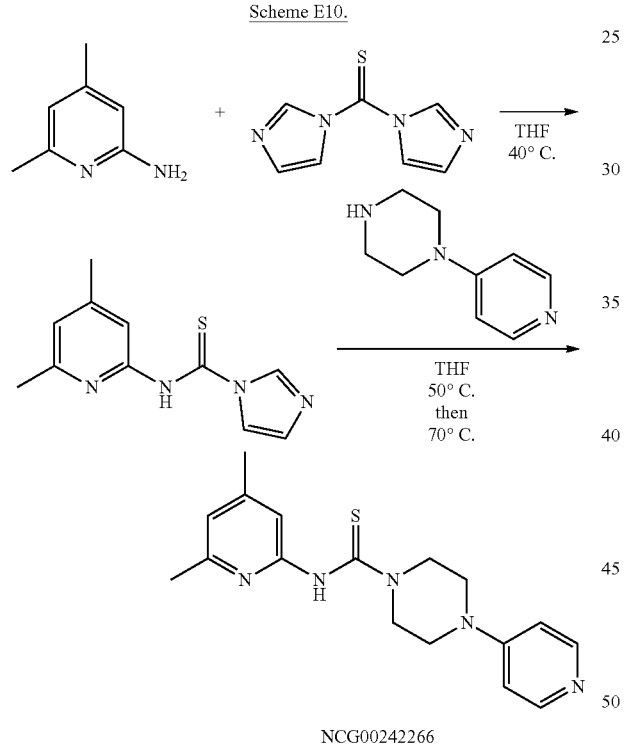

Scheme E10.

NCG00242266

To a solution of di(1H-imidzazol-1-yl)methanethione (1.64 g, 9.19 mmol) in THF (24 mL) was added 4,6-dimethylpyridine-2-amine (1.12 g, 9.19 mmol). The resulting reaction mixture was heated with stirring at 40° C. for 35 min. During the reaction, the mixture was sonicated in order to produce a homogeneous yellow slurry. To the resulting mixture was added 1-(pyridin-4-yl)piperazine (1.50 g, 9.19 mmol). The resulting reaction mixture became red and was heated with stirring at 50° C. for 2 hr, then at 70° C. for 0.5 hr. The reaction mixture was diluted with water and DCM. The layers were separated and the aqueous layer was re-extracted with DCM. The combined organic layers were dried with MgSO$_4$ and concentrated in vacuo. The resulting residue was taken up in DMSO and purified via reversed phase column chromatography (0 to 50% acetonitrile/water 0.1% TFA). The pure fractions were combined and most of the organic portion removed in vacuo. To the resulting mixture was added DCM as well as saturated aqueous sodium bicarbonate solution, in order to free base the product. The layers were separated and the aqueous layer was re-extracted with DCM three additional times. The combined organic layers were dried with MgSO$_4$ and concentrated in vacuo to afford N-(4,6-dimethylpyridin-2-yl)-4-(pyridin-4-yl)piperazine-1-carbothioamide (NCGC00242266 (Compound 71), 1.33 g, 44%) as a light yellow solid. HRMS: m/z (M+H)$^+$=328.1600 (Calculated for $C_{17}H_{22}N_5S$=328.1590), Retention time: 1.933 min; $^1$H NMR (400 MHz, DMSO-$d_6$) δ 9.71 (br s, 1H), 8.18-8.12 (m, 2H), 7.20 (s, 1H), 6.81-6.70 (m, 3H), 4.05-3.95 (m, 4H), 3.47-3.39 (m, 4H), 2.33 (s, 3H), 2.21 (s, 3H); $^{13}$C NMR (101 MHz, DMSO-$d_6$) δ 181.60, 155.19 (br), 154.29, 154.03, 150.25, 148.45 (br), 119.27, 115.87, 108.47, 47.93, 45.06, 23.47, 21.07.

Biological Assays

Example 11. Inhibition of PHGDH Activity

Compounds of the invention were assayed for inhibition of the activity phosphoglycerate dehydrogenase (PHGDH). The compounds were assayed in a mixture comprising PHGDH, PSAT1, PSPH, NADH, and glutamate. Diaphorase and resazurin were used as a fluorescent reporter system. Exemplary results are presented as calculated $IC_{50}$ values (Table E9). In Table E9 "A" represents a calculated $IC_{50}$ value of less than 5 μM; "B" represents a calculated $IC_{50}$ value of greater than or equal to 5 μM and less than 10 μM; C represents a calculated $IC_{50}$ value of greater than or equal to 10 μM or less than 20 μM, and "D" represents a calculated $IC_{50}$ value of greater than or equal to 20 μM.

TABLE E9

$IC_{50}$ values of exemplary compounds for inhibition of PHGDH.

| Compound No. | PHGDH $IC^{50}$ |
|---|---|
| 2 | C |
| 4 | B |
| 5 | D |
| 6 | C |
| 7 | D |
| 8 | D |
| 9 | D |
| 10 | D |
| 11 | D |
| 12 | D |
| 13 | D |
| 14 | D |
| 16 | D |
| 17 | D |
| 18 | D |
| 20 | D |
| 24 | B |
| 25 | B |
| 26 | B |
| 27 | D |
| 28 | A |
| 35 | B |
| 36 | A |
| 37 | D |
| 38 | B |
| 39 | C |
| 41 | B |
| 48 | C |
| 52 | D |
| 56 | B |
| 57 | B |

TABLE E9-continued

IC$_{50}$ values of exemplary compounds for inhibition of PHGDH.

| Compound No. | PHGDH IC$^{50}$ |
|---|---|
| 58 | B |
| 62 | D |
| 63 | D |
| 64 | B |
| 65 | B |
| 66 | C |
| 67 | B |
| 68 | B |
| 69 | B |
| 70 | B |
| 71 | D |
| 72 | A |
| 77 | D |
| 79 | C |
| 80 | D |
| 81 | B |
| 83 | D |
| 84 | D |
| 85 | C |
| 86 | C |
| 87 | D |
| 89 | C |
| 90 | B |
| 92 | D |
| 93 | B |
| 94 | B |
| 98 | A |
| 100 | A |
| 101 | D |
| 102 | D |
| 103 | C |
| 104 | D |
| 105 | C |
| 106 | C |
| 107 | C |
| 108 | C |
| 109 | D |
| 110 | B |
| 111 | B |
| 113 | C |
| 115 | C |
| 116 | B |
| 117 | A |
| 118 | D |
| 120 | D |
| 121 | D |
| 122 | A |
| 123 | D |
| 124 | C |
| 129 | D |
| 131 | D |
| 133 | D |
| 134 | B |
| 135 | A |
| 136 | C |
| 137 | C |
| 139 | D |
| 140 | D |
| 141 | A |
| 142 | B |
| 145 | D |
| 147 | C |
| 148 | C |
| 149 | C |
| 150 | D |
| 151 | D |
| 152 | D |
| 153 | C |
| 154 | D |
| 155 | C |
| 156 | D |
| 157 | D |
| 159 | D |
| 160 | D |
| 161 | D |
| 162 | D |
| 163 | C |
| 164 | C |
| 165 | D |
| 166 | D |
| 167 | D |
| 168 | D |
| 169 | B |
| 170 | B |
| 171 | B |
| 172 | B |
| 173 | B |
| 174 | B |
| 175 | A |
| 176 | B |
| 177 | C |
| 178 | B |
| 179 | A |
| 180 | B |
| 181 | C |
| 182 | B |
| 183 | B |
| 184 | B |
| 185 | B |
| 186 | C |
| 187 | D |
| 188 | A |
| 189 | C |
| 190 | A |
| 191 | D |
| 192 | C |
| 193 | A |
| 194 | B |
| 195 | A |
| 196 | D |
| 197 | D |
| 198 | D |
| 199 | D |
| 200 | C |
| 201 | C |
| 202 | C |
| 203 | D |
| 205 | D |
| 206 | D |
| 207 | D |
| 208 | C |
| 209 | B |
| 210 | C |
| 211 | C |
| 212 | B |
| 213 | C |
| 214 | B |
| 215 | B |
| 216 | C |
| 217 | C |
| 218 | B |
| 219 | B |
| 220 | D |
| 221 | D |
| 226 | C |
| 250 | A |
| 251 | A |
| 252 | A |
| 253 | C |
| 254 | A |
| 255 | A |
| 256 | D |
| 257 | D |
| 258 | A |
| 259 | D |
| 260 | D |
| 261 | B |
| 262 | A |
| 263 | A |
| 264 | A |
| 265 | A |
| 266 | A |

TABLE E9-continued

IC$_{50}$ values of exemplary compounds for inhibition of PHGDH.

| Compound No. | PHGDH IC$^{50}$ |
|---|---|
| 267 | A |
| 269 | A |
| 270 | D |
| 271 | D |
| 272 | D |
| 273 | C |
| 274 | C |
| 275 | A |
| 276 | D |
| 277 | C |
| 278 | C |
| 279 | C |
| 280 | C |
| 281 | C |
| 282 | C |
| 283 | D |
| 284 | C |
| 285 | C |
| 286 | C |
| 287 | D |
| 288 | C |
| 289 | C |
| 290 | C |
| 291 | A |
| 292 | A |
| 293 | C |
| 294 | C |
| 295 | B |
| 296 | A |
| 297 | A |
| 298 | A |
| 299 | A |
| 300 | B |
| 301 | D |
| 302 | B |
| 3 | D |
| 15 | D |
| 19 | D |
| 21 | D |
| 22 | B |
| 23 | D |
| 29 | B |
| 30 | A |
| 31 | C |
| 32 | B |
| 34 | C |
| 42 | D |
| 43 | D |
| 44 | D |
| 45 | C |
| 46 | C |
| 47 | D |
| 49 | C |
| 50 | C |
| 51 | D |
| 53 | D |
| 54 | B |
| 55 | D |
| 59 | C |
| 60 | D |
| 61 | C |
| 95 | D |
| 96 | D |
| 125 | D |
| 126 | C |
| 127 | D |
| 128 | D |
| 130 | C |
| 132 | C |
| 143 | B |
| 144 | D |
| 146 | C |
| 151 | D |
| 158 | B |
| 204 | C |
| 222 | D |
| 223 | C |
| 224 | D |
| 225 | C |
| 227 | C |
| 228 | A |
| 229 | B |
| 230 | A |
| 231 | D |
| 232 | B |
| 233 | B |
| 234 | D |
| 235 | D |
| 236 | B |
| 237 | D |
| 238 | D |
| 239 | C |
| 240 | D |
| 241 | D |
| 242 | A |
| 243 | A |
| 244 | A |
| 245 | D |
| 246 | B |
| 247 | A |
| 248 | D |
| 249 | D |

Example 12. Screening for PHGDH Inhibitors

Figure 1B:
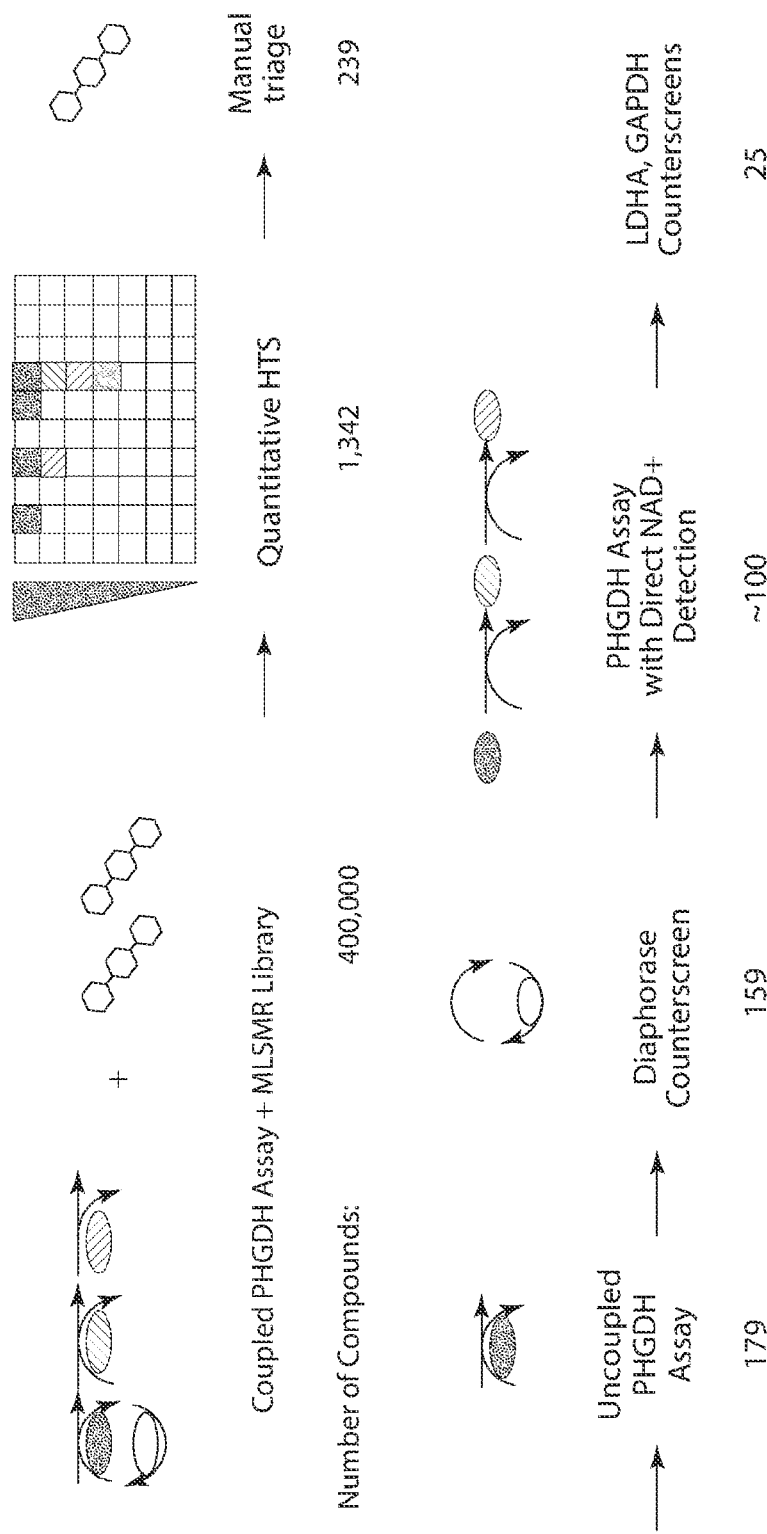
FIG. 1B. Design of PHGDH inhibitor screening process. Following HTS, manual triage selected synthetically tractable compounds and eliminated promiscuous inhibitors. Remaining compounds were confirmed and counterscreened to eliminate false positives and pan-dehydrogenase inhibitors. The number of compounds remaining is listed beneath each step.

Because the PHGDH-catalyzed reaction in isolation is at near thermodynamic equilibrium (See, e.g., Lund, K., Merrill, D. K. & Guynn, R. W. "The reactions of the phosphorylated pathway of L-serine biosynthesis: thermodynamic relationships in rabbit liver in vivo." *Arch Biochem Biophys* (1985)), a coupled primary screening assay was developed in which phosphoserine aminotransferase (PSAT1) and phosphoserine phosphatase (PSPH), the enzymes downstream of PHGDH, are included to minimize P-Pyr-mediated feedback inhibition of PHGDH and to pull the reaction forward (FIG. 1A). A coupled assay was used in a quantitative high-throughput screen to evaluate the dose response of 400,000 small molecules in the MLSMR library. In this endogenous pathway coupled assay, the production of NADH by PHGDH was measured through the diaphorase-mediated reduction of resazurin (See, e.g., Chakraborty, S., Sakka, M., Kimura, T. & Sakka, K. "Characterization of a dihydrolipoyl dehydrogenase having diaphorase activity of *Clostridium kluyveri*." *BioscL Biotechnol. Biochem.* 72, 982-988 (2008)). This screen yielded 1,342 compounds, which were triaged manually to remove promiscuous compounds (activity in >15% of assays run at the NIH) and enrich for families of compounds. The remaining 239 compounds were evaluated in an uncoupled PHGDH assay to determine if any were active against PHGDH, and counter-screened against diaphorase to eliminate inhibitors of the reporter enzyme. The remaining approximately 100 compounds were confirmed in a PHGDH assay with direct NAD$^+$ detection and counterscreened against LDHA and GAPDH to eliminate compounds active against glycolytic dehydrogenases. At the end of this process, approximately 25 PHGDH inhibiting compounds remained. FIG. 1B is a diagram illustrating the screening process. Compound 72 (NCT-502) is the original compound identified in the screen. Compound 267 (NCT-503) is a more soluble derivative of Compound 72 that was used for in vivo studies. Compound 71 (NCGC00242266) is an inactive derivative of Compound 72 used to exclude non-specific interactions of the thiourea group with other proteins.

Figure 1C:
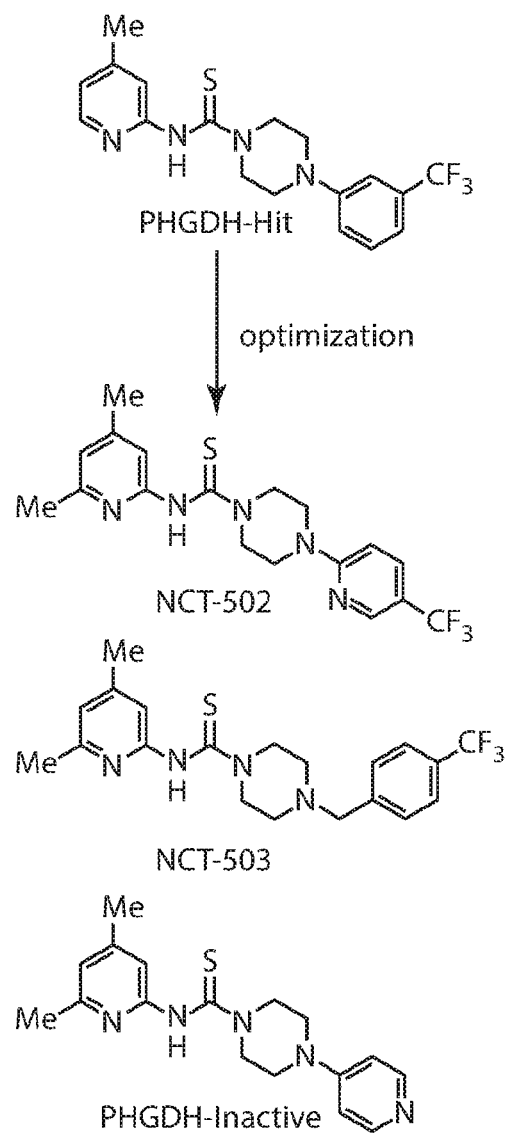
FIG. 1C. Piperazine-1-carbothioamide PHGDH inhibitors. PHGDH-hit was the initial hit in the screen; NCT-502 (Compound 72) was a derivative with improved potency, and NCT-503 has improved solubility and in vivo characteristics. The closely related inactive compound (referred to herein as "inactive compound") had no activity against PHGDH and served as a negative control.
Figure 5A:
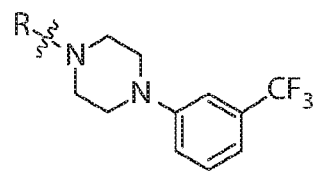
FIG. 5A. SAR of PHGDH inhibitors to improve potency and percent inhibition.

Ultimately, PHGDH-hit-1 was validated as a PHGDH inhibitor ($IC_{50}$=15.3 µM) containing a piperazine-1-carbothioamide scaffold (FIG. 1Q. Inhibitor optimization is shown in figure FIG. 5A. Addition of a methyl group to the 6-position of the pyridine ring improved potency (FIG. 5A, entry 5). Subsequently moving the trifluoromethyl group to the para-position and incorporating a nitrogen into the aromatic ring gave a considerable improvement in potency (NCT-502 (Compound 72), $IC_{50}$=2.6 µM, FIG. 1C) with reasonable in vitro ADME (FIG. 6A). Replacing the 2-pyridine-4-trifluoromethyl substituent with a 4 pyridinyl group resulted in a soluble compound (114 µM in PBS buffer) that did not inhibit PHGDH (PHGDH-Inactive; $IC_{50}$>100 µM; FIG. 1C), and was a key inactive control for subsequent experiments. Next, it was discovered that the piperazine N-aryl bond could be replaced with an JV-benzyl group, resulting in a improvement in potency, solubility, and microsomal stability yielding NCT-503 (Compound 267) (FIG. 1C, IC50=1.1 µM, FIG. 6A).

Example 13. Counter-Screening Against Other Proteins

Table E11 shows counter-screening data for PHGDH inhibiting compounds, against various enzymes. In Table E11 "A" represents a calculated $IC_{50}$ value of less than 10 µM; "B" represents a calculated $IC_{50}$ value of greater than or equal to 10 µM and less than 50 µM; "C" represents a calculated $IC_{50}$ value of greater than or equal to 50 µM or less than 100 µM; and "D" represents a calculated $IC_{50}$ value of greater than or equal to 100 µM. These compounds exhibit some activity towards ALDH1, but do not inhibit GAPDH.

NCT-502 (Compound 72), NCT-503 (Compound 267) and inactive compound were inactive against a panel of other dehydrogenases (FIG. 1D), and showed minimal cross-reactivity (<30% modulation of activity) in a panel of 168 GPCRs. Compounds in this class are known to inhibit bacterial phosphopantetheinyl transferase, but are inactive against the human ortholog (See, e.g., Foley, T. L. et al. "4-(3-Chloro-5-(trifluoromethyl)pyridin-2-yl)-N-(4-methoxypyridin-2-yl)piperazine-1-carbothioamide (ML267), a potent inhibitor of bacterial phosphopantetheinyl transferase that attenuates secondary metabolism and thwarts bacterial growth." *J Med Chem* 57, 1063-1078 (2014)).

TABLE E11

$IC_{50}$ values of exemplary compounds for inhibition of other proteins.

| Protein | Compound 72 (NCT-502) | Compound 267 (NCT-503) |
|---|---|---|
| PHGDH | A | A |
| ALDH | B | |
| GAPDH | D | D |
| HSD17B4 | D | |
| GPD1 | | D |
| GPD1L | | D |

Example 14. Inhibitor Kinetics

Figures 1D, 1E:
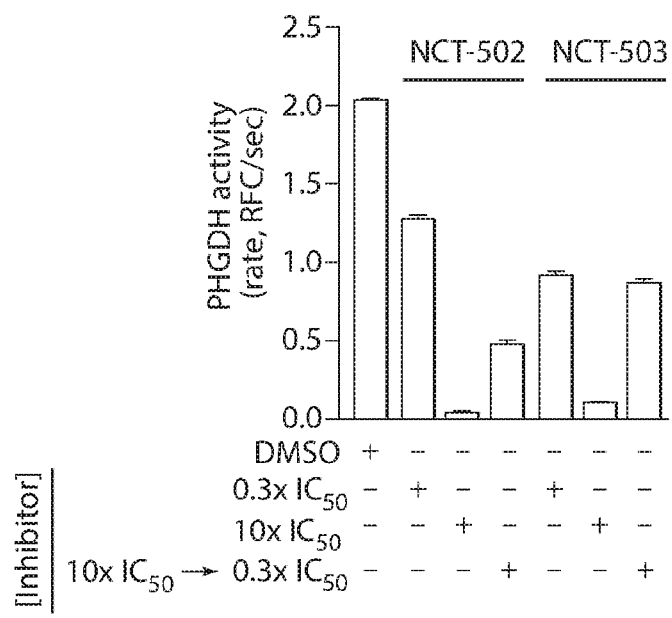
FIG. 1D. Counterscreening data for NCT-502 (Compound 72), NCT-503 (Compound 267), and the inactive compound. The compounds exhibit some activity against ALDH1 but no significant activity against dehydrogenases in glycolysis.
FIG. 1E. Dilution data demonstrating in vitro reversibility of NCT-502 (Compound 72) and NCT-503 (Compound 267).
Figure 1F:
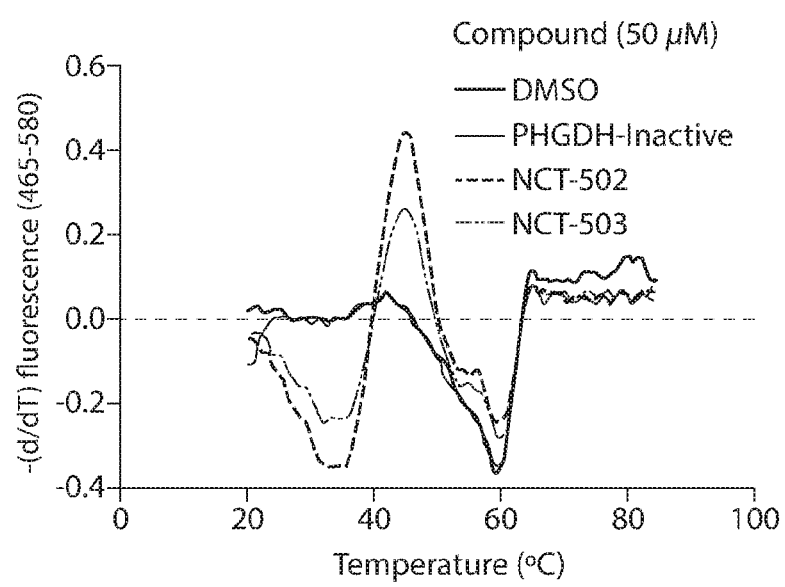
FIG. 1F. Melting temperature curves demonstrating NCT-502 (Compound 72) and NCT-503 (Compound 267)-induced destabilization of PHGDH.
Figure 2:
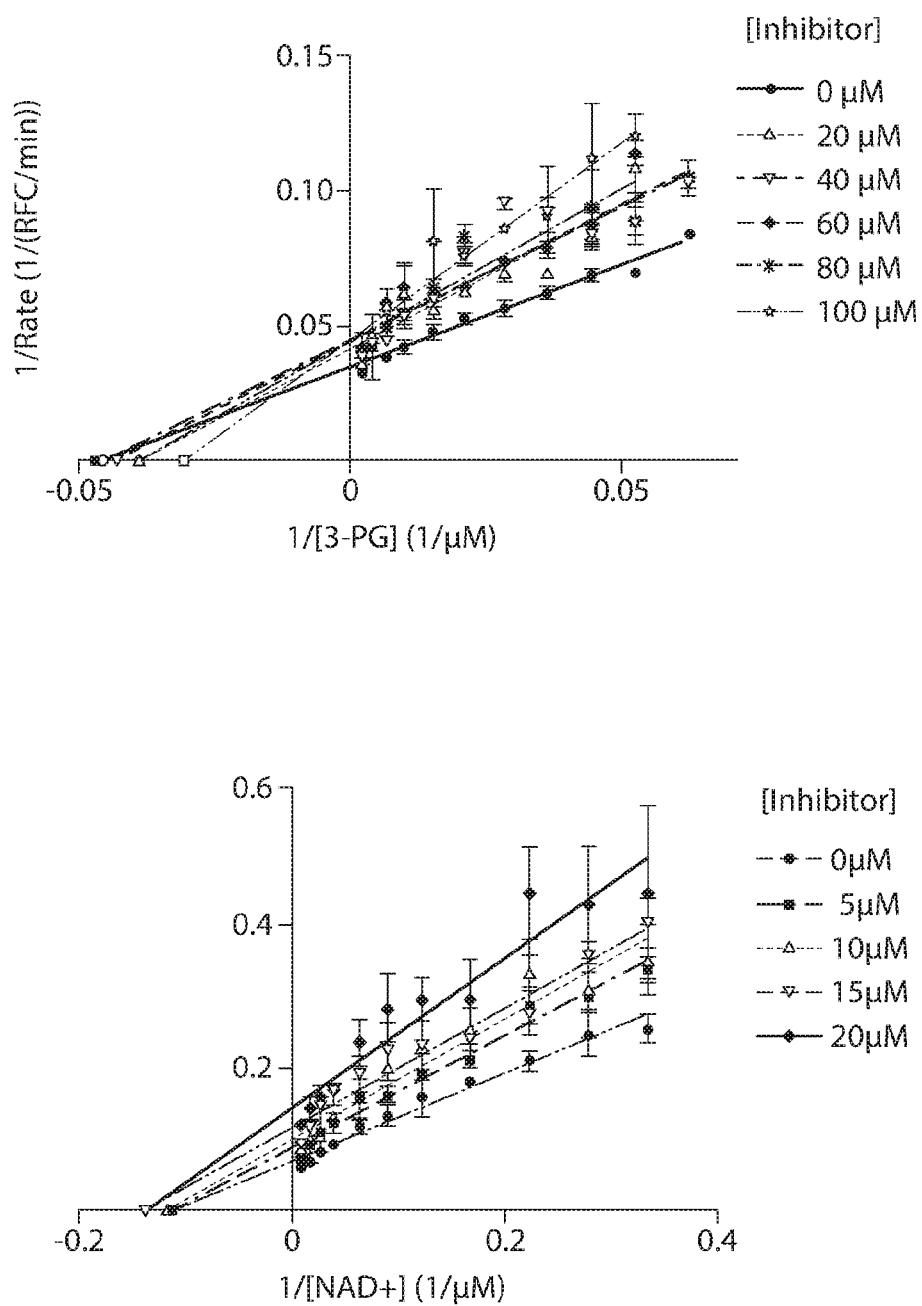
FIG. 2. Lineweaver-Burk plots for competition experiments of a PHGDH inhibitor against PHGDH substrates.

Competition experiments against substrates were carried out to determine the type of inhibition the compounds exhibit against PHGDH. FIG. 2 shows Lineweaver-Burk plots of Compound 267 (NCT-503) against the PHGDH substrate (3-phosphoglycerate) 3-PG and co-substrate $NAD^+$. This inhibitor exhibits mixed-mode inhibition with respect to 3-PG and non-competitive inhibition with respect to $NAD^+$, indicating that the inhibitor likely binds in or near the 3-PG binding pocket, which is consistent with the specificity of this compound towards PHGDH. Dilution experiments demonstrated reversible inhibition (FIG. 1E). NCT-502 (Compound 72) and NCT-503 (Compound 267) decreased the $T_m$ of PHGDH as measured by differential scanning fluorimetry, while the inactive compound did not, consistent with decreased stability of PHGDH induced by binding of active PHGDH inhibitors (FIG. 1F). Destabilization has been previously observed in the specific binding of small molecules to their protein targets (see, e.g., Hamiaux, C. et al. "DAD2 is an α/β hydrolase likely to be involved in the perception of the plant branching hormone, strigolactone." *Curr Biol* 22, 2032-2036 (2012)). NCT-503 (Compound 267) had reasonable aqueous solubility, and both NCT-502 (Compound 72) and NCT-503 (Compound 267) exhibited favorable absorption, distribution, metabolism and excretion (ADME) properties (FIG. 6A).

Example 15. Metabolomic Effect of Inhibition

Figure 3A:
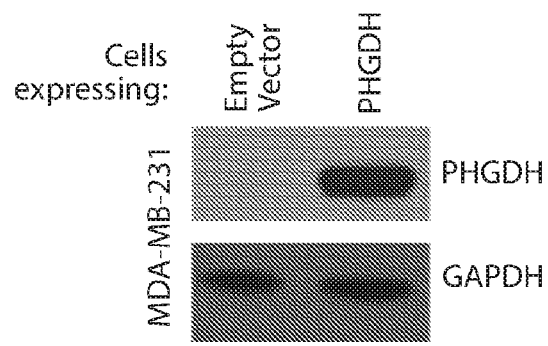
FIG. 3A. Western blot showing ectopic expression of PHGDH in constructed MDA-MB-231 breast cancer cell line and in the unmodified non-expressing control.

To examine target engagement of PHGDH inhibitors in cells, MDA-MB-231 cells that lack detectable expression of PHGDH and MDA-MB-231 cells that stably express full-length human PHGDH (MDA-MB-231-PHGDH) were treated with PHGDH inhibitors in RPMI lacking serine and glycine. A MDA-MB-231 cell line was constructed which expresses PHGDH for comparison against the MDA-MB-231 empty vector line. MDA-MB-231 breast cancer cells were infected with PHGDH-expressing retrovirus. The PHGDH blot is shown in FIG. 3A.

Figure 3B:
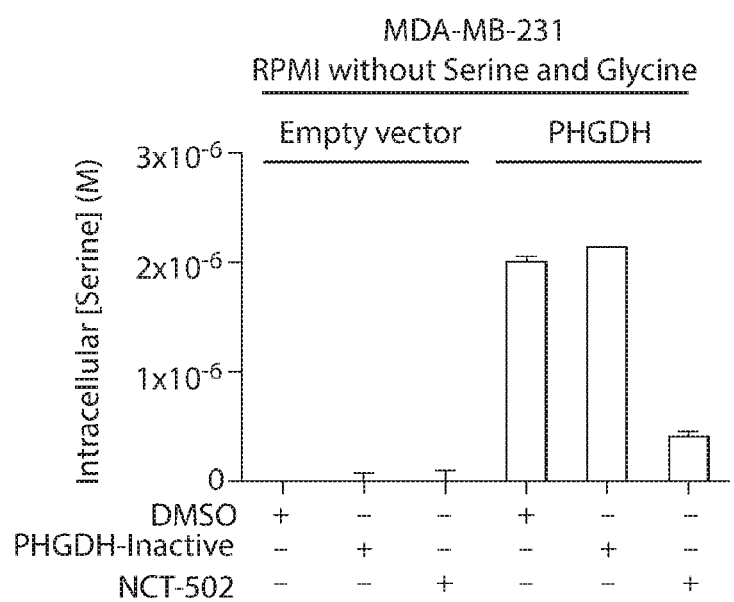
FIG. 3B. Graph showing intracellular serine levels in PHGDH for MDA-MB-231 (PHGDH expressing) and MDA-MB-231 (non-expressing) cells against Compound 267 (NCT-503), control Compound 71 (NCGC00242266), and DMSO control. NCT-502 (Compound 72) reduces intracellular serine concentrations in MDA-MB-231 cells expressing PHGDH in medium lacking serine and glycine. Inactive compound has no effect on intracellular serine concentrations.
Figure 3C:
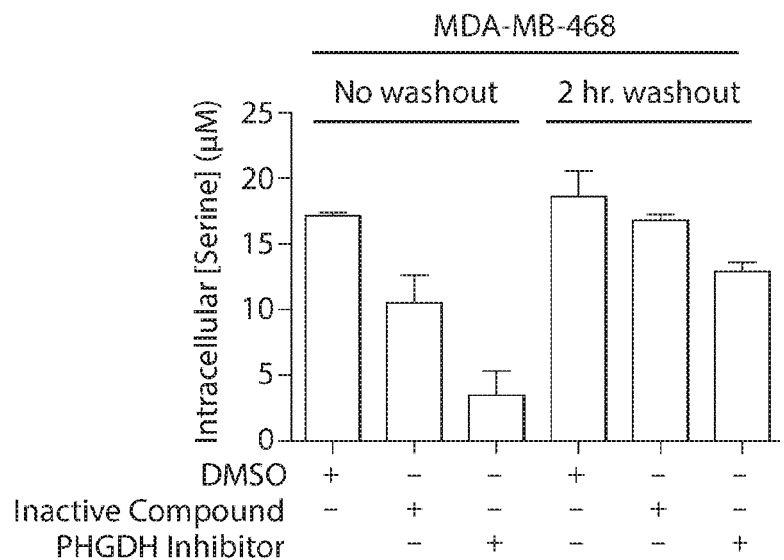
FIG. 3C. Graph showing intracellular serine levels in MDA-MB-468 (PHGDH expressing) cells with and without washout against Compound 267 (NCT-503), inactive Compound 71 (NCGC00242266), and DMSO control.

MDA-MB-231 cells and MDA-MB-231 cells over-expressing PHGDH were incubated with inactive or active PHGDH inhibitors in media lacking serine and glycine. MDA-MB-231 cells are incapable of synthesizing serine, but the addition of PHGDH permits these cells to synthesize serine. This is not reduced by control Compound 71 (NCGC00242266), but is reduced by Compound 267 (NCT-503), as shown by the measurement of the intracellular serine levels by liquid chromatography-mass spectrometry (LC-MS) (FIG. 3B). Concentrations of serine were determined by comparison with signals of internal standards and calibration curves. PHGDH inhibition reduces steady-state levels of intracellular serine in MDA-MB-231 cells over-expressing PHGDH. Studies were also performed in MDA-MB-468 cells, which over-express PHGDH and are PHGDH-dependent. As shown in FIG. 3C the inhibition for Compound 267 (NCT-503) is reversible.

Figure 3D:
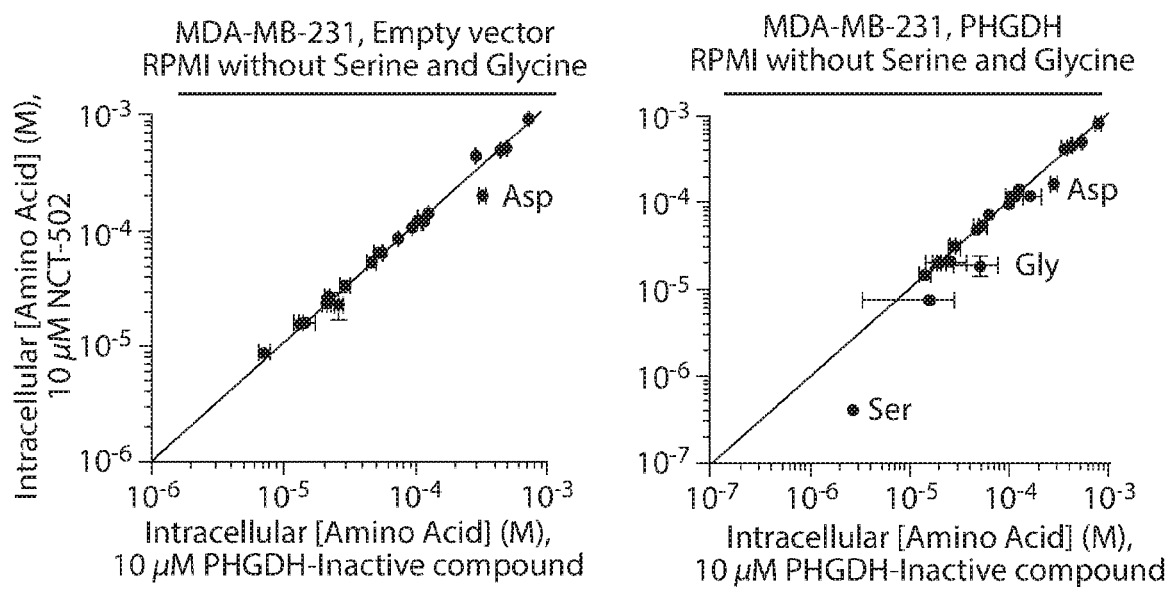
FIG. 3D. Graphs comparing intracellular amino acid levels in the presence of an Compound 267 (NCT-503) and inactive Compound 71 (NCGC00242266), for both PHGDH expressing and PHGDH non-expressing MDA-MB-231 cells. NCT-502 (Compound 72) treatment in media lacking serine and glycine decreases the concentrations of serine and glycine only in MDA-MB-231 cells expressing PHGDH, while sparing all other amino acids except for aspartate.

Measuring intracellular amino acids for MDA-MB-231 cells expressing PHGDH versus the control for both an inhibitor Compound 267 (NCT-503) and an inactive control Compound 71 (NCGC00242266), reveals that for the inhibitor only the concentrations of three amino acids: Aspartate, Serine, and Glycine, are reduced (FIG. 3D). Concentrations of amino acids were determined by comparison with the signals of internal standards and calibration curves. In MDA-MB-231-PHGDH cells, NCT-502 (Compound 72) treatment decreased intracellular serine (FIG. 3B) and glycine concentrations (FIG. 2D) and did not change the concentration of any other amino acid except for aspartate, which also decreased in parental MDA-MB-231 cells (FIG. 2D). However, MDA-MB-468 cells treated with NCT-503

(Compound 267) did not exhibit a decrease in aspartate suggesting that this effect is greater with NCT-502 (Compound 72).

Intracellular aspartate levels are influenced by electron transport chain activity in proliferating cells (See, e.g., Birsoy, K. et al. "An Essential Role of the Mitochondrial Electron Transport Chain in Cell Proliferation Is to Enable Aspartate Synthesis." Cell 162, 540-551 (2015); Sullivan, L. B. et al. "Supporting Aspartate Biosynthesis Is an Essential Function of Respiration in Proliferating Cells." Cell 162, 552-563 (2015)). To test the possibility that the compounds described herein might decrease aspartate by inhibiting the electron transport chain, oxygen consumption in MDA-MB-468 cells was measured following treatment with the PHGDH inhibitors and inactive compound. Both the active and inactive compounds decreased oxygen consumption (FIG. 6D), consistent with electron transport chain inhibition. At 50 µM, the inactive and active compounds equally inhibited oxygen consumption (FIG. 6D) but the active compounds inhibited the production of glucosederived serine substantially more than the inactive compound (FIG. 6E). NCT-503 (Compound 267) treatment also did not change intracellular glucose concentration (FIG. 6F). Use of our structurally related inactive compound as a control should separate the effect of our compounds on electron transport chain activity and on serine synthesis pathway activity.

Figure 3E:
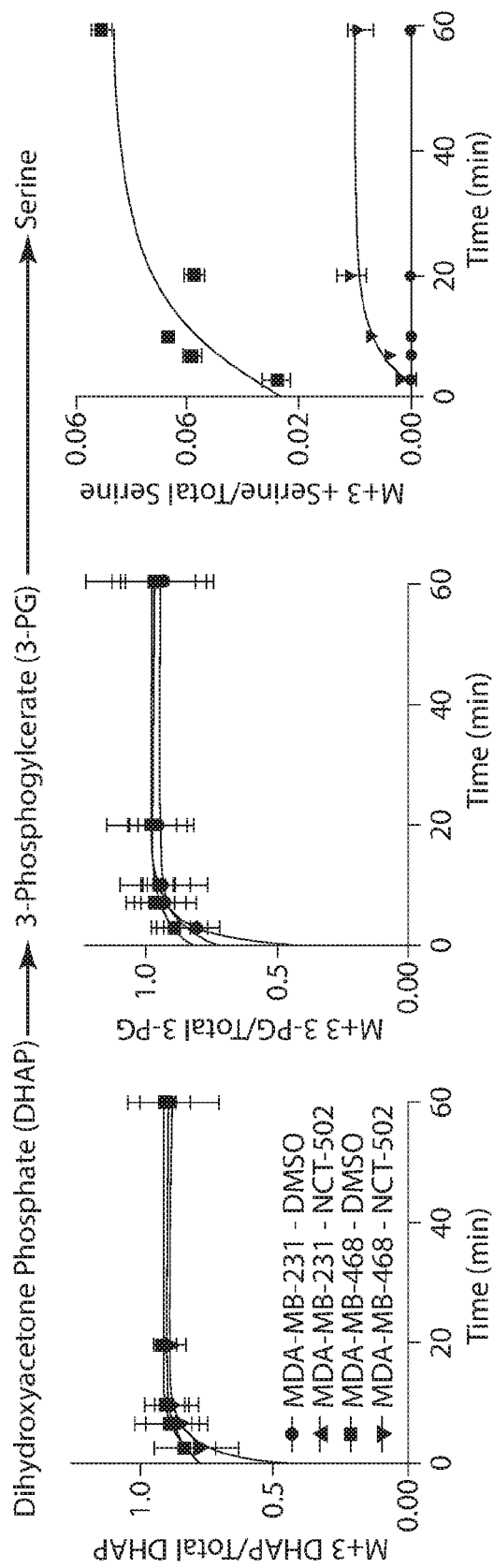
FIG. 3E. Graphs tracking the carbon-13 labeled-to-unlabeled ratio of glyceraldehyde-3-phosphate, 3-phosphoglycerate, and serine over time for Compound 267 (NCT-503) and DMSO control, for both MDA-MB-231 (non-expressing) and MDA-MB-468 (PHGDH expressing) cells. PHGDH inhibitors reduce M+3 serine produced from U-$^{13}$C glucose while sparing the labeling of the glycolytic intermediates M+3 dihydroxyacetone phosphate (DHAP) and M+3 3-phosphoglycerate.

To track the effects of PHGDH inhibition on glycolysis and serine biosynthesis, MDA-MB-231 and MDA-MB-468 cells were fed universally labeled carbon-13 glucose and the intracellular ratio of labeled to unlabeled glucose was measured at the times indicated in in FIG. 3E. PHGDH inhibition with Compound 267 (NCT-503) reduces the extent of labeled (glucose-derived) intracellular serine by >75%. The ratio for glyceraldehyde-3-phosphate (G3P) and 3-phosphoglycerate (3PG) remained unchanged, suggesting PHGDH inhibition does not reduce flux through glycolysis, but blocks flux through the serine biosynthesis pathway.

Figure 3F:
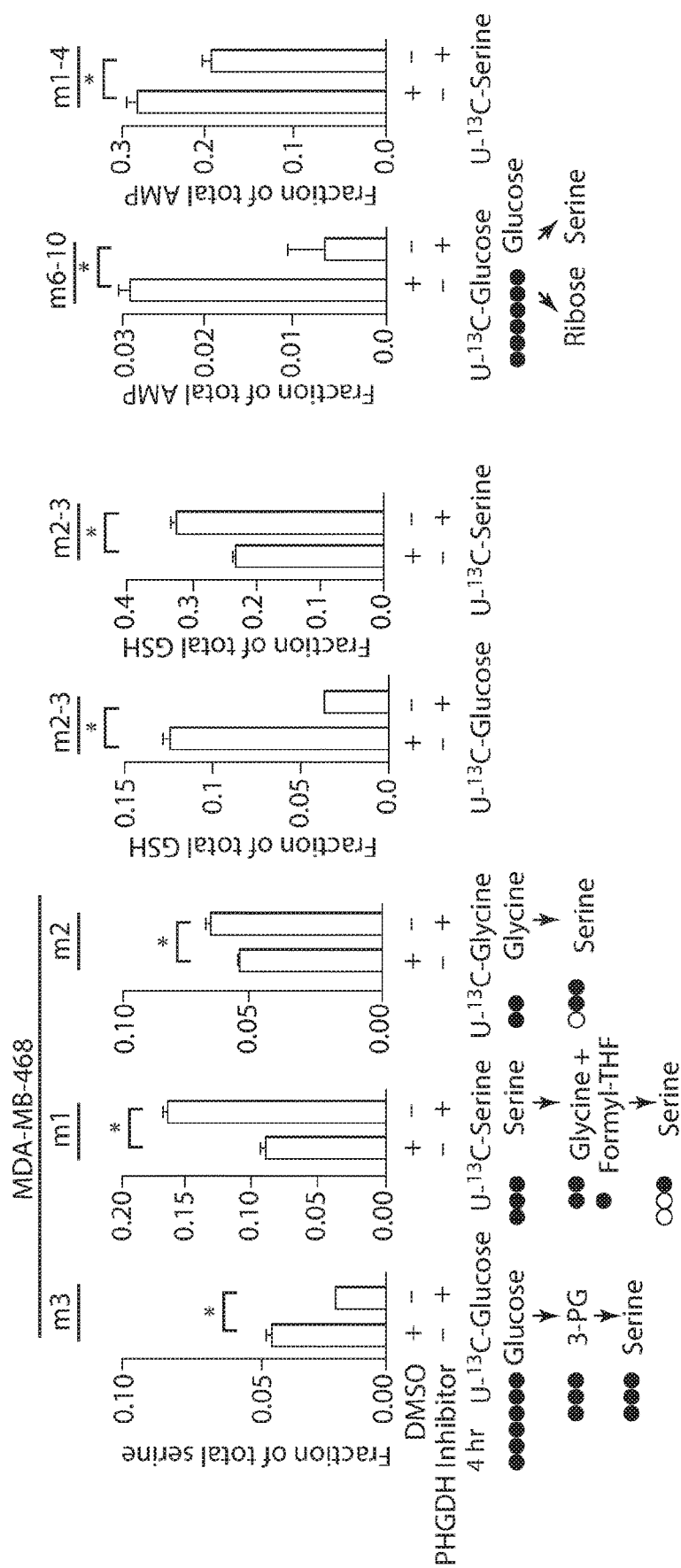
FIG. 3F. Graphs of tracking the carbon-13 labeled fraction of serine, glutathione (GSH), and adenosine monophosphate (AMP) in MDA-MB-468 cells with and without Compound 267 (NCT-503), in growth media with various carbon-13 labeled metabolites.
Figure 3G:
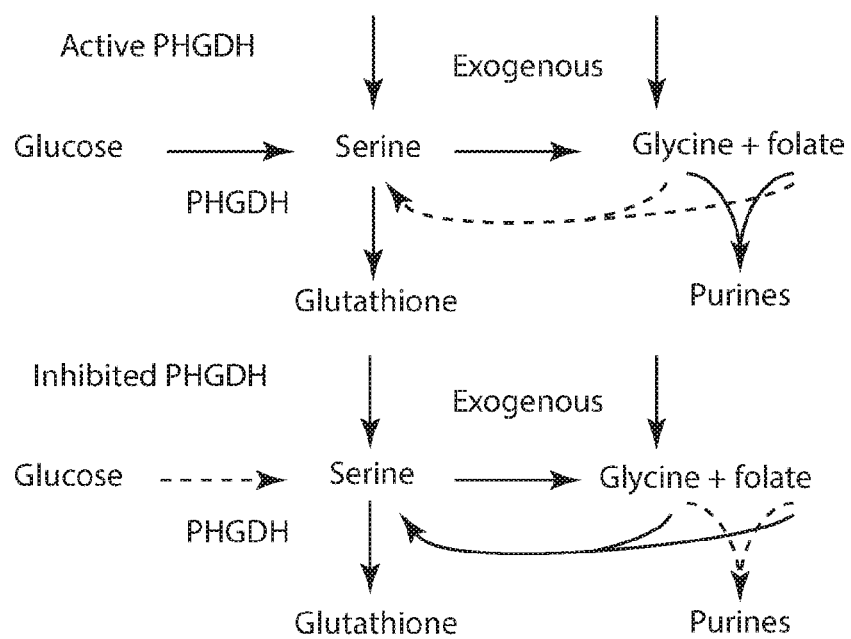
FIG. 3G. Diagram of the folate wasting model in the presence of a PHGDH inhibitor.

Exogenous serine is incapable of rescuing PHGDH inhibition (with Compound 267 (NCT-503)) due to a folate-wasting state induced by PHGDH inhibition, as evidenced by loss of incorporation of carbon-13 label from exogenous carbon-13 labeled serine into AMP in the presence of a PHGDH inhibitor (FIG. 3F). A model for folate wasting in the presence of PHGDH inhibition provided in FIG. 3G explains why exogenous serine is incapable of rescuing PHGDH inhibition.

Figure 3H:
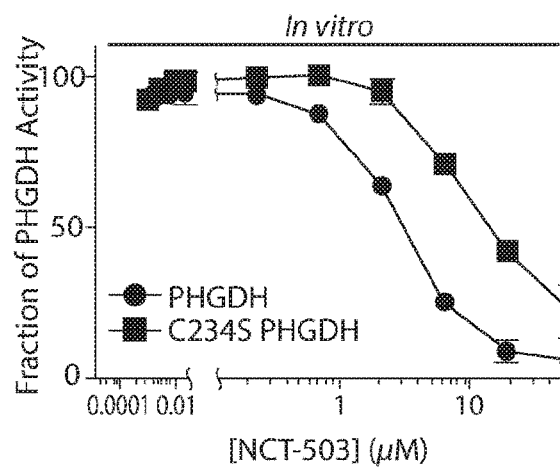
FIG. 3H. C234S PHGDH is less sensitive to NCT-503 (Compound 267) inhibition than wild type PHGDH in vitro.
Figure 3I:
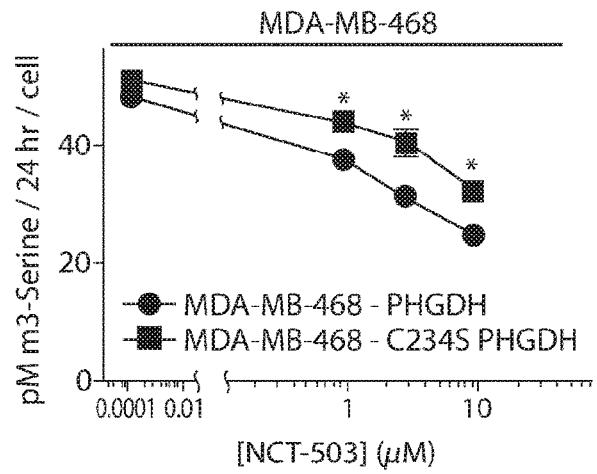
FIG. 3I. Expression of C234S PHGDH in MDA-MB-468 cells increases glucose-mediated serine flux in the presence of NCT-503 (Compound 267).

PHGDH target engagement by mutating cysteine 234 to serine (C234S) in the PHGDH active site was demonstrated (PDB: 2G76; FIG. 6H), which reduced the potency of NCT-503 (Compound 267)-mediated PHGDH inhibition by approximately 3-fold (FIG. 3H). Expression of C234S PHGDH in MDA-MB-468 partially restores serine flux in these cells in the presence of NCT-503 (Compound 267) (FIG. 3I) in spite of slightly decreased expression of PHGDH in these cells (FIG. 6I).

Figure 3J:
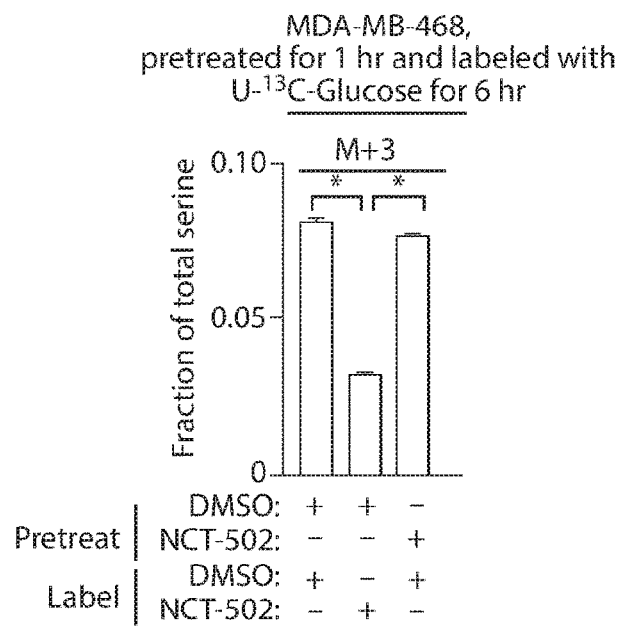
FIG. 3J. Intracellular synthesis of M+3-serine from U-$^{13}$C glucose following washout of NCT-502 (Compound 72) demonstrates PHGDH inhibitor reversibility. In this and all subsequent Figures, *, p<0.05.

NCT-502-mediated inhibition of serine synthesis was reversible in cells, as evidenced by resumption of the production of M+3 serine from U-$^{13}$C-glucose following washout of the inhibitor (FIG. 3J). Consistent with prior observations (See, e.g., Possemato, R. et al "Functional genomics reveal that the serine synthesis pathway is essential in breast cancer." 476, 346-350 (2011)), NCT-502 (Compound 72) also reduced the PSAT1-catalyzed production of M+5-α-ketoglutarate from U-$^{13}$C glutamate and $^{15}$N-serine from α-$^{15}$N-glutamate (generated from U-$^{13}$C glutamine and α-$^{15}$N-glutamine; FIGS. 6J and 6IQ. Therefore, NCT-502 (Compound 72) reversibly reduces serine synthesis in cells by engagement of PHGDH.

Example 16. Activity of PHGDH Inhibitors In Vitro and In Vivo

Figure 4A:
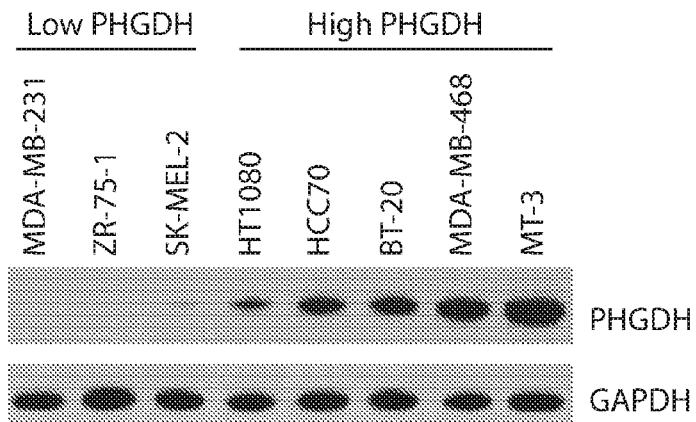
FIG. 4A. Western blot of PHGDH expression in tested cell lines.
Figure 4B:
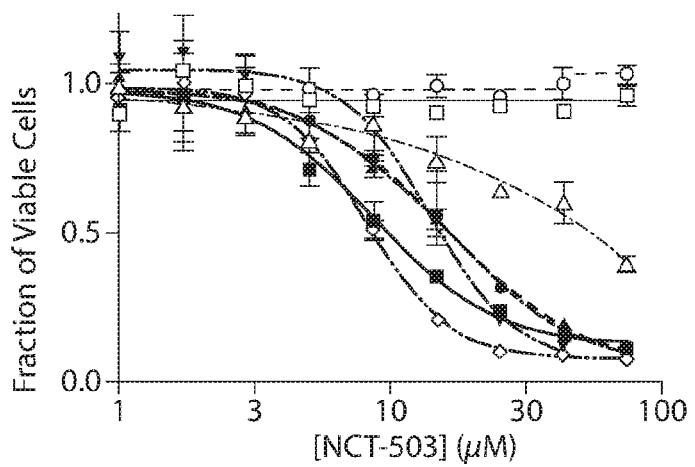
FIG. 4B. Selective toxicity of NCT-503 (Compound 267) towards five cell lines that overexpress PHGDH relative to three cell lines with low PHGDH expression.
Figure 4C:
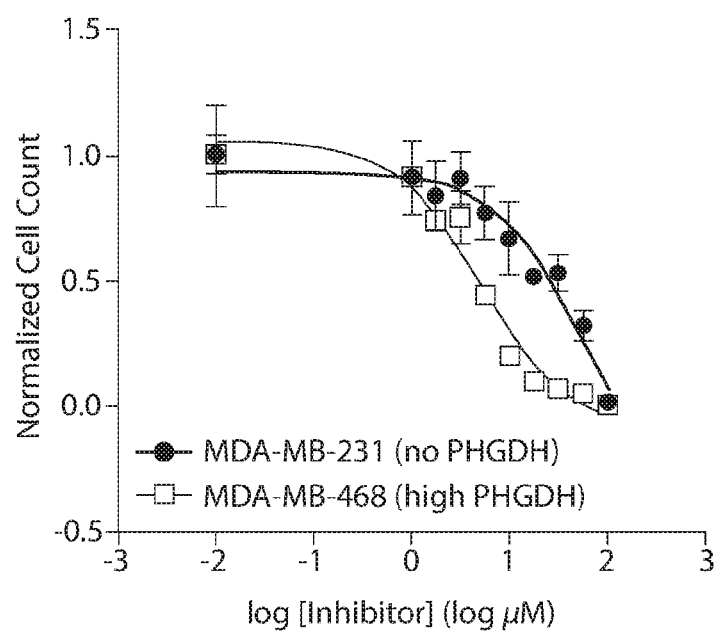
FIG. 4C. Graph of cell count vs. inhibitor concentration (Compound 267) for MDA-MB-231 (PHGDH-independent) and MDA-MB-468 (PHGDH-dependent) cells.
Figure 4D:
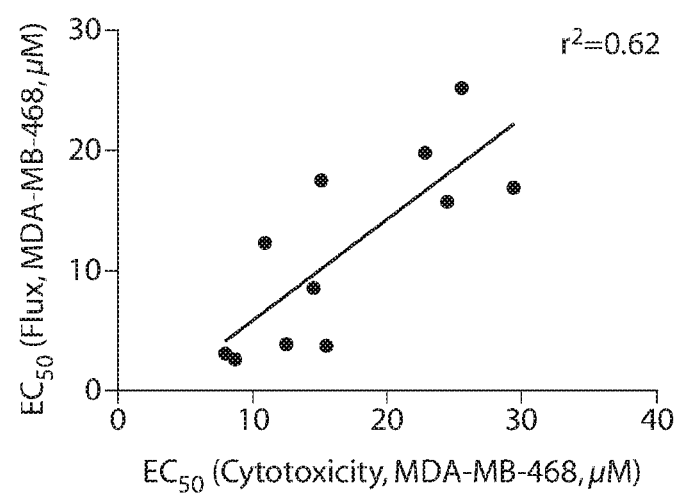
FIG. 4D. Graph comparing cytotoxicity EC50 with serine biosynthetic pathway flux $EC_{50}$ for multiple compounds of the invention (right). Graph showing compound cytotoxicity towards PHGDH-expressing MDA-MB-468 cells correlates with inhibition of M+3 serine production (left).
Figure 4D:
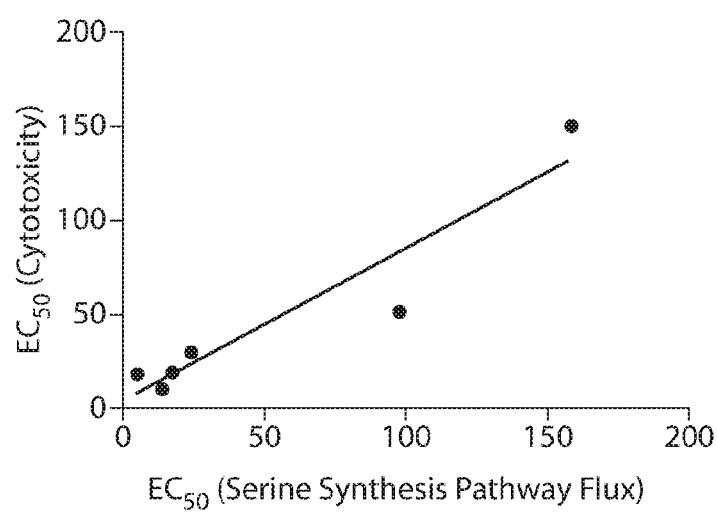
Figure 7A:
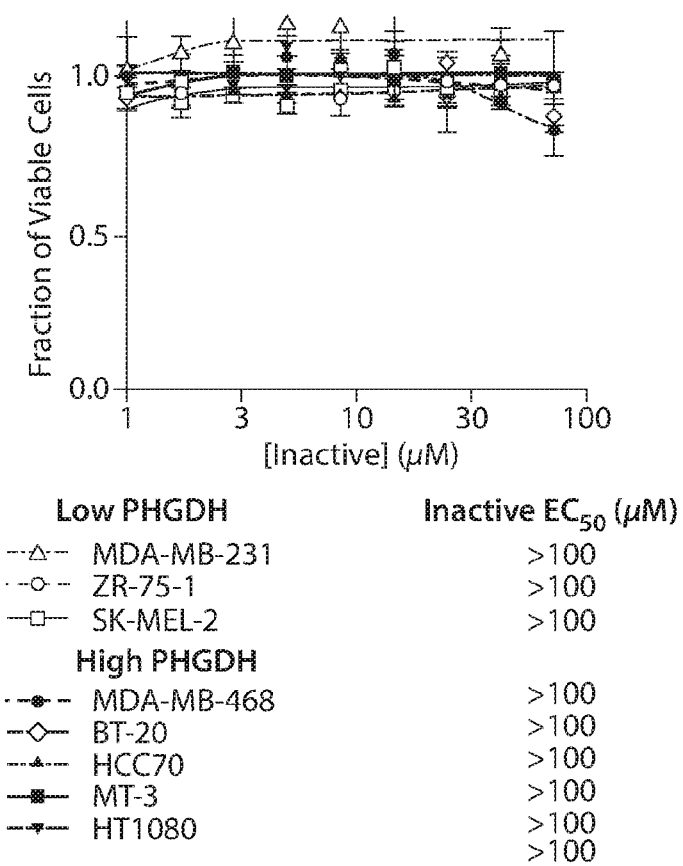
FIG. 7A. Inactive PHGDH inhibitor is not cytotoxic towards PHGDH-dependent or independent cell lines.
Figure 7B:
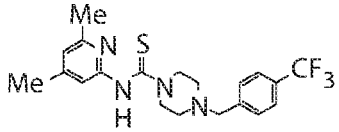
FIG. 7B. Compound structures and $EC_{50}$s for cytotoxicity and glucose to serine flux used for cytotoxicity-flux correlation.
Figure 7B:
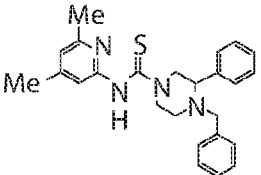
Figure 7B:
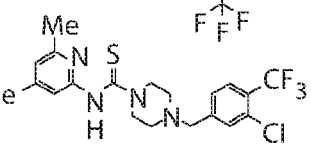
Figure 7B:
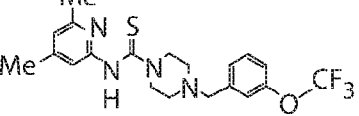
Figure 7B:
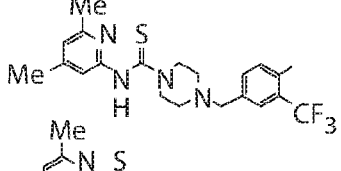
Figure 7B:
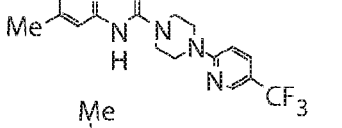
Figure 7B:
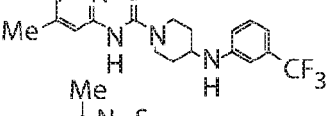
Figure 7B:
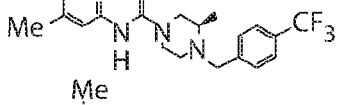
Figure 7B:
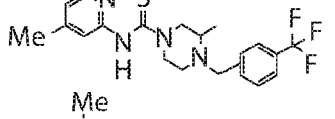
Figure 7B:
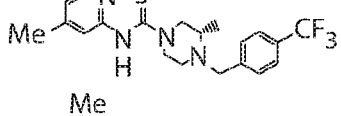
Figure 7B:
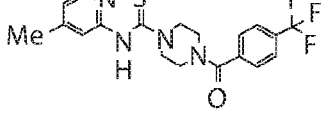

Knockdown of PHGDH is selectively toxic towards PHGDH-dependent cell lines, and minimally toxic towards PHGDH-independent cell lines. Treatment of three PHGDH-independent cell lines (MDA-MB-231, ZR-75-1, and SK-MEL-2; FIG. 4A), and five PHGDH-dependent cell lines (MDA-MB-468, BT-20, HCC70, HT1080, and MT-3; FIG. 4A) in dose-response with NCT-503 (Compound 267) demonstrated that PHGDH inhibitors had $EC_{50}$s of 8-16 µM for the PHGDH-dependent cell lines, a 6- to 10-fold higher EC50 for MDA-MB-231 cells, and no toxicity towards other PHGDH-independent cell lines (FIG. 4B). Assessing cell survival versus inhibitor concentration in PHGDH-dependent and PHGDH-independent cells demonstrates the selective cytotoxicity of the PHGDH inhibitors towards the dependent cells. Compound 267 (NCT-503) exhibits selective toxicity towards MDA-MB-468 (PHGDH-dependent) cells with an order of magnitude lower toxicity towards MDA-MB-231 (PHGDH-independent) cells, as shown in FIG. 4C. Cell count was determined by quantitating the amount of ATP present with CellTitreGlo® measurements 96 hours after dosage. The inactive compound was not toxic towards any of these cell lines (FIG. 7A). $EC_{50}$s for serine production from glucose of a set of piperazine-1-carbothioamides (Compound No.'s: 71, 72, 267, 250, 265, 275, 294, 295, 296, 297, 298, 299, 300, 301, and 302) showed a strong positive correlation with their EC so values for cytotoxicity in MDA-MB-468 cells (FIG. 4D FIG. 7B).

To test the in vivo effect of the inhibitors on the serine biosynthetic pathway, mice were treated with either vehicle or 35 mg/kg Compound 267 (NCT-503), followed by a tail vein injection of universally labeled carbon-13 glucose. The mice were sacrificed at the indicated times, and the fraction of labeled serine in the brain was determined by LC-MS and normalized to the fraction of labeled lactate (FIG. 4J). PHGDH inhibitors block incorporation of carbon-13 from universally labeled carbon-13 glucose into serine in the brains of mice.

Figures 6B, 6C:
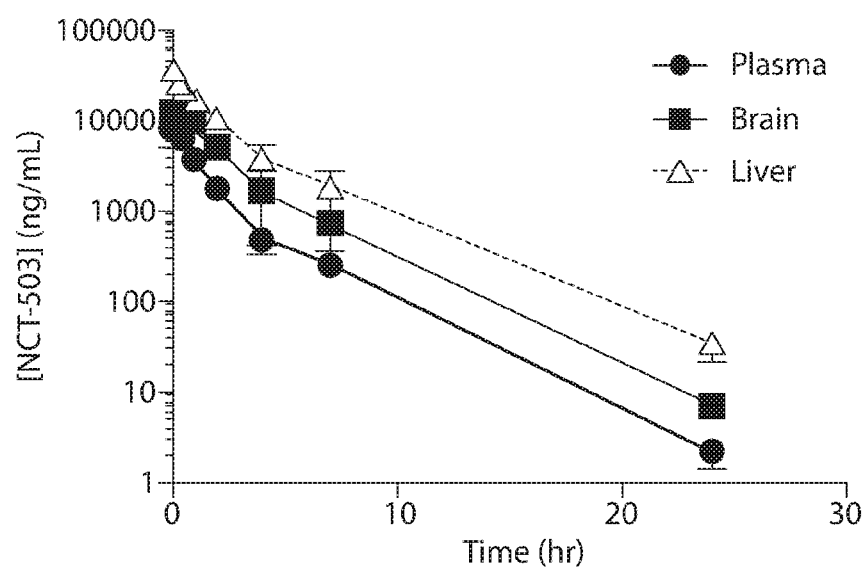
FIG. 6B. Pharmacokinetic parameters of NCT-503 (Compound 267) in plasma.
FIG. 6C. Pharmacokinetic profile of NCT-503 (Compound 267) in plasma, liver and brain following a single 30 mg/kg IP administration.
Figure 6H:
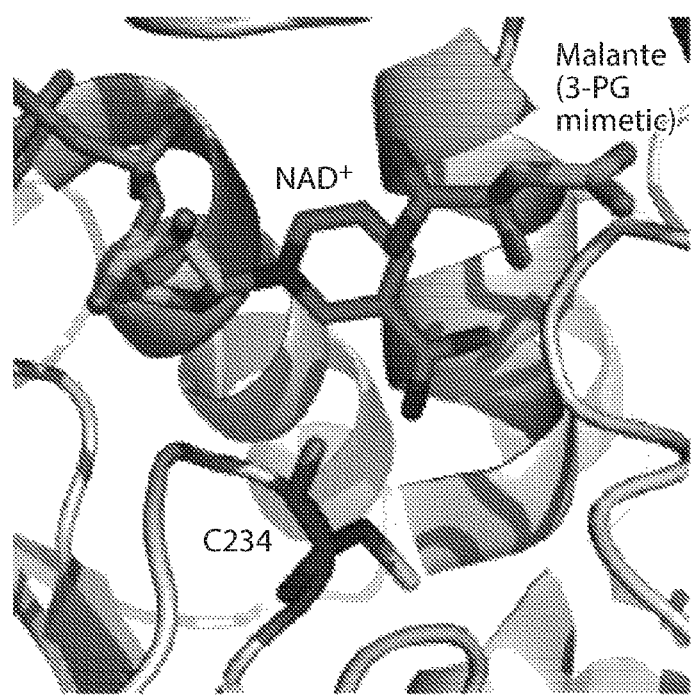
FIG. 6H. Location of cysteine 234 in the PHGDH active site. The C234S PHGDH mutation attenuates PHGDH inhibition by NCT-503 (Compound 267).
Figure 6I:
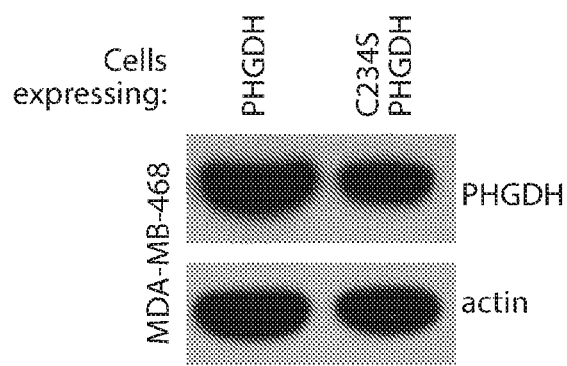
FIG. 6I. Similar expression of PHGDH in MDA-MB-468 cells expressing wild-type and C234S PHGDH.
Figure 6J:
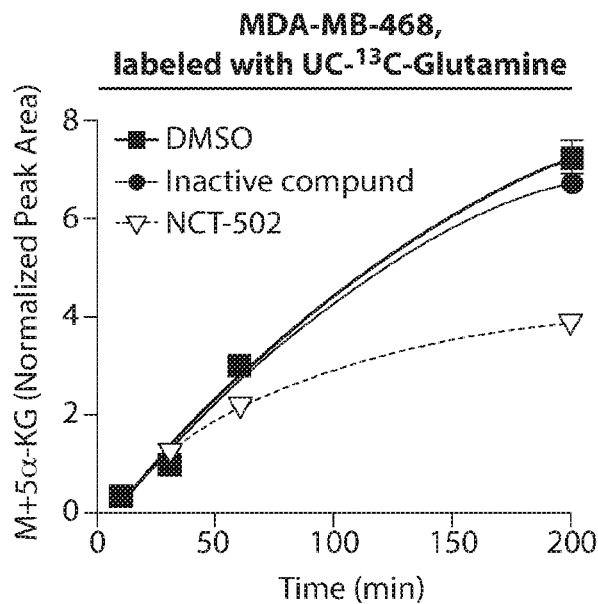
FIG. 6J. NCT-502 (Compound 72) decreases incorporation of U-$^{13}$-glutamine-derived carbon into α-ketoglutarate.
Figure 6K:
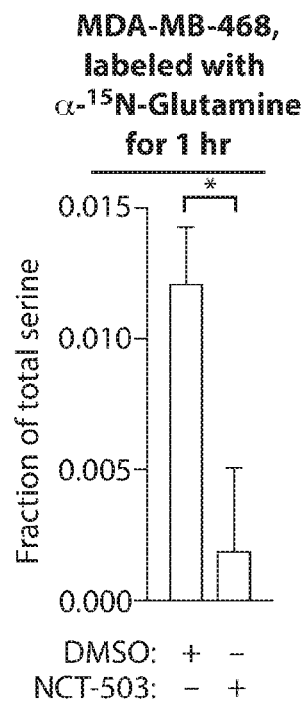
FIG. 6K. NCT-503 decreases incorporation of α-$^{15}$N-glutamine nitrogen into serine.

Pharmacokinetics to evaluate the utility of NCT-503 (Compound 267) as an in vivo inhibitor determined that the compound had good exposure ($AUC_{last}$=14,700 hour*ng/mL), half-life (2.5 hour) and $C_{max}$(~20 µM in plasma) following intraperitoneal administration with significant partitioning into the liver and brain (FIGS. 6B and 6C).

Figure 4E:
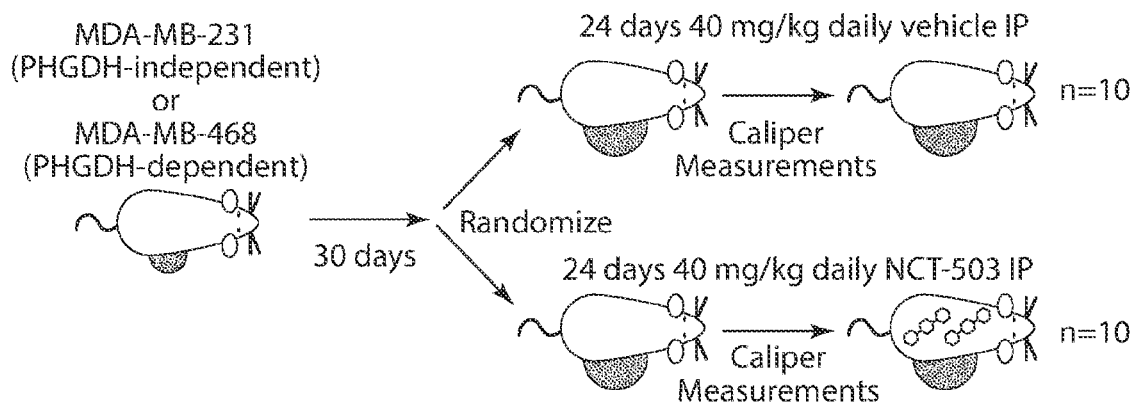
FIG. 4E. Design of a mouse experiment to evaluate PHGDH inhibitor toxicity towards MDA-MB-468, PHGDH-dependent orthotopic xenografts with sparing of MDA-MB-231, PHGDH-independent orthotopic xenografts.
Figure 4F:
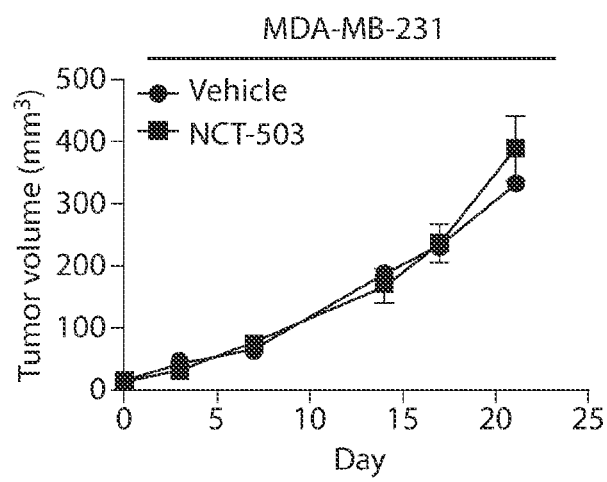
FIG. 4F. Graphs of tumor volume vs. time for MBA-MB-231 (PHGDH-independent) and MBA-MB-468 (PHGDH-dependent) tumors from single xenograft experiments with and without compound 267. NCT-503 (Compound 267) reduces the volume of MDA-MB-468 orthotopic xenografts while sparing the growth of MDA-MB-231 xenografts. The asterisk indicate statistically significant (p>0.025) data points. Error bars represent standard error of the mean.
Figure 4F:
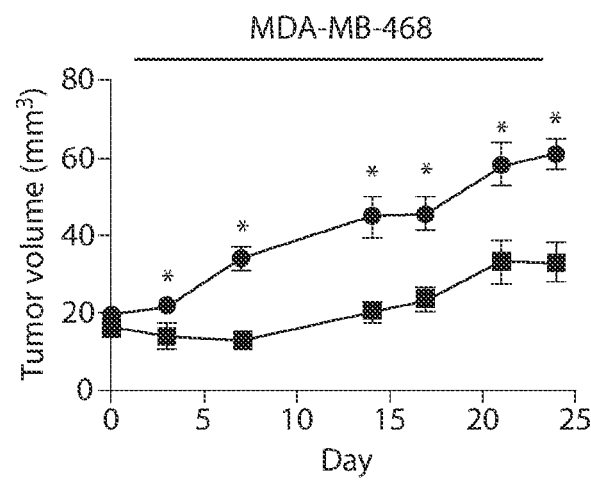
Figure 4G:
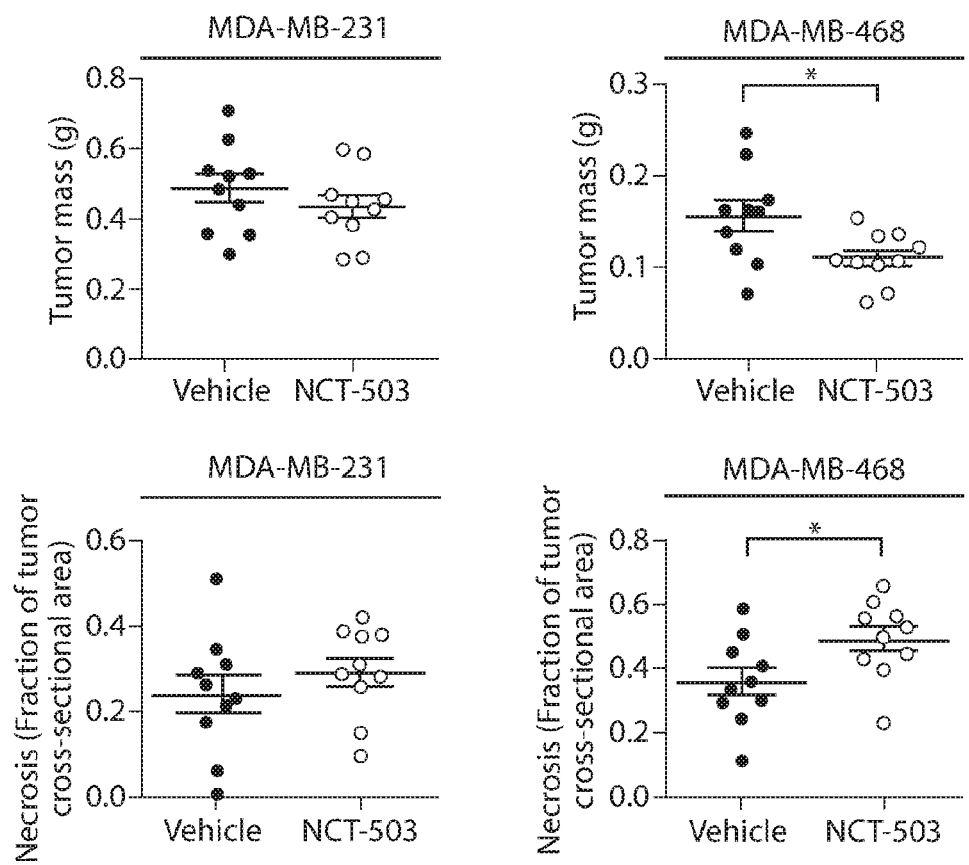
FIG. 4G. Graphs of tumor weight after 30 days for MB A-MB-231 (PHGDH-independent) and MBA-MB-468 (PHGDH-dependent) tumors from single xenograft experiments with and without Compound 267. NCT-503 (Compound 267) reduces the weight of MDA-MB-468 xenografts but not the weight of MDA-MB-231 xenografts. Error bars represent standard error of the mean.
Figure 4H:
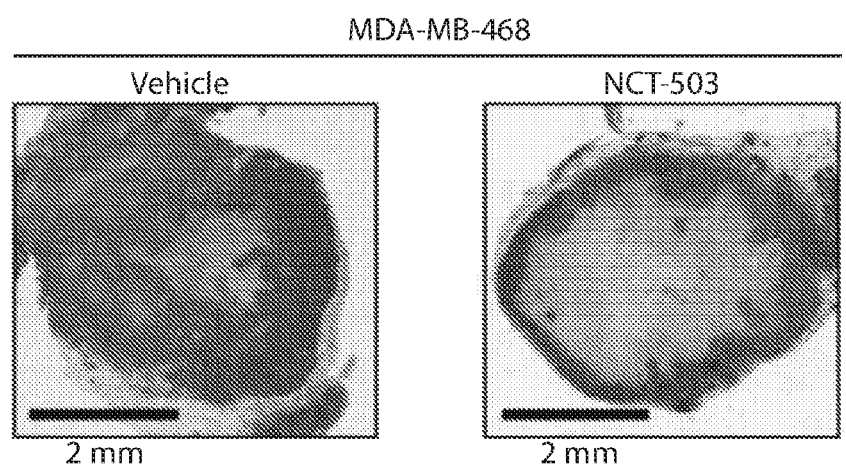
FIG. 4H. NCT-503 (Compound 267) increases the fraction of necrosis in MDA-MB-468 orthotopic xenografts but not in MDA-MB-231 orthotopic xenografts. Scale bars, 2 mm.
Figure 7C:
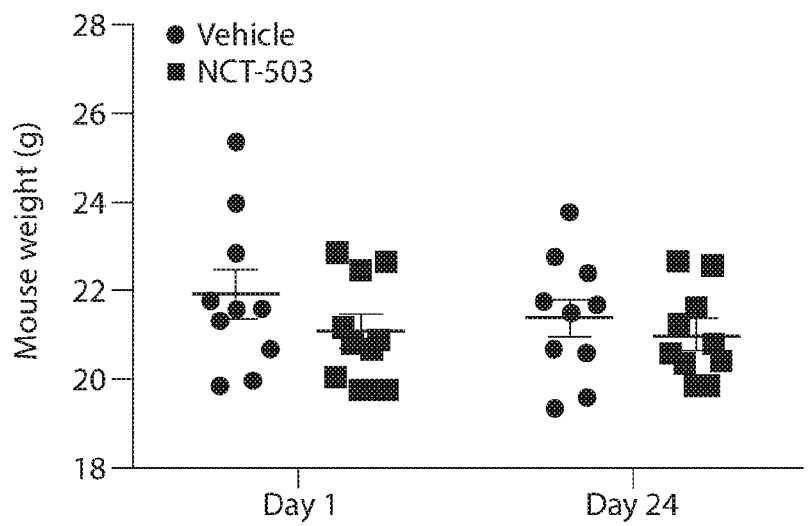
FIG. 7C. Mice treated with NCT-503 (Compound 267) daily for 24 days do not lose weight relative to vehicle-treated mice.

To evaluate NCT-503 (Compound 267) activity in vivo, MDA-MB-231 and MDA-MB-468 orthotopic xenografts were treated with vehicle or NCT-503 (Compound 267) (40 mg/kg daily, IP, FIG. 4E). PHGDH inhibitor treatment reduced the growth and weight of PHGDH-dependent MDA-MB-468 xenografts but did not affect the growth or weight of PHGDH-independent MDA-MB-231 xenografts (FIGS. 4F and 4G). PHGDH inhibition also selectively increased necrosis in MDA-MB-468 xenografts, but not in MDA-MB-231 xenografts (FIG. 4H). Importantly, mice treated with the compound did not lose weight during the 24-day treatment (FIG. 7C) in spite of the potential systemic toxicities of inhibiting serine biosynthesis (FIG. 6C). Levels of NCT-503 (Compound 267) in tumors were ~3 µM at the conclusion of the experiment, validating exposure of the tumor to compound.

Figure 4I:
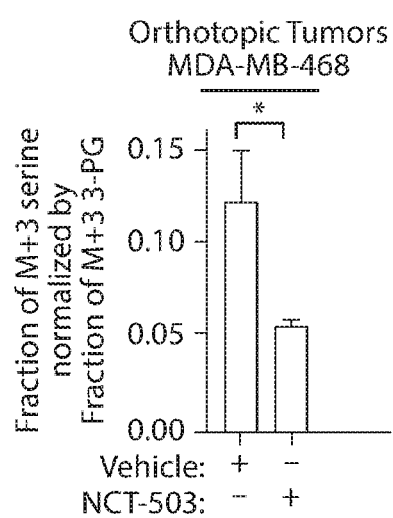
FIG. 4I. Following infusion of U-$^{13}$C glucose, NCT-503 (Compound 267) reduces the fraction of M+3 serine (normalized to M+3 3-PG) in MDA-MB-468 orthotopic xenografts.
Figure 4J:
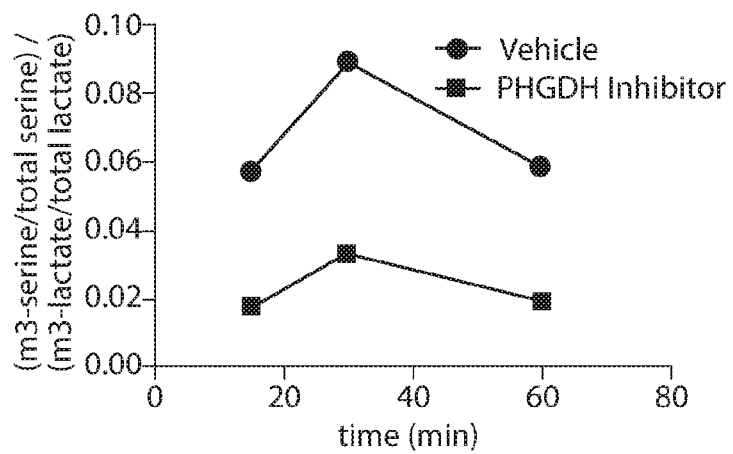
FIG. 4J. Graph of the ratio of the fraction of labeled serine to the fraction of labeled lactate in the brain for mice treated with either vehicle or 35 mg/kg PHGDH inhibitor and injected with carbon-13 glucose.
Figure 4K:
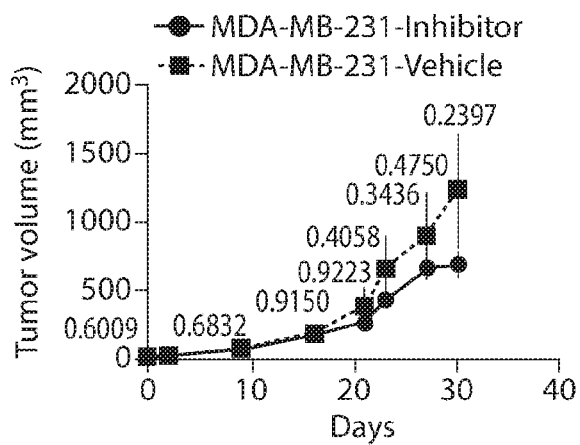
FIG. 4K. Graphs of tumor volume vs. time for MBA-MB-231 (PHGDH-independent) and MBA-MB-468 (PHGDH-dependent) tumors from paired xenograft experiments with and without Compound 267.
Figure 4K:
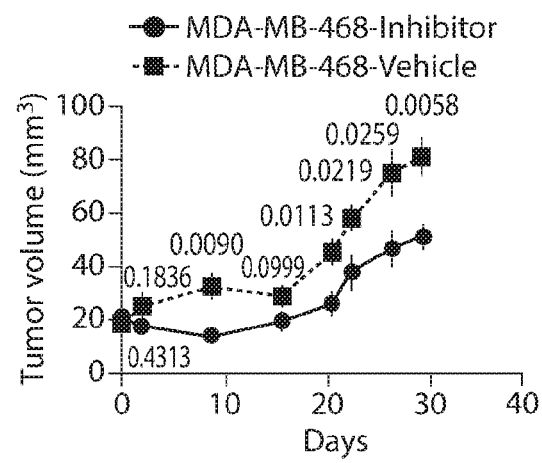
Figure 7D:
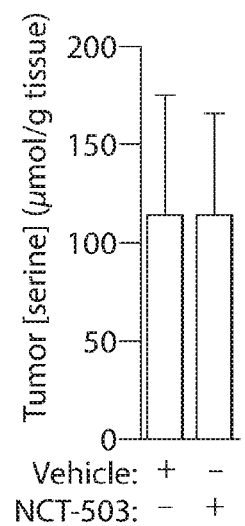
FIG. 7D. Tumors from both treated and untreated mice have similar intratumoral serine concentrations.

We evaluated target engagement in NOD.SCID mice by treating mice bearing MDA-MB-468 tumors with vehicle or NCT-503 (Compound 267) and infusing the animals with U-$^{13}$C-glucose. MDA-MB-468 tumors in NCT-503 (Compound 267)-treated mice exhibited decreased production of glucose-derived serine (FIG. 4I), while intratumoral serine concentrations did not change with NCT-503 (Compound 267) treatment (FIG. 7D). Thus, the PHGDH inhibitors described herein engage PHGDH in tumors and recapitulate the selective toxicity of PHGDH knockdown in vivo.

Figure 8A:
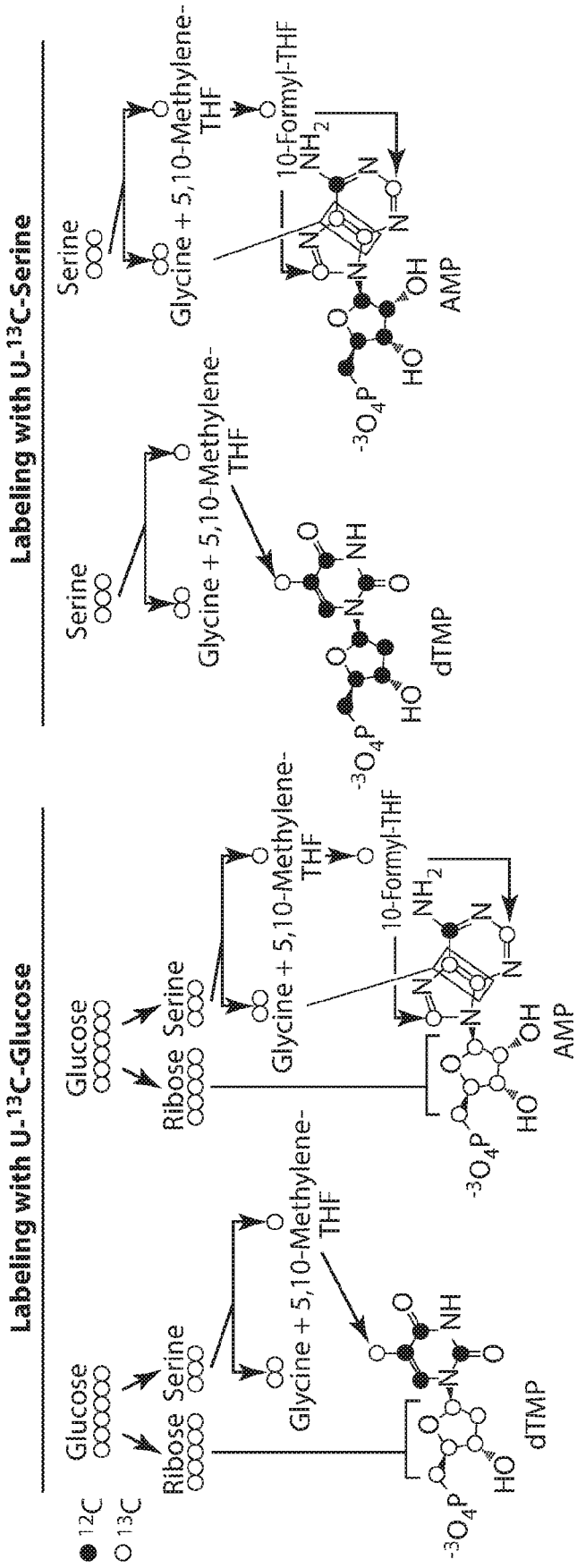
FIG. 8A. PHGDH inhibition in a PHGDH-dependent cell line unexpectedly reduces the incorporation of exogenous serine into dTMP and AMP. Incorporation of $^{13}$C from glucose, glucose-derived serine, and exogenous serine into nucleotides.
Figure 8B:
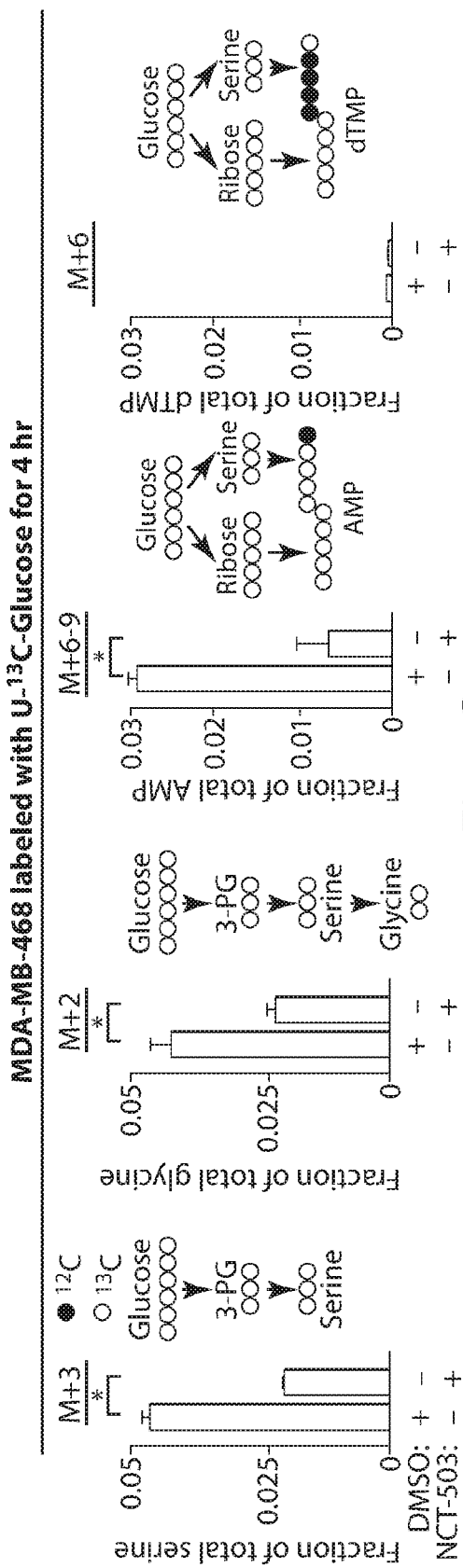
FIG. 8B. 10 μM NCT-503 (Compound 267) treatment for four hours reduces the synthesis of glucose-derived serine and decreases the incorporation of $^{13}$C from glucose via serine into AMP.
Figure 9A:
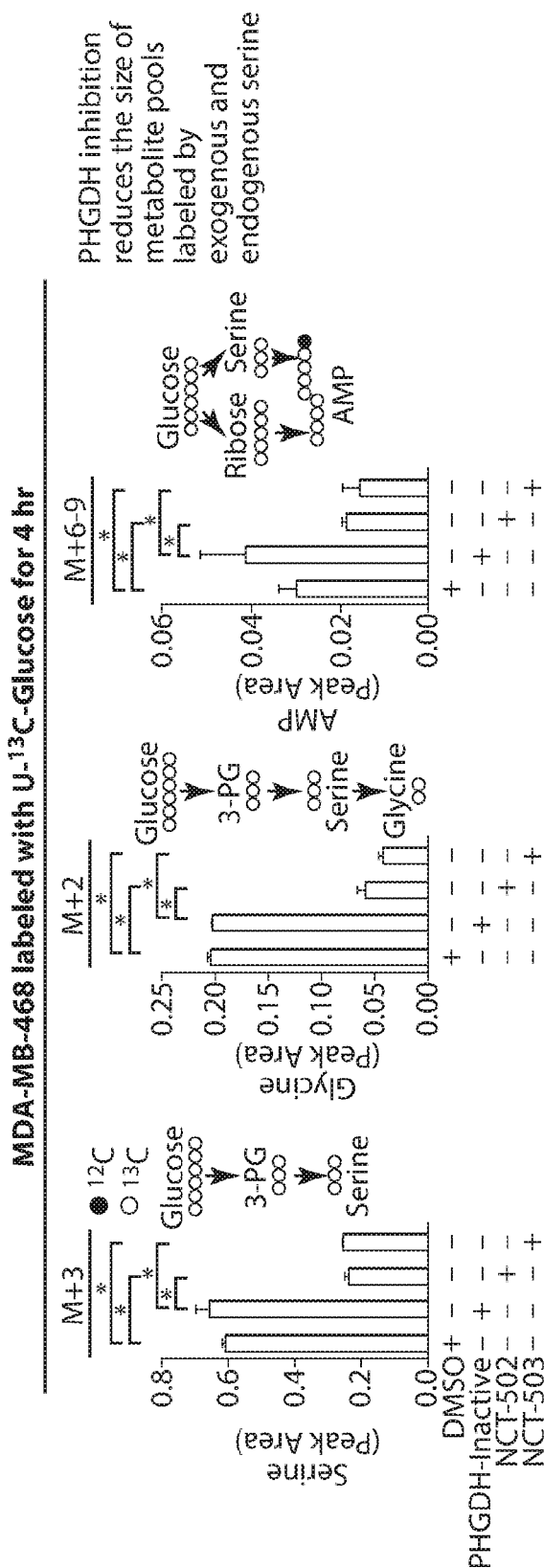
FIG. 9A. PHGDH inhibition in a PHGDH-dependent cell line reduces the size of metabolite pools labeled by endogenous and exogenous serine. All pools are normalized by total cell volume from an independently counted, identically treated plate. Pools of M+3 serine, M+2 glycine and M+6-9 AMP derived from U-$^{13}$C-glucose are unaffected by inactive compound but decrease in response to 10 μM NCT-502 (Compound 72) or NCT-503 (Compound 267) treatment.
Figure 9B:
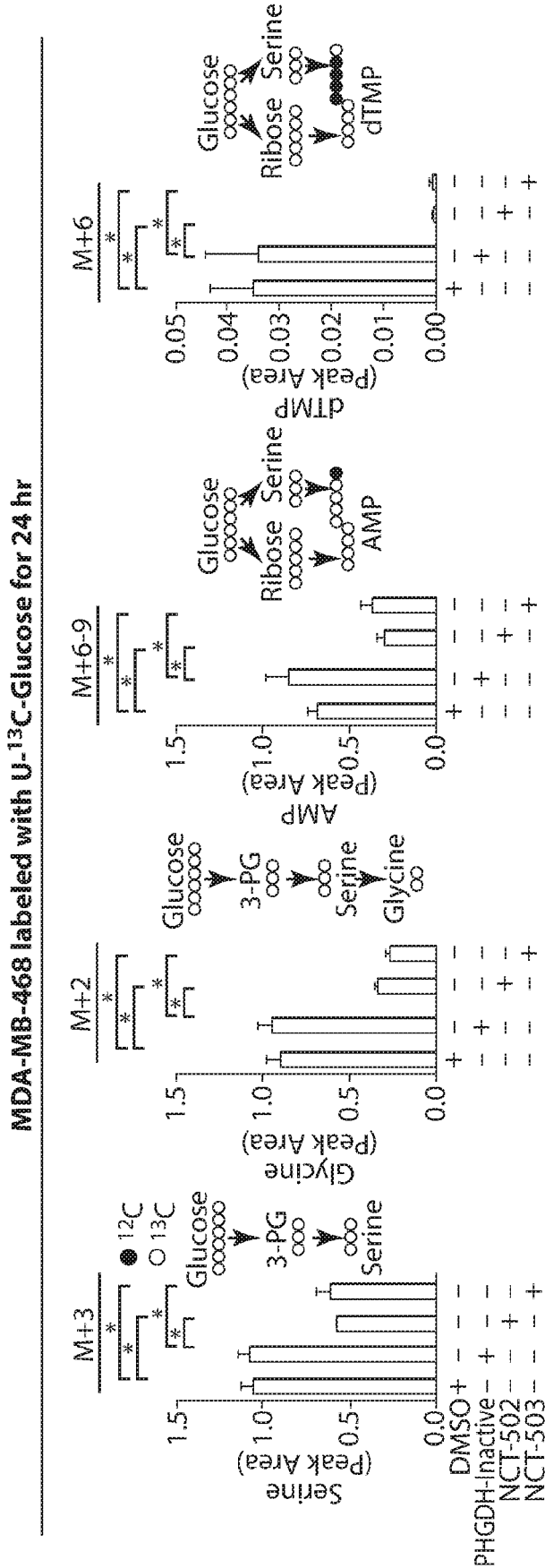
FIG. 9B. The same results persist at 24 hours. In addition, 10 μM NCT-502 (Compound 72) or NCT-503 (Compound 267) both reduce the M+6 dTMP pool size.

Example 17. PHGDH Inhibition Affects the Fate of Both Exogenous and Endogenous Serine PHGDH knockdown and small molecule PHGDH inhibitors are selectively toxic towards PHGDH-dependent cells and tumors even when serine is present (all cells in FIG. 4B were treated in RPMI containing 288 μM serine; see FIG. 7D for intratumoral serine concentrations). For this reason, the fates of both glucose-derived serine and exogenous serine were examined in PHGDH-dependent cells following acute PHGDH inhibition. Serine is incorporated into the purine ring of AMP via 10-formyltetrahydrofolate and glycine, and into the methyl group of the pyrimidine moiety of dTMP via 5,10-methylene-tetrahydrofolate (FIG. 8A). The production of M+3 serine and labeled nucleotides in cells fed U-$^{13}$C-glucose was measured. As expected, PHGDH inhibition reduced the production of M+3-serine and its product, M+2 glycine, from U-$^{13}$Cglucose (FIG. 8B, FIG. 9A), resulting in the incorporation of less $^{13}$C into AMP and dTMP via M+3 serine (FIG. 8B). The loss of incorporation of glucose-derived serine carbons into both AMP and dTMP persisted at 24 hours (FIG. 8A, FIG. 9B).

Figure 8C:
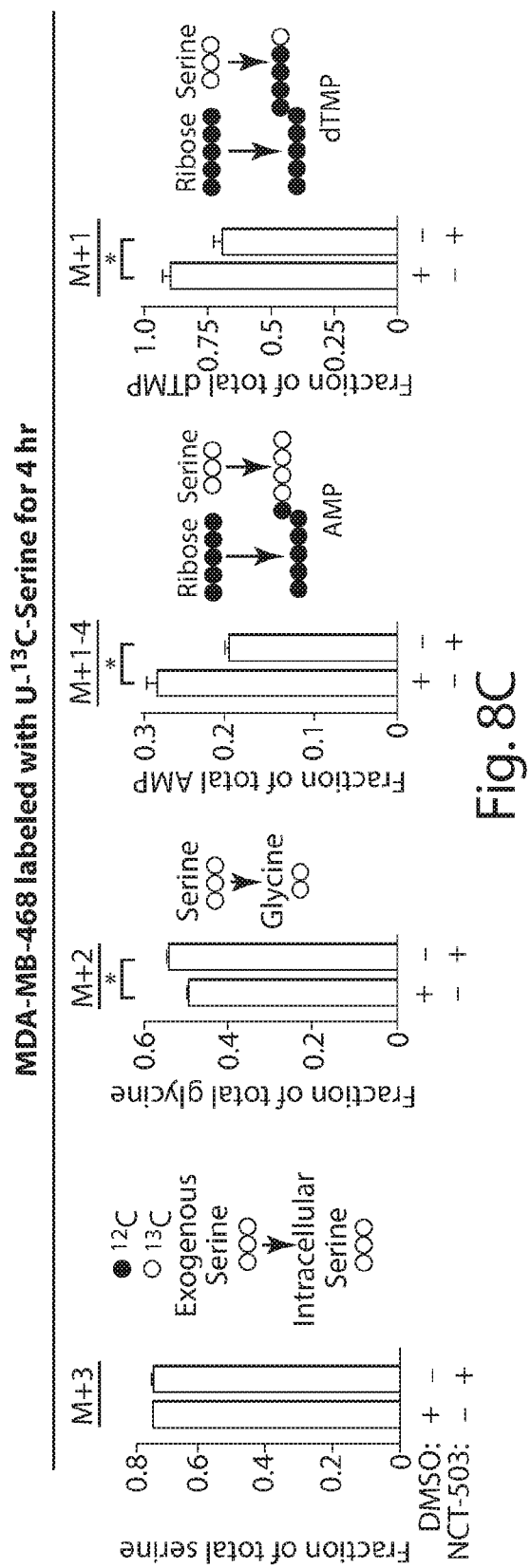
FIG. 8C. 10 μM NCT-503 (Compound 267) treatment for four hours in the presence of exogenous U-$^{13}$C-serine does not increases the proportion of labeled serine but increases the fraction of labeled glycine, consistent with decreased synthesis of unlabeled serine. Unexpectedly, NCT-503 (Compound 267) reduces the incorporation of one-carbon units from exogenous U-$^{13}$C-serine into AMP and dTMP.
Figure 9C:
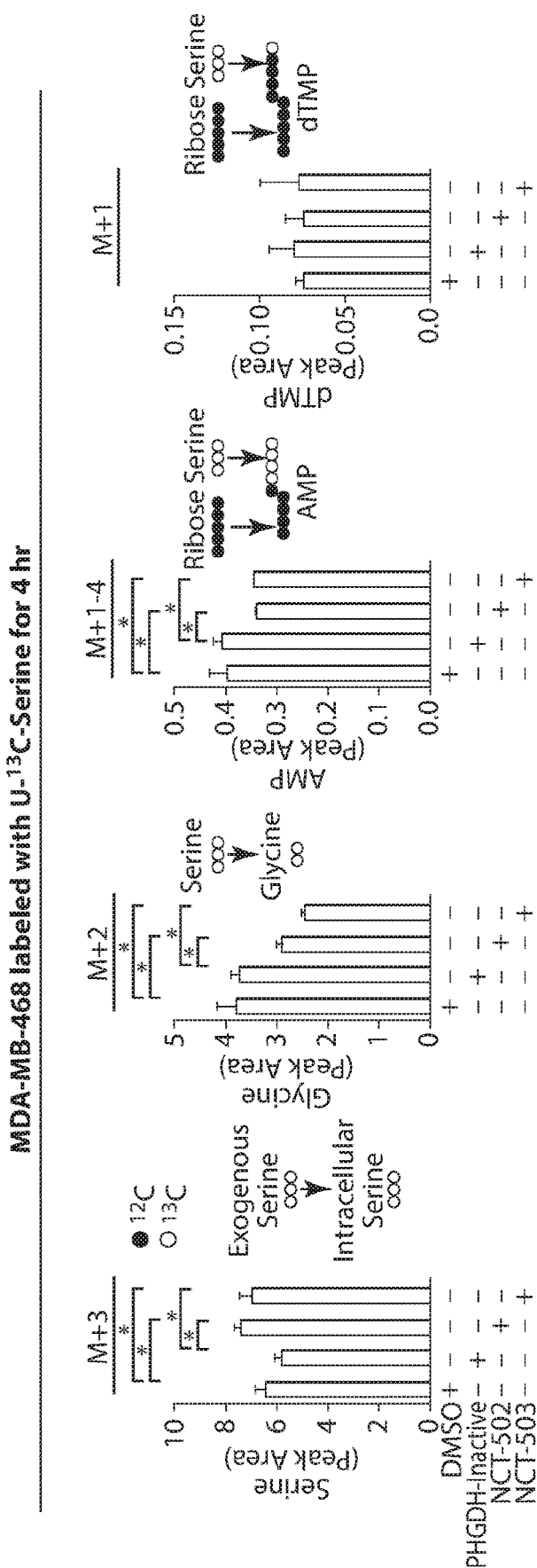
FIG. 9C. Neither NCT-502 (Compound 72) or NCT-503 (Compound 267) affect the M+3 serine pool size at 4 hours, but both decrease the M+2 glycine and M+1-4 AMP pools.
Figure 9D:
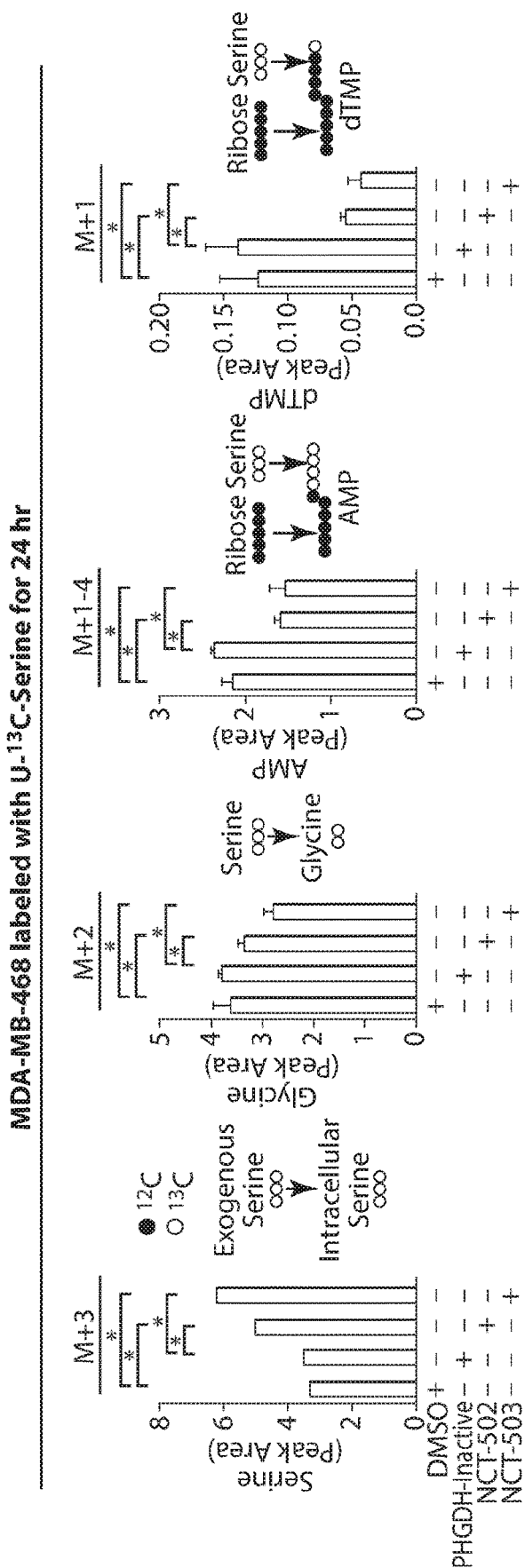
FIG. 9D. At 24 hours, both 10 μM NCT-502 (Compound 72) and NCT-503 (Compound 267) significantly decrease the size M+1-4 AMP and M+1 dTMP pools generated by U-$^{13}$C-serine labeling.
Figure 10C:
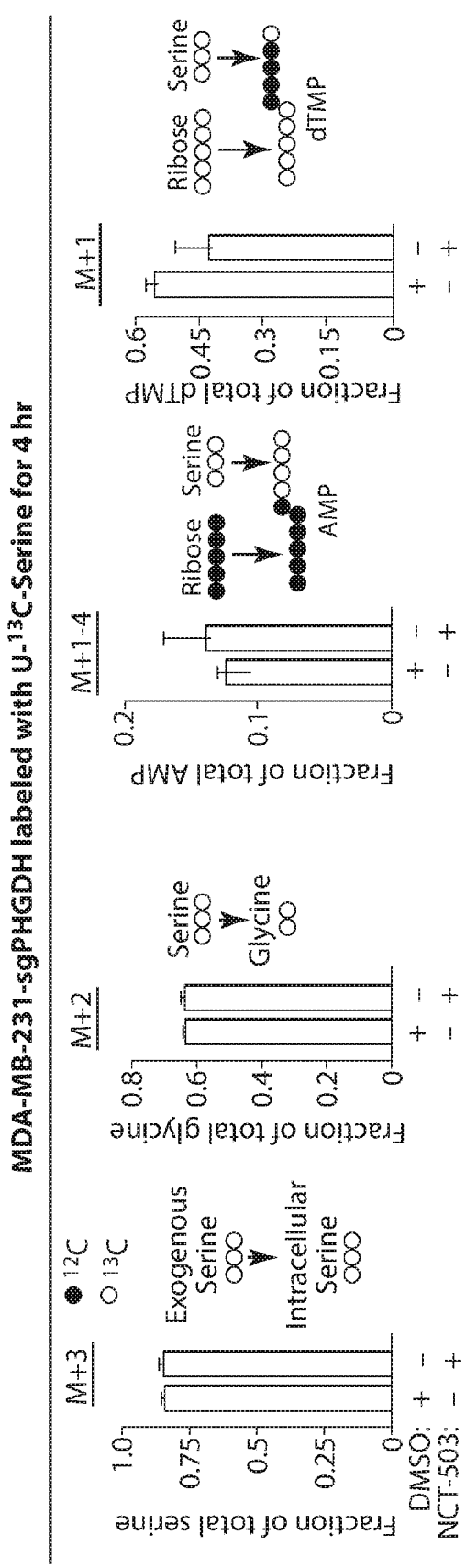
Figure 10D:
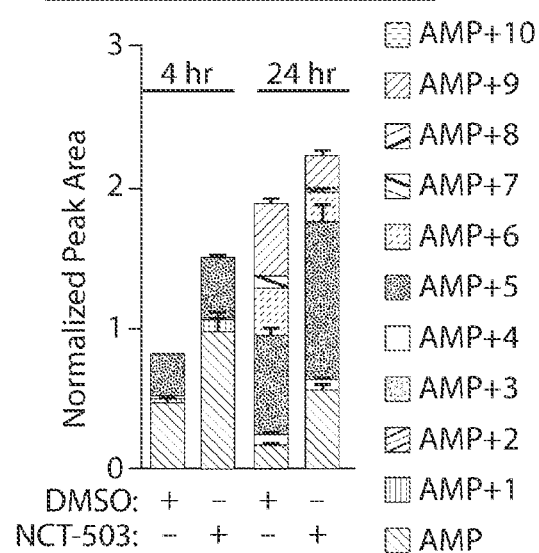
Figure 10E:
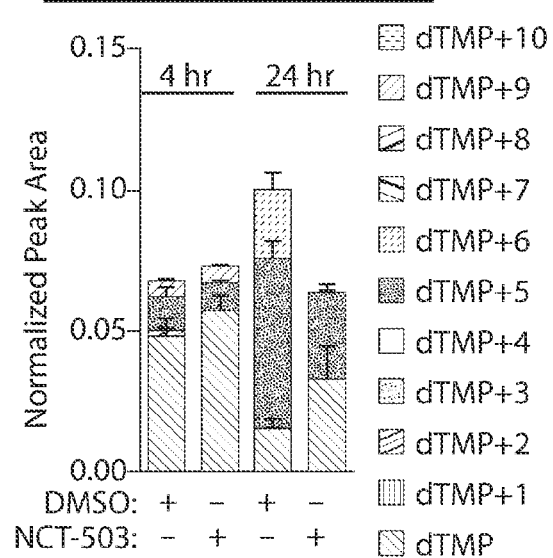

To determine the fate of exogenous serine, cells were fed U-$^{13}$C-serine instead of unlabeled serine in the medium. PHGDH inhibition did not block the uptake (FIGS. 9C, 9D) or change the fraction of M+3-serine in MDA-MB-468 cells and, as expected, increased the incorporation of exogenous, labeled serine into glycine (FIG. 8C). Unexpectedly, NCT-503 (Compound 267) treatment for 4 hours decreased the incorporation of $^{13}$C from exogenous U-$^{13}$C-serine into AMP and dTMP (FIG. 8C, FIG. 9Q, effects which persisted at 24 hours of treatment as a reduction in labeled pool size (FIG. 10B, FIG. 11D, FIG. 12 A, FIG. 12B). The inhibitor did not have these effects on MDA-MB-231 cells that lack PHGDH (FIG. 10C).

Example 18. The Serine Synthesis Pathway Regulates One-Carbon Unit Availability

Exogenous and endogenous serine are incorporated into AMP via glycine and 10-formyl-tetrahydrofolate, and into dTMP via 5,10-methylene tetrahydrofolate (5,10-CH$_2$-THF) generated by the mitochondrial serine hydroxymethyl transferase (SHMT2) or the cytosolic serine hydroxymethyl transferase (SHMT1). SHMT1 is also capable of synthesizing serine from 5,10-CH$_2$-THF and glycine (See, e.g., Narkewicz, M. R., Sauls, S. D., Tjoa, S. S., Teng, C. & Fennessey, P. V. "Evidence for intracellular partitioning of serine and glycine metabolism in Chinese hamster ovary cells." *Biochem J* 313 (Pt 3), 991-996 (1996)). As a defect in serine import was not observed (FIG. 8B; FIGS. 9C and 9D), consumption of serine-derived 5,10-CH$_2$-THF by SHMT1 may generate serine at the expense of dTMP synthesis when the serine synthesis pathway is inhibited. Moreover, attenuation of SHMT1 activity may redirect one-carbon units from both exogenous and endogenous serine towards nucleotide synthesis.

Figure 11A:
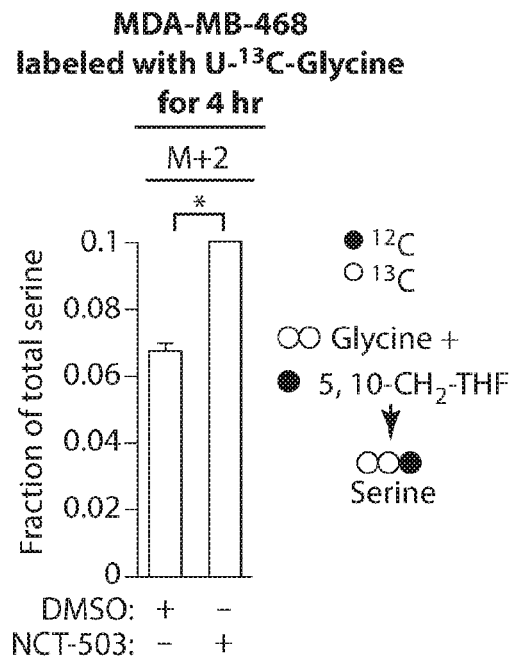
FIG. 11A. SHMT1 mediates the loss of nucleotide labeling induced by PHGDH inhibition. NCT-503 (Compound 267) induces increased synthesis of M+2 serine from M+2 glycine and unlabeled 5,10-$CH_2$-THF (5,10-Methylenetetrahydrofolate) in a PHGDH-dependent cell line.
Figure 11B:
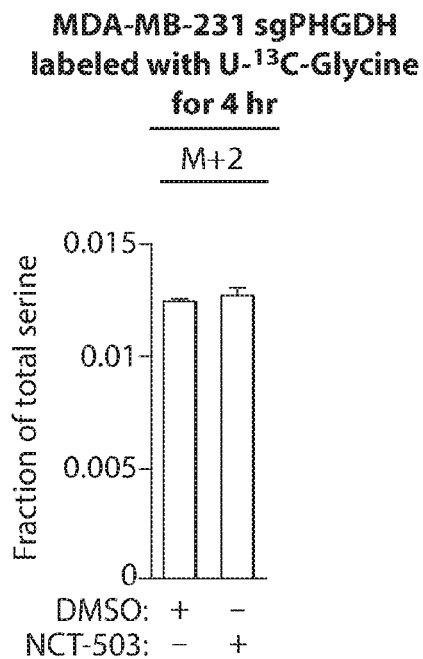
FIG. 11B. MDA-MB-231 cells lacking PHGDH do not synthesize a significantly different amount of M+2 serine from M+2 glycine following PHGDH inhibitor treatment.
Figure 11C:
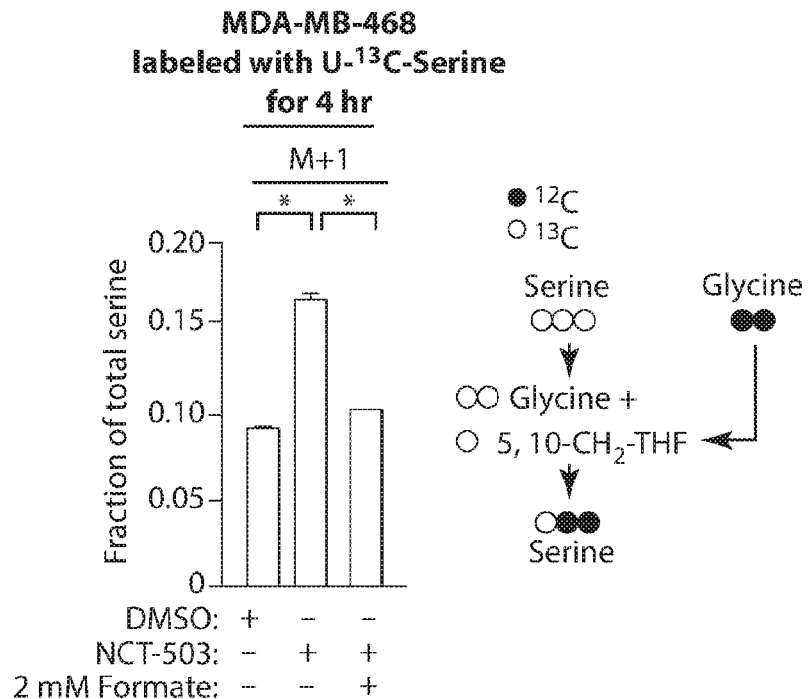
FIG. 11C. Serine synthesis pathway activity, or a serine synthesis pathway intermediate, represses SHMT1 activity. SHMT1 catalyzes serine synthesis from glycine and 5,10-$CH_2$-THF.
Figure 11D:
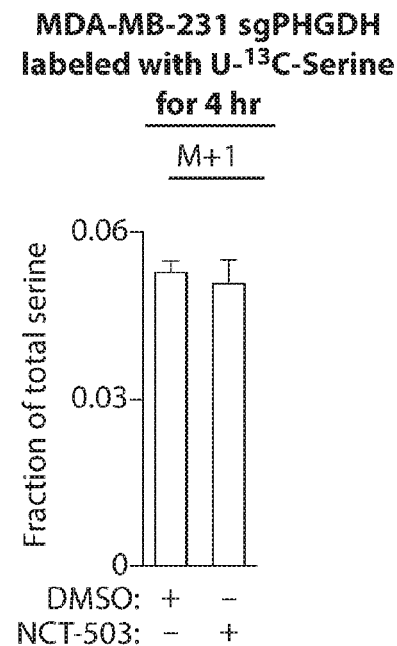
FIG. 11D. Probable SHMT1-catalyzed synthesis of M+1-serine from unlabeled glycine and $^{13}$C-serine-derived 5,10-methylene THF (5,10-$CH_2$-THF) increases with PHGDH inhibition (10 μM NCT-503 (Compound 267)) and is suppressed by exogenous unlabeled formate.
Figure 11E:
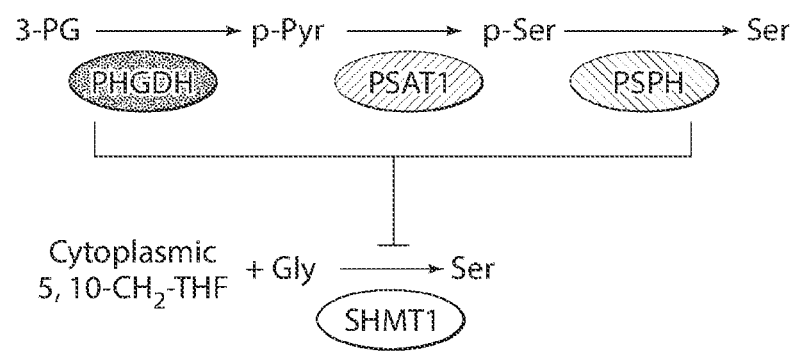
FIG. 11E. NCT-503 (Compound 267) does not induce increased M+1 serine labeling in MDA-MB-231 cells lacking PHGDH.

In agreement with this, MDA-MB-468 cells fed exogenous U-$^{13}$C-glycine exhibit increased production of M+2 serine in the presence of NCT-503 (Compound 267) (FIG. 11A; FIG. 13A). This did not occur in MDA-MB-231 cells lacking PHGDH (FIG. 11B FIG. 13B). Increased SHMT1 activity in the presence of U-$^{13}$C-serine should increase the amount of serine containing a single $^{13}$C derived from 5,10-$^{13}$CH$_2$-THF and unlabeled glycine from the cytosolic pool. Consistent with this hypothesis, NCT-503 (Compound 267) treatment increased the fraction of M+1 serine in MDA-MB-468 cells fed with U-$^{13}$C-serine (FIG. 11Q. The addition of unlabeled formate reduced M+1 serine production from U-$^{13}$C-serine, which demonstrates that the M+1 serine arose from unlabeled glycine and 5,10-$^{13}$CH$_2$-THF (FIG. 11C, FIG. 13Q. Cells lacking PHGDH did not exhibit increased M+1 serine production from M+3 serine following NCT-503 (Compound 267) treatment (FIG. 11D). These data support a hypothesis in which the glucose-derived serine biosynthesis pathway inhibits SHMT1 (FIG. 11E) to prevent wasting of 5,10-CH$_2$-THF while serine synthesis is ongoing.

Figure 11F:
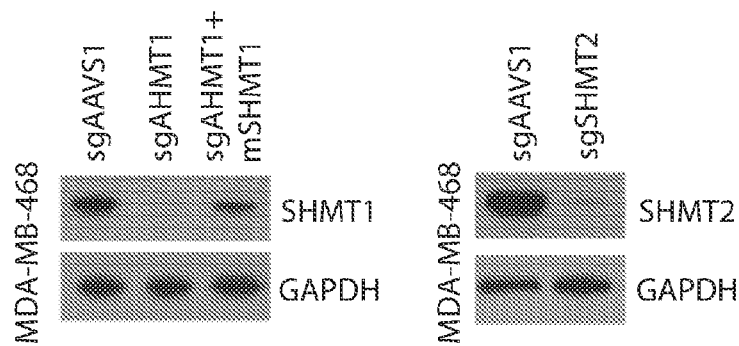
FIG. 11F. Cas9 and sgRNA-mediated deletion of SHMT1 and SHMT2 in MDA-MB-468 cells, with rescue of SHMT1 expression with mouse SHMT1.
Figure 11G:
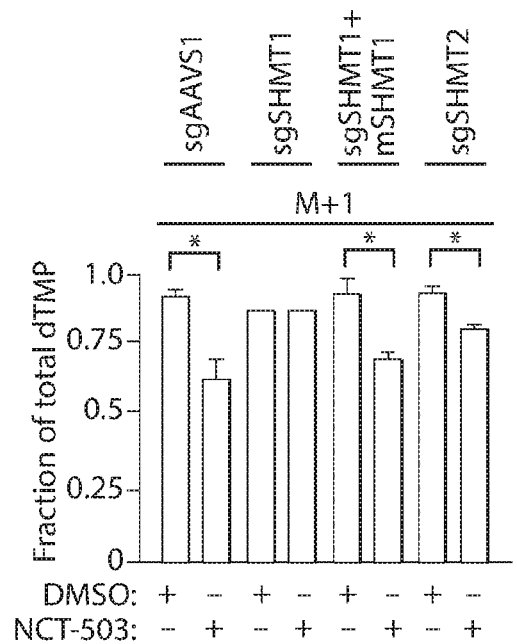
FIG. 11G. SHMT1 deletion restores incorporation of carbon from U-$^{13}$C serine into dTMP in the presence of PHGDH inhibitor. Mouse SHMT1 expression restores decreased dTMP labeling induced by PHGDH inhibition. SHMT2 knockout does not block PHGDH inhibitor-mediated loss of dTMP labeling.
Figure 11H:
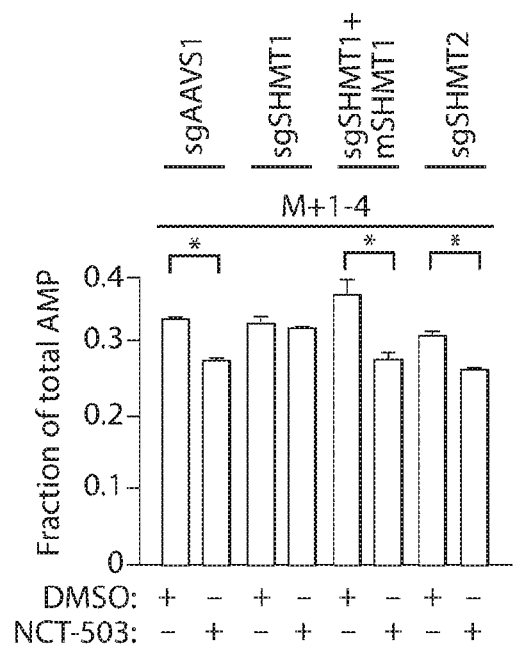
FIG. 11H. SHMT1 deletion restores incorporation of carbon from U-$^{13}$C serine into AMP in the presence of a PHGDH inhibitor. Mouse SHMT1 restores PHGDH inhibitor-mediated loss of AMP labeling by U-$^{13}$C serine.
Figure 11I:
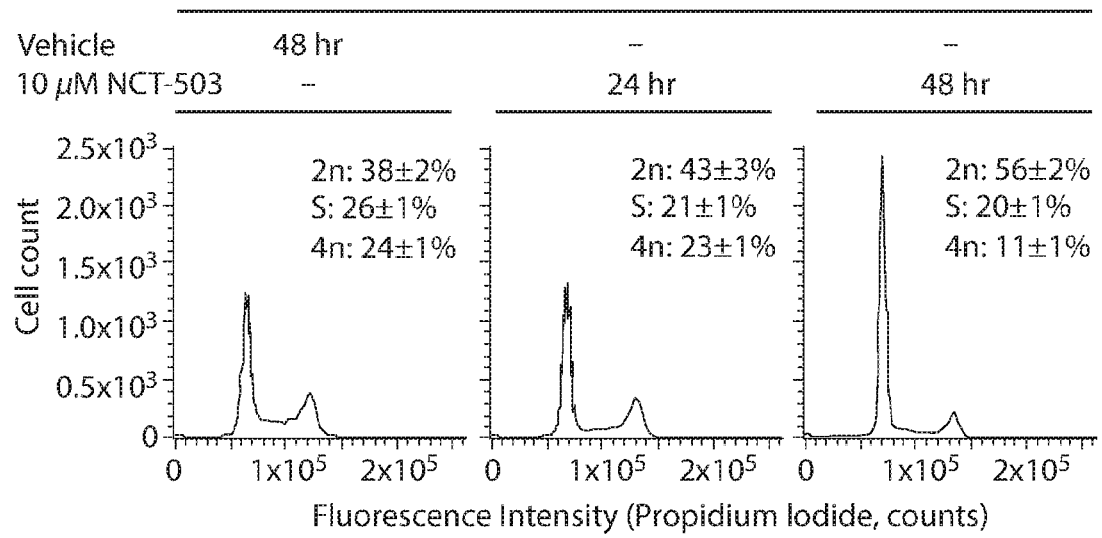
FIG. 11I. NCT-503 (Compound 267) treatment induces $G_1$/S cell cycle arrest in MDA-MB-468 cells, consistent with a defect in nucleotide synthesis.
Figure 11J:
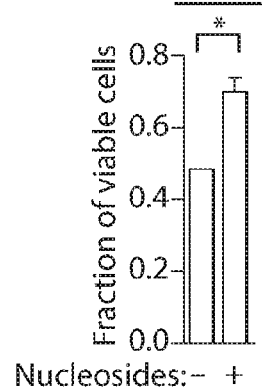
FIG. 11J. Nucleoside supplementation partially rescues PHGDH inhibitor toxicity.

MDA-MB-468 cells were generated in which cytosolic SHMT1 or mitochondrial SHMT2 was deleted with CRISPR/Cas9 (FIG. 11F). Loss of SHMT1, but not SHMT2, restored the incorporation of serine-derived carbon into AMP and dTMP in the presence of a PHGDH inhibitor (FIGS. 11g and 11h). Expression of an sgRNA-resistant mouse SHMT1 (FIG. 11F) restored the loss of U-$^{13}$C-serine incorporation into AMP and dTMP induced by PHGDH inhibition (FIGS. 11g and 11h). Serine synthesis-mediated inhibition of SHMT1 directs the incorporation of serine-derived one-carbon units into AMP and dTMP. Consistent with this hypothesis, NCT-503 (Compound 267) caused G$_1$/S arrest after 48 hours (FIG. 11I) and supplementation of RPMI with nucleosides reduced the toxicity of PHGDH inhibition (FIG. 11J).

As described herein, PHGDH inhibitors have been identified that inhibit the synthesis of glucose-derived serine through direct target engagement. Counter-screens of these compounds against dehydrogenases, steady state metabolite profiling, and $^{13}$C labeling studies confirmed the effectiveness of the PHGDH inhibitors in cells (in vitro) and in vivo.

Figure 11K:
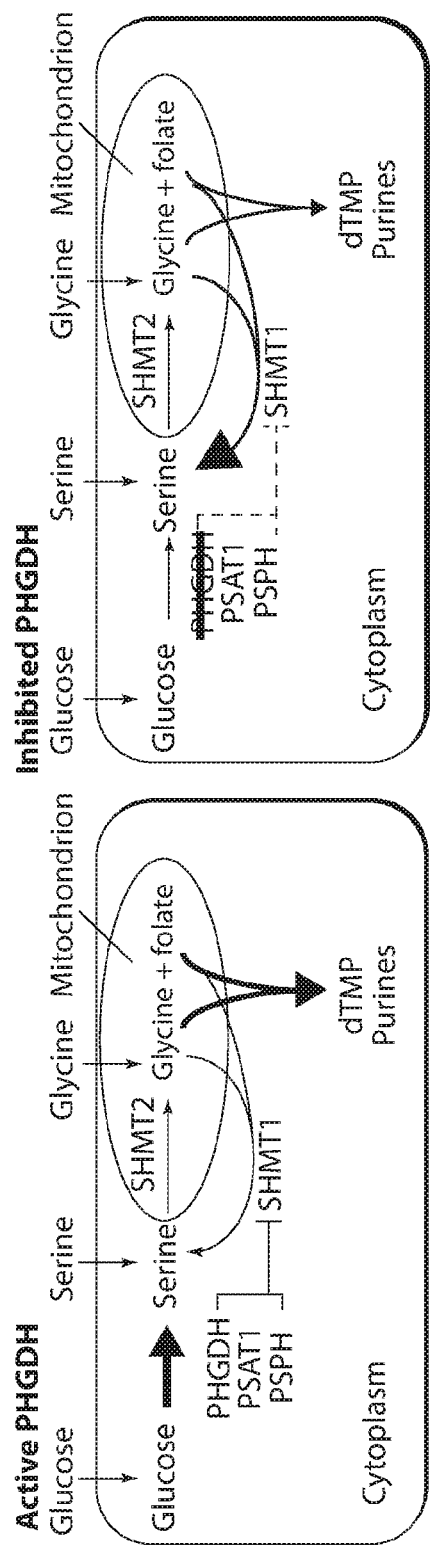
FIG. 11K. Model of one-carbon unit wasting induced by PHGDH inhibition. Suppression of PHGDH activity increases the activity of SHMT1, which consumes one-carbon units to resynthesize serine but reduces the availability of one-carbon units needed for purine and dTMP synthesis.
Figure 12A:
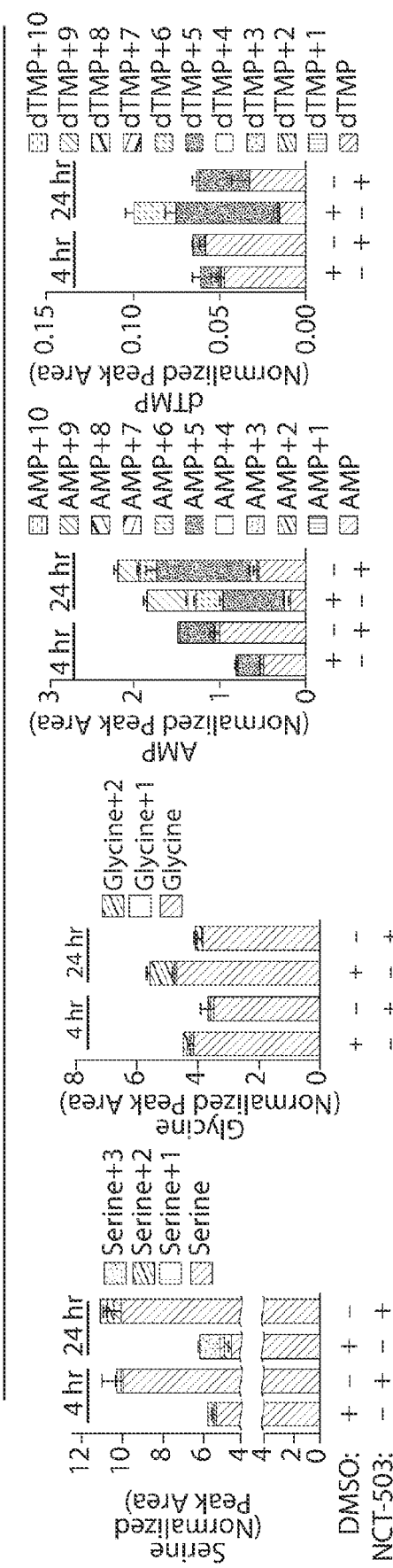
FIG. 12A. Isotopomer distributions of serine, glycine, AMP, and dTMP following PHGDH inhibitor treatment.
Figure 12B:
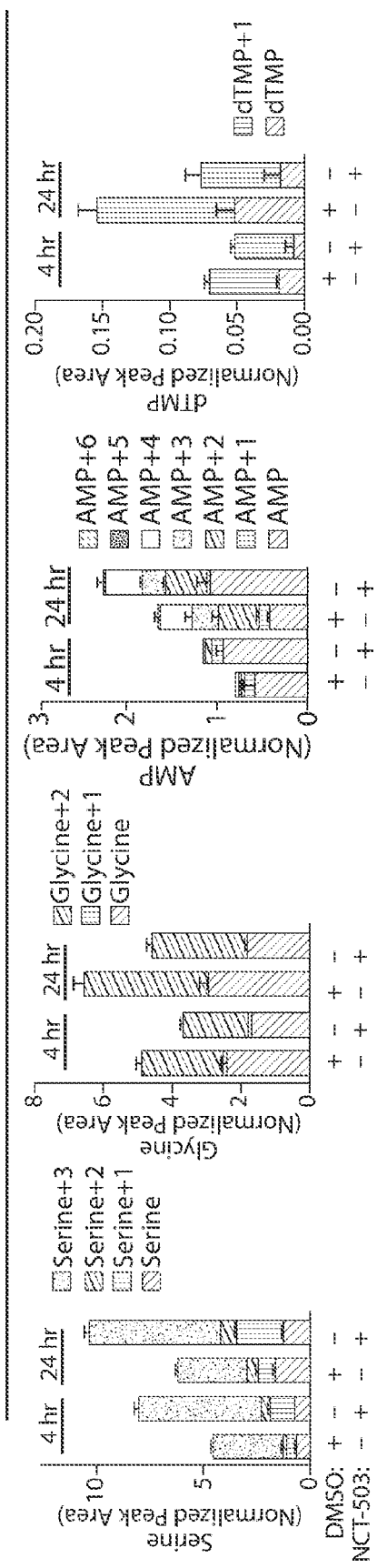
FIG. 12B. Pool sizes following labeling with U-$^{13}$C glucose. Labeled serine and glycine decrease at 4 and 24 hours, and labeled and unlabeled dTMP pools decrease at 24 hours following NCT-503 (Compound 267) treatment. Pool sizes following labeling with U-$^{13}$C serine. Incorporation of $^{13}$C into dTMP decreases at 24 hours following PHGDH inhibitor treatment.

The PHGDH inhibitors described herein show that the serine synthesis pathway not only generates serine, but also ensures that one-carbon units derived from both endogenous and exogenous serine are available for nucleotide synthesis by reducing SHMT1 activity (FIG. 11K). One-carbon unit wasting induced by PHGDH inhibition and SHMT1 activation reduces one-carbon unit incorporation into nucleotides even in the presence of ample serine, and may contribute to the inability of exogenous serine to rescue PHGDH inhibition or knockdown.

Substantial genetic evidence supports the importance of the serine synthesis pathway in the survival and proliferation of various cancers including, but not limited to, breast cancer, melanoma, and non-small cell lung cancer cells. The selective toxicity and tolerability of the compounds described herein in vitro and in vivo show that the PHGDH-inhibiting compounds can be therapeutically useful.

Biological Methods

Materials

The following antibodies were used: antibodies to PHGDH (HPA021241) and SHMT2 (HPA020549) from Sigma, an antibody to SHMT1 (12612) from Cell Signaling Technologies, an antibody to GAPDH (GT239) from GeneTex, and an antibody to actin (sc-1616) from Santa Cruz Biotechnologies. BT-20 (HTB-19), HCC70 (CRL-2315), HT1080 (CCL-121), MDA-MB-468 (HTB-132), MDA-MB-231 (HTB-26), SK-MEL-2 (HTB-68), and ZR-75-1 (CRL-1500) cells were from ATCC and MT-3 (ACC 403) cells were from DSMZ. Cell lines were directly obtained from authenticated sources and were not STR profiled. The BT-20 cell line has previously been misidentified but this PHGDH-amplified cell line has previously been used to demonstrate selective toxicity of PHGDH knockdown. Cell lines were verified to be free of mycoplasma contamination by PCR (See, e.g., Young, L., Sung, J., Stacey, G. & Masters, J. R. "Detection of *Mycoplasma* in cell cultures." *Nat Protoc* 5, 929-934 (2010)). 3-Phosphoglycerate (P8877), NAD+ (N0632), glutamate (49621), DL-glyceraldehyde 3-phosphate (G5251), dihydroxyacetone phosphate (D7137), glycerol-3-phosphate (G7886), TCEP (646547), diaphorase (D5540), and resazurin (R7017) were from Sigma. U-$^{13}$C-glucose (CLM-1396-1), U-$^{13}$C-serine (CLM-1574-H-0.25), U-$^{13}$C-glycine (CLM-1017-1), Phe-d8 (DLM-372) and Val-d8 (DLM-311) were from Cambridge Isotope Laboratories. Matrigel (536230) was from BD Biosciences. Protein concentrations were determined using Bio-Rad Protein assay (Bio-Rad 500-0006). Amino acid-free and glucose-free RPMI was from US Biological. All LC-MS reagents were Optima grade (Fisher).

Protein Overexpression and Purification cDNAs to human PHGDH, PSAT1, PSPH, GAPDH, GPD1, and GPD1L were PCR amplified from human liver cDNA prepared from human liver mRNA using Superscript III (Life Technologies) and cloned into pET30-2 with an N-terminal 6×His Tag. Proteins were expressed in Rosetta (DE3)pLysS *E. coli* (EMD Millipore) grown to an OD of 0.6 and induced with 1 mM IPTG for 16 hours at 16° C. Bacteria were lysed at 4° C. in a French press and purified by Ni$^{2+}$ affinity chromatography on a 5 mL HiTrap chelating HP column (GE Healthcare) attached to an AktaPURE FPLC system (GE Healthcare) using a gradient of 0-500 mM imidazole in 50 mM Na-Phosphate pH 8 and 300 mM NaCl. Peak fraction purity was assessed by SDS gel electrophoresis. Pure fractions were combined, concentrated in 15 mL UltraFree 30 concentrators (EMD Millipore) and loaded onto a HiLoad Superdex 200 prep grade 16/60 column equilibrated in 20 mM Tris pH 7.4, 100 mM NaCl, and 1 mM TCEP. Peak fractions were concentrated to [protein]≥5 mg/mL, flash frozen in liquid nitrogen, and stored at −80° C. prior to use.

Enzyme Assays

PHGDH assay buffer contained 50 mM TEA pH 8.0, 10 mM MgCl$_2$, 0.05% BSA, and 0.01% Tween-20. PHGDH enzyme buffer consisted of assay buffer with 20 nM PHGDH and 0.2 mg/mL diaphorase. PHGDH substrate buffer contained 0.3 mM NAD 1.25 mM glutamate, 0.1 mM 3-phosphoglycerate, 0.2 mM resazurin, 1 μM PSAT1, and 1 μM PSPH. qHTS was performed in 1536-well plates dispensed with a BioRAPTR FRD. Each well contained equal volumes of substrate buffer and assay buffer. Plates were read at 0 minutes and 20 minutes at room temperature with a ViewLux uHTS Microplate Imager (PerkinElmer). Follow-up assays were performed in black 384-well plates (Greiner) in 20 μL of enzyme buffer to which compounds were added in dose-response with an HP D300 digital dispenser (Hewlett-Packard), followed by addition of 20 μL of substrate buffer. Plates were incubated at room temperature (25° C.) and read at 0 and 20 minutes with a Spectramax M5 plate reader (Molecular Devices) in fluorescence intensity mode with a $\lambda_{ex}$=550 nm and $\lambda_{em}$=600 nm (emission cutoff=590 nm).

GAPDH substrate buffer contained 210 mM Tris pH 7.4, 2.5 mM NaH$_2$PO$_4$ pH 7.4, 2 mM DL-Glyceraldehyde 3-phosphate, 1.75 mM MgCl$_2$, 0.01 mM NAD+, 0.11 mM resazurin, 0.2 mg/mL BSA, and 0.01% Tween-20. GAPDH enzyme buffer contained 50 mM Tris pH 7.4, 100 mM NaCl, 0.02 mM TCEP, 0.01 mM EDTA, 0.1 mg/mL BSA, 0.42 mg/mL diaphorase, and 2.5 nM GAPDH. The GAPDH, GPD1, and GPD1L assays were run in 384-well plates using the same protocol and readout as the PHGDH assay. GPD1 substrate buffer contained 114 mM Tris pH 7.4, 0.25 mM DHAP, 1.14 mM MgCl$_2$, 0.011 mM NADH, 0.06 mg/mL BSA, and 0.011% Tween-20. GPD1 enzyme buffer contained 50 mM Tris pH 7.4, 100 mM NaCl, 0.08 mM TCEP, 0.4 mg/mL BSA, 0.03 μM EDTA, and 0.8 nM GPD1. 70 μL of substrate buffer were mixed with 10 μL enzyme buffer. GPD1L substrate buffer contained 200 mM Tris pH 7.4, 0.05 mM sn-G3-P, 2 mM MgCl$_2$, 0.04 mM NAD+, 0.11 mM resazurin, 0.1 mg/mL BSA, and 0.02% Tween-20. GPD1L enzyme buffer contained 50 mM Tris pH 7.4, 100 mM NaCl, 0.02 mM TCEP, 0.42 mg/mL diaphorase, 0.1 mg/mL BSA, 0.008 μM EDTA, and 16 nM GPD1L. 40 μL of substrate buffer were mixed with 40 μL of enzyme buffer.

The GAPDH and GPD1L assays were read using the same protocol as the PHGDH assay. The GPD1 assay was read using loss of NADH fluorescence ($\lambda_{ex}$=340 nm and $\lambda_{em}$=460 nm).

Binding Assays

Differential scanning fluorimetry assays were carried out in 20 mM TEA pH 8, 100 mM NaCl, 1× SYPRO Orange (Sigma), 2 μM PHGDH in a volume of 10 μL. Unfolding was monitored using a LightCycler 480 II real-time PCR instrument ($\lambda_{ex}$=465 nm and $\lambda_{em}$=580 nm) over a linear 20 to 85° C. gradient. Plots of the first derivative of fluorescence vs. temperature were generated in LightCycler software.

Cell Culture

All cells were grown as adherent cell lines in RPMI supplemented with 10% IFS and penicillin/streptomycin. Media for metabolite profiling experiments utilized dialyzed inactivated fetal serum (IFS), prepared by dialyzing IFS for 72 hours using SnakeSkin 3.5K MWCO dialysis tubing against a 10-fold higher volume of phosphate-buffered saline (PBS) with a complete PBS exchange every 12 hours.

Overexpression of PHGDH

Full length human PHGDH was cloned into pMXS-IRES-BLAST which was used to generate retrovirus in supernatants using transient transfection (See, e.g., Luo, B. ei al. "Highly parallel identification of essential genes in cancer cells." *Proceedings of the National Academy of Sciences* 105, 20380-20385 (2008)). MDA-MB-231 cells were transduced with retrovirus by spin infection (2250 rpm for 30 minutes) in polybrene. After 24 hours, cells were selected with 2 μg/mL puromycin.

CRISP-Cas9 Mediated Gene Knockout

We used CRISPR/Cas-9 mediated genome editing to achieve gene knockout, using pLentiCRISPR (Addgene Plasmid #49535) in which the sgRNA and Cas9 are delivered on a single plasmid. Editing of the PHGDH locus in MDA-MB-231 cells was accomplished by transfection of cells with the pLENTICRISPR plasmid into which a sgRNA targeting the PHGDH locus had been cloned. Transfected cells were subjected to single cell cloning by limiting dilution in 96 well plates. Editing of the PHGDH locus was confirmed by Sanger sequencing of the targeted locus. PHGDH null clones exhibited biallelic insertion or deletion of a single "A" at the targeted site and were compared to unedited control clones.

Editing of the SHMT1 and SHMT2 loci in MDA-MB-468 cells was accomplished by infection of cells with lentivirus delivering sgRNA and Cas9. Lentiviruses were generated in supernatants using transient transfection (See, e.g., Luo, B. et al. "Highly parallel identification of essential genes in cancer cells." *Proceedings of the National Academy of Sciences* 105, 20380-20385 (2008)) and MDA-MB-468 cells were transduced by spin infection at 2250 rpm for 30 minutes in the presence of polybrene followed by overnight incubation. Lentiviruses with a sgRNA against AAVS1 served as a negative control, and uninfected cells were used as negative controls for transduction.

After transduction, infected MDA-MB-486 cells were selected with puromycin for three days. Loss of SHMT1 and SHMT2 expression was confirmed by Western blotting. For addback experiments, mouse SHMT1 was cloned into pLJM5 (Addgene Plasmid #61614). Lentivirus production and MDA-MB-468 infection were as above. Following spin infection at 2250 rpm and incubation for 24 hours, cells were selected with hygromycin (Sigma) for one week and re-selected with puromycin for 24 hours. All cells were seeded into medium lacking antibiotics for 24 hours prior to further experiments. The following target site sequences (See, e.g., Wang, T., Wei, J. J., Sabatini, D. M. & Lander, E. S. "Genetic screens in human cells using the CRISPR-Cas9 system." *Science* 343, 80-84 (2014)) were used:

```
AAVS1:
                                   (SEQ ID NO: 1)
GGGGCCACTAGGGACAGGAT;

PHGDH:
                                   (SEQ ID NO: 2)
AAAGCAGAACCTTAGCAAAG;

SHMT1:
                                   (SEQ ID NO: 3)
GAACGGGGCGTATCTCATGG;

SHMT2:
                                   (SEQ ID NO: 4)
GAGAAGGACAGGCAGTGTCG.
```

Cytotoxicity Experiments

Cells were seeded in white 96-well plates (Greiner) at a density of 2000 cells/well (MDA-MB-468, BT-20, MT-3) or 1000 cells/well (all other cell lines) and allowed to attach for 24 hours. Compounds were prepared in DMSO and dispensed using an HP D300 compound dispenser. Cell viability was assessed with Cell Titer-Glo (Promega) at four days following treatment and luminescence measured with a SpectraMax M5 Plate Reader (Molecular Devices). Luminescence was normalized to an untreated control in identical medium. For rescue experiments, RPMI was supplemented with 40 µM adenosine, uridine, guanosine, cytidine, deoxyadenosine, thymidine, deoxyguanosine, and deoxycytidine and the medium was replaced daily.

Oxygen Consumption Measurements

Oxygen consumption of intact MDA-MB-468 cells was measured using an XF24 Extracellular Flux Analyzer (Seahorse Bioscience). 85,000 cells were plated in RPMI media and exposed to compounds at 10 and 50 µM. Each measurement represents the average of six independent wells.

Metabolite Profiling: Steady-State and Labeling Experiments

Cells were evenly seeded at 400,000 cells per well of a 6-well plate and allowed to attach for 24 hours. Prior to all labeling experiments, cells were pretreated with 10 µM compound or an equivalent volume of DMSO in RPMI for 1 hour. For steady-state metabolite concentrations, cells were washed with PBS prior to pretreatment and treatment in RPMI lacking serine and glycine. For labeling experiments, U-$^{13}$C-glucose, U-$^{13}$C-serine, or U-$^{13}$C-glycine replaced the corresponding unlabeled RPMI component. Cells were washed in 4° C. 0.9% (w/v) NaCl in LCMS-grade water and extracted in 1 mL/well of 80:20 (v/v) methanol:water with 0.01 ng/mL Val-d8 and Phe-d8 as internal extraction standards. The extraction solvent was dried under nitrogen gas and metabolite samples were stored at −80° C. until analysis. Triplicate identically seeded wells were trypsinized and analyzed with a Multisizer Coulter Counter (Beckman Coulter) to obtain cell counts and total cell volumes for normalization.

Liquid Chromatography-Mass Spectrometry

Dried metabolites were resuspended in 100 µL water, centrifuged at 13,000×g at 4° C. for 10 minutes, and the supernatant recovered for analysis. Chromatographic separation was achieved by injecting 1 pi of sample on a SeQuant ZIC-pHILIC Polymeric column (2.1 3 150 mm 5 mM, EMD Millipore). Flow rate was set to 0.1 ml per minute, column compartment was set to 25° C., and autosampler sample tray was set to 4° C. Mobile Phase A consisted of 20 mM ammonium carbonate, 0.1% ammonium hydroxide. Mobile Phase B was 100% acetonitrile. The mobile phase gradient (% B) was as follows: 0 min 80%, 30 min 20%, 31 min 80%, 42 min 80%. All mobile phase was introduced into the ionization source set with the following parameters: sheath gas=40, auxiliary gas=15, sweep gas=5, spray voltage=−3.1 kV or +3.0 kV, capillary temperature=275° C., S-lens RF level=40, probe temperature=350° C. Metabolites were monitored using a polarity-switching full-scan method and identified by accurate mass (±20 ppm) and retention time within 15 seconds of a previously run pure standard. Metabolite peaks were identified and integrated with Xcalibur v.2.2 software (Thermo Fisher Scientific) and normalized to internal standard and to total cell volume, m/z ratios for stable isotopically labeled metabolites were obtained from IsoMETLIN (See, e.g., Cho, K. et al. "isoMETLIN: a database for isotope-based metabolomics." *Anal Chem* 86, 9358-9361 (2014)) and corrected for natural abundance.

Mouse Orthotopic Xenografts

Female NOD.CB17-Prkdc$^{scid}$/J mice, 6-8 weeks old, were obtained from Jackson Laboratories. All animals were provided with food ad libitum for the duration for the duration of the experiment. The animals were allocated randomly for induction with MDA-MB-231 or MDA-MB-468 tumors and tumor group was assigned blindly. 500,000 MDA-MB-231 or MDA-MB-468 cells were injected into the 4$^{th}$ mammary fat pad of each mouse. After 30 days, the tumors were palpable, and the mice were pooled by tumor type and divided randomly to two groups, which were assigned blindly to vehicle or NCT-503 treatment. NCT-503 (Compound 267) was prepared in a vehicle of 5% ethanol, 35% PEG 300 (Sigma), and 60% of an aqueous 30% hydroxypropyl-β-cyclodextrin (Sigma) solution, and injected intraperitoneally once daily. Dose was adjusted to mouse weight, and the volume of injection did not exceed 150 µL. Caliper measurements were obtained twice weekly and tumor volumes were calculated with the modified ellipsoid formula: volume=0.5×width$^2$×length.

For quantitation of necrotic regions, fixed tumors were embedded and sections stained with hematoxylin and eosin. Slides were scanned with a Leica Aperio AT2 brightfield scanner. Tumor and necrotic cross-sectional regions were manually delineated and measured using Leica ImageScope software to calculate the percentage of necrosis.

Glucose Infusions in Mice

Chronic catheters were surgically implanted into the jugular veins of normal or tumor bearing animals 3-4 days prior to infusions. Animals were fasted for 6 hours (morning fast) and infusions were performed in free-moving, conscious animals at 1:00 pm for all studies to minimize metabolic changes associated with circadian rhythm. Following administration of either vehicle or NCT-503 (Compound 267) at 30 mg/kg, a constant infusion of U-$^{13}$C-glucose (30 mg/kg/min) (Cambridge Isotope Laboratories) was administered for a 3-hour duration. Animals were terminally anesthetized with sodium pentobarbital and all tissues were fully harvested in less than 5 minutes to preserve the metabolic state. Tumors and adjacent lung tissue were carefully dissected and rapidly frozen using a BioSqueezer (BioSpec Products) to ensure rapid quenching of metabolism throughout the tissue section. Tissues were stored at −80 C and extracted with 80:20 (v/v) methanol: water in the same manner as cells prior to LCMS analysis.

Statistics and Animal-Model Statements

All experiments consisted of at least three biological replicates unless otherwise stated, with the exception of the xenograft based experiments, which were performed once with groups of ten mice. All center values shown in graphs refer to the mean. Error bars represent standard deviations unless otherwise stated. Asterisks in figure legends represent $p<0.05$. f-tests were heteroscedastic to allow for unequal variance and distributions assumed to follow a Student's t distribution, and these assumptions are not contradicted by the data. All t-tests were two-sided. No statistical methods were used to predetermine sample size. No samples or animals were excluded from analyses. Animals were blindly and randomly assigned to tumor type and to the vehicle or treatment groups. All experiments involving mice were carried out with approval from the Committee for Animal Care at MIT and under the supervision of the MIT Division of Comparative Medicine in accordance with the MIT Policy on the use of animals in research and teaching.

EQUIVALENTS AND SCOPE

In the claims articles such as "a," "an," and "the" may mean one or more than one unless indicated to the contrary or otherwise evident from the context. Claims or descriptions of a given product or process that include "or" between one or more members of a group are considered satisfied if one, more than one, or all of the group members are present, employed, or otherwise relevant, unless indicated to the contrary or otherwise evident from the context. The invention includes embodiments of a given product or process in or to which exactly one member of the group is present, employed, or otherwise relevant. The invention includes embodiments of a given product or process in or to which multiple members of the group are present, employed, or otherwise relevant. The invention includes embodiments of a given product or process in or to which the entire group is present, employed, or otherwise relevant.

Furthermore, the invention encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, in instances referring to the invention or aspects of the invention as comprising particular elements or features (or both), certain embodiments of the invention or aspects of the invention consist or consist essentially of such elements or features (or both). For purposes of simplicity, those embodiments have not been specifically set forth in haec verba herein. It is also noted that the terms "comprising" and "containing" are intended to be open and permit the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (II):

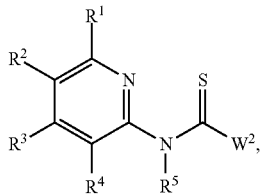

or a pharmaceutically acceptable salt thereof, wherein:

$W^2$ is of formula:

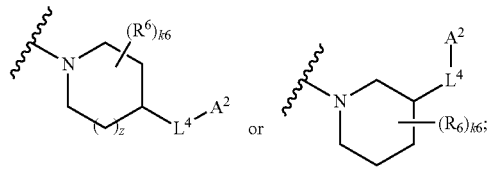

$L^2$ is —$CH_2$—;

L is —$CH_2$—;

$A^2$ is of the formula:

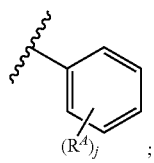

$R^A$ is halogen, nitrile, nitro, optionally substituted alkyl, optionally substituted alkenyl, optionally substituted carbocyclyl, optionally substituted heterocyclyl, optionally substituted aryl, optionally substituted heteroaryl, —$OR^b$, —$NR^cR^d$, —$SR^e$, —C(=O)$R^f$, —C(=O)$OR^b$, —C(=O)$NR^cR^d$, —S(=O)$R^f$, —S(=O)$OR^b$, —S(=O)$NR^cR^d$, —S(=O)$_2R^f$, —S(=O)$_2OR^b$, or —S(=O)$_2NR^cR^d$;

j is 0 or 1;

$R^1$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^b$, —$NR^cR^d$, —$SR^e$, —C(=O)$R^f$, —C(=O)$OR^b$, —C(=O)$NR^cR^d$, —S(=O)$R^f$, —S(=O)$OR^b$, —S(=O)$NR^cR^d$, —S(=O)$_2R^f$, —S(=O)$_2OR^b$, or —S(=O)$_2NR^cR^d$;

$R^2$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^b$, —$NR^cR^d$, —$SR^e$, —C(=O)$R^f$, —C(=O)$OR^b$, —C(=O)$NR^cR^d$, —S(=O)$R^f$, —S(=O)$OR^b$, —S(=O)$NR^cR^d$, —S(=O)$_2R^f$, —S(=O)$_2OR^b$, or —S(=O)$_2NR^cR^d$;

$R^3$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^b$, —$NR^cR^d$, —$SR^e$, —C(=O)$R^f$, —C(=O)$OR^b$, —C(=O)$NR^cR^d$, —S(=O)$R^f$, —S(=O)$OR^b$, —S(=O)$NR^cR^d$, —S(=O)$_2R^f$, —S(=O)$_2OR^b$, or —S(=O)$_2NR^cR^d$;

$R^4$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^b$, —$NR^cR^d$, —$SR^e$, or —C(=O)$R^f$, —C(=O)$OR^b$, —C(=O)$NR^cR^d$, —S(=O)$R^f$, —S(=O)$OR^b$, —S(=O)$NR^cR^d$, —S(=O)$_2R^f$, —S(=O)$_2OR^b$, or —S(=O)$_2NR^cR^d$;

$R^5$ is hydrogen, optionally substituted $C_1$-$C_6$ alkyl, or a nitrogen protecting group;

each $R^6$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^b$, —$NR^cR^d$, —$SR^e$, —C(=O)$R^f$, —C(=O)$OR^b$, or —C(=O)$NR^cR^d$;

each $R^a$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each $R^b$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each of $R^c$ and $R^d$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or $R^c$ and $R^d$ are joined to form an optionally substituted heterocyclic or optionally substituted heteroaryl ring;

each $R^e$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a sulfur protecting group;

each $R^f$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

k6 is 0, 1, 2, 3, or 4; and z is 1 or 2.

2. The compound of claim 1, wherein $R^5$ is hydrogen.

3. The compound of claim 1, wherein k6 is 0.

4. The compound of claim 1, wherein the compound is of formula:

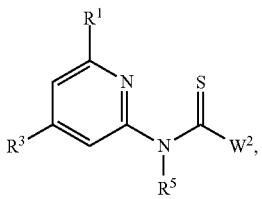

or a pharmaceutically acceptable salt thereof.

5. The compound of claim 1, wherein the compound is of formula:

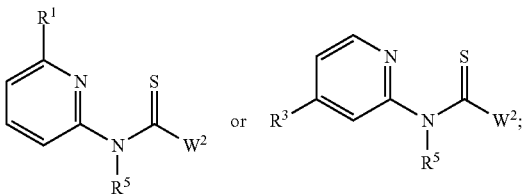

or a pharmaceutically acceptable salt thereof.

6. The compound of claim 1, wherein $W^2$ is:

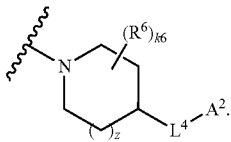

7. The compound of claim 1, wherein $W^2$ is:

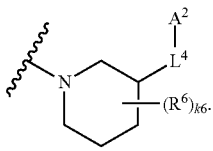

8. The compound according to claim 1, wherein the compound is:

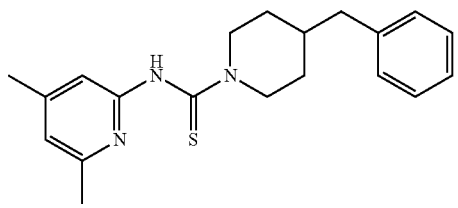

or a pharmaceutically acceptable salt thereof.

9. A pharmaceutical composition comprising a compound of claim 1, or a pharmaceutically acceptable salt thereof, and a pharmaceutically acceptable excipient.

10. A method of treating a disease in a subject in need thereof, the method comprising administering to the subject a therapeutically effective amount of a compound of Formula (II):

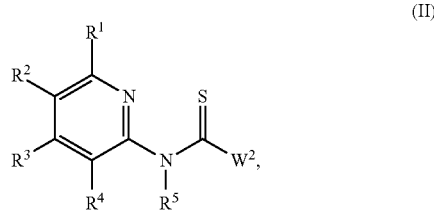

(II)

or a pharmaceutically acceptable salt thereof, wherein:

$W^2$ is of formula:

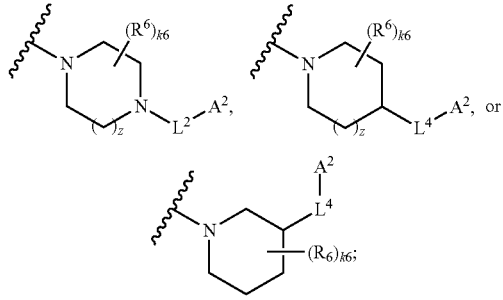

$L^2$ is —CH$_2$—;
$L^4$ is —CH$_2$—;
$A^2$ is of the formula:

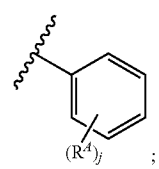

$R^A$ is halogen, nitrile, nitro, optionally substituted alkyl, optionally substituted alkenyl, optionally substituted carbocyclyl, optionally substituted heterocyclyl, optionally substituted aryl, optionally substituted heteroaryl, —OR$^b$, —NR$^c$R$^d$, —SR$^e$, —C(=O)R$^f$, —C(=O)OR$^b$, —C(=O)NR$^c$R$^d$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

j is 0 or 1;

$R^1$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^b$, —NR$^c$R$^d$, —SR$^e$, —C(=O)R$^f$, —C(=O)OR$^b$, —C(=O)NR$^c$R$^d$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

$R^2$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^b$, —$NR^cR^d$, —$SR^e$, —$C(=O)R^f$, —$C(=O)OR^b$, —$C(=O)NR^cR^d$, —$S(=O)R^f$, —$S(=O)OR^b$, —$S(=O)NR^cR^d$, —$S(=O)_2R^f$, —$S(=O)_2OR^b$, or —$S(=O)_2NR^cR^d$;

$R^3$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^b$, —$NR^cR^d$, —$SR^e$, —$C(=O)R^f$, —$C(=O)OR^b$, —$C(=O)NR^cR^d$, —$S(=O)R^f$, —$S(=O)OR^b$, —$S(=O)NR^cR^d$, —$S(=O)_2R^f$, —$S(=O)_2OR^b$, or —$S(=O)_2NR^cR^d$;

$R^4$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^b$, —$NR^cR^d$, —$SR^e$, or —$C(=O)R^f$, —$C(=O)OR^b$, —$C(=O)NR^cR^d$, —$S(=O)R^f$, —$S(=O)OR^b$, —$S(=O)NR^cR^d$, —$S(=O)_2R^f$, —$S(=O)_2OR^b$, or —$S(=O)_2NR^cR^d$;

$R^5$ is hydrogen, optionally substituted $C_1$-$C_6$ alkyl, or a nitrogen protecting group;

each $R^6$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^b$, —$NR^cR^d$, —$SR^e$, —$C(=O)R^f$, —$C(=O)OR^b$, or —$C(=O)NR^cR^d$;

each $R^a$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each $R^b$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each of $R^c$ and $R^d$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or $R^c$ and $R^d$ are joined to form an optionally substituted heterocyclic or optionally substituted heteroaryl ring;

each $R^e$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a sulfur protecting group;

each $R^f$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

k6 is 0, 1, 2, 3, or 4; and z is 1 or 2;

provided that the compound is not N-(4,6-dimethylpyridin-2-yl)-4-(3-(trifluoromethyl)benzyl)piperazine-1-carbothioamide; wherein the disease is pulmonary fibrosis, renal cell carcinoma, or breast cancer.

11. The method of claim 10, wherein the disease is pulmonary fibrosis or renal cell carcinoma.

12. The method of claim 10, wherein the disease is breast cancer.

13. A method of inhibiting the activity of a phosphoglycerate dehydrogenase (PHGDH) in a subject or biological sample, the method comprising administering to the subject or contacting the biological sample with an effective amount of a compound of Formula (II):

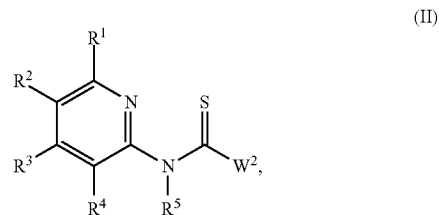

(II)

or a pharmaceutically acceptable salt thereof, wherein:

$W^2$ is of formula:

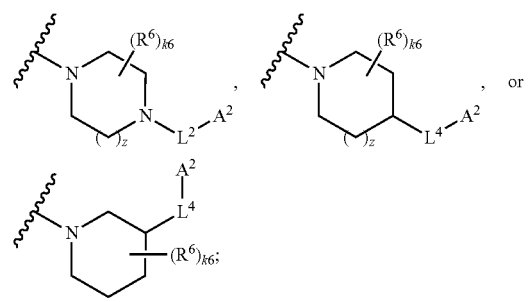

, or $L^2$ is —$CH_2$—;

$L^4$ is —$CH_2$—;

$A^2$ is of the formula:

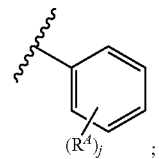

;

$R^A$ is halogen, nitrile, nitro, optionally substituted alkyl, optionally substituted alkenyl, optionally substituted carbocyclyl, optionally substituted heterocyclyl, optionally substituted aryl, optionally substituted heteroaryl, —$OR^b$, —$NR^cR^d$, —$SR^e$, —$C(=O)R^f$, —$C(=O)OR^b$, —$C(=O)NR^cR^d$, —$S(=O)R^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

j is 0 or 1;

R$^1$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^b$, —NR$^c$R$^d$, —SR$^e$, —C(=O)R$^f$, —C(=O)OR$^b$, —C(=O)NR$^c$R$^d$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

R$^2$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^b$, —NR$^c$R$^d$, —SR$^e$, —C(=O)R$^f$, —C(=O)OR$^b$, —C(=O)NR$^c$R$^d$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

R$^3$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^b$, —NR$^c$R$^d$, —SR$^e$, —C(=O)R$^f$, —C(=O)OR$^b$, —C(=O)NR$^c$R$^d$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

R$^4$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^b$, —NR$^c$R$^d$, —SR$^e$, or —C(=O)R$^f$, —C(=O)OR$^b$, —C(=O)NR$^c$R$^d$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

R$^5$ is hydrogen, optionally substituted C$_1$-C$_6$ alkyl, or a nitrogen protecting group;

each R$^6$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^b$, —NR$^c$R$^d$, —SR$^e$, —C(=O)R$^f$, —C(=O)OR$^b$, or —C(=O)NR$^c$R$^d$;

each R$^a$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each R$^b$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each of R$^c$ and R$^d$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or R$^c$ and R$^d$ are joined to form an optionally substituted heterocyclic or optionally substituted heteroaryl ring;

each R$^e$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a sulfur protecting group;

each R$^f$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

k6 is 0, 1, 2, 3, or 4; and z is 1 or 2;

provided that the compound is not N-(4,6-dimethylpyridin-2-yl)-4-(3-(trifluoromethyl)benzyl)piperazine-1-carbothioamide.

14. A method of inducing cell death in PHGDH-dependent cells in a subject or biological sample, the method comprising administering to the subject or contacting the biological sample with an effective amount of a compound Formula (II):

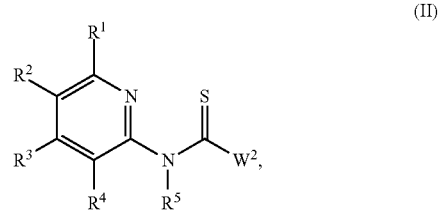

or a pharmaceutically acceptable salt thereof, wherein:
W$^2$ is of formula:

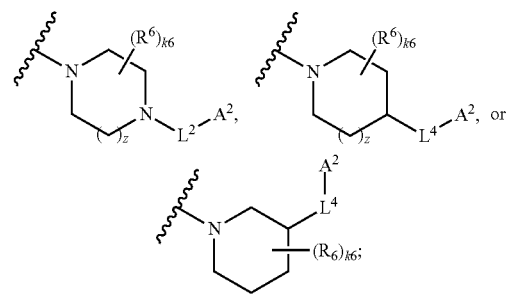

L$^2$ is —CH$_2$—;
L$^4$ is —CH$_2$—;
A$^2$ is of the formula:

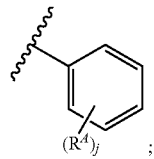

R$^A$ is halogen, nitrile, nitro, optionally substituted alkyl, optionally substituted alkenyl, optionally substituted carbocyclyl, optionally substituted heterocyclyl, optionally substituted aryl, optionally substituted heteroaryl, —OR$^b$, —NR$^c$R$^d$, —SR$^e$, —C(=O)R$^f$, —C(=O)OR$^b$, —C(=O)NR$^c$R$^d$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

j is 0 or 1;

R$^1$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^b$, —NR$^c$R$^d$, —SR$^e$, —C(=O)R$^f$, —C(=O)OR$^b$, —C(=O)NR$^c$R$^d$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

R$^2$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^b$, —NR$^c$R$^d$, —SR$^e$, —C(=O)R$^f$, —C(=O)OR$^b$, —C(=O)NR$^c$R$^d$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

R$^3$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^b$, —NR$^c$R$^d$, —SR$^e$, —C(=O)R$^f$, —C(=O)OR$^b$, —C(=O)NR$^c$R$^d$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

R$^4$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^b$, —NR$^c$R$^d$, —SR$^e$, or —C(=O)R$^f$, —C(=O)OR$^b$, —C(=O)NR$^c$R$^d$, —S(=O)R$^f$, —S(=O)OR$^b$, —S(=O)NR$^c$R$^d$, —S(=O)$_2$R$^f$, —S(=O)$_2$OR$^b$, or —S(=O)$_2$NR$^c$R$^d$;

R$^5$ is hydrogen, optionally substituted C$_1$-C$_6$ alkyl, or a nitrogen protecting group;

each R$^6$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^b$, —NR$^c$R$^d$, —SR$^e$, —C(=O)R$^f$, —C(=O)OR$^b$, or —C(=O)NR$^c$R$^d$;

each R$^a$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each R$^b$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each of R$^c$ and R$^d$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, or R$^c$ and R$^d$ are joined to form an optionally substituted heterocyclic or optionally substituted heteroaryl ring;

each R$^e$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a sulfur protecting group;

each R$^f$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

k6 is 0, 1, 2, 3, or 4; and z is 1 or 2;

provided that the compound is not N-(4,6-dimethylpyridin-2-yl)-4-(3-(trifluoromethyl)benzyl)piperazine-1-carbothioamide.

15. A method of treating a disease in a subject in need thereof, the method comprising administering to the subject a therapeutically effective amount of a compound selected from the group consisting of:

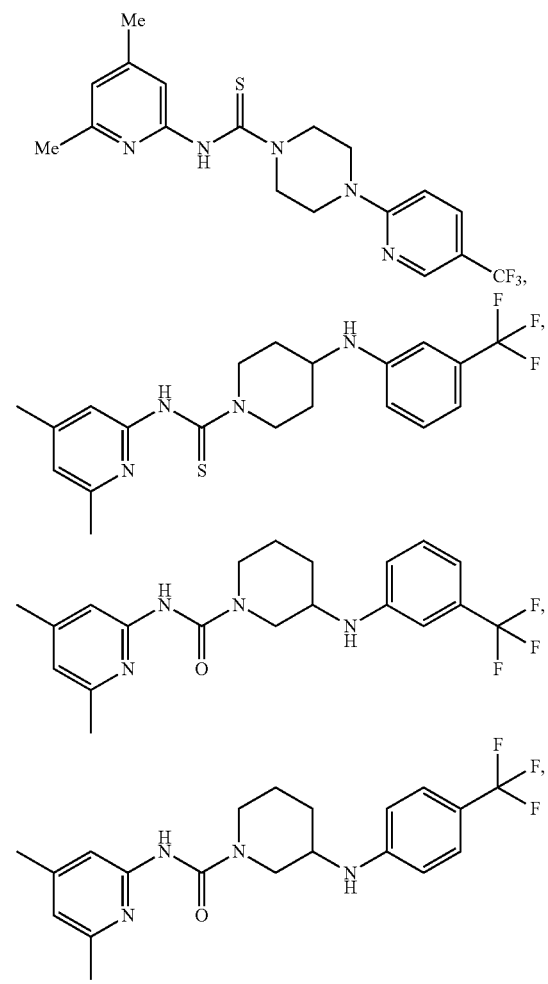

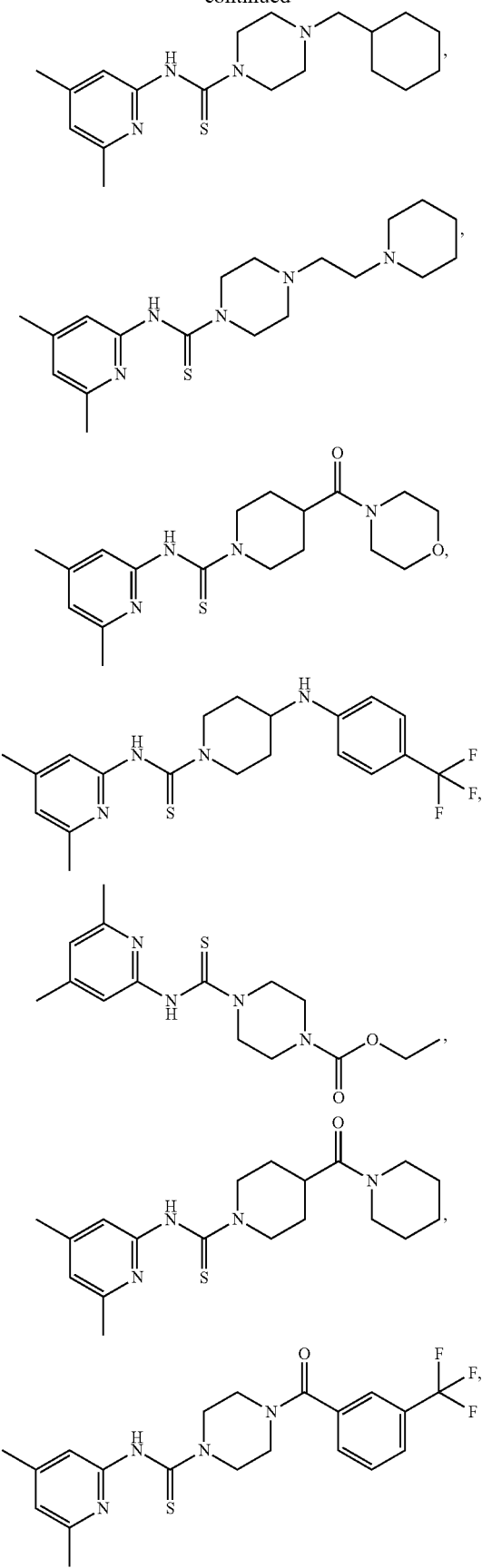

-continued
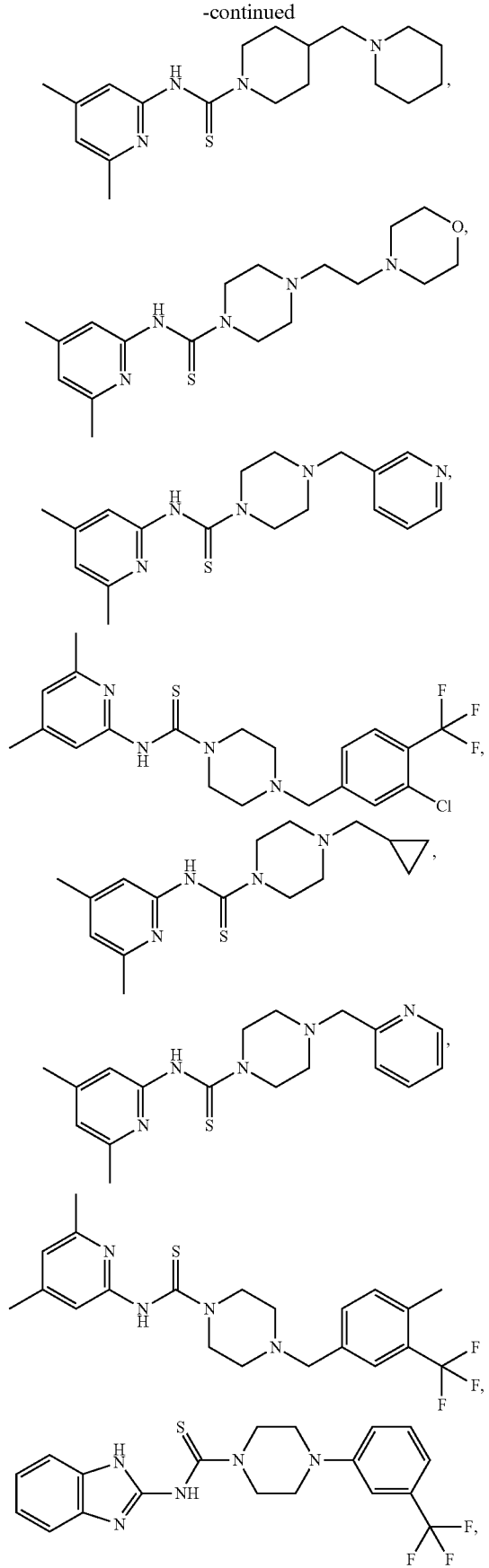
-continued
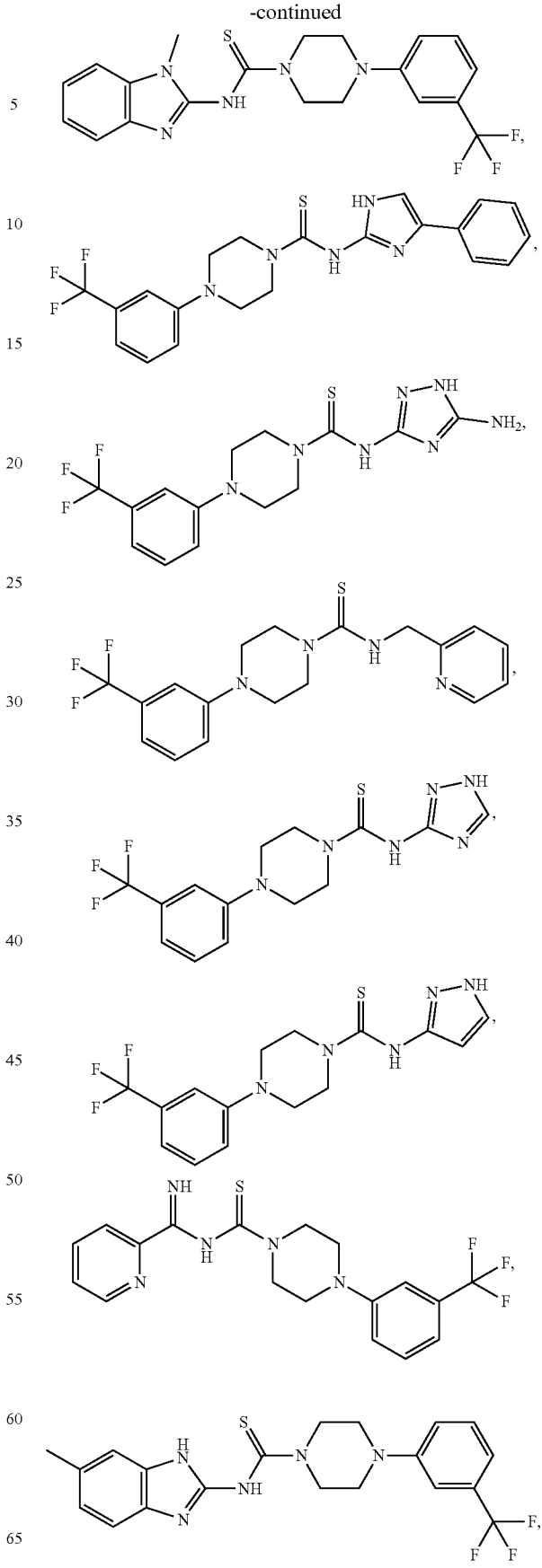

-continued

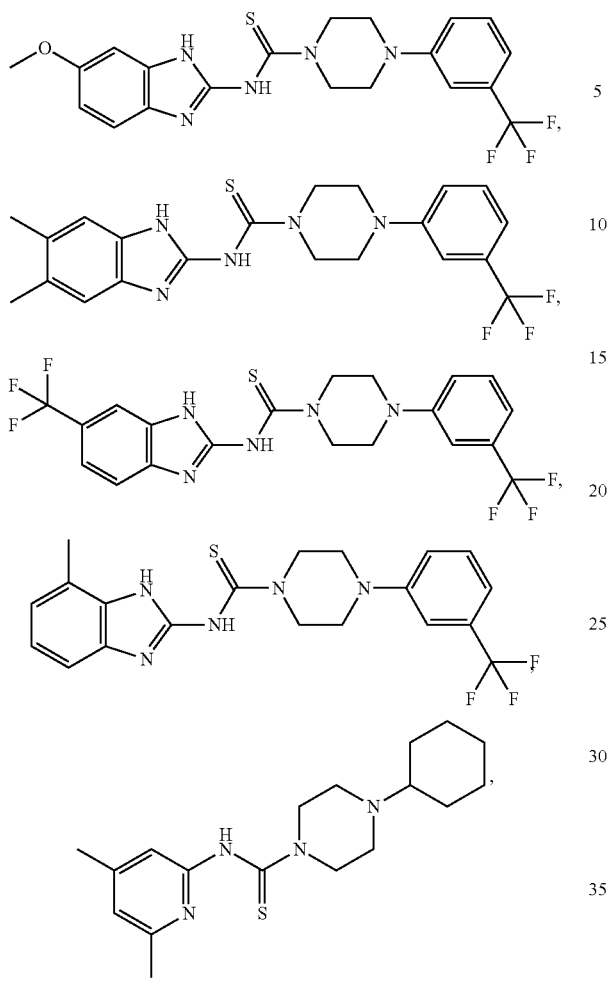

and pharmaceutically acceptable salts thereof; wherein the disease is pulmonary fibrosis, renal cell carcinoma, or breast cancer.

16. The method of claim 15, wherein the disease is pulmonary fibrosis or renal cell carcinoma.

17. The method of claim 15, wherein the disease is breast cancer.

18. A method of inhibiting the activity of a phosphoglycerate dehydrogenase (PHGDH) in a subject or biological sample, the method comprising administering to the subject or contacting the biological sample with a compound selected from the group consisting of:

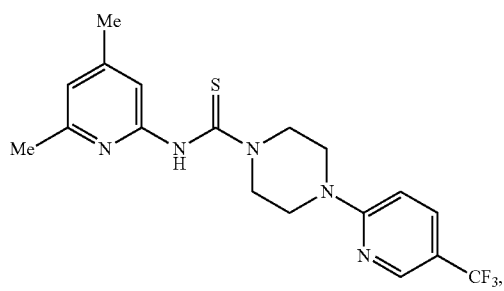 [SMILES: Cc1cc(C)nc(NC(=S)N2CCN(c3ccc(C(F)(F)F)cn3)CC2)c1]

-continued

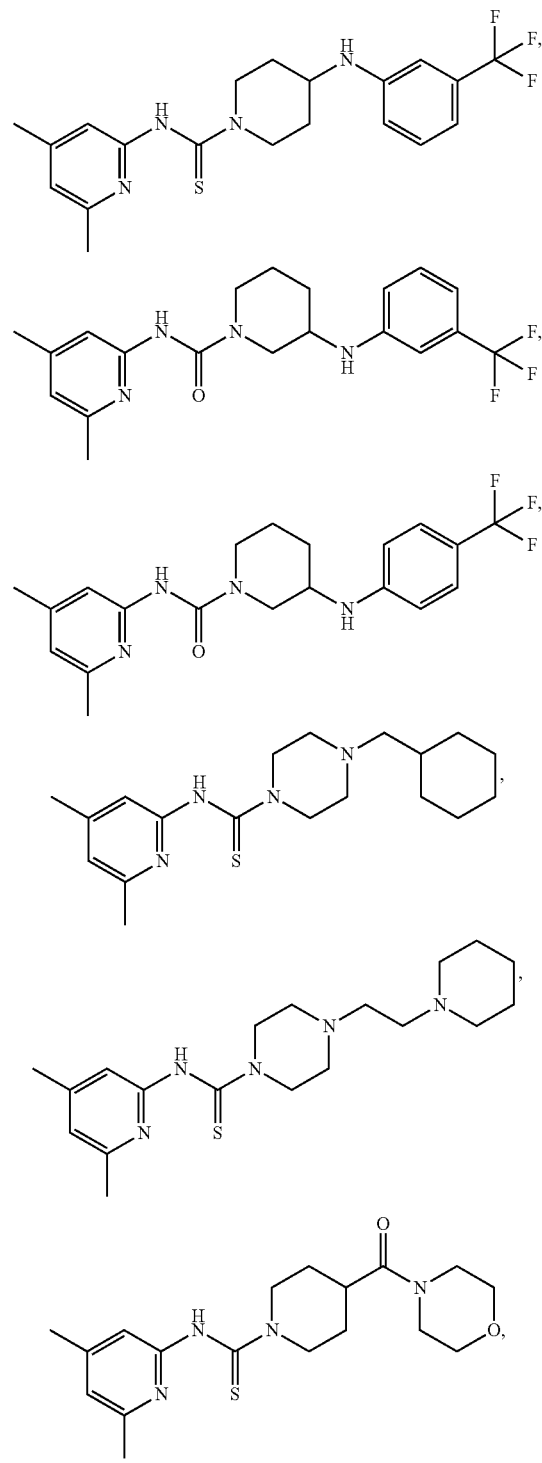

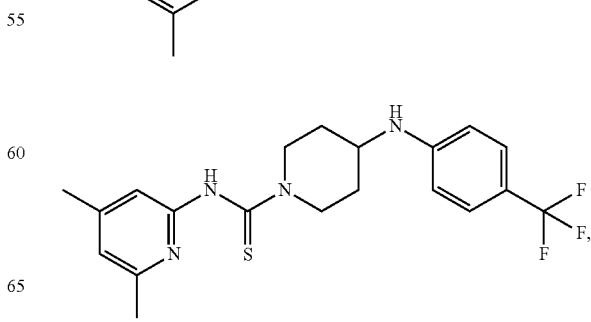

307
-continued
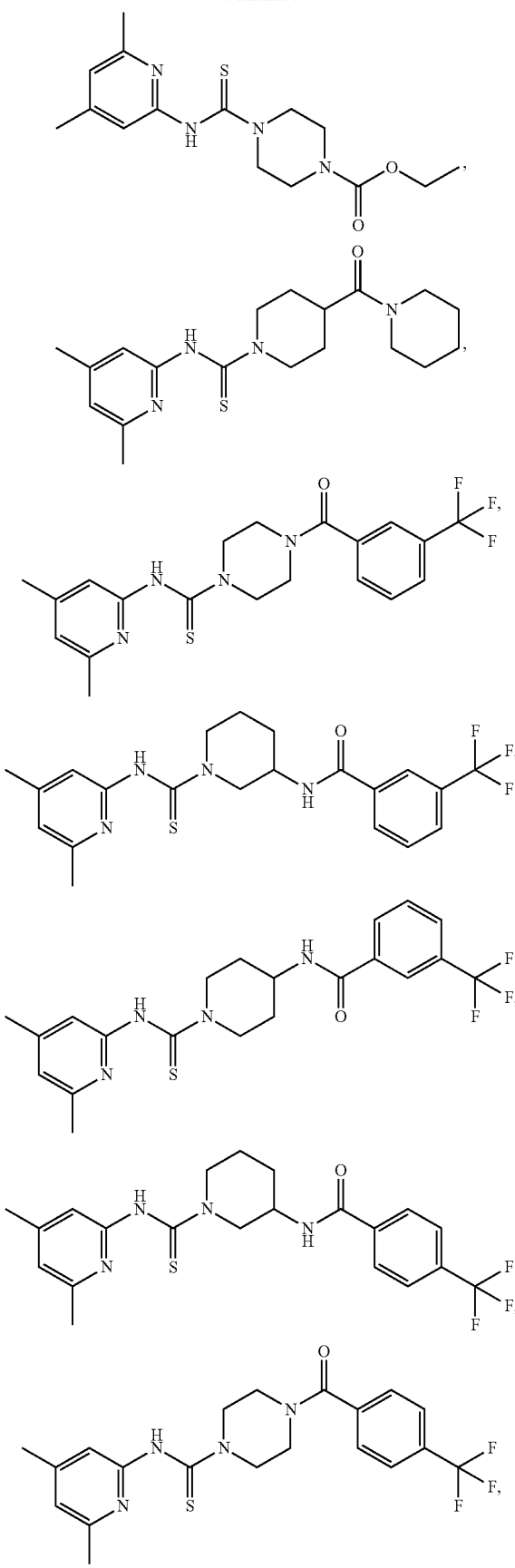
308
-continued
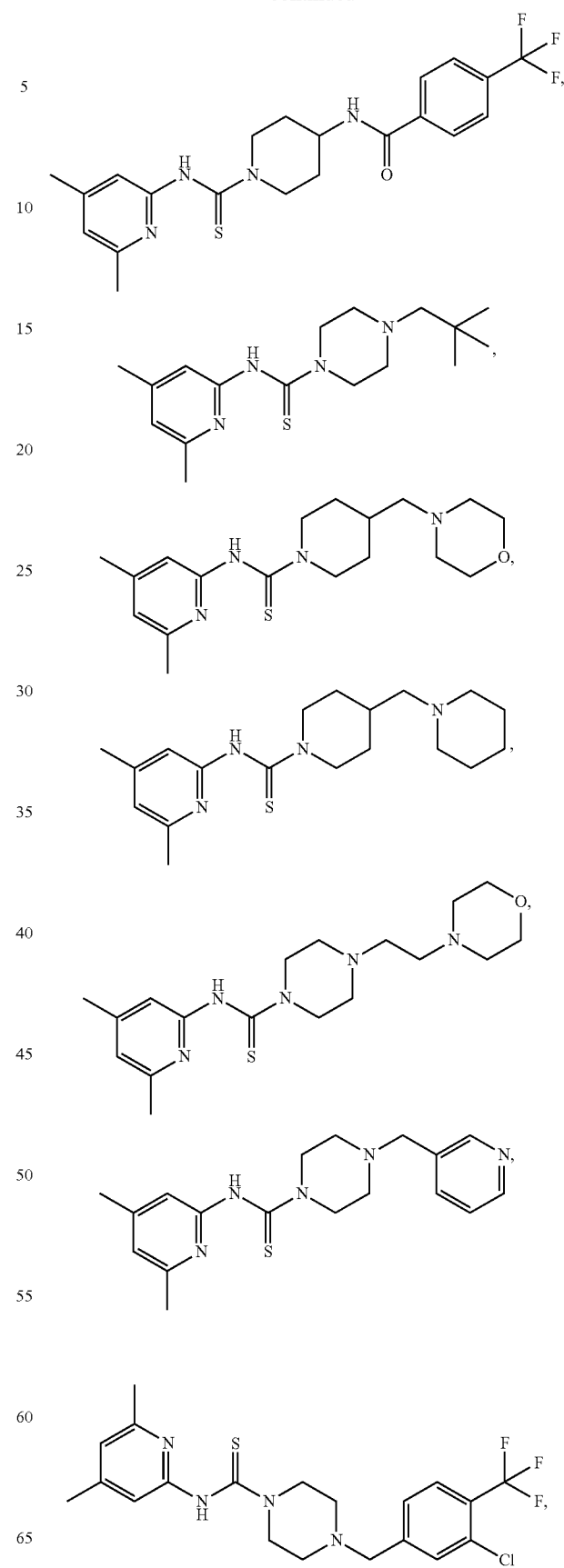

309
-continued
310
-continued
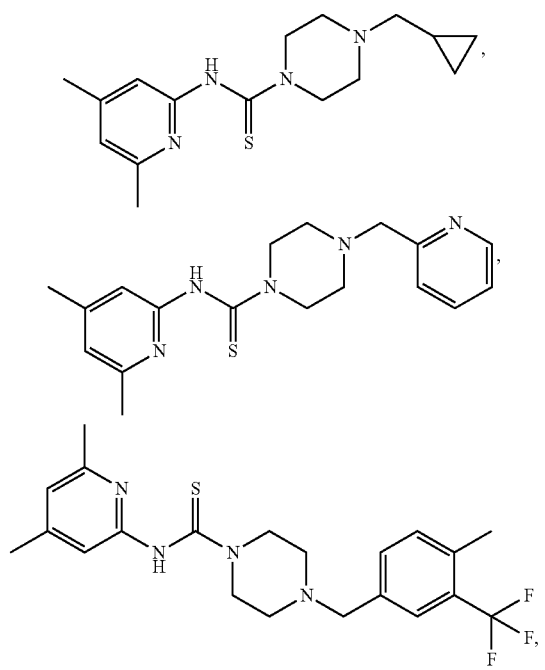
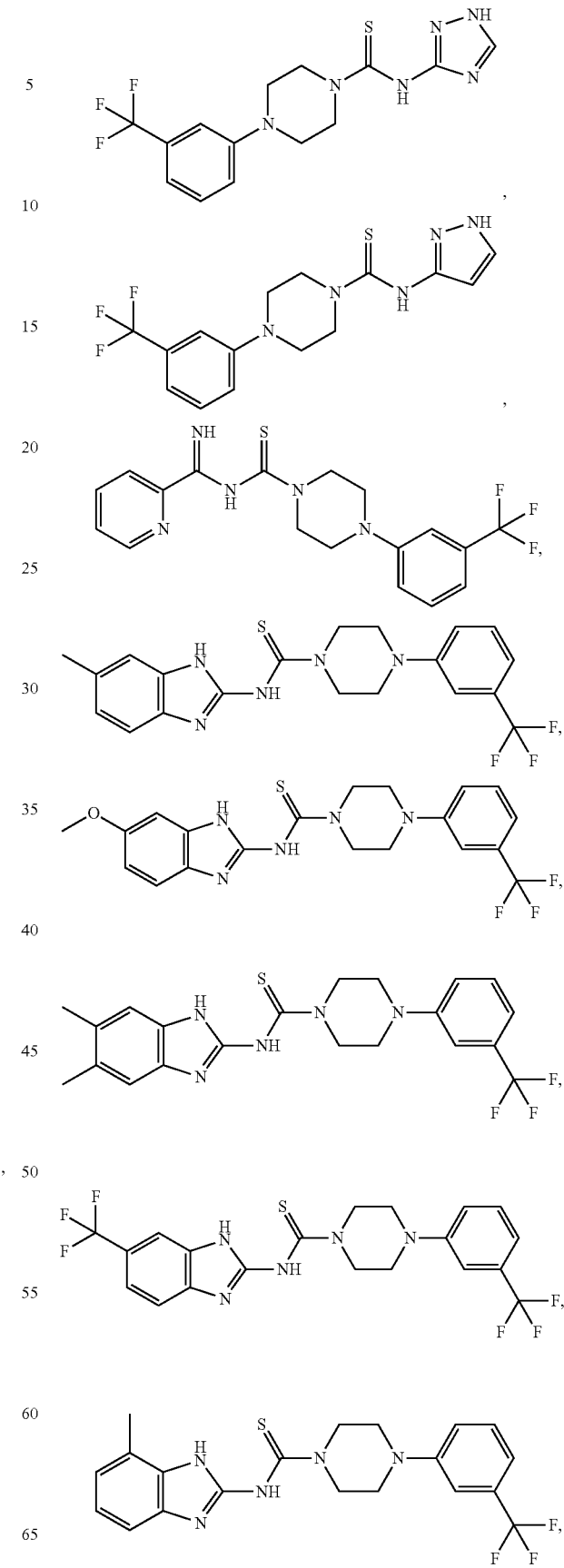

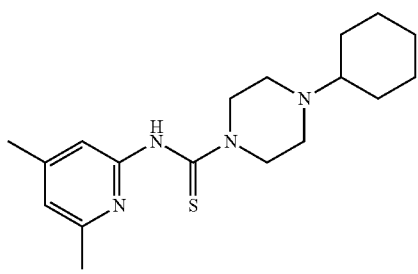
and pharmaceutically acceptable salts thereof.
19. A method of inducing cell death in PHGDH-dependent cells in a subject or biological sample, the method comprising administering to the subject or contacting the biological sample with a selected from the group consisting of:
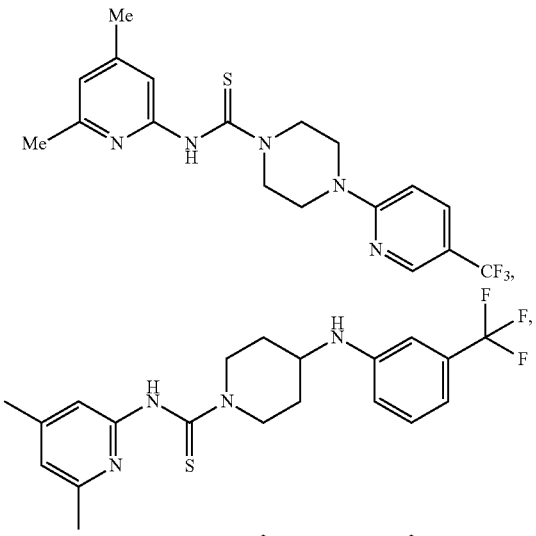
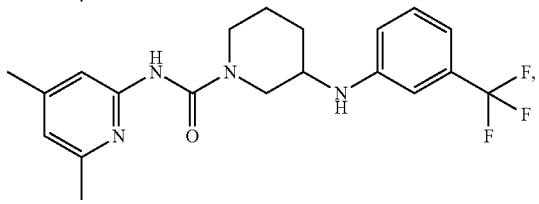
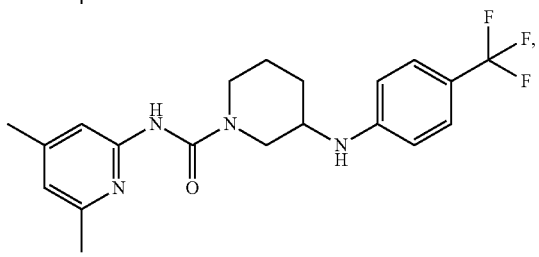
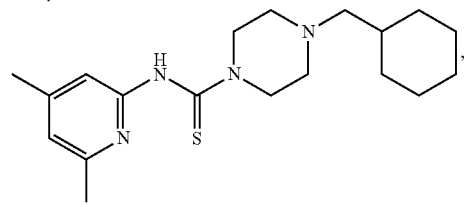
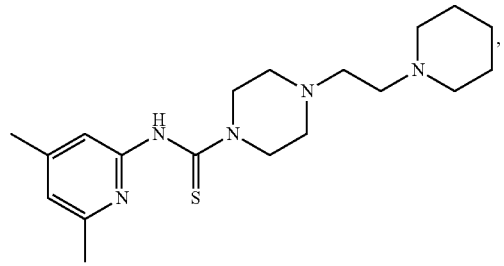
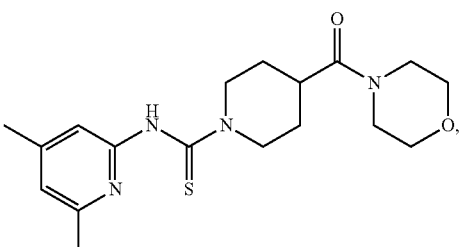
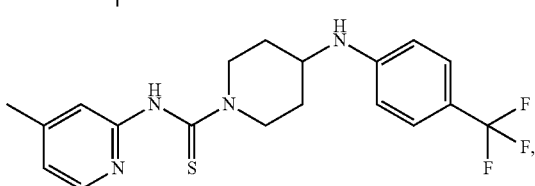
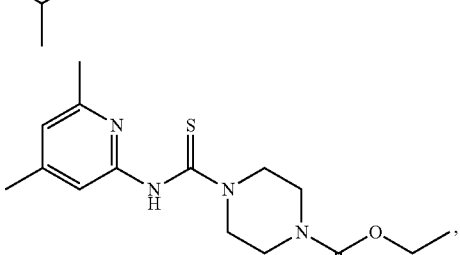
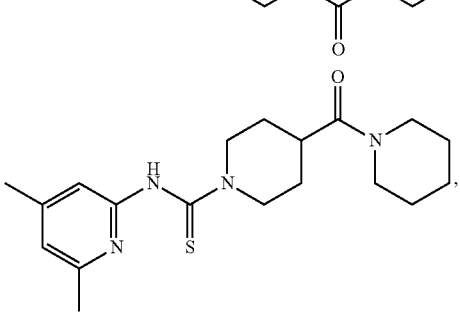
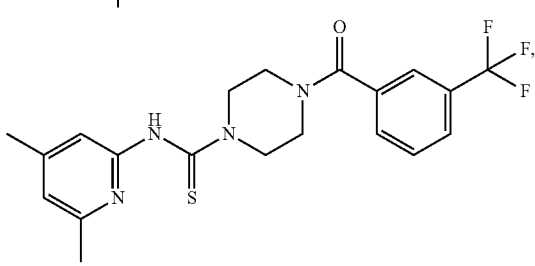
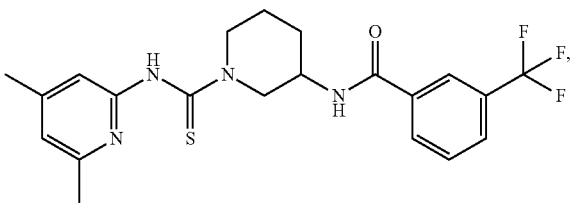

313
-continued
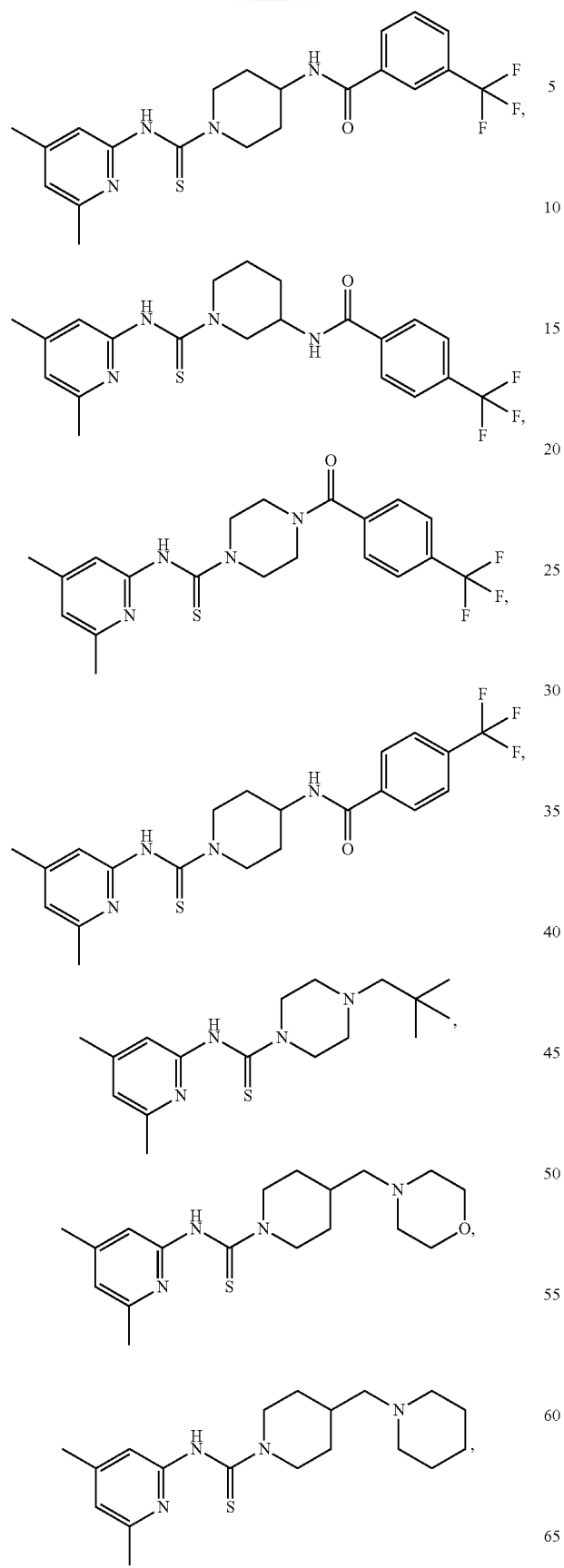
314
-continued
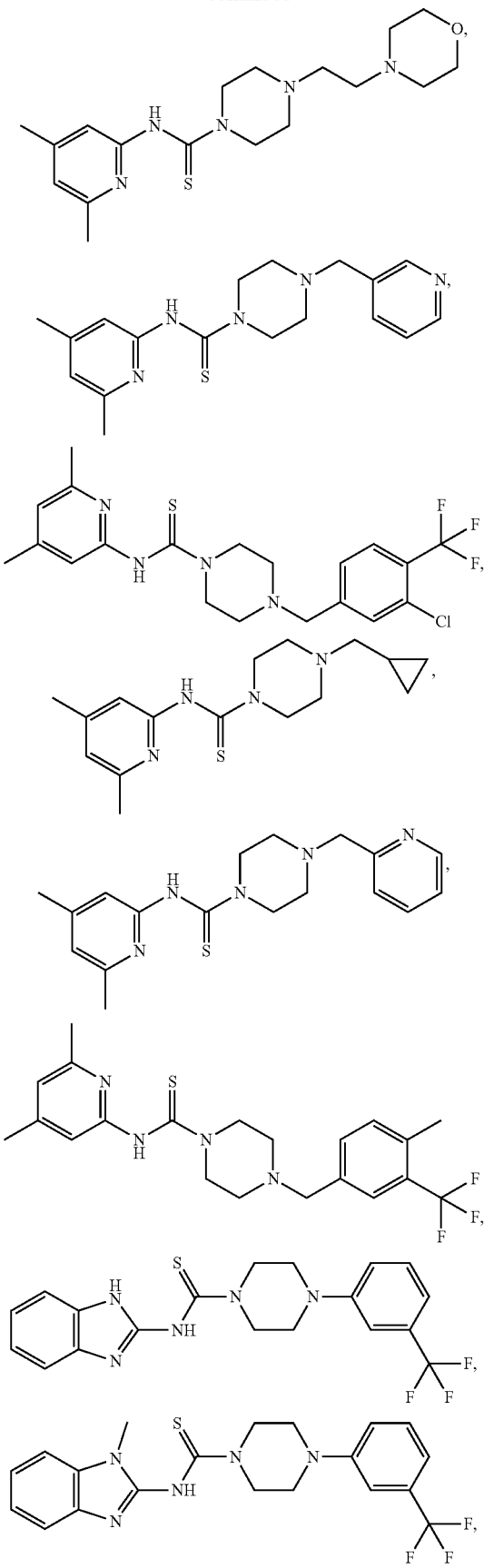

-continued

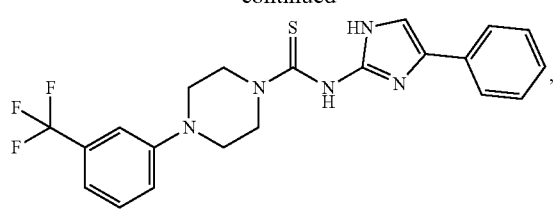

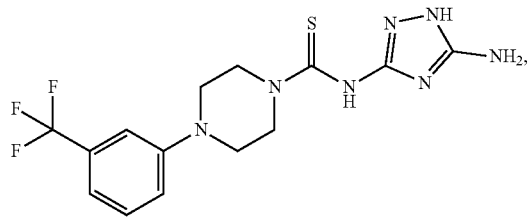

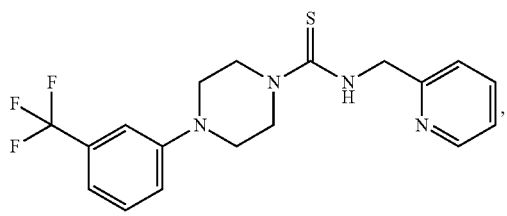

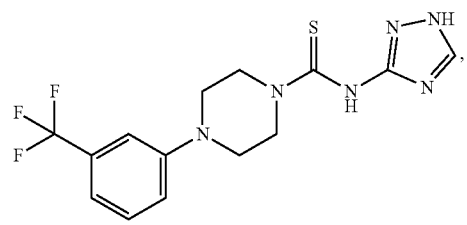

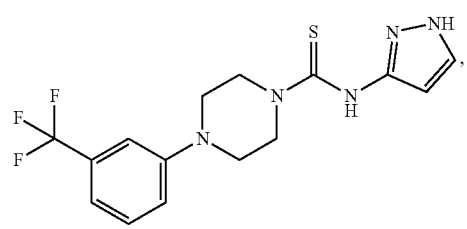

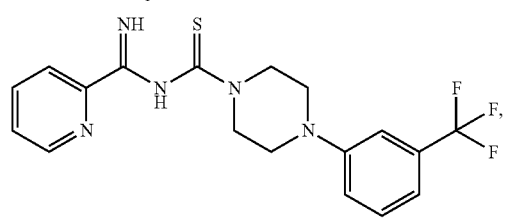

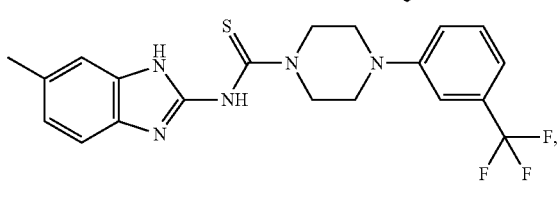

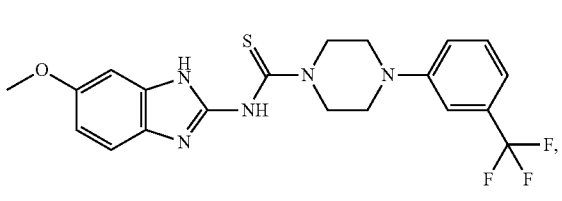

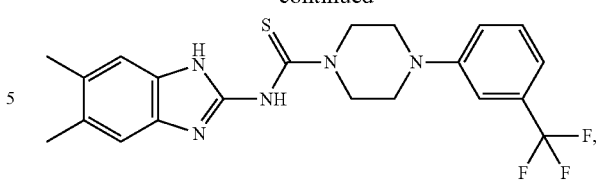

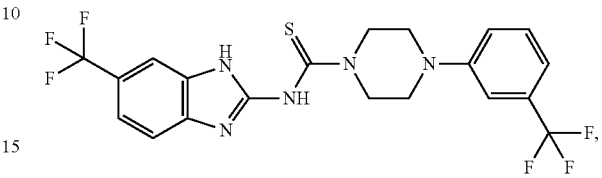

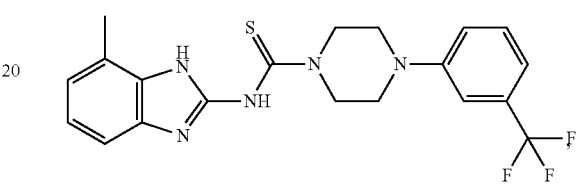

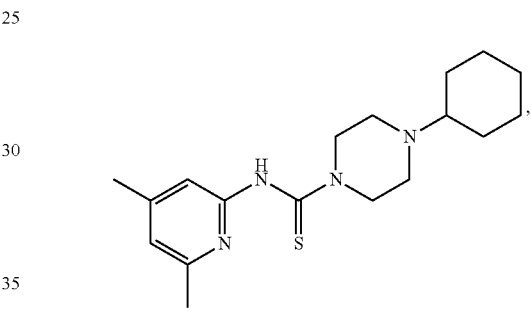

and pharmaceutically acceptable salts thereof.

20. The method of claim 13, wherein the method is for inhibiting the activity of a phosphoglycerate dehydrogenase (PHGDH) in a biological sample.

21. The method of claim 14 wherein the method is for inducing cell death in PHGDH-dependent cells in a biological sample.

22. The method of claim 18, wherein the method is for inhibiting the activity of a phosphoglycerate dehydrogenase (PHGDH) in a biological sample.

23. The method of claim 19, wherein the method is for inducing cell death in PHGDH-dependent cells in a biological sample.

24. The method of claim 10 wherein the compound is the following:

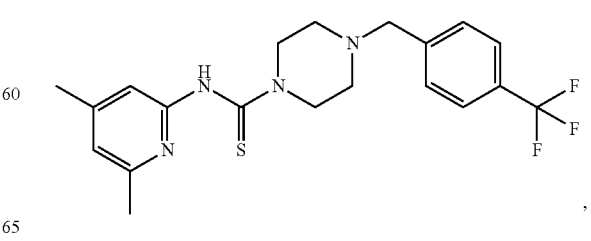

or a pharmaceutically acceptable salt thereof.

25. The method of claim 15, wherein the compound is the following:
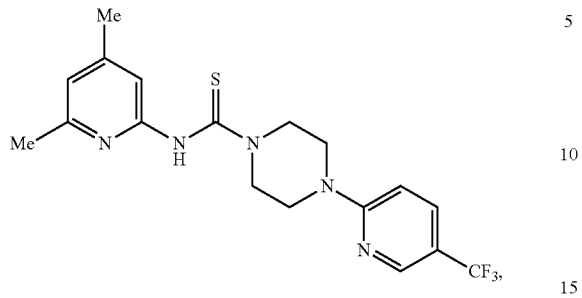
or a pharmaceutically acceptable salt thereof.
* * * * *

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleotide
```

<400> SEQUENCE: 1
ggggccacta gggacaggat                                                      20

<210> SEQ ID NO 2
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 2
aaagcagaac cttagcaaag                                                      20

<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 3
gaacggggcg tatctcatgg                                                      20

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4
gagaaggaca ggcagtgtcg                                                      20

<210> SEQ ID NO 5
<211> LENGTH: 533
<212> TYPE: PRT
<213> ORGANISM: Homo sapiens

<400> SEQUENCE: 5

Met Ala Phe Ala Asn Leu Arg Lys Val Leu Ile Ser Asp Ser Leu Asp
1               5                   10                  15

Pro Cys Cys Arg Lys Ile Leu Gln Asp Gly Gly Leu Gln Val Val Glu
            20                  25                  30

Lys Gln Asn Leu Ser Lys Glu Glu Leu Ile Ala Glu Leu Gln Asp Cys
        35                  40                  45

Glu Gly Leu Ile Val Arg Ser Ala Thr Lys Val Thr Ala Asp Val Ile
    50                  55                  60

Asn Ala Ala Glu Lys Leu Gln Val Val Gly Arg Ala Gly Thr Gly Val
65                  70                  75                  80

Asp Asn Val Asp Leu Glu Ala Ala Thr Arg Lys Gly Ile Leu Val Met
                85                  90                  95

Asn Thr Pro Asn Gly Asn Ser Leu Ser Ala Ala Glu Leu Thr Cys Gly
            100                 105                 110

Met Ile Met Cys Leu Ala Arg Gln Ile Pro Gln Ala Thr Ala Ser Met
        115                 120                 125

Lys Asp Gly Lys Trp Glu Arg Lys Lys Phe Met Gly Thr Glu Leu Asn
    130                 135                 140

Gly Lys Thr Leu Gly Ile Leu Gly Leu Gly Arg Ile Gly Arg Glu Val
145                 150                 155                 160

```
Ala Thr Arg Met Gln Ser Phe Gly Met Lys Thr Ile Gly Tyr Asp Pro
                165                 170                 175

Ile Ile Ser Pro Glu Val Ser Ala Ser Phe Gly Val Gln Gln Leu Pro
            180                 185                 190

Leu Glu Glu Ile Trp Pro Leu Cys Asp Phe Ile Thr Val His Thr Pro
        195                 200                 205

Leu Leu Pro Ser Thr Thr Gly Leu Leu Asn Asp Asn Thr Phe Ala Gln
    210                 215                 220

Cys Lys Lys Gly Val Arg Val Val Asn Cys Ala Arg Gly Gly Ile Val
225                 230                 235                 240

Asp Glu Gly Ala Leu Leu Arg Ala Leu Gln Ser Gly Gln Cys Ala Gly
                245                 250                 255

Ala Ala Leu Asp Val Phe Thr Glu Glu Pro Pro Arg Asp Arg Ala Leu
                260                 265                 270

Val Asp His Glu Asn Val Ile Ser Cys Pro His Leu Gly Ala Ser Thr
            275                 280                 285

Lys Glu Ala Gln Ser Arg Cys Gly Glu Glu Ile Ala Val Gln Phe Val
        290                 295                 300

Asp Met Val Lys Gly Lys Ser Leu Thr Gly Val Val Asn Ala Gln Ala
305                 310                 315                 320

Leu Thr Ser Ala Phe Ser Pro His Thr Lys Pro Trp Ile Gly Leu Ala
                325                 330                 335

Glu Ala Leu Gly Thr Leu Met Arg Ala Trp Ala Gly Ser Pro Lys Gly
                340                 345                 350

Thr Ile Gln Val Ile Thr Gln Gly Thr Ser Leu Lys Asn Ala Gly Asn
            355                 360                 365

Cys Leu Ser Pro Ala Val Ile Val Gly Leu Leu Lys Glu Ala Ser Lys
370                 375                 380

Gln Ala Asp Val Asn Leu Val Asn Ala Lys Leu Leu Val Lys Glu Ala
385                 390                 395                 400

Gly Leu Asn Val Thr Thr Ser His Ser Pro Ala Ala Pro Gly Glu Gln
                405                 410                 415

Gly Phe Gly Glu Cys Leu Leu Ala Val Ala Leu Ala Gly Ala Pro Tyr
                420                 425                 430

Gln Ala Val Gly Leu Val Gln Gly Thr Thr Pro Val Leu Gln Gly Leu
            435                 440                 445

Asn Gly Ala Val Phe Arg Pro Glu Val Pro Leu Arg Arg Asp Leu Pro
            450                 455                 460

Leu Leu Leu Phe Arg Thr Gln Thr Ser Asp Pro Ala Met Leu Pro Thr
465                 470                 475                 480

Met Ile Gly Leu Leu Ala Glu Ala Gly Val Arg Leu Leu Ser Tyr Gln
                485                 490                 495

Thr Ser Leu Val Ser Asp Gly Glu Thr Trp His Val Met Gly Ile Ser
            500                 505                 510

Ser Leu Leu Pro Ser Leu Glu Ala Trp Lys Gln His Val Thr Glu Ala
        515                 520                 525

Phe Gln Phe His Phe
    530
```